(12) United States Patent
Wan et al.

(10) Patent No.: US 12,098,214 B2
(45) Date of Patent: Sep. 24, 2024

(54) COMBINATION THERAPIES FOR TREATING CANCER

(71) Applicant: ALX Oncology Inc., South San Francisco, CA (US)

(72) Inventors: Hong Wan, Foster City, CA (US); Bang Janet Sim, South San Francisco, CA (US); Sophia Randolph, Chico, CA (US); Jaume Pons, San Francisco, CA (US); Tracy Chia-Chien Kuo, San Carlos, CA (US)

(73) Assignee: ALX Oncology Inc., South San Francisco, CA (US)

( * ) Notice: Subject to any disclaimer, the term of this patent is extended or adjusted under 35 U.S.C. 154(b) by 0 days.

(21) Appl. No.: 17/743,350

(22) Filed: May 12, 2022

(65) Prior Publication Data

US 2022/0363779 A1    Nov. 17, 2022

Related U.S. Application Data

(60) Provisional application No. 63/193,581, filed on May 26, 2021, provisional application No. 63/188,388, filed on May 13, 2021.

(51) Int. Cl.
*C07K 16/32* (2006.01)
*A61K 39/00* (2006.01)
*A61P 35/00* (2006.01)

(52) U.S. Cl.
CPC .............. *C07K 16/32* (2013.01); *A61P 35/00* (2018.01); *A61K 2039/505* (2013.01); *C07K 2317/24* (2013.01); *C07K 2319/02* (2013.01); *C07K 2319/03* (2013.01); *C07K 2319/30* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 5,116,964 A | 5/1992 | Capon et al. |
| 5,306,809 A | 4/1994 | Boon et al. |
| 5,478,925 A | 12/1995 | Wallach et al. |
| 5,505,931 A | 4/1996 | Pribish |
| 5,648,237 A | 7/1997 | Carter |
| 5,697,901 A | 12/1997 | Eriksson |
| 5,972,707 A | 10/1999 | Roy et al. |
| 6,174,529 B1 | 1/2001 | Michael et al. |
| 6,261,554 B1 | 7/2001 | Valerio et al. |
| 6,541,615 B1 | 4/2003 | Ullrich et al. |
| 6,591,129 B1 | 7/2003 | Ben-Haim et al. |
| 6,613,332 B1 | 9/2003 | Michael et al. |
| 7,402,155 B2 | 7/2008 | Palasis et al. |
| 7,514,229 B2 | 4/2009 | Jamieson et al. |
| 7,662,367 B2 | 2/2010 | Desjarlais et al. |
| 7,691,970 B2 | 4/2010 | Skerra et al. |
| 7,892,558 B2 | 2/2011 | Zagury |
| 8,216,805 B2 | 7/2012 | Carter et al. |
| 8,377,448 B2 | 2/2013 | Smith et al. |
| 8,399,219 B2 | 3/2013 | Stagliano et al. |
| 8,518,404 B2 | 8/2013 | Daugherty et al. |
| 8,518,869 B2 | 8/2013 | Hallström et al. |
| 8,529,898 B2 | 9/2013 | Daugherty et al. |
| 8,541,203 B2 | 9/2013 | Daugherty et al. |
| 8,562,997 B2 | 10/2013 | Jaiswal et al. |
| 8,603,778 B2 | 12/2013 | Heavner et al. |
| 8,613,922 B2 | 12/2013 | Clemmons et al. |
| 8,728,476 B2 | 5/2014 | Van Den Berg |
| 8,748,399 B2 | 6/2014 | Bedzyk et al. |
| 8,993,266 B2 | 3/2015 | Stagliano et al. |
| 9,017,675 B2 | 4/2015 | Liu et al. |
| 9,169,321 B2 | 10/2015 | Daugherty et al. |
| 9,352,037 B2 | 5/2016 | Van Den Berg |
| 9,382,320 B2 | 7/2016 | Liu et al. |
| 9,394,365 B1 | 7/2016 | Eisenbach-Schwartz et al. |
| 9,475,882 B2 | 10/2016 | Clemmons et al. |
| 9,512,225 B2 | 12/2016 | Eisenbach-Schwartz et al. |
| 9,512,227 B2 | 12/2016 | Eisenbach-Schwartz et al. |
| 9,534,052 B2 | 1/2017 | Eisenbach-Schwartz et al. |
| 9,546,206 B2 | 1/2017 | Ring et al. |
| 9,562,087 B2 | 2/2017 | Ring et al. |
| 9,845,345 B2 | 12/2017 | Ring et al. |
| 9,944,911 B2 | 4/2018 | Ring et al. |
| 10,179,171 B2 | 1/2019 | Govindan et al. |
| 10,259,859 B2 | 4/2019 | Pons et al. |
| 10,406,179 B2 | 9/2019 | Shizuru et al. |

(Continued)

FOREIGN PATENT DOCUMENTS

| | | |
|---|---|---|
| CA | 3063099 A1 | 12/2018 |
| CN | 102257001 A | 11/2011 |
| CN | 102596233 A | 7/2012 |
| CN | 102939303 A | 2/2013 |
| CN | 103635490 A | 3/2014 |

(Continued)

OTHER PUBLICATIONS

Kauder et al (PLoS ONE, 2018, 13(8) e0201832, internet pp. 1-33).*
Chow et al (Journal of Clinical Oncology, 2019; 37, No. 15_suppl, abstract 2514).*
NCT03013218 (History of Changes for study NCT03013218, published Dec. 11, 2019, pp. 1-8).*
NCT04499924 (History of Changes for study NCT04499924, published Nov. 19, 2020, pp. 1-14).*
De Vita et al (Future Oncology, 2019, 15:2723-2731).*
Abrahao-Machado et al. (2016). "HER2 testing in gastric cancer: an update," World J. Gastroenterol. 22(19):4619-4625.

(Continued)

*Primary Examiner* — Laura B Goddard
(74) *Attorney, Agent, or Firm* — MORRISON & FOERSTER LLP

(57) ABSTRACT

Provided are methods of treating cancer that comprise administering a polypeptide (e.g. a fusion polypeptide) that comprises a SIRPα D1 domain variant and an Fc domain variant in combination with at least one chemotherapy agent and/or at least one therapeutic antibody. Also provided are related kits.

6 Claims, 6 Drawing Sheets

Specification includes a Sequence Listing.

(56) References Cited

U.S. PATENT DOCUMENTS

| | | |
|---|---|---|
| 10,696,730 B2 | 6/2020 | Pons et al. |
| 10,894,831 B2 | 1/2021 | Schnorr et al. |
| 10,907,209 B2 | 2/2021 | Wang et al. |
| 11,208,459 B2 | 12/2021 | Pons et al. |
| 11,208,481 B2 | 12/2021 | Ring et al. |
| 11,419,897 B2 | 8/2022 | Shizuru et al. |
| 11,608,377 B2 | 3/2023 | Schnorr et al. |
| 11,613,564 B2 | 3/2023 | Pons et al. |
| 11,639,376 B2 | 5/2023 | Pons et al. |
| 2004/0213792 A1 | 10/2004 | Clemmons et al. |
| 2007/0148201 A1 | 6/2007 | Skerra et al. |
| 2008/0160013 A1 | 7/2008 | Clemmons et al. |
| 2009/0068195 A1 | 3/2009 | Vugmeyster et al. |
| 2010/0189651 A1 | 7/2010 | Stagliano et al. |
| 2010/0215640 A1 | 8/2010 | Clemmons et al. |
| 2010/0239578 A1 | 9/2010 | Danska et al. |
| 2010/0239579 A1 | 9/2010 | Smith et al. |
| 2011/0081345 A1 | 4/2011 | Moore et al. |
| 2011/0110938 A1 | 5/2011 | Chiu et al. |
| 2011/0184145 A1 | 7/2011 | Silence et al. |
| 2011/0237498 A1 | 9/2011 | Raymond et al. |
| 2012/0189625 A1 | 7/2012 | Wang et al. |
| 2012/0283408 A1 | 11/2012 | Lee et al. |
| 2013/0011401 A1 | 1/2013 | Huber et al. |
| 2014/0010810 A1 | 1/2014 | West et al. |
| 2014/0023664 A1 | 1/2014 | Lowman et al. |
| 2014/0024111 A1 | 1/2014 | Kannan et al. |
| 2014/0051634 A1 | 2/2014 | Hallström et al. |
| 2014/0113348 A1 | 4/2014 | Williams et al. |
| 2014/0140926 A1 | 5/2014 | Discher et al. |
| 2014/0161800 A1 | 6/2014 | Blankenship et al. |
| 2014/0193408 A1 | 7/2014 | Huber et al. |
| 2014/0242095 A1 | 8/2014 | Wang et al. |
| 2015/0071905 A1 | 3/2015 | Ring et al. |
| 2015/0203559 A1 | 7/2015 | Stagliano et al. |
| 2015/0329616 A1 | 11/2015 | Uger et al. |
| 2015/0353642 A1 | 12/2015 | Tykocinski |
| 2015/0376288 A1 | 12/2015 | Weiskopf et al. |
| 2016/0000909 A1 | 1/2016 | Eisenbach-Schwartz et al. |
| 2016/0008429 A1 | 1/2016 | Willingham et al. |
| 2016/0008463 A1 | 1/2016 | Eisenbach-Schwartz et al. |
| 2016/0045532 A1 | 2/2016 | Roberts et al. |
| 2016/0069898 A1 | 3/2016 | Weiskopf et al. |
| 2016/0144009 A1 | 5/2016 | Tseng et al. |
| 2016/0152715 A1 | 6/2016 | Wong et al. |
| 2016/0177276 A1 | 6/2016 | Lo et al. |
| 2016/0186150 A1 | 6/2016 | Deming et al. |
| 2016/0193295 A1 | 7/2016 | Kannan et al. |
| 2016/0194406 A1 | 7/2016 | Leeper et al. |
| 2016/0244522 A1 | 8/2016 | Van Den Berg |
| 2016/0297866 A1 | 10/2016 | Clemmons et al. |
| 2016/0304609 A1 | 10/2016 | Liu et al. |
| 2017/0029508 A1 | 2/2017 | Eisenbach-Schwartz et al. |
| 2017/0044258 A1 | 2/2017 | Van Den Berg |
| 2017/0107270 A1* | 4/2017 | Pons .................. A61P 11/06 |
| 2017/0281791 A1 | 10/2017 | Govindan et al. |
| 2017/0285037 A1 | 10/2017 | Kulangara et al. |
| 2018/0037652 A1 | 2/2018 | Liu et al. |
| 2018/0105600 A1 | 4/2018 | Pons et al. |
| 2018/0141986 A1 | 5/2018 | Tian et al. |
| 2018/0155405 A1 | 6/2018 | Ring et al. |
| 2018/0195054 A1 | 7/2018 | Ring et al. |
| 2018/0312563 A1 | 11/2018 | Uger et al. |
| 2018/0312587 A1 | 11/2018 | Van Eenennaam et al. |
| 2018/0371435 A1 | 12/2018 | Deming et al. |
| 2019/0093174 A1 | 3/2019 | Wang et al. |
| 2019/0169266 A1 | 6/2019 | Pons et al. |
| 2020/0239543 A1 | 7/2020 | Pons et al. |
| 2020/0263154 A1 | 8/2020 | Deming et al. |
| 2020/0392199 A1 | 12/2020 | Pons et al. |
| 2020/0400662 A1 | 12/2020 | Wan et al. |
| 2021/0070838 A1 | 3/2021 | Pons et al. |
| 2021/0154269 A1 | 5/2021 | Wan et al. |
| 2021/0388329 A1 | 12/2021 | Deming et al. |
| 2022/0064293 A1 | 3/2022 | Ring et al. |
| 2022/0196651 A1 | 6/2022 | Pons et al. |
| 2022/0213166 A1 | 7/2022 | Pons et al. |
| 2022/0242928 A1 | 8/2022 | Pons et al. |
| 2022/0401516 A1 | 12/2022 | Pons et al. |
| 2023/0218719 A1 | 7/2023 | Wan et al. |
| 2023/0340433 A1 | 10/2023 | Deming et al. |
| 2024/0075101 A1 | 3/2024 | Wan et al. |

FOREIGN PATENT DOCUMENTS

| | | |
|---|---|---|
| CN | 104812413 A | 7/2015 |
| CN | 107252476 A | 10/2017 |
| CN | 108350048 A | 7/2018 |
| CO | 20180002471 A2 | 5/2018 |
| EA | 15538 B1 | 8/2011 |
| EP | 2429574 B1 | 5/2015 |
| EP | 3128005 A1 | 2/2017 |
| EP | 3287470 A1 | 2/2018 |
| JP | 2011500005 A | 1/2011 |
| JP | 2012533631 A | 12/2012 |
| JP | 2013541542 A | 11/2013 |
| JP | 2015504899 A | 2/2015 |
| WO | WO-1993000077 A1 | 1/1993 |
| WO | WO-1999040940 A1 | 8/1999 |
| WO | WO-2000077026 A1 | 12/2000 |
| WO | WO-2001048020 A1 | 7/2001 |
| WO | WO-2003031650 A2 | 4/2003 |
| WO | WO-2003095618 A2 | 11/2003 |
| WO | WO-2004011618 A2 | 2/2004 |
| WO | WO-2004096133 A2 | 11/2004 |
| WO | WO-2005108415 A2 | 11/2005 |
| WO | WO-2007084344 A2 | 7/2007 |
| WO | WO-2009046541 A1 | 4/2009 |
| WO | WO-2009091601 A1 | 7/2009 |
| WO | WO-2009131453 A1 | 10/2009 |
| WO | WO-2010070047 A1 | 6/2010 |
| WO | WO-2010096838 A2 | 8/2010 |
| WO | WO-2010130053 A1 | 11/2010 |
| WO | WO-2011011315 A1 | 1/2011 |
| WO | WO-2011066501 A1 | 6/2011 |
| WO | WO-2011076781 A1 | 6/2011 |
| WO | WO-2011143624 A2 | 11/2011 |
| WO | WO-2012048332 A2 | 4/2012 |
| WO | WO-2012130831 A1 | 10/2012 |
| WO | WO-2012142515 A2 | 10/2012 |
| WO | WO-2012172521 A1 | 12/2012 |
| WO | WO-2013032948 A1 | 3/2013 |
| WO | WO-2013063076 A1 | 5/2013 |
| WO | WO-2013109752 A1 | 7/2013 |
| WO | WO-2014045022 A2 | 3/2014 |
| WO | WO-2014094122 A1 | 6/2014 |
| WO | WO-2014121093 A1 | 8/2014 |
| WO | WO-2014124028 A1 | 8/2014 |
| WO | WO-2014149477 A1 | 9/2014 |
| WO | WO-2014160183 A1 | 10/2014 |
| WO | WO-2014179132 A1 | 11/2014 |
| WO | WO-2014186761 A2 | 11/2014 |
| WO | WO-2015041987 A1 | 3/2015 |
| WO | WO-2015042557 A1 | 3/2015 |
| WO | WO-2015048329 A2 | 4/2015 |
| WO | WO-2015057834 A1 | 4/2015 |
| WO | WO-2015116933 A2 | 8/2015 |
| WO | WO-2015136541 A2 | 9/2015 |
| WO | WO-2016022971 A1 | 2/2016 |
| WO | WO-2016022994 A2 | 2/2016 |
| WO | WO-2016023001 A1 | 2/2016 |
| WO | WO-2016023040 A1 | 2/2016 |
| WO | WO-2016024021 A1 | 2/2016 |
| WO | WO-2016033201 A1 | 3/2016 |
| WO | WO-2016044021 A1 | 3/2016 |
| WO | WO-2016057980 A1 | 4/2016 |
| WO | WO-2016063233 A1 | 4/2016 |
| WO | WO-2016065329 A1 | 4/2016 |
| WO | WO-2016081423 A1 | 5/2016 |
| WO | WO-2016138306 A1 | 9/2016 |
| WO | WO-2016169261 A1 | 10/2016 |
| WO | WO-2016187226 A1 | 11/2016 |
| WO | WO-2017009829 A1 | 1/2017 |
| WO | WO-2017027422 A1 | 2/2017 |

(56) References Cited

FOREIGN PATENT DOCUMENTS

| WO | WO-2017068164 A1 | 4/2017 |
|---|---|---|
| WO | WO-2017177333 A1 | 10/2017 |
| WO | WO-2017178653 A2 | 10/2017 |
| WO | WO-2018057669 A1 | 3/2018 |
| WO | WO-2018068028 A1 | 4/2018 |
| WO | WO-2018081897 A1 | 5/2018 |
| WO | WO-2018081898 A1 | 5/2018 |
| WO | WO-2018107058 A1 | 6/2018 |
| WO | WO-2018149938 A1 | 8/2018 |
| WO | WO-2018176132 A1 | 10/2018 |
| WO | WO-2018210795 A1 | 11/2018 |
| WO | WO-2019023347 A1 | 1/2019 |
| WO | WO-2020047326 A2 | 3/2020 |
| WO | WO-2020243338 A1 | 12/2020 |
| WO | WO-2020247820 A1 | 12/2020 |
| WO | WO-2021108693 A1 | 6/2021 |
| WO | WO-2021247430 A1 | 12/2021 |
| WO | WO-2022010806 A1 | 1/2022 |
| WO | WO-2022120286 A1 | 6/2022 |
| WO | WO-2022241157 A1 | 11/2022 |
| WO | WO-2023235754 A1 | 12/2023 |

OTHER PUBLICATIONS

Anonymous (2019). "A Phase 1 Dose Escalation Trial of Intratumoral Injections of TTI-621 in Subjects With Relapsed and Refractory Percutaneously-Accessible Solid Tumors and Mycosis Fungoide," clinical trials.gov, pp. 1-5, Retrieved Jan. 25, 2021 <https://clinicaltrials.gov/ct2/history/NCT02890368?V_13=View#StudyPageTop>.

Anonymous (2019). "A Phase 1a/1b Dose Escalation and Expansion Trial of TTI-621, a Novel Biologic Targeting CD47, in Subjects With Relapsed or Refractory Hematologic Malignancies and Selected Solid Tumors," clinical trials.gov, pp. 1-7, Retrieved Jan. 25, 2021 <https://clinicaltrials.gov/ct2/history/NCT02663518?V_21=View#StudyPageTop>.

Anonymous (2019). "A Phase 1a/1b Dose Escalation and Expansion Trial of TTI-622 in Patients With Advanced Relapsed or Refractory Lymphoma or Myeloma," clinicaltrials.gov, pp. 1-4, Retrieved Jan. 25, 2021 <https://clinicaltrials.gov/ct2/history/NCT03530683?V_10=View#StudyPageTop>.

Ansell et al. (2017). "TTI-621 (SIRPαFc), an Immune Checkpoint Inhibitor Blocking the CD47 "Do Not Eat" Signal, Induces Objective Responses in Patients with Advanced, Relapsed/Refractory Diffuse Large B-Cell Lymphoma (DLBCL)," Blood, 130 (Supplement 1): 4116, Abstract.

Ayyappan et al. (2018) "Marginal Zone Lymphoma: Clinicopathologic Variations and Approaches to Therapy," Curr Oncol Rep. 20(4):687, 11 pages.

Balsas et al. (2017) "SOX11 promotes tumor protective microenvironment interactions through CXCR4 and FAK regulation in mantle cell lymphoma," Blood, 130(4):501-513.

Barclay et al. (Jun. 2006). "The SIRP family of receptors and immune regulation," Nat. Rev. Immunol. 6(6):457-464.

Borrok et al. (epub Jul. 10, 2012). "Revisiting the role of glycosylation in the structure of human IgG Fc." ACS Chemical Biology 7(9):1596-1602.

Casara et al. (2018). "S55746 is a novel orally active BCL-2 selective and potent inhibitor that impairs hematological tumor growth," Oncotarget. 9(28): 20075-20088.

CDC (2020). "United States Cancer Statistics (USCS)," retrieved Sep. 8, 2020 from <https://www.cdc.gov/cancer/uscs/>, 2 pages.

Cheson et al. (2014) "Recommendations for Initial Evaluation, Staging and Response Assessment of Hodgkin and Non-Hodgkin Lymphoma: The Lugano Classification." J. Clin Oncol. 32:3059-3067.

Ciobanu et al. (2013) "Indolent Lymphoma: Diagnosis and Prognosis in Medical Practice." Maedica (Buchar), 8(4):338-342.

Clinical Trials, History of Changes for Study: NCT02358031: A Study of Pembrolizumab (MK-3475) for First Line Treatment of Recurrent or Metastatic Squamous Cell Cancer of the Head and Neck (MK-3475-048/KEYNOTE-048), retrieved Apr. 21, 2022 from https://clinicaltrials.gov/ct2/show/NCT02358031, 13 pages.

Croxtall et al. (2010). "Trastuzumab In HER2-Positive Metastatic Gastric Cancer," Drugs, 70(17): 2259-2267.

Dreyling et al. (2013). "ESMO Consensus Guidelines: Marginal Cell Lymphoma, Mantle Cell Lymphoma, Peripheral T-cell Lymphoma," Ann Oncol. 24(4):857-877.

Dreyling et al. (2014). "Mantle Cell Lymphoma: Biology, Clinical Presentation, and Therapeutic Approaches," Am Soc Clin Oncol Educ Book, pp. 191-198.

Eisenhauer et al. (2009). "New response evaluation criteria in solid tumours: revised RECIST guideline (version 1.1)," Eur J. Cancer. 45:228-247.

European Medicines Agency "Herceptin, Annex I, Summary of Product Characteristics," retrieved Sep. 8, 2020 from <https://www.ema.europa.eu/en/documents/product- information/herceptin-epar-product-information_en.pdf>, 91 pages.

European Medicines Agency "KEYTRUDA, Annex I, Summary of Product Characteristics," retrieved Sep. 8, 2020 from <https://www.ema.europa.eu/en/documents/product-information/keytruda-epar-product-information_en.pdf>, 156 pages.

European Medicines Agency "MabThera, Annex I, Summary of Product Characteristics," retrieved Sep. 8, 2020 from <https://www.ema.europa.eu/en/documents/product-information/mabthera-epar-product-information_en.pdf>, 149 pages.

European Search Report mailed on Nov. 7, 2016 for European Application No. 16183261.3, filed on Aug. 8, 2016, 14 pages.

European Search Report mailed on Oct. 23, 2015 for European Application No. 13738232.1, filed on Jan. 17, 2013, seven pages.

FDA "Summary of Safety and Effectiveness Data," PD-L1 IHC 22C3 pharmDx, retrieved Sep. 8, 2020 from <www.accessdata.fda.gov/cdrh_docs/pdf15/p150013b.pdf>, 22 pages.

FDA (2012). "RITUXAN (rituximab) Label," Highlights of Prescribing Information, retrieved Sep. 8, 2020 from <https://www.accessdata.fda.gov/drugsatfda_docs/label/2012/103705s5367s5388lbl.pdf>, 40 pages.

FDA (2016). "KEYTRUDA® (pembrolizumab) Label," Highlights of Prescribing Information, retrieved Sep. 8, 2020 from <https://www.accessdata.fda.gov/drugsatfda_docs/label/2016/125514s012lbl.pdf>, 26 pages.

FDA (2017). "HERCEPTIN® (trastuzumab) Label," Highlights of Prescribing Information, retrieved Sep. 8, 2020 from <https://www.accessdata.fda.gov/drugsatfda_docs/label/2017/103792s5337lbl.pdf>, 38 pages.

Fehrenbacher et al. (2016). "Atezolizumab versus docetaxel for patients with previously treated non-small-cell lung cancer (POPLAR): a multicentre, open-label, phase 2 randomised controlled trial," Lancet, 387(10030):1837-46.

Garon et al. (2015). "Pembrolizumab for the Treatment of Non-Small-Cell Lung Cancer," New Engl J Med. 372:2018-28.

GenBank Accession No. NP_037148.2, (ROD Sep. 1, 2016, last updated Apr. 16, 2017), "tyrosine-protein phosphatase non-receptor type substrate 1 precursor [Rattus norvegicus]," located at <http://www.ncbi.nlm.nih.gov/protein/NP_037148.2>, last visited on Jun. 9, 2017, four pages.

Gunasekaran et al. (epub Apr. 16, 2010). "Enhancing antibody Fc heterodimer formation through electrostatic steering effects: applications to bispecific molecules and monovalent IgG," J Biol Chem. 285(25):19637-19646.

Hatherley et al. (epub Jul. 23, 2009). "Structure of signal-regulatory protein alpha: a link to antigen receptor evolution," J Biol Chem. 284(39):26613-26619.

Hatherley et al. (epub Mar. 16, 2007). "The structure of the macrophage signal regulatory protein alpha (SIRPalpha) inhibitory receptor reveals a binding face reminiscent of that used by T cell receptors." J Biol Chem. 282(19):14567-14575.

Hatherley et al. (Jul. 25, 2008). "Paired receptor specificity explained by structures of signal regulatory proteins alone and complexed with CD47," Mol. Cell. 31(2):266-277.

(56) References Cited

OTHER PUBLICATIONS

Herbst et al. (2016). "Pembrolizumab versus docetaxel for previously treated, PD-L1-positive, advanced non-small-cell lung cancer (KEYNOTE-010): a randomised controlled trial," The Lancet, 387:1540-50.

Hezareh et al. (2001) "Effector function activities of a panel of mutants of a broadly neutralizing antibody against human immunodeficiency virus type 1," J Virol., 75(24):12161-8.

Ho et al. (2015). "'Velcro' Engineering of High Affinity CD47 Ectodomain as Signal Regulatory Protein α (SIRPα) Antagonists That Enhance Antibody-Dependent Cellular Phagocytosis," J Biol Chem, 290(20):12650-63.

Husain et al. (2018). "Expanding the Boundaries of Biotherapeutics with Bispecific Antibodies," Biodrugs 32(5): 441-464.

Hwang et al. (2017). "Response Evaluation of Chemotherapy for Lung Cancer." Tuberc Respir Dis (Seoul). 80(2):136-142.

Icard, P. et al. (epub Jul. 25, 2012). "A global view of the biochemical pathways involved in the regulation of the metabolism of cancer cells," Biochim Biophys Acta. 1826(2):423-433.

International Preliminary Report on Patentability mailed on Feb. 23, 2017 for PCT Application No. PCT/US2015/044528, filed on Aug. 10, 2015, 11 pages.

International Preliminary Report on Patentability mailed on Jan. 24, 2017, for PCT Application No. PCT/US2016/045914, filed on Aug. 5, 2016, 20 pages.

International Preliminary Report on Patentability mailed on Jul. 31, 2014 for PCT Application No. PCT/US2013/021937, filed on Jan. 17, 2013, 7 pages.

International Search Report mailed on Dec. 22, 2015 for PCT Application No. PCT/US2015/044528, filed on Aug. 10, 2015, four pages.

International Search Report mailed on Jan. 24, 2017, for PCT Application No. PCT/US2016/045914, filed on Aug. 5, 2016, six pages.

International Search Report mailed on May 21, 2013, for PCT Application No. PCT/US2013/021937, filed on Jan. 17, 2013, five pages.

Jang et al. (2013). "Comparison of RECIST version 1.0 and 1.1 in assessment of tumor response by computed tomography in advanced gastric cancer," Chin J. Cancer Res. 25(6):689-694.

Jawa et al. (epub Sep. 25, 2013). "T-cell dependent immunogenicity of protein therapeutics: Preclinical assessment and mitigation," Clin Immunol. 149(3):534-555.

Jin et al. (2018) "Pharmacokinetic and pharmacodynamic characterization of ALX148, a CD47 blocker, in patients with advanced malignancy and non-Hodgkin lymphoma," Soc Immunotherpay of Cancer Conference, #P340.

Keytruda package insert (2016). Highlights of Prescribing Information, Reference ID: 4003165, 29 pages.

Kharitonenkov et al., "A family of proteins that inhibit signalling through tyrosine kinase receptors," Nature (Mar. 13, 1997), 386(6621):181-186.

Kim et al. (2008). "Association of CD47 with natural killer cell-mediated cytotoxicity of head-and-neck squamous cell carcinoma lines," Tumour Biol., 29(1):28-34.

Kim et al. (2015). "Single-Lesion Measurement per Organ for Assessing Tumor Response in Advanced Gastric Cancer," Oncology. 88:69-75.

Kim et al. (2019). "A Phase 1 Study of ALX148, a CD47 Blocker, in Combination with Rituximab in Patients with Non-Hodgkin Lymphoma," Blood, 134, Supplement_1, Abstract #1953.

Kurokawa et al. (2013) "Which is the optimal response criteria for evaluating preoperative treatment in esophageal cancer: RECIST or histology?" Ann Surg Oncol. 20(9):3009-3014.

Kwon et al. (Dec. 21, 1999). "Elimination of residual metastatic prostate cancer after surgery and adjunctive cytotoxic T lymphocyte-associated antigen 4 (CTLA-4) blockade immunotherapy," Proc. Natl. Acad. Sci. USA. 96(26):15074-15079.

Lala et al. (2018). "Clinical outcomes with therapies for previously treated recurrent/metastatic head-and-neck squamous cell carcinoma (R/M HNSCC): a systematic literature review," Oral Oncol., 84:108-120.

Larouche et al. (2010). "Lymphoma recurrence 5 years or later following diffuse large B-cell lymphoma: clinical characteristics and outcome," J Clin Oncol, 28(12):2094-100.

Lee et al. (Dec. 1, 2007). "Novel structural determinants on SIRP alpha that mediate binding to CD47," The Journal of Immunology 179(11):7741-7750.

Lee et al. (epub Sep. 7, 2010). "The role of cis dimerization of signal regulatory protein alpha (SIRPalpha) in binding to CD47," J Biol Chem. 285(49):37953-37963.

Lin et al. (epub Jul. 17, 2012). "Soluble extracellular domains of human SIRPα and CD47 expressed in *Escherichia coli* enhances the phagocytosis of leukemia cells by macrophages in vitro," Protein Expr Purif. 85(1):109-116.

Liu et al. (2007, epub Oct. 3, 2006). "Functional elements on SIRPalpha IgV domain mediate cell surface binding to CD47," Journal of Molecular Biology 365(3):680-693.

Liu et al. (2015). "CD47 blockade triggers T cell-mediated destruction of immunogenic tumors," Nature Medicine, 21(10):1209-15.

Liu et al. (Feb. 15, 2004). "Peptide-mediated inhibition of neutrophil transmigration by blocking CD47 interactions with signal regulatory protein alpha," J Immunol. 172 (4) 2578-2585.

Lordick et al. (2016). "Oesophageal cancer: ESMO Clinical Practice Guidelines for diagnosis, treatment and follow-up," Ann Oncol. 27(suppl 5): v50-v57.

Miller et al. (1981). Reporting results of cancer treatment, Cancer. 47:207-214.

Montoto et al. (2007). "Risk and clinical implications of transformation of follicular lymphoma to diffuse large B-cell lymphoma," J Clin Oncol (2007) 25(17):2426-33.

Mosely et al. (2016) "Rational Selection of Syngeneic Preclinical Tumor Models for Immunotherapeutic Drug Discovery." Cancer Immunol Res., 5(1): 29-41.

Nakaishi et al. (2008, epub Nov. 7, 2007). "Structural insight into the specific interaction between murine SHPS-1/SIRP alpha and its ligand CD47," J Mol Biol. 375(3):650-660.

NCT03013218, History of Changes, Oct. 24, 2017, "A Study of ALX148 in Patients With Advanced Solid Tumors and Lymphoma," 5 pages.

NICE (Jul. 2016). "Non-Hodgkin's Lymphoma: Diagnosis and Management," London, National Institute for Health and Care Excellence (NICE), Guideline No. 52, 26 pages.

Nishino et al. (2013). "Developing a Common Language for Tumor Response to Immunotherapy: Immune-Related Response Criteria Using Unidimensional Measurements," Clinical Cancer Research, 19(14):3936-43.

Oken et al. (1982). "ECOG Performance Status," as published in "Toxicity and Response Criteria of the Eastern Cooperative Oncology Group," Am J Clin Oncol, 5:649-655, retrieved Sep. 8, 2020 from <http://www.npcrc.org/files/news/ECOG_performance_status.pdf>, 1 page.

Oldenborg et al. (Jun. 16, 2000). "Role of CD47 as a marker of self on red blood cells," Science 288(5473):2051-2054.

Reck et al. (2016) "Pembrolizumab versus Chemotherapy for PD-L1-Positive Non-Small-Cell Lung Cancer." NEJM. 375: 1823-1833.

Ridgway et al. (Jul. 1996). "Knobs-into-holes' engineering of antibody CH3 domains for heavy chain heterodimerization," Protein Eng. 9(7):617-621.

Rischin et al. (2019). "Protocol-specified final analysis of the phase 3 KEYNOTE-048 trial of pembrolizumab (pembro) as first-line therapy for recurrent/metastatic head and neck squamous cell carcinoma (R/M HNSCC)," Journal of Clinical Oncology, May 20, 37, No. 15_suppl, abstract # 6000.

Rudikoff et al. (1982). Single amino acid substitution altering antigen.

Sazinsky et al. (2008). "Aglycosylated immunoglobulin G1 variants productively engage activating Fc receptors," Proc Natl Acad Sci U S A, 105(51): 20167-20172.

(56) References Cited

OTHER PUBLICATIONS

Shimoyama (2014). "Unraveling trastuzumab and lapatinib inefficiency in gastric cancer: Future steps (Review)," Molecular and Clinical Oncology 2: 175-181.

Sim et al. (2019). "Discovery of high affinity, pan-allelic, and pan-mammalian reactive antibodies against the myeloid checkpoint receptor SIRPα," mAbs, 11(6): 1-17.

Soto-Pantoja et al. (2014). "CD47 in the tumor microenvironment limits cooperation between antitumor T-cell immunity and radiotherapy," Cancer Research, 74(23): 6771-83.

Spiess et al. (2015). "Alternative molecular formats and therapeutic applications for bispecific antibodies," Molecular Immunology 67(2): 95-106.

Stong et al. (1985). "Human acute leukemia cell line with the t(4;11) chromosomal rearrangement exhibits B lineage and monocytic characteristics," Blood. 65(1): 21-31.

Subramanian et al. (2007, epub Nov. 10, 2006). "Phylogenetic divergence of CD47 interactions with human signal regulatory protein alpha reveals locus of species specificity. Implications for the binding site," J Biol Chem. 282(3):1805-1818.

Takenaka et al. (epub Nov. 4, 2007). "Polymorphism in SIRPα modulates engraftment of human hematopoietic stem cells," Nat Immunol. 8(12):1313-1323.

Therasse et al. (2000). "New Guidelines to Evaluate the Response to Treatment in Solid Tumors," J. Natl Cancer Inst. 92:205-216.

Tsai et al. (epub Mar. 17, 2010). "Self inhibition of phagocytosis: the affinity of 'marker of self CD47 for SIRPalpha dictates potency of inhibition but only at low expression levels," Blood Cells Mol Dis. 45(1):67-74.

Tse et al. (2008). "ABT-263: a potent and orally bioavailable Bcl-2 family inhibitor," Cancer Res, 68(9): 3421-3429.

Tseng et al. (2013). "Anti-CD47 antibody-mediated phagocytosis of cancer by macrophages primes an effective antitumor T-cell response," Proc Natl Acad Sci USA, 110(27): 11103-11108.

Venclyxto Label, Highlights of Prescribing Information, 2016, FDA, retrieved Feb. 8, 2021 from www.accessdata.fda.gov/drugsatfda_docs/label/2016/208573s000lbl.pdf>, 25 pages.

Venclyxto Product Information, 2020, EMA, retrieved Feb. 8, 2021 from <www.ema.europa.eu/en/medicines/human/EPAR/venclyxto#product-information-section>, 6 pages.

VOSE (2017). "Mantle cell lymphoma: 2017 update on diagnosis, risk-stratification, and clinical management," Am J. Hematol. 92(8):806-813.

Wan et al. (2019). "Pharmacodynamic Biomarker Characterization of ALX148, a CD47 Blocker, in Combination with Established Anticancer Antibodies in Patients with Advanced Malignancy," Society for Immunotherapy of Cancer (SITC), Abstract #P449.

Wang et al. (1995). "Active immunotherapy of cancer with a nonreplicating recombinant fowlpox virus encoding a model tumor-associated antigen," J. Immunol. 154:4685-4692.

Weiskopf (2017.) "Cancer immunotherapy targeting the CD47/SIRPα axis," European Journal of Cancer, vol. 76, pp. 100-109.

Who (1979) Handbook for Reporting Results of Cancer Treatment. Geneva: World Health Organization Offset Publication, No. 48, 46 pages.

Who Cancer Fact Sheets (2018), "All Cancers," the Global Cancer Observatory, retrieved Sep. 8, 2020 from <https://gco.iarc.fr/today/data/factsheets/cancers/39-All-cancers-fact-sheet.pdf>, 2 pages.

Wilson et al. (Jul. 1984). "The structure of an antigenic determinant in a protein," Cell 37(3):767-778.

Wray et al. (2016) "Therapy Response Assessment and Patient Outcomes in Head and Neck Squamous Cell Carcinoma: FDG PET Hopkins Criteria Versus Residual Neck Node Size and Morphologic Features." Am J. Roentgenology, 207:641-647.

Written Opinion mailed on Dec. 22, 2015 for PCT Application No. PCT/US2015/044528, filed on Aug. 10, 2015, nine pages.

Written Opinion mailed on Jan. 24, 2017 for PCT Application No. PCT/US2016/045914, filed on Aug. 5, 2016, 19 pages.

Written Opinion of the International Searching Authority mailed on May 21, 2013 for PCT Application No. PCT/US2013/021937, filed on Jan. 17, 2013, five pages.

Wu et al. (2018). "Anti-CD47 treatment enhances anti-tumor T-cell immunity and improves immunosuppressive environment in head and neck squamous cell carcinoma," Oncoimmunology,7(4):e1397248, pp. 1-12.

Yamao et al. (Feb. 3, 1997). "Mouse and human SHPS-1: molecular cloning of cDNAs and chromosomal localization of genes," Biochem Biophys Res Commun. 231(1):61-67.

Yanagawa et al. (2012) "Evaluation of response to neoadjuvant chemotherapy for esophageal cancer: PET response criteria in solid tumors versus response evaluation criteria in solid tumors," J Nucl Med. 53(6):872-880.

Yu et al. (2015). "PD-1 blockade attenuates immunosuppressive myeloid cells due to inhibition of CD47/SIRPα axis in HPV negative head and neck squamous cell carcinoma," Oncotarget, 6(39): 42067-42080.

Zhang et al. (2016.) "Blocking CD47 and autophagy for the therapy of non-small cell lung cancer," Annals of Oncology, vol. 27, Supplement 9, 399P.

International Search Report mailed on Jul. 25, 2022 for PCT Application No. PCT/US2022/029056, filed on May 12, 2022, 7 pages.

U.S. Appl. No. 17/932,180, filed Sep. 14, 2022 for Deming et al., titled "SIRP-Alpha Variant Constructs and Uses Thereof ,".

U.S. Appl. No. 18/185,255, filed Mar. 16, 2023 for Pons et al., titled "Constructs Having a SIRP-Alpha Domain or Variant Thereof,".

U.S. Appl. No. 18/342,331, filed Jun. 27, 2023 for Wan et al., titled "Combination Therapies for Treating Cancer,".

U.S. Appl. No. 18/452,972, filed Aug. 21, 2023 for Pons et al., titled "Methods of Treating Cancer,".

Anonymous (2021). "ASPEN-01: a Phase 1 study of ALX148, a CD47 blocker, in combination with trastuzumab, ramucirumab, and paclitaxel in patients with 2nd line HER2-positive advanced gastric or gastroesophageal cancer", Retrieved Jul. 12, 2022 from <https://ir.alxoncology.com/static-files/16e6c9e0-e0fa-425d-a5b8-b6fd00431c74>, 22 pages.

Brown et a. (2001). "Integrin-associated protein (CD47) and its ligands," Trends Cell Biol., 11(3):130-5.

Carboplatin Label, Package Insert, 2012, retrieved Feb. 8, 2021 from <www.accessdata.fda.gov/drugsatfda_docs/label/2012/077139Orig1s016lbl.pdf>, 7 pages.

Chao et al. (2010). "Anti-CD47 antibody synergizes with rituximab to promote phagocytosis and eradicate non-Hodgkin lymphoma," Cell., 142(4):699-713.

Chao et al. (2011). "Extranodal dissemination of non-Hodgkin lymphoma requires CD47 and is inhibited by anti-CD47 antibody therapy," Blood, 118(18):4890-4891.

Chow et al. (2020). "A phase I study of ALX148, a CD47 blocker, in combination with standard anticancer antibodies and chemotherapy regimens in patients with advanced malignancy," Journal of Clinical Oncology., 38:15_suppl, Abstract 3056.

CISplatin Label, 2015, FDA, retrieved Feb. 8, 2021 from <www.accessdata.fda.gov/drugsatfda_docs/label/2015/018057s083lbl.pdf>, 11 pages.

Edris et al. (2012). "Antibody therapy targeting the CD47 protein is effective in a model of aggressive metastatic leiomyosarcoma," PNAS USA, 109:6656-61.

FDA (2019). "Highlights of Prescribing Information, ENHERTU," Retrieved Aug. 5, 2022 from <https://www.accessdata.fda.gov/drugsatfda_docs/label/2019/761139s000lbl.pdf>, 16 pages.

Gabrilovich et al. (2012). "Coordinated regulation of myeloid cells by tumours," Nat Rev Immunol. 12(4):253-68.

Goto et al. (2014). "Efficacy of anti-CD47 antibody-mediated phagocytosis with macrophages against primary effusion lymphoma," Eur J. Cancer, 50(10):1836-1846.

Jaiswal et al. (2010). "Macrophages as mediators of tumor immunosurveillance," Trends Immunol, 31(6):212-219.

Kabat et al. (1991). Sequences of proteins of immunological interest, 5th ed. U.S. Dept. of Health and Human Services, Public Health Service, National Institutes of Health: Bethesda, MD, 12 pages.

(56) References Cited

OTHER PUBLICATIONS

Kauder et al. (2018). "ALX148 blocks CD47 and enhances innate and adaptive antitumor immunity with a favorable safety profile," PLoS One., 13(8):e0201832, 33 pages.

Kim et al. (2012). "Anti-CD47 antibodies promote phagocytosis and inhibit the growth of human myeloma cells," Leukemia, 26:2538-2545.

Lakhani et al. (2021). "Evorpacept alone and in combination with pembrolizumab or trastuzumab in patients with advanced solid tumours (ASPEN-01): a first-in-human, open-label, multicentre, phase 1 dose-escalation and dose-expansion study," Lancet Oncology, 22(12):1740-1751.

Lee et al. (2020). "404 ALX148, a CD47 blocker, in combination with standard chemotherapy and antibody regimens in patients with gastric/gastroesophageal junction (GC) cancer and head and neck squamous cell carcinoma (HNSCC)," Journal for Immuno Therapy of Cancer 8(Suppl 3):A345-A246.

Makiyama et al. (2020). "Randomized, Phase II Study of Trastuzumab Beyond Progression in Patients with HER2-Positive Advance Gastric or Gastroesophageal Junction Cancer," J Clin Oncol., 38(17):1919-1927.

Miller et al. (2019) "Quantitative high-throughput screening assays for the discovery and development of SIRPα-CD47 interaction inhibitors." PLoS ONE 14(7): e0218897, 21 pages.

Murata et al. (2018). "Anti-human SIRPα antibody is a new tool for cancer immunotherapy," Cancer Sci 109(5):1300-1308.

Oldenborg (2013). "CD47: A Cell Surface Glycoprotein Which Regulates Multiple Functions of Hematopoietic Cells in Health and Disease," ISRN Hematol (2013), Article ID 614619, 19 pages.

Paraplatin Label, 2020, FDA, retrieved Feb. 8, 2021 from <www.accessdata.fda.gov/drugsatfda_docs/label/2010/020452s005lbl.pdf>, 21 pages.

Patel et al. (2020). "Targeted Therapies in Advanced Gastric Cancer," Curr Treat Options Oncol., 21(9):70, 14 pages.

Petrova et al. (2016.) "TTI-621 (SIRPαFc): a CD47-Blocking Innate Immune Checkpoint Inhibitor with Broad Antitumor Activity and Minimal Erythrocyte Binding," Clin Cancer Res, 23(4):1068-1079.

Platinol label, 2011, FDA, retrieved Feb. 8, 2021 from <www.accessdata.fda.gov/drugsatfda_docs/label/2011/018057s080lbl.pdf>, 15 pages.

Poklar et al. (1996). "Influence of cis-platin intrastrand crosslinking on the conformation, thermal stability and energetic of a 20-mer DNA duplex," Proc. Natl. Acad. Sci. U.S.A., 93(15): 7606-11.

Ring et al. (2017). "Anti-SIRPα antibody immunotherapy enhances neutrophil and macrophage antitumor activity," PNAS USA 114(49):E10578-E10585.

Rudd et al. (1995). "Persistence of cisplatin-induced DNA interstrand crosslinking in peripheral blood mononuclear cells from elderly and young individuals," Cancer Chemother. Pharmacol., 35 (4):323-6.

Russ et al. (2018). "Blocking 'don't eat me' signal of CD47-SIRPα in hematological malignancies, an in-depth review," Blood Rev. Nov. 2018, 32(6):480-489, 24 pages.

Sasikumar et al. "Abstract B007: Potent antitumor activity of a novel and orally available small-molecule antagonist targeting the CD47/SIRPa pathway" CR-NCI-EORTC International Conference: Molecular Targets and Cancer Therapeutics; Oct. 26-30, 2017, Philadelphia, PA; Mol Cancer Ther, Published Jan. 1, 2018, (17) (1 Supplement) B007, 4 pages.

Shitara et al. (2020). "Trastuzumab Deruxtecan in Previously Treated HER2-Positive Gastric Cancer," N Engl J Med, 382:2419-2430.

U.S. Appl. No. 17/334,151, filed on May 28, 2021 for Pons et al.

Weiskopf et al. (epub May 30, 2013). "Engineered SIRPα variants as immunotherapeutic adjuvants to anticancer antibodies," Science, 341(6141):88-91.

Wilke et al. (2014). "Ramucirumab plus paclitaxel versus placebo plus paclitaxel in patients with previously treated advanced gastric or gastro-oesophageal junction adenocarcinoma (RAINBOW): a double-blind, randomised phase 3 trial," Lancet Oncol., 15(11):1224-35.

Willingham et al. (2012). "The CD47-signal regulatory protein alpha (SIRPa) interaction is a therapeutic target for human solid tumors," Proc Natl Acad Sci USA, 109(17):6662-6667.

Yanigata et al. (2017). "Anti-SIRPα antibodies as a potential new tool for cancer immunotherapy," JCI Insight, 2:e89140, 16 pages.

Zhang et al. (2018). "Disrupting CD47-SIRPa axis alone or combined with autophagy depletion for the therapy of glioblastoma," Carcinogenesis, 39:689-699.

Zhao et al. (epub Oct. 31, 2011). "CD47-signal regulatory protein-a (SIRPα) interactions form a barrier for antibody-mediated tumor cell destruction," Proc Natl Acad Sci USA, 108(45):18342-18347.

Anonymous (2023). "A Study of Evorpacept (ALX148) in Patients With Advanced HER2+ GastricCancer (ASPEN-06)," clinicaltrials.gov, pp. 1 to 11, Retrieved Mar. 19, 2024 from < https://www.clinicaltrials.gov/study/NCT05002127#study-plan>.

Anonymous (2023). "ALX Oncology Reports Positive Interim Phase 2 ASPEN-06 Clinical Trial Results of Evorpacept for the Treatment of Advanced HER2-Positive Gastric Cancer" 2 pages.

FDA (2020). "Highlights of Prescribing Information, TUKYSA," Drug Label, 20 pages.

Garrido et al. (2016). "The safety and efficacy of ramucirumab in combination with paclitaxel for the treatment of advanced gastric or gastro-esophageal junction adenocarcinoma," Expert Rev Anticancer Ther., 16(10):1005-10.

International Search Report and Written Opinion mailed Apr. 23, 2021 for PCT Application No. PCT/US2020/062402, filed on Nov. 25, 2020, 16 pages.

Xie et al. (2023.) "An agonistic anti-signal regulatory protein alpha antibody for chronic inflammatory diseases," Cell Reports Med. 4:101130.

Yoshida et al. (2015). "CD47 is an adverse prognostic factor and a therapeutic target in gastric cancer," Cancer Med., 4(9): 1322-1333.

Zhang et al. (2015.) "SIRP/CD47 Signaling in Neurological Disorders," Brain Res, 1623:74-80.

U.S. Appl. No. 18/441,339, filed Feb. 14, 2024 for Deming et al., titled "SIRP-Alpha Variant Constructs and Uses Thereof,".

U.S. Appl. No. 18/540,092, filed Dec. 14, 2023 for Pons et al., titled "Constructs Having a Sirp-Alpha Domain or Variant Thereof,".

* cited by examiner

US 12,098,214 B2

COMBINATION THERAPIES FOR TREATING CANCER

CROSS REFERENCE TO RELATED APPLICATIONS

This application claims the priority benefit of U.S. Provisional Application No. 63/188,388, filed on May 13, 2021, and of U.S. Provisional Application No. 63/193,581, filed on May 26, 2021, the contents of each of which are incorporated by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 757972001600SEQLIST.txt, date recorded: May 12, 2022, size: 302,942 bytes).

FIELD OF THE INVENTION

The present invention relates to methods of treating cancer that comprise administering an agent that blocks the interaction between CD47 (e.g., hCD47) and SIRPα (e.g., hSIRPα) in conjunction with a chemotherapy agent and at least one additional anti-cancer agent and/or at least one additional mode of cancer therapy.

BACKGROUND

Many cancers have a poor prognosis, even when treated with available therapeutics. There is a need in the art for new treatments to provide additional therapeutic options and improve outcomes for cancer patents.

Tumor cells manipulate the myeloid compartment to evade the anti-tumor host immune response (Gabrilovich et al., Nat Rev Immunol (2012) 12(4):253-68). For example, while CD47 expressed on the surface of normal cells binds SIRPα on macrophages and provides a "don't eat me" signal, tumor cells have also been found to overexpress CD47 to evade the macrophage component of immune surveillance (Oldenborg, ISRN Hematol (2013) 614619).

Macrophage-mediated destruction of cancer cells requires both the disruption of "don't eat me" signals (e.g., CD47-SIRPα) and the activation of "eat me" signals. Neither component alone is sufficient to trigger maximal phagocytic reaction against tumor cells. As described above, CD47 provides a fundamental "don't eat me" signal through its interaction with SIRPα on macrophages. The pro-phagocytic "eat me" signal can be provided to the same macrophages by binding to their activating Fc gamma receptors. For example, the pro-phagocytic "eat me" signal can be provided by binding of anti-tumor antibodies to Fc receptors on macrophages.

All references cited herein, including patent applications, patent publications, and UniProtKB/Swiss-Prot Accession numbers are herein incorporated by reference in their entirety, as if each individual reference were specifically and individually indicated to be incorporated by reference.

BRIEF SUMMARY

In some embodiments, provided is a method of treating cancer in an individual, comprising administering to the individual an effective amount of: (a) a polypeptide comprising a SIRPα D1 domain variant and an Fc domain variant, (b) an anti-HER2 antibody, (c) an anti-VEGF2 antibody, and (d) paclitaxel; wherein the SIRPα D1 domain variant comprises the amino acid sequence of SEQ ID NO: 81 or SEQ ID NO: 85; wherein the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat, wherein the cancer is gastric cancer or gastroesophageal junction (GEJ) cancer, and wherein the individual has received at least one prior therapy for the gastric or the GEJ cancer. In some embodiments, the gastric cancer or GEJ cancer is a HER2-overexpressing (e.g., HER2$^+$) gastric cancer or a HER2-overexpressing GEJ cancer. In some embodiments, the individual has received prior therapy with an anti-HER2 antibody, with an anti-HER2 antibody and a fluoropyrimidine, with an anti HER2 antibody and a platinum-based chemotherapy agent, or with a platinum-based chemotherapy agent. In some embodiments, individual has progressed during or after a treatment with an anti-HER2 antibody, an anti-HER2 antibody and a fluoropyrimidine, an anti HER2 antibody and a platinum-based chemotherapy agent, or a platinum-based chemotherapy agent. In some embodiments, the anti-HER2 antibody is trastuzumab. In some embodiments, the anti-VEGF antibody is ramucirumab. In some embodiments, the polypeptide comprising the SIRPα D1 domain variant and the Fc domain variant is administered at a dose between about 10 to about 60 mg/kg once a week (qw), such as 10 mg/kg, 15 mg/kg, or 30 mg/kg once a week. In some embodiments, the polypeptide comprising the SIRPα D1 domain variant and the Fc domain variant is administered at a dose of 10 mg/kg, 15 mg/kg, or 30 mg/kg once every two weeks. In some embodiments, the trastuzumab is administered at an initial dose of 8 mg/kg followed by 6 mg/kg once every three weeks. In some embodiments, the trastuzumab is administered at an initial dose of 6 mg/kg followed by 4 mg/kg once every two weeks (e.g., an initial dose of 6 mg/kg, followed by a 4 mg/kg dose two weeks after the initial 6 mg/kg dose, followed by a 4 mg/kg dose every two weeks after the first 4 mg/kg dose). In some embodiments, the paclitaxel is administered at a dose of 80 mg/m2 on days 1, 8, and 15 of a 28-day cycle. In some embodiments, among a population of patients receiving the treatment, the overall response rate (ORR) of the population is greater than 65%, 70%, 75%, 80%, 85%, 90%, or 95%.

In some embodiments, the polypeptide comprising a SIRPα D1 domain variant and an Fc domain variant forms a homodimer. In some embodiments, the individual is a human.

In some embodiments, provided is a kit comprising a polypeptide comprising a SIRPα D1 domain variant and an Fc domain variant in a pharmaceutically acceptable carrier, for use in combination with an anti-HER2 antibody, an anti-VEGFR2 antibody, and paclitaxel; wherein the SIRPα D1 domain variant comprises the amino acid sequence of SEQ ID NO: 81 or SEQ ID NO: 85; wherein the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat, and wherein the kit comprises instructions for administering the polypeptide comprising a SIRPα D1 domain variant and an Fc domain variant in combination with the anti-HER2 antibody, the anti-VEGFR2 antibody, and the paclitaxel to an individual with gastric cancer or gastroesophageal junction (GEJ) cancer who has received at least one prior therapy for the gastric or the GEJ cancer. In some embodiments, the gastric cancer or GEJ cancer is HER2$^+$ gastric cancer or HER2$^+$ GEJ cancer. In some embodiments, the anti-HER2 antibody is trastuzumab. In some embodiments, the anti-VEGFR2 antibody is ramucirumab. In some embodiments, the individual received prior therapy (or therapies) with an anti-HER2 antibody (e.g., trastuzumab) and/or a fluoropyrimidine, and/or a platinum-based chemotherapeutic agent. In some embodiments, the gastric cancer or GEJ cancer in the individual progressed during or after prior therapy (or therapies) comprising anti-HER2 antibody (e.g., trastuzumab) and/or a fluoropyrimidine, and/or a platinum-based chemotherapeutic agent. In some embodiments, the individual failed (e.g., relapsed after or did not respond to) prior therapy (or therapies) comprising anti-HER2 antibody (e.g., trastuzumab) and/or a fluoropyrimidine, and/or a platinum-based chemotherapeutic agent. In some embodiments, the prior therapy (or therapies) comprised an anti-HER2 antibody and a fluoropyrimidine (e.g., administered during the same line of therapy or during different lines of therapy). In some embodiments, the prior therapy (or therapies) comprised an anti-HER2 antibody and a platinum-based chemotherapy agent (e.g., administered during the same line of therapy or during different lines of therapy).

DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figure 1:
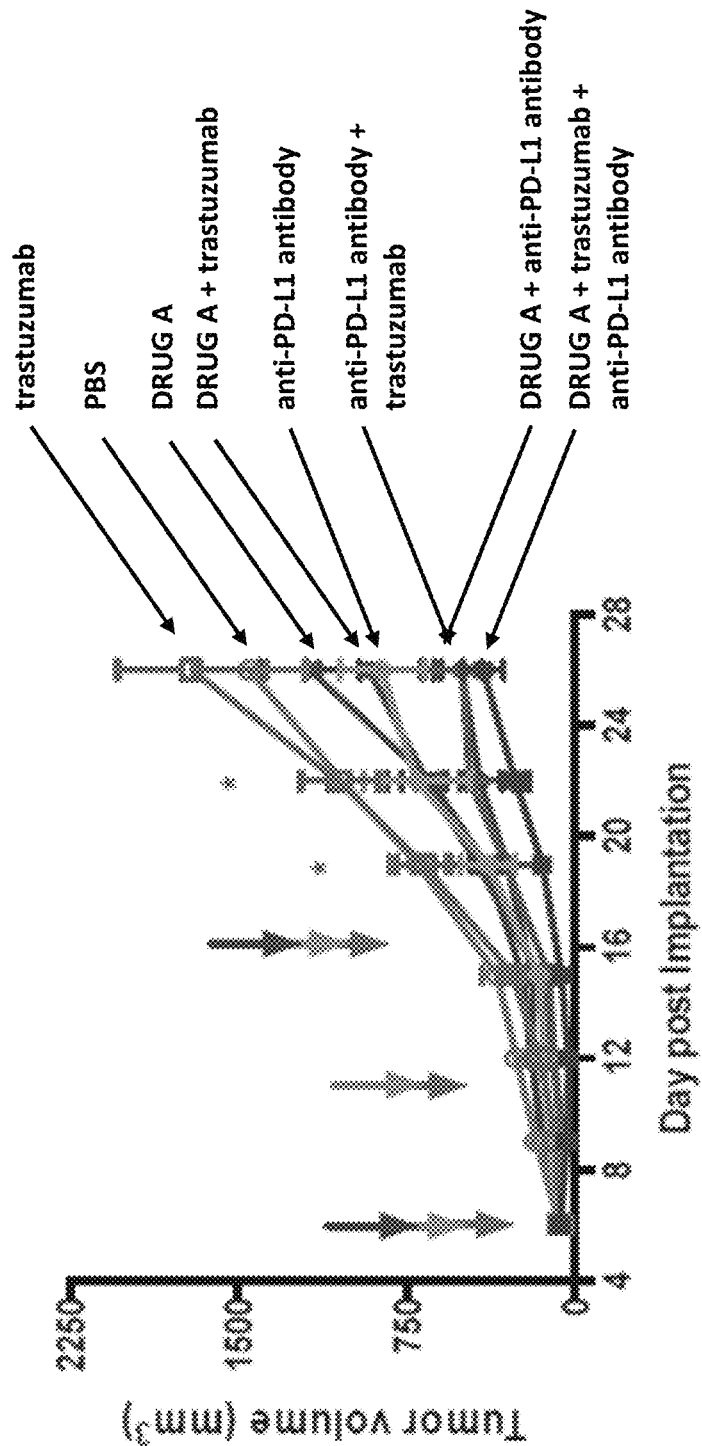
FIG. 1 provides the results of experiments that were performed to determine the effect of DRUG A in combination with (a) an anti-HER2 antibody, (b) an anti-PD-L1 antibody, or (c) an anti-HER2 antibody and an anti-PD-L1 on tumor growth in a MC38 m:h chimeric colon cancer model in mice.

The following description sets forth exemplary methods, parameters and the like. It should be recognized, however, that such description is not intended as a limitation on the scope of the present disclosure but is instead provided as a description of exemplary embodiments.

Definitions

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description or the claims, such terms are intended to be inclusive in a manner similar to the term "comprising."

As used herein, the terms "treatment", "treating", and the like, refer to administering an agent, or carrying out a procedure, for the purposes of obtaining an effect. In some embodiments, the effect is prophylactic in terms of completely or partially preventing a disease or symptom thereof. In some embodiments, the effect is therapeutic in terms of affecting a partial or complete cure for a disease or symptoms of the disease.

As used herein, the term "antibody" refers to intact antibodies; antibody fragments, provided that they exhibit the desired biological activity (e.g. epitope binding); monoclonal antibodies; polyclonal antibodies; monospecific antibodies; multi-specific antibodies (e.g., bispecific antibodies); and antibody-like proteins.

As used herein, the term "antibody variable domain" refers to the portions of the light and heavy chains of an antibody that include amino acid sequences of complementary determining regions (CDRs, e.g., CDR L1, CDR L2, CDR L3, CDR H1, CDR H2, and CDR H3) and framework regions (FRs).

As used herein, the term "linker" refers to a linkage between two elements, e.g., protein domains. In some embodiments, a linker can be a covalent bond or a spacer. The term "spacer" refers to a moiety (e.g., a polyethylene glycol (PEG) polymer) or an amino acid sequence (e.g., a 1-200 amino acid sequence) occurring between two polypeptides or polypeptide domains to provide space or flexibility (or both space and flexibility) between the two polypeptides or polypeptide domains. In some embodiments, an amino acid spacer is part of the primary sequence of a polypeptide (e.g., joined to the spaced polypeptides or polypeptide domains via the polypeptide backbone).

As used herein, the term "effective amount" refers to an amount of a polypeptide or a pharmaceutical composition containing a polypeptide described herein, e.g., a polypeptide having a SIRPα D1 domain or variant thereof, that is sufficient and effective in achieving a desired therapeutic effect in treating a patient having a disease, such as a cancer, e.g., solid tumor or hematological cancer. In some embodiments, an effective amount of polypeptide will avoid adverse side effects.

As used herein, the term "pharmaceutical composition" refers to a medicinal or pharmaceutical formulation that includes an active ingredient as well as excipients or diluents (or both excipients and diluents) and enables the active ingredient to be administered by suitable methods of administration. In some embodiments, the pharmaceutical compositions disclosed herein include pharmaceutically acceptable components that are compatible with the polypeptide. In some embodiments, the pharmaceutical composition is in tablet or capsule form for oral administration or in aqueous form for intravenous or subcutaneous administration, for example by injection.

As used herein, the terms "subject," "individual," and "patient" are used interchangeably to refer to a vertebrate, for example, a mammal. Mammals include, but are not limited to, murines, simians, humans, farm animals, sport animals, and pets. Tissues, cells, and their progeny of a biological entity obtained in vivo or cultured in vitro are also encompassed. None of the terms entail supervision of a medical professional.

As used herein, the term "affinity" or "binding affinity" refers to the strength of the binding interaction between two molecules. Generally, binding affinity refers to the strength of the sum total of non-covalent interactions between a molecule and its binding partner, such as a SIRPα D1 domain variant and CD47. Unless indicated otherwise, binding affinity refers to intrinsic binding affinity, which reflects a 1:1 interaction between members of a binding pair. The binding affinity between two molecules is commonly described by the dissociation constant (KD) or the association constant (KA). Two molecules that have low binding affinity for each other generally bind slowly, tend to dissociate easily, and exhibit a large KD. Two molecules that have high affinity for each other generally bind readily, tend to remain bound longer, and exhibit a small KD. In some embodiments, the KD of two interacting molecules is determined using known methods and techniques, e.g., surface plasmon resonance (SPR). KD can be calculated as the ratio of koff/kon.

As used herein, the term "$K_D$, less than" refers to a numerically smaller $K_D$ value and an increasing binding affinity relative to the recited KD value. As used herein, the term "KD greater than" refers to a numerically larger KD value and a decreasing binding affinity relative to the recited KD value.

As used herein, "in conjunction with" refers to administration of one treatment modality in addition to another treatment modality. As such, "in conjunction with" refers to administration of one treatment modality before, during, or after administration of the other treatment modality to the individual.

Overview

Provided herein are methods of treating cancer in an individual (e.g., a human individual) that comprises administering to the individual an effective amount of (a) an agent that blocks the interaction between CD47 (e.g., hCD47) and SIRPα (e.g., hSIRPα) and (b) a chemotherapy agent (e.g., at least one chemotherapy agent, such as at least two, at least three, or at least four chemotherapy agents). In some embodiments the method further comprises administering to the individual an effective amount of a therapeutic antibody (e.g., at least one therapeutic antibody, such as at least two, at least three, or at least four therapeutic antibodies). Additionally or alternatively, in some embodiments the method further comprises administering to the individual an effective amount of an immunotherapeutic agent (e.g., at least one immunotherapeutic agent, such as at least two, at least three, or at least four immunotherapeutic agents). Additionally or alternatively, in some embodiments, the method comprises administering the polypeptide and the chemotherapy agent in combination with one or more additional modes of therapy, including, but not limited to, e.g., radiation therapy, surgery, cryoablation, and bone marrow transplant.

In some embodiments, the agent that blocks the interaction between CD47 (e.g., hCD47) and SIRPα (e.g., hSIRPα) is a small molecule inhibitor of the CD47-SIRPα pathway (e.g., RRX-001 and others). See, e.g., Miller et al. (2019) "Quantitative high-throughput screening assays for the discovery and development of SIRPα-CD47 interaction inhibitors." *PLoS ONE* 14(7): e0218897 and Sasikumar et al. ACR-NCI-EORTC International Conference: Molecular Targets and Cancer Therapeutics; Oct. 26-30, 2017; Philadelphia, PA; Abstract B007.

In some embodiments, the agent that blocks the interaction between CD47 (e.g., hCD47) and SIRPα (e.g., hSIRPα) binds CD47 (e.g., hCD47). In some embodiments, the agent binds CD47 (e.g., hCD47) with a $K_D$ of about 10 nM or better (such as at least about any one of 9 nM, 8 nM, 7 nM, 6 nM, 5 nM, 3 nM, 2 nM, 1 nM, 750 pM, 500 pM, 250 pM, 200 pM, 100 pM, 50 pM, 25 pM, 20 pM 10 pM or less than 10 pM). In some embodiments, the agent that binds CD47 (e.g., hCD47) exhibits at least about 50% CD47 receptor occupancy (e.g., at least about any one of 50%, 55%, 60%, 65%, 70%, 75%, 80%, 85%, 90%, 95%, 99%, or about 100%) in a human subject. In some embodiments, the agent that binds CD47 (e.g., hCD47) has an EC50 of about 80 ng/ml or less, e.g., about any one of 75, 70, 65, 60, 55, 50, 45, 40, 35, 30, 25, 20, 15, 10, or 5 ng/ml. In some embodiments, the agent that binds CD47 (e.g., hCD47) is an anti-CD47 antibody (e.g., a therapeutic anti-CD47 antibody) or an antigen-binding fragment thereof. In some embodiments, the antigen binding fragment is a Fab, a Fab', a Fab'-SH, an F(ab')2, an Fv, an scFv, a one-armed antibody, or a diabody. In some embodiments, the anti-CD47 antibody is a monospecific antibody. In some embodiments, the anti-CD47 antibody is a multispecific (e.g., bispecific) antibody. In some embodiments the term "anti-CD47 antibody" encompasses antibody-based constructs (such as multispecific constructs) including, without limitation triomabs, DARTs (i.e., dual-affinity re-targeting antibodies), TandAbs (i.e., tandem diabodies), tandem scFvs, CrossMabs, DNLs (i.e., dock and lock antibodies), DVD-Ig (i.e., dual variable domain immunoglobulins), tetravalent bispecific IgGs, nanobodies, dual targeting domains, and ART-Igs (i.e., asymmetric reengineering technology-immunoglobulins). Additional details regarding exemplary antibody constructs (both monospecific and multispecific) are provided in Husain et al. (2018) *Biodrugs* 32(5): 441-464 and Spiess et al. (2015) *Molecular Immunology* 67(2): 95-106. In some embodiments, the anti-CD47 antibody is Hu5F9-G4, B6H12.2, BRIC126, CC-90002, SRF231, or IBI188 (from Innovent Biologics) (see, e.g., Zhao et al. (2011), *PNAS USA* 108:18342-18347; Chao et al. (2010) *Cell* 142:699-713, Kim et al. (2012) *Leukemia* 26:2538-2545; Chao et al. (2011) *Blood* 118:4890-4891; Goto et al. (2014) *Eur J. Cancer* 50:1836-1846; and Edris et al. (2012) *PNAS USA* 109:6656-61 for additional information about these anti-CD47 antibodies).

In some embodiments, the agent that blocks the interaction between CD47 (e.g., hCD47) and SIRPα (e.g., hSIRPα) binds SIRPα (e.g., hSIRPα). In some embodiments, the agent binds SIRPα (e.g., hSIRPα) with a $K_D$ of about 10 nM or better (such as at least about any one of 9 nM, 8 nM, 7 nM, 6 nM, 5 nM, 3 nM, 2 nM, 1 nM, 750 pM, 500 pM, 250 pM, 200 pM, 100 pM, 50 pM, 25 pM, 20 pM 10 pM or less than 10 pM). In some embodiments, the agent that binds SIRPα (e.g., hSIRPα) exhibits at least about 50% SIRPα receptor occupancy (e.g., at least about any one of 50%, 55%, 60%, 65%, 70%, 75%, 80%, 85%, 90%, 95%, 99%, or about 100%) in a human subject. In some embodiments, the agent that binds SIRPα (e.g., hSIRPα) has an EC50 of about 80 ng/ml or less, e.g., about any one of 75, 70, 65, 60, 55, 50, 45, 40, 35, 30, 25, 20, 15, 10, or 5 ng/ml. In some embodiments, the agent that binds SIRPα (e.g., hSIRPα) is an anti-SIRPα antibody (e.g., a therapeutic anti-SIRPα antibody) or an antigen-binding fragment thereof. In some embodiments, the antigen binding fragment is a Fab, a Fab', a Fab'-SH, an F(ab')2, an Fv, an scFv, a one-armed antibody, or a diabody. In some embodiments, the anti-SIRPα antibody is a monospecific antibody or monospecific antibody construct (including, but not limited to those described above). In some embodiments, the anti-SIRPα antibody is a multispecific (e.g., bispecific) antibody or a multispecific antibody construct (including, but not limited to those described above). In some embodiments, the anti-SIRPα antibody is KWAR23, SE12C3, 040, or MY-1 (see, e.g., Ring et al. (2017) *PNAS USA* 114(49): E10578-E10585); Murata et al. (2018) Cancer Sci 109(5):1300-1308; and Yanigata et al. (2017) JCI Insight 2:e89140 for additional information about these anti-SIRPα antibodies). In some embodiments, the anti-SIRPα antibody is an antibody described in WO 2018/057669; US-2018-0105600-A1; US20180312587; WO2018107058; WO2019023347; US20180037652; WO2018210795; WO2017178653; WO2018149938; WO2017068164; and WO2016063233, the contents of which are incorporated herein by reference in their entireties.

In some embodiments, the agent that blocks the interaction between CD47 (e.g., hCD47) and SIRPα (e.g., hSIRPα) is an anti-SIRPβ antibody or an anti-SIRPγ antibody (e.g., an anti-SIRPβ antibody or anti-SIRPγ antibody that is capable of binding SIRPα), or an antigen-binding fragment thereof. In some embodiments, the agent is an antibody (or antigen binding fragment thereof) that is capable of bind two or more of SIRPα, SIRPβ, and SIRPγ. In some embodiments, such antibody binds SIRPα (e.g., hSIRPα) with a $K_D$ of about 10 nM or better (such as at least about any one of 9 nM, 8 nM, 7 nM, 6 nM, 5 nM, 3 nM, 2 nM, 1 nM, 750 pM, 500 pM, 250 pM, 200 pM, 100 pM, 50 pM, 25 pM, 20 pM, 10 pM or less than 10 pM). In some embodiments, the antibody exhibits at least about 50% SIRPα receptor occupancy (e.g., at least about any one of 50%, 55%, 60%, 65%, 70%, 75%, 80%, 85%, 90%, 95%, 99%, or about 100%) in a human subject. In some embodiments, the antibody has an EC50 of about 80 ng/ml or less, e.g., about any one of 75, 70, 65, 60, 55, 50, 45, 40, 35, 30, 25, 20, 15, 10, or 5 ng/ml. In some embodiments, the antigen binding fragment is a Fab, a Fab', a Fab'-SH, an F(ab')2, an Fv, an scFv, a one-armed antibody, or a diabody. In some embodiments, the antibody is a monospecific antibody or monospecific antibody construct (including, but not limited to those described above). In some embodiments, the antibody is a multispecific (e.g., bispecific) antibody or a multispecific antibody construct (including, but not limited to those described above).

In some embodiments, the agent that blocks the interaction between CD47 (e.g., hCD47) and SIRPα (e.g., hSIRPα) is a fusion polypeptide comprising a moiety that binds CD47. In some embodiments, the fusion polypeptide comprises an antibody Fc region and a moiety that binds CD47. In some embodiments, the portion of the fusion polypeptide that binds CD47 (e.g., hCD47) binds CD47 (e.g., hCD47) with a $K_D$ of about 10 nM or better (such as at least about any one of 9 nM, 8 nM, 7 nM, 6 nM, 5 nM, 3 nM, 2 nM, 1 nM, 750 pM, 500 pM, 250 pM, 200 pM, 100 pM, 50 pM, 25 pM, 20 pM, 10 pM or less than 10 pM). In some embodiments, the fusion polypeptide exhibits at least about 50% CD47 receptor occupancy (e.g., at least about any one of 50%, 55%, 60%, 65%, 70%, 75%, 80%, 85%, 90%, 95%, 99%, or about 100%) in a human subject. In some embodiments, the fusion polypeptide has an EC50 of about 80 ng/ml or less, e.g., about any one of 75, 70, 65, 60, 55, 50, 45, 40, 35, 30, 25, 20, 15, 10, or 5 ng/ml. In some embodiments, the fusion polypeptide comprises WT human antibody Fc region. In some embodiments, the fusion polypeptide comprises an Fc variant (e.g., a variant of a WT human antibody Fc region) that exhibits reduced (e.g., such as ablated) effector function as compared to a WT Fc region. Exemplary Fc variants are described in WO 2017/027422 and US 2017/0107270, the contents of which are incorporated herein by reference in their entireties. In some embodiments, moiety that binds CD47 (e.g., hCD47) is a WT SIRPα (e.g., hSIRPα), or a WT SIRPγ (e.g., hSIRPγ). In some embodiments, moiety that binds CD47 (e.g., hCD47) is a CD47-binding fragment (e.g., d1 domain) of a WT SIRPα (e.g., hSIRPα), or a WT SIRPγ (e.g., hSIRPγ). In some embodiments, the moiety that binds CD47 (e.g., hCD47) is a SIRPα variant, a SIRPγ variant, a SIRPβ variant, or a CD47-binding fragment thereof (e.g., the d1 domain). Exemplary SIRPγ variants, SIRPβ1 variant, and SIRPβ2 variants are described in, e.g., WO 2013/109752; US 2015/0071905; U.S. Pat. No. 9,944,911; WO 2016/023040; WO 2017/027422; US 2017/0107270; U.S. Pat. Nos. 10,259,859; 9,845,345; WO2016187226; US20180155405; WO2017177333; WO2014094122; US2015329616; US20180312563; WO2018176132; WO2018081898; WO2018081897; PCT/US2019/048921; US20180141986A1; and EP3287470A1, the contents of which are incorporated herein by reference in their entireties.

In some embodiments, the agent that blocks the interaction between CD47 (e.g., hCD47) and SIRPα (e.g., hSIRPα) is a fusion polypeptide comprising an antibody Fc region and a SIRPα variant. In some embodiments, the SIRPα variant binds CD47 (e.g., hCD47) with a $K_D$ of about 10 nM or better (such as at least about any one of 9 nM, 8 nM, 7 nM, 6 nM, 5 nM, 3 nM, 2 nM, 1 nM, 750 pM, 500 pM, 250 pM, 200 pM, 100 pM, 50 pM, 25 pM, 20 pM, 10 pM or less than 10 pM). In some embodiments, the fusion polypeptide exhibits at least about 50% CD47 receptor occupancy (e.g., at least about any one of 50%, 55%, 60%, 65%, 70%, 75%, 80%, 85%, 90%, 95%, 99%, or about 100%) in a human subject. In some embodiments, the fusion polypeptide has an EC50 of about 80 ng/ml or less, e.g., about any one of 75, 70, 65, 60, 55, 50, 45, 40, 35, 30, 25, 20, 15, 10, or 5 ng/ml. In some embodiments, the fusion polypeptide comprises WT human antibody Fc region. In some embodiments, the fusion polypeptide comprises an Fc variant (e.g., a variant of a WT human antibody Fc region) that exhibits reduced (e.g., such as ablated) effector function as compared to a WT Fc region, such as those described in the references cited herein. In some embodiments, the fusion polypeptide comprises a SIRPα variant described in WO 2013/109752; US 2015/0071905; WO 2016/023040; WO 2017/027422; US 2017/0107270; U.S. Pat. Nos. 10,259,859; 9,845,345; WO2016187226; US20180155405; WO2017177333; WO2014094122; US2015329616; US20180312563; WO2018176132; WO2018081898; WO2018081897; US20180141986A1; and EP3287470A1, the contents of which are incorporated herein by reference in their entireties. In some embodiments, the fusion polypeptide comprising an antibody Fc region and a SIRPα variant is TTI-621, TTI-622, or IMM01 (see, e.g., Petrova et al. (2017) Clin Cancer Res 23:1086-1079; Russ et al. (2018) Blood Rev 50268-960X(17)30093-0; Zhang, X, Chen, W, Fan, J et al. Disrupting CD47-SIRPα axis alone or combined with autophagy depletion for the therapy of glioblastoma. Carcinogenesis 2018; 39: 689-99).

In some embodiments, the agent that blocks the interaction between CD47 (e.g., hCD47) and SIRPα (e.g., hSIRPα) is a fusion polypeptide comprising a SIRPα D1 domain variant (e.g., a SIRPα D1 domain variant described herein) and an Fc domain variant (e.g., an Fc domain variant described herein).

In some embodiments, provided is a method of treating cancer (e.g., gastric cancer or gastroesophageal cancer) in an individual (e.g., a human individual), comprising administering to the individual an effective amount of (a) an agent that blocks the interaction between CD47 (e.g., hCD47) and SIRPα (e.g., hSIRPα) (b) an anti-HER2 antibody, (c) an anti-VEGFR2 antibody, and (d) paclitaxel. In some embodiments, the agent that blocks the interaction between CD47 and SIRPα is a polypeptide comprising a SIRPα D1 domain variant and an Fc domain variant) wherein the SIRPα D1 domain variant comprises the amino acid sequence of SEQ ID NO: 81 or SEQ ID NO: 85, wherein the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat.

Further details regarding the methods of treatment with polypeptides comprising a SIRPα D1 domain variant and an Fc domain variant are described below. See also WO 2017/027422, U.S. Pat. No. 10,259,859, and PCT/US20/62402 the contents of each of which are incorporated by reference herein in their entireties.

Signal-Regulatory Protein α (SIRPα) D1 Domain and Variants Thereof

Disclosed herein, in some embodiments, are polypeptides comprising a signal-regulatory protein α (SIRP-α) D1 variant comprising a SIRPα D1 domain, or a fragment thereof, that comprises an amino acid mutation at residue 80 relative to a wild-type SIRPα D1 domain (e.g., a wild-type SIRPα D1 domain set forth in SEQ ID NO: 1 or 2); and at least one additional amino acid mutation relative to a wild-type SIRPα D1 domain (e.g., a wild-type SIRPα D1 domain set forth in SEQ ID NO: 1 or 2) at a residue selected from the group consisting of: residue 6, residue 27, residue 31, residue 47, residue 53, residue 54, residue 56, residue 66, and residue 92.

Also disclosed herein, in some embodiments, are polypeptides comprising an Fc domain variants, wherein an Fc domain variant dimer comprises two Fc domain variants, wherein each Fc domain variant independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

Signal-regulatory protein α ("SIRP-α" or "SIRP-alpha") is a transmembrane glycoprotein belonging to the Ig superfamily that is widely expressed on the membrane of myeloid cells. SIRPα interacts with CD47, a protein broadly expressed on many cell types in the body. The interaction of SIRPα with CD47 prevents engulfment of "self" cells, which can otherwise be recognized by the immune system. It has been observed that high CD47 expression on tumor cells can act, in acute myeloid leukemia and several solid tumor cancers, as a negative prognostic factor for survival.

Native SIRPα comprises 3 highly homologous immunoglobulin (Ig)-like extracellular domains—D1, D2, and D3. The SIRPα D1 domain ("D1 domain") refers to the membrane distal, extracellular domain of SIRPα and mediates binding of SIRPα to CD47. As used herein, the term "SIRPα polypeptide" refers to any SIRPα polypeptide or fragment thereof that is capable of binding to CD47. There are at least ten variants of wild-type human SIRPα. Table 1 shows the amino acid sequences of the D1 domains of the naturally occurring wild-type human SIRPα D1 domain variants (SEQ ID NOs:1 and 2). In some embodiments, a SIRPα polypeptide comprises a SIRPα D1 domain. In some embodiments, a SIRPα polypeptide comprises a wild-type D1 domain, such as those provided in SEQ ID NOs: 1 and 2. In some embodiments, a SIRPα polypeptide includes a D2 or D3 domain (or both a D2 and a D3 domain) (see Table 3) of a wild-type human SIRPα.

TABLE 1

Sequences of Wild-Type SIRPα D1 Domains

| SEQ ID NO: | Description | Amino Acid Sequence |
|---|---|---|
| 1 | Wild-type D1 domain variant 1 | EEELQVIQPDKSVLVAAGETATLRCTATSLIPVGPIQ WFRGAGPGRELIYNQKEGHFPRVTTVSDLTKRNNM DFSIRIGNITPADAGTYYCVKFRKGSPDDVEFKSGA GTELSVRAKPS |

TABLE 1-continued

Sequences of Wild-Type SIRPα D1 Domains

| SEQ ID NO: | Description | Amino Acid Sequence |
|---|---|---|
| 2 | Wild-type D1 domain variant 2 | EEELQVIQPDKSVSVAAGESAILHCTVTSLIPVGPIQ WFRGAGPARELIYNQKEGHFPRVTTVSESTKRENM DFSISISNITPADAGTYYCVKFRKGSPDTEFKSGAGT ELSVRAKPS |
| 11 | Wild-type pan-D1 domain | EEX$_1$LQVIQPDKX$_2$VX$_3$VAAGEX$_4$AX$_5$LX$_6$CTX$_7$TSLIP VGPIQWFRGAGPX$_8$RELIYNQKEGHFPRVTTVSX$_9$X$_{10}$ TKRX$_{11}$NMDFX$_{12}$IX$_{13}$IX$_{14}$NITPADAGTYYCVKFRKGS X$_{15}$X$_{16}$DX$_{17}$EFKSGAGTELSVRX$_{18}$KPS |
|  | Amino acid substitutions relative to SEQ ID NO: 11 | X$_1$ is E or G; X$_2$ is S or F; X$_3$ is L or S; X$_4$ is T or S; X$_5$ is T or I; X$_6$ is R, H, or L; X$_7$ is A or V; X$_8$ is G or A; X$_9$ is D or E; X$_{10}$ is L or S; X$_{11}$ is N or E or D; X$_{12}$ is S or P; X$_{13}$ is R or S; X$_{14}$ is G or S; X$_{15}$ is P or absent; X$_{16}$ is D or P; X$_{17}$ is V or T; and X$_{18}$ is A or G |

As used herein, the term "SIRPα D1 domain variant" refers to a polypeptide comprising a SIRPα D1 domain or a CD47-binding portion of a SIRPα polypeptide that has a higher affinity to CD47 than wild-type SIRPα. A SIRPα D1 domain variant comprises at least one amino acid substitution, deletion, or insertion (or a combination thereof) relative to a wild-type SIRPα.

In some embodiments, SIRPα D1 domain variants disclosed herein comprise a SIRPα D1 domain or variant thereof. In some embodiments, a SIRPα D1 domain variant comprises one or more amino acid substitutions, insertions, additions, or deletions relative to a wild-type D1 domain shown in SEQ ID NOs: 1 and 2. Table 2 lists exemplary amino acid substitutions in each SIRPα D1 domain variant (SEQ ID NOs: 13-14). In some embodiments, the SIRPα D1 domain polypeptide or SIRPα D1 domain variant comprises a fragment of the D1 domain. In some embodiments, the SIRPα polypeptide fragment or SIRPα D1 domain variant fragment comprises an amino acid sequence of less than 10 amino acids in length, about 10 amino acids in length, about 20 amino acids in length, about 30 amino acids in length, about 40 amino acids in length, about 50 amino acids in length, about 60 amino acids in length, about 70 amino acids in length, about 80 amino acids in length, about 90 amino acids in length, about 100 amino acids in length, or more than about 100 amino acids in length. In some embodiments, the SIRPα D1 domain fragments retain the ability to bind to CD47.

In some embodiments, a polypeptide of the disclosure comprising a SIRPα D1 domain variant binds with higher binding affinity to CD47 than a wild-type human SIRPα D1 domain. In some embodiments, the SIRPα D1 domain variant binds to human CD47 with at least 1-fold (e.g., at least 1.5-fold, 2-fold, 2.5-fold, 3-fold, 3.5-fold, 4-fold, 5-fold or greater than 5-fold) affinity than the affinity of a naturally occurring D1 domain. In some embodiments, the SIRPα D1 domain variant binds to human CD47 with at least 1-fold (e.g., at least 10-fold, 100-fold, 1000-fold or greater than 1000-fold) affinity than the affinity of a naturally occurring D1 domain.

As used herein, the term "optimized affinity" or "optimized binding affinity" refers to an optimized strength of the binding interaction between a polypeptide disclosed herein, including a SIRPα D1 domain variant, and CD47. For example, in some embodiments, the polypeptide binds primarily or with higher affinity to CD47 on cancer cells and does not substantially bind or binds with lower affinity to CD47 on non-cancer cells. In some embodiments, the binding affinity between the polypeptide and CD47 is optimized such that the interaction does not cause clinically relevant toxicity or decreases toxicity compared to a variant which binds with maximal affinity. In some embodiments, in order to achieve an optimized binding affinity between a polypeptide provided herein and CD47, the polypeptide including a SIRPα D1 domain variant is developed to have a lower binding affinity to CD47 than which is maximally achievable. In some embodiments, the SIRPα D1 domain variants disclosed herein cross react with rodent, non-human primate (NHP), and human CD47.

As used herein, the term "immunogenicity" refers to the property of a protein (e.g., a therapeutic protein) which causes an immune response in the host as though it is a foreign antigen. The immunogenicity of a protein can be assayed in vitro in a variety of different ways, such as through in vitro T-cell proliferation assays.

As used herein, the term "minimal immunogenicity" refers to an immunogenicity of a protein (e.g., a therapeutic protein) that has been modified, e.g., through amino acid substitutions, to be lower (e.g., at least 10%, 25%, 50%, or 100% lower) than the immunogenicity before the amino acid substitutions are introduced (e.g., an unmodified protein). In some embodiments, a protein (e.g., a therapeutic protein) is modified to have minimal immunogenicity and causes no or very little host immune response even though it is a foreign antigen.

In some embodiments, the SIRPα D1 domain variant demonstrates minimal immunogenicity. In some embodiments, a SIRPα polypeptide of the disclosure administered to a subject has the same amino acid sequence as that of the SIRPα polypeptide in a biological sample of the subject, except for amino acid changes which increase affinity of the SIRPα D1 domain variant. In some embodiments, the polypeptide variants disclosed herein lower the risk of side effects compared to anti-CD47 antibodies or wild-type SIRPα. In some embodiments, the polypeptide variants disclosed herein lower the risk of anemia compared to anti-CD47 antibodies or wild-type SIRPα. In some embodiments, the polypeptide variants disclosed herein do not cause acute anemia in rodent or non-human primates (NHP) studies.

Table 2 lists specific amino acid substitutions in a SIRPα D1 domain variant relative to each D1 domain sequence. In some embodiments, a SIRPα D1 domain variant includes one or more (e.g., two, three, four, five, six, seven, eight, nine, ten, eleven, twelve, thirteen, fourteen or more) of the substitutions listed in Table 2. In some embodiments, a SIRPα D1 domain variant includes at most fourteen amino acid substitutions relative to a wild-type D1 domain. In some embodiments, a SIRPα D1 domain variant includes at most ten amino acid substitutions relative to a wild-type D1 domain. In some embodiments, a SIRPα D1 domain variant includes at most seven amino acid substitutions relative to a wild-type D1 domain. In some embodiments, a SIRPα D1 domain variant of the disclosure has at least 90% (e.g., at least 92%, 95%, 97% or greater than 97%) amino acid sequence identity to a sequence of a wild-type D1 domain.

In some embodiments, a SIRPα D1 domain variant is a chimeric SIRPα D1 domain variant that includes a portion of two or more wild-type D1 domains or variants thereof (e.g., a portion of one wild-type D1 domain or variant thereof and a portion of another wild-type D1 domain or variant thereof). In some embodiments, a chimeric SIRPα D1 domain variant includes at least two portions (e.g., three, four, five or more portions) of wild-type D1 domains or variants thereof, wherein each of the portions is from a different wild-type D1 domain. In some embodiments, a chimeric SIRPα D1 domain variant further includes one or more amino acid substitutions listed in Table 2.

V, or L; $X_7$ is K or R; $X_8$ is E or Q; $X_9$ is H, P, or R; $X_{10}$ is L, T, or G; $X_{11}$ is K or R; $X_{12}$ is V or I; $X_{13}$ is F, L, or V; and $X_{14}$ is F or V; and wherein the variant comprises at least one amino acid substitution relative to a wild-type SIRPα D1 domain that comprises the sequence of SEQ ID NO: 1.

In some embodiments, a polypeptide comprises a SIRPα D1 domain variant that comprises the sequence of SEQ ID NOs: 13, wherein $X_1$ is L, I, or V. In any of the aforementioned embodiments, $X_2$ is V, L, or, I. In some embodiments, $X_3$ is A or V. In some embodiments, $X_4$ is A, I, or L. In some embodiments, $X_5$ is I, T, S, or F. In some embodiments, $X_6$ is E, V, or L. In some embodiments, $X_7$ is K or R. In some embodiments, $X_8$ is E or Q. In some embodiments, $X_9$ is H, P, or R. In some embodiments, $X_{10}$ is L, T, or G. In some embodiments, $X_{11}$ is K or R. In some embodiments, $X_{12}$ is V or I. In some embodiments, $X_{13}$ is F, L, V. In some embodiments, $X_{14}$ is F or V. In some embodiments, the polypeptide of this aspect of the disclosure includes no more than six amino acid substitutions relative to the wild-type SIRPα D1 domain that comprises the sequence of SEQ ID NO: 1.

In some embodiments, the polypeptide binds CD47 with at least 10-fold greater binding affinity than the wild-type SIRPα D1 domain that comprises the sequence of SEQ ID NO: 1. In some embodiments, the polypeptide binds CD47 with at least 100-fold greater binding affinity than the

TABLE 2

Amino Acid Substitutions in a SIRPα D1 Domain Variant

| SEQ ID NO: | Description | Amino Acid Sequence |
|---|---|---|
| 13 | D1 domain v1 | EEEX$_1$QX$_2$IQPDKSVLVAAGETX$_3$TLRCTX$_4$TSLX$_5$PVG PIQWFRGAGPGRX$_6$LIYNQX$_7$X$_8$GX$_9$FPRVTTVSDX$_{10}$T X$_{11}$RNNMDFSIRIGNITPADAGTYYCX$_{12}$KX$_{13}$RKGSPDD VEX$_{14}$KSGAGTELSVRAKPS |
| — | Amino acid substitutions relative to SEQ ID NO: 13 | $X_1$ = L, I, V; $X_2$ = V, L, I; $X_3$ = A, V; $X_4$ = A, I, L; $X_5$ = I, T, S, F; $X_6$ = E, V, L; $X_7$ = K, R; $X_8$ = E, Q; $X_9$ = H, P, R; $X_{10}$ = L, T, G; $X_{11}$ = K, R; $X_{12}$ = V, I; $X_{13}$ = F, L, V; $X_{14}$ = F, V |
| 14 | D1 domain v2 | EEEX$_1$QX$_2$IQPDKSVSVAAGESX$_3$ILHCTX$_4$TSLX$_5$PVGP IQWFRGAGPARX$_6$LIYNQX$_7$X$_8$GX$_9$FPRVTTVSEX$_{10}$TX$_{11}$ RENMDFSISISNITPADAGTYYCX$_{12}$KX$_{13}$RKGSPDTEX$_{14}$ KSGAGTELSVRAKPS |
| — | Amino acid substitutions relative to SEQ ID NO: 14 | $X_1$ = L, I, V; $X_2$ = V, L, I; $X_3$ = A, V; $X_4$ = V, I, L; $X_5$ = I, T, S, F; $X_6$ = E, V, L; $X_7$ = K, R; $X_8$ = E, Q; $X_9$ = H, P, R; $X_{10}$ = S, T, G; $X_{11}$ = K, R; $X_{12}$ = V, I; $X_{13}$ = F, L, V; $X_{14}$ = F, V |
| 23 | Pan D1 domain | EEX$_1$X$_2$QX$_3$IQPDKX$_4$VX$_5$VAAGEX$_6$X$_7$X$_8$LX$_9$CTX$_{10}$TSL X$_{11}$PVGPIQWFRGAGPX$_{12}$RX$_{13}$LIYNQX$_{14}$X$_{15}$GX$_{16}$FPRV TTVSX$_{17}$X$_{18}$TX$_{19}$RX$_{20}$NMDFX$_{21}$IX$_{22}$IX$_{23}$NITPADAGTYY CX$_{24}$KX$_{25}$RKGSPDX$_{26}$X$_{27}$EX$_{28}$KSGAGTELSVRX$_{29}$KPS |
| — | Amino acid substitutions relative to SEQ ID NO: 23 | $X_1$ = E, G; $X_2$ = L, I, V; $X_3$ = V, L, I; $X_4$ = S, F; $X_5$ = L, S; $X_6$ = S, T; $X_7$ = A, V; $X_8$ = I, T; $X_9$ = H, R; $X_{10}$ = A, V, I, L; $X_{11}$ = I, T, S, F; $X_{12}$ = A, G; $X_{13}$ = E, V, L; $X_{14}$ = K, R; $X_{15}$ = E, Q; $X_{16}$ = H, P, R; $X_{17}$ = D, E; $X_{18}$ = S, L, T, G; $X_{19}$ = K, R; $X_{20}$ = E, D; $X_{21}$ = S, P; $X_{22}$ = S, R; $X_{23}$ = S, G; $X_{24}$ = V, I; $X_{25}$ = F, L, V; $X_{26}$ = D or absent; $X_{27}$ = T, V; $X_{28}$ = F, V; and $X_{29}$ = A, G |

In some embodiments, a polypeptide comprises a SIRPα D1 domain variant that comprises a sequence of: EEEX$_1$QX$_2$IQPDKSVLVAAGETX$_3$TLRCTX$_4$TSLX$_5$PV-GPIQWFRGAGPGRX$_6$LIYNQX$_7$X$_8$G X$_9$FPRVTTVSDX$_{10}$TX$_{11}$RNNMDFSIRIGNITPADAGT-YYCX$_{12}$KX$_{13}$RKGSPDDVEX$_{14}$KSGA GTELSVRAKPS (SEQ ID NO: 13), wherein $X_1$ is L, I, or V; $X_2$ is V, L, or, I; $X_3$ is A or V; $X_4$ is A, I, or L; $X_5$ is I, T, S, or F; $X_6$ is E, wild-type SIRPα D1 domain that comprises the sequence of SEQ ID NO: 1. In some embodiments, the polypeptide binds CD47 with at least 1000-fold greater binding affinity than the wild-type SIRPα D1 domain that comprises the sequence of SEQ ID NO: 1. In some embodiments, a SIRPα D1 domain variant polypeptide or fragment thereof binds to CD47 with a KD less than $1\times10^{-8}$M, less than $5\times10^{-9}$M, less than $1\times10^{-9}$M, less $5\times10^{-10}$ M, less than $1\times10^{-10}$ M or less than $1×10^{-11}$M. In some embodiments, a SIRPα D1 domain variant polypeptide or fragment thereof binds to CD47 with a KD between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide includes a SIRPα D1 domain variant that comprises a sequence of: EEEX$_1$QX$_2$IQPDKSVSVAAGES X$_3$ILHCTX$_4$TSLX$_5$PVGPIQWFRGAGPARX$_6$LIYNQX$_7$- X$_8$G X$_9$FPRVTTVSEX$_{10}$TX$_{11}$RENMDFSISISNITPADAGTY YCX$_{12}$KX$_{13}$RKGSPDTEX$_{14}$KSGAGT ELSVRAKPS (SEQ ID NO: 14), wherein X$_1$ is L, I, or V; X$_2$ is V, L, or, I; X$_3$ is A or V; X$_4$ is V, I, or L; X$_5$ is I, T, S, or F; X$_6$ is E, V, or L; X$_7$ is K or R; X$_8$ is E or Q; X$_9$ is H, P, or R; X$_{10}$ is S, T, or G; X$_{11}$ is K or R; X$_{12}$ is V or I; X$_{13}$ is F, L, or V; and X$_{14}$ is F or V; and wherein the variant comprises at least one amino acid substitution relative to a wild-type SIRPα D1 domain that comprises the sequence of SEQ ID NO: 2.

In some embodiments in this aspect of the disclosure, the polypeptide comprises the sequence of SEQ ID NO: 14, wherein X$_1$ is L, I, or V. In some embodiments, X$_2$ is V, L, or, I. In some embodiments, X$_3$ is A or V. In some embodiments, X$_4$ is V, I, or L. In some embodiments, X$_5$ is I, T, S, or F. In some embodiments, X$_6$ is E, V, or L. In some embodiments, X$_7$ is K or R. In some embodiments, X$_8$ is E or Q. In some embodiments, X$_9$ is H, P, or R. In some embodiments, X$_{10}$ is S, T, or G. In some embodiments, X$_{11}$ is K or R. In some embodiments, X$_{12}$ is V or I. In some embodiments, X$_{13}$ is F, L, or V. In some embodiments, X$_{14}$ is F or V. In some embodiments, the polypeptide of this aspect of the disclosure includes no more than six amino acid substitutions relative to the wild-type SIRPα D1 domain that comprises the sequence of SEQ ID NO: 2.

In some embodiments, the polypeptide binds CD47 with at least 10-fold greater binding affinity than the wild-type SIRPα D1 domain having the sequence of SEQ ID NO: 2. In some embodiments, the polypeptide binds CD47 with at least 100-fold greater binding affinity than the wild-type SIRPα D1 domain having the sequence of SEQ ID NO: 2. In some embodiments, the polypeptide binds CD47 with at least 1000-fold greater binding affinity than the wild-type SIRPα D1 domain having the sequence of SEQ ID NO: 2. In some embodiments, a SIRPα D1 domain variant polypeptide or fragment thereof binds to CD47 with a K$_D$ less than $1×10^{-8}$M, less than $5×10^{-9}$M, less than $1×10^{-9}$M, less $5×10^{-10}$M, less than $1×10^{-10}$M or less than $1×10^{-11}$M. In some embodiments, a SIRPα D1 domain variant polypeptide or fragment thereof binds to CD47 with a K$_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide includes a SIRPα D1 domain variant having a sequence of: EEX$_1$X$_2$QX$_3$IQPDKX$_4$VX$_5$VAAGEX$_6$X$_7$X$_8$LX$_9$CTX$_{10}$T SLX$_{11}$PVGPIQWFRGAGPX$_{12}$RX$_{13}$LIY NQX$_{14}$X$_{15}$GX$_{16}$FPRVTTVSX$_{17}$X$_{18}$TX$_{19}$RX$_{20}$NMDFX$_{21}$ IX$_{22}$IX$_{23}$NITPADAGTYYCX$_{24}$KX$_{25}$RK GSPDX$_{26}$X$_{27}$EX$_{28}$KSGAGTELSVRX$_{29}$KPS (SEQ ID NO: 23), wherein X$_1$ is E or G; X$_2$ is L, I, or V; X$_3$ is V, L, or, I; X$_4$ is S or F; X$_5$ is L or S; X$_6$ is S or T; X$_7$ is A or V; X$_8$ is I or T; X$_9$ is H or R; X$_{10}$ is A, V, I, or L; X$_{11}$ is I, T, S, or F; X$_{12}$ is A or G; X$_{13}$ is E, V, or L; X$_{14}$ is K or R; X$_{15}$ is E or Q; X$_{16}$ is H, P, or R; X$_{17}$ is D or E; X$_{18}$ is S, L, T, or G; X$_{19}$ is K or R; X$_{20}$ is E or D; X$_{21}$ is S or P; X$_{22}$ is S or R; X$_{23}$ is S or G; X$_{24}$ is V or I; X$_{25}$ is F, L, V; X$_{26}$ is D or absent; X$_{27}$ is T or V; X$_{28}$ is F or V; and X$_{29}$ is A or G; and wherein the variant comprises at least one amino acid substitution relative to a wild-type SIRPα D1 domain having the sequence of SEQ ID NO: 1 or 2.

In any of the aforementioned embodiments in this aspect of the disclosure, X$_2$ is L, I, or V. In any of the aforementioned embodiments, X$_3$ is V, L, or, I. In embodiments, X$_4$ is S or F. In some embodiments, X$_5$ is L or S. In some embodiments, X$_6$ is S or T. In some embodiments, X$_7$ is A or V. In some embodiments, X$_8$ is I or T. In some embodiments, X$_9$ is H or R. In some embodiments, X$_{10}$ is A, V, I, or L. In some embodiments, X$_{11}$ is I, T, S, or F. In some embodiments, X$_{12}$ is A or G. In some embodiments, X$_{13}$ is E, V, or L. In some embodiments, X$_{14}$ is K or R. In some embodiments, X$_{15}$ is E or Q. In some embodiments, X$_{16}$ is H, P, or R. In some embodiments, X$_{17}$ is D or E. In some embodiments, X$_{18}$ is S, L, T, or G. In some embodiments, X$_{19}$ is K or R. In some embodiments, X$_{20}$ is E or D. In some embodiments, X$_{21}$ is S or P. In some embodiments, X$_{22}$ is S or R. In some embodiments, X$_{23}$ is S or G. In some embodiments, X$_{24}$ is V or I. In some embodiments, X$_{25}$ is F, L, V. In some embodiments, X$_{26}$ is D or absent. In some embodiments, X$_{27}$ is T or V. In some embodiments, X$_{28}$ is F or V. In some embodiments, X$_{29}$ is A or G. In some embodiments, the polypeptide of this aspect of the disclosure includes no more than six amino acid substitutions relative to the wild-type SIRPα D1 domain having the sequence of SEQ ID NO: 1 or 2.

In some embodiments, the polypeptide binds CD47 with at least 10-fold greater binding affinity than the wild-type SIRPα D1 domain having the sequence of SEQ ID NO: 1 or 2. In some embodiments, the polypeptide binds CD47 with at least 100-fold greater binding affinity than the wild-type SIRPα D1 domain having the sequence of SEQ ID NO: 1 or 2. In some embodiments, the polypeptide binds CD47 with at least 1000-fold greater binding affinity than the wild-type SIRPα D1 domain having the sequence of SEQ ID NO: 1 or 2. In some embodiments, a SIRPα D1 domain variant polypeptide or fragment thereof binds to CD47 with a K$_D$ less than $1×10^{-8}$M, less than $5×10^{-9}$M, less than $1×10^{-9}$M, less $5×10^{-10}$ M, less than $1×10^{-10}$ M or less than $1×10^{-11}$ M. In some embodiments, a SIRPα D1 domain variant polypeptide or fragment thereof binds to CD47 with a K$_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide of the disclosure including a SIRPα D1 domain variant further comprises a D2 domain having the sequence of SEQ ID NO: 24, a D3 domain having the sequence of SEQ ID NO: 25, or a D2 domain having the sequence of SEQ ID NO: 24 and a D3 domain having the sequence of SEQ ID NO: 25 of a wild-type human SIRPα as shown in Table 3. In some embodiments, the SIRPα D1 domain variant further comprises a fragment or variant of a D2 domain or a fragment or variant of a D3 domain. In some embodiments, the SIRPα D1 domain variant further comprises a fragment or variant of a D2 domain and a fragment or variant of a D3 domain. In some embodiments, a SIRPα D1 domain variant is joined to a D2 or D3 domain by way of a linker. In some embodiments, a SIRPα D1 domain variant is joined to a D2 and D3 domain by way of a linker.

TABLE 3

Amino Acid Sequences of SIRPα D2 and D3 Domains

| SEQ ID NO: | Description | Amino Acid Sequence |
|---|---|---|
| 24 | SIRPα D2 domain | APVVSGPAARATPQHTVSFTCESHGFSPRDITLKWFKN GNELSDFQTNVDPVGESVSYSIHSTAKVVLTREDVHSQ VICEVAHVTLQGDPLRGTANLSETIR |
| 25 | SIRPα D3 domain | VPPTLEVTQQPVRAENQVNVTCQVRKFYPQRLQLTWLE NGNVSRTETASTVTENKDGTYNWMSWLLVNVSAHRDDV KLTCQVEHDGQPAVSKSHDLKVS |

In some embodiments, a polypeptide of the disclosure including a SIRPα D1 domain variant is attached to an Fc domain variant in order to improve the pharmacokinetic properties of the polypeptide, e.g., increase serum half-life. In some embodiments, a SIRPα D1 domain variant is attached to an Fc domain variant that is unable to dimerize. In some embodiments, Fc domain variants serve to increase the serum half-life of the polypeptides described herein. In some embodiments, a polypeptide of the disclosure including a SIRPα D1 domain variant does not include the sequence of any one of SEQ ID NOs: 26-36 shown in Table 4.

In some embodiments, the polypeptides and polypeptide constructs described herein are utilized in vitro for binding assays, such as immune assays. For example, in some embodiments, the polypeptides and polypeptide constructs described herein are utilized in liquid phase or bound to a solid phase carrier. In some embodiments, polypeptides utilized for immunoassays are detectably labeled in various ways.

In some embodiments, polypeptides and polypeptide constructs described herein are bound to various carriers and used to detect the presence of specific antigen expressing cells. Examples of carriers include glass, polystyrene, polypropylene, polyethylene, dextran, nylon, amylases, natural and modified celluloses, polyacrylamides, agaroses, and magnetite. The nature of the carrier can be either soluble or insoluble.

Various different labels and methods of labeling are known. Examples of labels include enzymes, radioisotopes, fluorescent compounds, colloidal metals, chemiluminescent compounds, and bio-luminescent compounds. Various techniques for binding labels to polypeptides disclosed herein are available.

In some embodiments, the polypeptides are coupled to low molecular weight haptens. These haptens are then specifically detected by means of a second reaction. For

TABLE 4

| SEQ ID NO: | AMINO ACID SEQUENCE |
|---|---|
| 26 | EEELQVIQPDKSVSVAAGESAILHCTITSLIPVGPIQWFRGAGPARELIYNQRE GHFPRVTTVSETTRRENMDFSISISNITPADAGTYYCVKFRKGSPDTEVKSGA GTELSVRAKPS |
| 27 | EEEVQVIQPDKSVSVAAGESAILHCTLTSLIPVGPIQWFRGAGPARVLIYNQR QGHFPRVTTVSEGTRRENMDFSISISNITPADAGTYYCIKFRKGSPDTEFKSG AGTELSVRAKPS |
| 28 | EEEVQIIQPDKSVSVAAGESVILHCTITSLTPVGPIQWFRGAGPARLLIYNQRE GPFPRVTTVSETTRRENMDFSISISNITPADAGTYYCVKLRKGSPDTEFKSGA GTELSVRAKPS |
| 29 | EEELQIIQPDKSVSVAAGESAILHCTITSLSPVGPIQWFRGAGPARVLIYNQRQ GPFPRVTTVSEGTKRENMDFSISISNITPADAGTYYCIKLRKGSPDTEFKSGA GTELSVRAKPS |
| 30 | EEEIQVIQPDKSVSVAAGESVIIHCTVTSLFPVGPIQWFRGAGPARVLIYNQR QGRFPRVTTVSEGTKRENMDFSISISNITPADAGTYYCVKVRKGSPDTEVKS GAGTELSVRAKPS |
| 31 | EEEVQIIQPDKSVSVAAGESIILHCTVTSLFPVGPIQWFRGAGPARVLIYNQRE GRFPRVTTVSEGTRRENMDFSISISNITPADAGTYYCIKLRKGSPDTEFKSGA GTELSVRAKPS |
| 32 | EEEVQLIQPDKSVSVAAGESAILHCTVTSLFPVGPIQWFRGAGPARVLIYNQR EGPFPRVTTVSEGTKRENMDFSISISNITPADAGTYYCIKFRKGSPDTEVKSG AGTELSVRAKPS |
| 33 | EEELQIIQPDKSVLVAAGETATLRCTITSLFPVGPIQWFRGAGPGRVLIYNQR QGPFPRVTTVSDTTKRNNMDFSIRIGNITPADAGTYYCIKFRKGSPDDVEFKS GAGTELSVRAKPS |
| 34 | EEELQIIQPDKSVSVAAGESAILHCTITSLFPVGPIQWFRGAGPARLLIYNQRQ GPFPRVTTVSETTKRENMDFSISISNITPADAGTYYCVKFRKGSPDTEFKSGA GTELSVRAKPS |
| 35 | EEEVQIIQPDKSVSVAAGESAILHCTITSLFPVGPIQWFRGAGPARVLIYNQKQ GPFPRVTTISETTRRENMDFSISISNITPADAGTYYCIKFRKGSPDTEFKSGAG TELSVRAKPS |
| 36 | EEELQIIQPDKSVSVAAGESAILHCTITSLTPVGPIQWFRGAGPARVLIYNQRQ GPFPRVTTVSEGTRRENMDFSISISNITPADAGTYYCIKFRKGSPDTEVKSGA GTELSVRAKPS | example, in some embodiments, the hapten biotin is used with avidin or the haptens dinitrophenol, pyridoxal, or fluorescein are detected with specific anti-hapten antibodies (e.g., anti-dinitrophenol antibodies, anti-pyridoxal antibodies, and anti-fluorescein antibodies respectively).

SIRPα D1 Domain Variants with Altered Glycosylation Patterns

Disclosed herein, in some embodiments, are polypeptides comprising a signal-regulatory protein α (SIRP-α) D1 variant comprising a SIRPα D1 domain, or a fragment thereof, having an amino acid mutation at residue 80 relative to a wild-type SIRPα D1 domain (e.g., a wild-type SIRPα D1 domain set forth in SEQ ID NO: 1 or 2); and at least one additional amino acid mutation relative to a wild-type SIRPα D1 domain (e.g., a wild-type SIRPα D1 domain set forth in SEQ ID NO: 1 or 2) at a residue selected from the group consisting of: residue 6, residue 27, residue 31, residue 47, residue 53, residue 54, residue 56, residue 66, and residue 92.

Also disclosed herein, in some embodiments, are polypeptides comprising an Fc domain variant, wherein an Fc domain variant dimer comprises two Fc domain variants, wherein each Fc domain variant independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

In some embodiments, a polypeptide in a composition disclosed herein comprises a SIRPα D1 domain variant that has reduced or minimal glycosylation. The D1 domain of SEQ ID NOs: 1 and 2 in Table 1 each contains a single potential N-linked glycosylation site at amino acid N80 in the sequence N80ITP. Expression of a SIRPα D1 domain in Chinese Hamster Ovary (CHO) cells results in a major band of 16 kDa (non-glycosylated) and a minor band of higher molecular weight that was removed by Endo Hf. Endo Hf is a recombinant protein fusion of Endoglycosidase H and maltose binding protein. Endo Hf cleaves within the chitobiose core of high mannose and some hybrid oligosaccharides from N-linked glycoproteins. This implies that a proline at amino acid position 83 can reduce the efficiency of glycosylation, leading to a protein with different degrees of glycosylation and therefore heterogeneity. For drug development, heterogeneity can give rise to challenges in process development. Therefore, to investigate the possibility of generating homogenous, non-glycosylated forms of SIRPα D1 domain variants, in some embodiments, amino acid N80 of a SIRPα D1 variant is mutated to Ala. In some embodiments, to make a non-glycosylated, SIRPα D1 domain variant, amino acid N80 in a SIRPα D1 domain variant is replaced by any amino acid, including any naturally and non-naturally occurring amino acid, e.g., N80A and N80Q. In some embodiments, a SIRPα D1 domain variant comprises an N80A mutation and at least 1 additional mutation (e.g., at least 2, 3, 4, 5, 6, 7, 8, 9, or 10 additional mutations or more). In some embodiments, the additional mutation is in the CD47 binding site. In some embodiments, the additional mutation is in the hydrophobic core of the D1 domain.

In some embodiments, a polypeptide in a composition disclosed herein includes a SIRPα D1 domain variant that has increased glycosylation relative to a wild-type SIRPα D1 domain. Another option to increase homogeneity of the final product is to enhance the efficiency of glycosylation at amino acid N80 and generate SIRPα D1 domain variants with increased glycosylation relative to a wild-type. In some embodiments, the amino acid P83 in the sequence NITP83 affects the degree of glycosylation at amino acid N80. In some embodiments, changing P83 to any amino acid increases the efficiency of glycosylation at N80. In some embodiments, amino acid P83 in a SIRPα D1 domain variant is replaced by any amino acid, including naturally and non-naturally amino acids, e.g., P83V, P83A, P83I, and P83L. In some embodiments, a polypeptide of the disclosure is expressed in a cell that is optimized not to glycosylate proteins that are expressed by such cell, for example by genetic engineering of the cell line (e.g., genetically engineered yeast or mammalian host) or modifications of cell culture conditions such as addition of kifunensine or by using a naturally non-glycosylating host such as a prokaryote (*E. coli*, etc.).

Table 5 lists specific amino acid substitutions in a SIRPα D1 domain variant relative to each D1 domain variant sequence. In some embodiments, a SIRPα D1 domain variant includes one or more (e.g., two, three, four, five, six, seven, eight, nine, ten, eleven, twelve, thirteen, fourteen or more) of the substitutions listed in Table 5. In some embodiments, the SIRPα D1 domain variants are not glycosylated or are minimally glycosylated. In some embodiments, the SIRPα D1 domain variants are fully glycosylated or almost fully glycosylated. In some embodiments, a SIRPα D1 domain variant includes at most fourteen amino acid substitutions relative to a wild-type D1 domain. In some embodiments, a SIRPα D1 domain variant includes at most ten amino acid substitutions relative to a wild-type D1 domain. In some embodiments, a SIRPα D1 domain variant includes at most seven amino acid substitutions relative to a wild-type D1 domain. In some embodiments, a SIRPα D1 domain variant of the disclosure has at least 90% (e.g., at least 92%, 95%, 97% or greater than 97%) amino acid sequence identity to a sequence of a wild-type D1 domain.

In some embodiments, a SIRPα D1 domain variant is a chimeric SIRPα D1 domain variant that includes a portion of two or more wild-type D1 domains or variants thereof (e.g., a portion of one wild-type D1 domain or variant thereof and a portion of another wild-type D1 domain or variant thereof). In some embodiments, a chimeric SIRPα D1 domain variant includes at least two portions (e.g., three, four, five or more portions) of wild-type D1 domains or variants thereof, wherein each of the portions is from a different wild-type D1 domain. In some embodiments, a chimeric SIRPα D1 domain variant further includes one or more amino acid substitutions listed in Table 5.

TABLE 5

Amino Acid Substitutions in a SIRPα D1 Domain Variant

| SEQ ID NO: | Description | Amino Acid Sequence |
|---|---|---|
| 37 | D1 domain v1 | EEEX$_1$QX$_2$IQPDKSVLVAAGETX$_3$TLRCTX$_4$TSLX$_5$PVG PIQWFRGAGPGRX$_6$LIYNQX$_7$X$_8$GX$_9$FPRVTTVSDX$_{10}$T X$_{11}$RNNMDFSIRIGX$_{12}$ITX$_{13}$ADAGTYYCX$_{14}$KX$_{15}$RKGSP DDVEX$_{16}$KSGAGTELSVRAKPS |

TABLE 5-continued

Amino Acid Substitutions in a SIRPα D1 Domain Variant

| SEQ ID NO: | Description | Amino Acid Sequence |
|---|---|---|
| — | Amino acid substitutions relative to SEQ ID NO: 37 | $X_1$ = L, I, V; $X_2$ = V, L, I; $X_3$ = A, V; $X_4$ = A, I, L; $X_5$ = I, T, S, F; $X_6$ = E, V, L; $X_7$ = K, R; $X_8$ = E, Q; $X_9$ = H, P, R; $X_{10}$ = L, T, G; $X_{11}$ = K, R; $X_{12}$ = N, A, C, D, E, F, G, H, I, K, L, M, P, Q, R, S, T, V, W, Y; $X_{13}$ = P, A, C, D, E, F, G, H, I, K, L, M, N, Q, R, S, T, V, W, Y; $X_{14}$ = V, I; $X_{15}$ = F, L, V; $X_{16}$ = F, V |
| 38 | D1 domain v2 | EEE$X_1$Q$X_2$IQPDKSVSVAAGES$X_3$ILHCT$X_4$TSL$X_5$PVGP IQWFRGAGPAR$X_6$LIYNQ$X_7$G$X_8$G$X_9$FPRVTTVSE$X_{10}$T$X_{11}$ RENMDFSISIS$X_{12}$IT$X_{13}$ADAGTYYC$X_{14}$K$X_{15}$RKGSPDT E$X_{16}$KSGAGTELSVRAKPS |
| — | Amino acid substitutions relative to SEQ ID NO: 38 | $X_1$ = L, I, V; $X_2$ = V, L, I; $X_3$ = A, V; $X_4$ = V, I, L; $X_5$ = I, T, S, F; $X_6$ = E, V, L; $X_7$ = K, R; $X_8$ = E, Q; $X_9$ = H, P, R; $X_{10}$ = S, T, G; $X_{11}$ = K, R; $X_{12}$ = N, A, C, D, E, F, G, H, I, K, L, M, P, Q, R, S, T, V, W, Y; $X_{13}$ = P, A, C, D, E, F, G, H, I, K, L, M, N, Q, R, S, T, V, W, Y; $X_{14}$ = V, I; $X_{15}$ = F, L, V; $X_{16}$ = F, V |
| 47 | Pan D1 domain | EE$X_1$$X_2$Q$X_3$IQPDK$X_4$V$X_5$VAAGE$X_6$$X_7$$X_8$L$X_9$CT$X_{10}$TSL $X_{11}$PVGPIQWFRGAGP$X_{12}$R$X_{13}$LIYNQ$X_{14}$$X_{15}$G$X_{16}$FPRV TTVS$X_{17}$$X_{18}$T$X_{19}$R$X_{20}$NMDF$X_{21}$I$X_{22}$I$X_{23}$$X_{24}$IT$X_{25}$ADAGT YYC$X_{26}$K$X_{27}$RKGSPD$X_{28}$$X_{29}$E$X_{30}$KSGAGTELSVR$X_{31}$KP S |
| — | Amino acid substitutions relative to SEQ ID NO: 47 | $X_1$ = E, G; $X_2$ = L, I, V; $X_3$ = V, L, I; $X_4$ = S, F; $X_5$ = L, S; $X_6$ = S, T; $X_7$ = A, V; $X_8$ = I, T; $X_9$ = H, R, L; $X_{10}$ = A, V, I, L; $X_{11}$ = I, T, S, F; $X_{12}$ = A, G; $X_{13}$ = E, V, L; $X_{14}$ = K, R; $X_{15}$ = E, Q; $X_{16}$ = H, P, R; $X_{17}$ = D, E; $X_{18}$ = S, L, T, G; $X_{19}$ = K, R; $X_{20}$ = E, N; $X_{21}$ = S, P; $X_{22}$ = S, R; $X_{23}$ = S, G; $X_{24}$ = any amino acid; $X_{25}$ = any amino acid; $X_{26}$ = V, I; $X_{27}$ = F, L, V; $X_{28}$ = D or absent; $X_{29}$ = T, V; $X_{30}$ = F, V; and $X_{31}$ = A, G |
| 48 | Pan D1 domain | EEELQ$X_1$IQPDKSV$X_2$VAAGE$X_3$A$X_4$L$X_5$CT$X_6$TSL$X_7$PV GPIQWFRGAGP$X_8$R$X_9$LIYNQ$X_{10}$$X_{11}$G$X_{12}$FPRVTTVS$X_{13}$ $X_{14}$TKR$X_{15}$NMDFSI$X_{16}$I$X_{17}$$X_{18}$ITPADAGTYYC$X_{19}$KFR KG$X_{20}$$X_{21}$$X_{22}$D$X_{23}$EFKSGAGTELSVRAKPS |
| — | Amino acid substitutions relative to SEQ ID NO: 48 | $X_1$ = V, I; $X_2$ = L, S; $X_3$ = T, S; $X_4$ = T, I; $X_5$ = R, H; $X_6$ = A, V, I; $X_7$ = I, R, Y, K, F; $X_8$ = G, A; $X_9$ = E, V; $X_{10}$ = K, R; $X_{11}$ = E, D, Q; $X_{12}$ = H, P; $X_{13}$ = D, E; $X_{14}$ = S, L, T; $X_{15}$ = N, E; $X_{16}$ = R, S; $X_{17}$ = G, S; $X_{18}$ = N, A; $X_{19}$ = V, I; $X_{20}$ = S, I, M; $X_{21}$ = P or absent; $X_{22}$ = D, P; and $X_{23}$ = V, T |
| 49 | Pan D1 domain | EEELQ$X_1$IQPDKSVLVAAGETATLRCT$X_2$TSL$X_3$PVGPI QWFRGAGPGR$X_4$LIYNQ$X_5$$X_6$G$X_7$FPRVTTVSD$X_8$TKR NNMDFSIRIG$X_9$ITPADAGTYYC$X_{10}$KFRKGSPDDVEF KSGAGTELSVRAKPS |
| — | Amino acid substitutions relative to SEQ ID NO: 49 | $X_1$ = V, I, L; $X_2$ = A, I, V, L; $X_3$ = I, F, S, T; $X_4$ = E, V, L; $X_5$ = K, R; $X_6$ = E, Q; $X_7$ = H, P, R; $X_8$ = L, T, S, G; $X_9$ = A; and $X_{10}$ = V, I |
| 50 | Pan D1 domain | EEELQ$X_1$IQPDKSVSVAAGESAILHCT$X_2$TSL$X_3$PVGPI QWFRGAGPAR$X_4$LIYNQ$X_5$$X_6$G$X_7$FPRVTTVSE$X_8$TKR ENMDFSISIS$X_9$ITPADAGTYYC$X_{10}$KFRKGSPDTEFKS GAGTELSVRAKPS |
| — | Amino acid substitutions relative to SEQ ID NO: 50 | $X_1$ = V, I; $X_2$ = V, I; $X_3$ = I, F; $X_4$ = E, V; $X_5$ = K, R; $X_6$ = E, Q; $X_7$ = H, P; $X_8$ = S, T; $X_9$ = N, A; and $X_{10}$ = V, I |
| 51 | Pan D1 domain | EEELQ$X_1$IQPDKSVLVAAGETATLRCT$X_2$TSL$X_3$PVGPI QWFRGAGPGR$X_4$LIYNQ$X_5$EG$X_6$FPRVTTVSD$X_7$TKRN NMDFSIRIG$X_8$ITPADAGTYYC$X_9$KFRKGSPDDVEFKS GAGTELSVRAKPS |
| — | Amino acid substitutions relative to SEQ ID NO: 51 | $X_1$ = V, I; $X_2$ = A, I; $X_3$ = I, F; $X_4$ = E, V; $X_5$ = K, R; $X_6$ = H, P; $X_7$ = L, T; $X_8$ = N, A; and $X_9$ = V, I |

TABLE 5-continued

Amino Acid Substitutions in a SIRPα D1 Domain Variant

| SEQ ID NO: | Description | Amino Acid Sequence |
|---|---|---|
| 52 | Pan D1 domain | EEELQX$_1$IQPDKSVLVAAGETATLRCTX$_2$TSLX$_3$PVGPI QWFRGAGPGRELIYNQX$_4$EGX$_5$FPRVTTVSDX$_6$TKRN NMDFSIRIGX$_7$ITPADAGTYYCVKFRKGSPDDVEFKSG AGTELSVRAKPS |
| — | Amino acid substitutions relative to SEQ ID NO: 52 | X$_1$ = V, L, I; X$_2$ = A, I, L; X$_3$ = I, T, S, F; X$_4$ = K, R; X$_5$ = H, P, R; X$_6$ = L, T, G; and X$_7$ = N, A |
| 212 | Pan D1 domain | EEELQX$_1$IQPDKSVSVAAGESAILHCTX$_2$TSLX$_3$PVGPI QWFRGAGPARELIYNQX$_4$EGX$_5$FPRVTTVSEX$_6$TKREN MDFSISISX$_7$ITPADAGTYYCVKFRKGSPDTEFKSGAG TELSVRAKPS |
| — | Amino acid substitutions relative to SEQ ID NO: 212 | X$_1$ = V, L, I; X$_2$ = V, I, L; X$_3$ = I, T, S, F; X$_4$ = K, R; X$_5$ = H, P, R; X$_6$ = S, T, G; and X$_7$ = N, A |
| 218 | Pan D1 domain | EEELQX$_1$IQPDKSVLVAAGETATLRCTX$_2$TSLX$_3$PVGPI QWFRGAGPGRX$_4$LIYNQX$_5$X$_6$GX$_7$FPRVTTVSDX$_8$TKR NNMDFSIRIGX$_9$X$_{10}$X$_{11}$X$_{12}$ADAGTYYCX$_{13}$KFRKGSPD DVEFKSGAGTELSVRAKPS |
| — | Amino acid substitutions relative to SEQ ID NO: 218 | X$_1$ = V, L, or I; X$_2$ = A, V, L, or I; X$_3$ = , S, T, or F; X$_4$ = E, L, or V; X$_5$ = K or R; X$_6$ = E or Q; X$_7$ = H, R or P; X$_8$ = S,G, L or T, X$_9$ = any amino acid; X$_{10}$ = any amino acid; X$_{11}$ = any amino acid; X$_{12}$ = any amino acid; and X$_{13}$ = V or I |
| 219 | Pan D1 domain | EEELQX$_1$IQPDKSVLVAAGETATLRCTX$_2$TSLX$_3$PVGPI QWFRGAGPGRX$_4$LIYNQX$_5$X$_6$GX$_7$FPRVTTVSDX$_8$TKR NNMDFSIRIGX$_9$ITX$_{10}$ADAGTYYCX$_{11}$KFRKGSPDDVE FKSGAGTELSVRAKPS |
| — | Amino acid substitutions relative to SEQ ID NO: 219 | X$_1$ = V, L or I; X$_2$ = A, V, L, or I; X$_3$ = I, S, T or F; X$_4$ = E, L, or V; X$_5$ = K or R; X$_6$ = E or Q; X$_7$ = H, R or P; X$_8$ = S,G, L, or T; X$_9$ = N; X$_{10}$ = any amino acid other than P ; and X$_{11}$ = V or I |

In some embodiments, a polypeptide includes a SIRPα D1 domain variant having a sequence of: EEEX$_1$QX$_2$IQPDKSVLVAAGETX$_3$TLRCTX$_4$TSLX$_5$PV-GPIQWFRGAGPGRX$_6$LIYNQX$_7$X$_8$GX$_9$FPRVTTVSDX$_{10}$TX$_{11}$RNNMDFSIRIGX$_{12}$ITX$_{13}$ADAGTYYCX$_{14}$KX$_{15}$RKGSPDDVEX$_{16}$KS GAG-TELSVRAKPS (SEQ ID NO: 37), wherein X$_1$ is L, I, or V; X$_2$ is V, L, or, I; X$_3$ is A or V; X$_4$ is A, I, or L; X$_5$ is I, T, S, or F; X$_6$ is E, V, or L; X$_7$ is K or R; X$_8$ is E or Q; X$_9$ is H, P, or R; X$_{10}$ is L, T, or G; X$_{11}$ is K or R; X$_{12}$ is N, A, C, D, E, F, G, H, I, K, L, M, P, Q, R, S, T, V, W, or Y; X$_{13}$ is P, A, C, D, E, F, G, H, I, K, L, M, N, Q, R, S, T, V, W, or Y; X$_{14}$ is V or I; X$_{15}$ is F, L, or V; and X$_{16}$ is F or V; and wherein the variant comprises at least one amino acid substitution relative to a wild-type SIRPα D1 domain having the sequence of SEQ ID NO: 1.

In some embodiments in this aspect of the disclosure, a polypeptide includes a SIRPα D1 domain variant having a sequence of SEQ ID NO: 37, wherein X$_1$ is L, I, or V. In some embodiments, X$_2$ is V, L, or, I. In some embodiments, X$_3$ is A or V. In some embodiments, X$_4$ is A, I, or L. In some embodiments, X$_5$ is I, T, S, or F. In some embodiments, X$_6$ is E, V, or L. In some embodiments, X$_7$ is K or R. In some embodiments, X$_8$ is E or Q. In some embodiments, X$_9$ is H, P, or R. In some embodiments, X$_{10}$ is L, T, or G. In some embodiments, X$_{11}$ is K or R. In some embodiments, X$_{12}$ is N, A, C, D, E, F, G, H, I, K, L, M, P, Q, R, S, T, V, W, or Y. In some embodiments, X$_{13}$ is P, A, C, D, E, F, G, H, I, K, L, M, N, Q, R, S, T, V, W, or Y. In some embodiments, X$_{14}$ is V or I. In some embodiments, X$_{15}$ is F, L, V. In some embodiments, X$_{16}$ is F or V.

In some embodiments, a polypeptide provided herein includes no more than ten amino acid substitutions relative to the wild-type SIRPα D1 domain having the sequence of SEQ ID NO: 1. In some embodiments, the polypeptide provided herein includes no more than seven amino acid substitutions relative to the wild-type SIRPα D1 domain having the sequence of SEQ ID NO: 1.

In some embodiments, the polypeptide binds CD47 with at least 10-fold greater binding affinity than the wild-type SIRPα D1 domain having the sequence of SEQ ID NO: 1. In some embodiments, the polypeptide binds CD47 with at least 100-fold greater binding affinity than the wild-type SIRPα D1 domain having the sequence of SEQ ID NO: 1. In some embodiments, the polypeptide binds CD47 with at least 1000-fold greater binding affinity than the wild-type SIRPα D1 domain having the sequence of SEQ ID NO: 1. In some embodiments, a SIRPα D1 domain variant polypeptide or fragment thereof binds to CD47 with a K$_D$ less than $1\times10^{-8}$M, less than $5\times10^{-9}$M, less than $1\times10^{-9}$M, less $5\times10^{-10}$ M, less than $1\times10^{-10}$ M or less than $1\times10^{-11}$M. In some embodiments, a SIRPα D1 domain variant polypeptide or fragment thereof binds to CD47 with a K$_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide includes a SIRPα D1 domain variant having a sequence of: EEEX$_1$QX$_2$IQPDKSVSVAAGESX$_3$ILHCTX$_4$TSLX$_5$PV GPIQWFRGAGPARX$_6$LIYNQX$_7$X$_8$G X$_9$FPRVTTVSEX$_{10}$TX$_{11}$RENMDFSISISX$_{12}$ITX$_{13}$ADA-GTYYCX$_{14}$KX$_{15}$RKGSPDTEX$_{16}$KSGA GTELSVRAKPS (SEQ ID NO: 38), wherein X$_1$ is L, I, or V; X$_2$ is V, L, or, I; X$_3$ is A or V; X$_4$ is V, I, or L; X$_5$ is I, T, S, or F; X$_6$ is E, V, or L; X$_7$ is K or R; X$_8$ is E or Q; X$_9$ is H, P, or R; X$_{10}$ is S, T, or G; X$_{11}$ is K or R; X$_{12}$ is N, A, C, D, E, F, G, H, I, K, L, M, P, Q, R, S, T, V, W, or Y; X$_{13}$ is P, A, C, D, E, F, G, H, I, K, L, M, N, Q, R, S, T, V, W, or Y; X$_{14}$ is V or I; X$_{15}$ is F, L, or V; and X$_{16}$ is F or V; and wherein the variant comprises at least one amino acid substitution relative to a wild-type SIRPα D1 domain having the sequence of SEQ ID NO: 2.

In some embodiments in this aspect of the disclosure, a polypeptide includes a SIRPα D1 domain variant having a sequence of SEQ ID NO: 38, wherein X$_1$ is L, I, or V. In some embodiments, X$_2$ is V, L, or, I. In some embodiments, X$_3$ is A or V. In some embodiments, X$_4$ is V, I, or L. In some embodiments, X$_5$ is I, T, S, or F. In some embodiments, X$_6$ is E, V, or L. In some embodiments, X$_7$ is K or R. In some embodiments, X$_8$ is E or Q. In some embodiments, X$_9$ is H, P, or R. In some embodiments, X$_{10}$ is S, T, or G. In some embodiments, X$_{11}$ is K or R. In some embodiments, X$_{12}$ is N, A, C, D, E, F, G, H, I, K, L, M, P, Q, R, S, T, V, W, or Y. In some embodiments, X$_{13}$ is P, A, C, D, E, F, G, H, I, K, L, M, N, Q, R, S, T, V, W, or Y. In some embodiments, X$_{14}$ is V or I. In some embodiments, X$_{15}$ is F, L, or V. In some embodiments, X$_{16}$ is F or V.

In some embodiments, a polypeptide includes a SIRPα D1 domain variant having no more than ten amino acid substitutions relative to the wild-type SIRPα D1 domain having the sequence of SEQ ID NO: 2. In some embodiments, a polypeptide includes a SIRPα D1 domain variant having no more than seven amino acid substitutions relative to the wild-type SIRPα D1 domain having the sequence of SEQ ID NO: 2.

In some embodiments, the polypeptide binds CD47 with at least 10-fold greater binding affinity than the wild-type SIRPα D1 domain having the sequence of SEQ ID NO: 2. In some embodiments, the polypeptide binds CD47 with at least 100-fold greater binding affinity than the wild-type SIRPα D1 domain having the sequence of SEQ ID NO: 2. In some embodiments, the polypeptide binds CD47 with at least 1000-fold greater binding affinity than the wild-type SIRPα D1 domain having the sequence of SEQ ID NO: 2. In some embodiments, a SIRPα D1 domain variant polypeptide or fragment thereof binds to CD47 with a K$_D$ less than $1\times10^{-8}$M, less than $5\times10^{-9}$M, less than $1\times10^{-9}$M, less $5\times10^{-10}$ M, less than $1\times10^{-10}$ M or less than $1\times10^{-11}$ M. In some embodiments, a SIRPα D1 domain variant polypeptide or fragment thereof binds to CD47 with a K$_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In another aspect, the disclosure features a polypeptide including a SIRPα D1 domain variant having a sequence of: EEX$_1$X$_2$QX$_3$IQPDKX$_4$VX$_5$VAAGEX$_6$X$_7$X$_8$LX$_9$CTX$_{10}$T-SLX$_{11}$PVGPIQWFRGAGPX$_{12}$RX$_{13}$LIY NQX$_{14}$X$_{15}$GX$_{16}$FPRVTTVSX$_{17}$X$_{18}$TX$_{19}$RX$_{20}$NMDFX$_{21}$-IX$_{22}$IX$_{23}$X$_{24}$ITX$_{25}$ADAGTYYCX$_{26}$KX$_{27}$RKGSPDX$_{28}$-X$_{29}$EX$_{30}$KSGAGTELSVRX$_{31}$KPS (SEQ ID NO: 47), wherein X$_1$ is E or G; X$_2$ is L, I, or V; X$_3$ is V, L, or, I; X$_4$ is S or F; X$_5$ is L or S; X$_6$ is S or T; X$_7$ is A or V; X$_8$ is I or T; X$_9$ is H, R, or L; X$_{10}$ is A, V, I, or L; X$_{11}$ is I, T, S, or F; X$_{12}$ is A or G; X$_{13}$ is E, V, or L; X$_{14}$ is K or R; X$_{15}$ is E or Q; X$_{16}$ is H, P, or R; X$_{17}$ is D or E; X$_{18}$ is S, L, T, or G; X$_{19}$ is K or R; X$_{20}$ is E or N; X$_{21}$ is S or P; X$_{22}$ is S or R; X$_{23}$ is S or G; X$_{24}$ is any amino acid; X$_{25}$ is any amino acid; X$_{26}$ is V or I; X$_{27}$ is F, L, V; X$_{28}$ is D or absent; X$_{29}$ is T or V; X$_{30}$ is F or V; and X$_{31}$ is A or G; and wherein the variant comprises at least one amino acid substitution relative to a wild-type SIRPα D1 domain having the sequence of SEQ ID NO: 1 or 2.

In some embodiments, the polypeptide comprises the sequence of SEQ ID NO: 47, wherein X$_1$ is E or G. In any of the aforementioned embodiments in this aspect of the disclosure, X$_2$ is L, I, or V. In any of the aforementioned embodiments, X$_3$ is V, L, or, I. In any of the aforementioned embodiments, X$_4$ is S or F. In any of the aforementioned embodiments, X$_5$ is L or S. In any of the aforementioned embodiments, X$_6$ is S or T. In any of the aforementioned embodiments, X$_7$ is A or V. In any of the aforementioned embodiments, X$_8$ is I or T. In any of the aforementioned embodiments, X$_9$ is H or R. In any of the aforementioned embodiments, X$_{10}$ is A, V, I, or L. In any of the aforementioned embodiments, X$_{11}$ is I, T, S, or F. In any of the aforementioned embodiments, X$_{12}$ is A or G. In any of the aforementioned embodiments, X$_{13}$ is E, V, or L. In any of the aforementioned embodiments, X$_{14}$ is K or R. In any of the aforementioned embodiments, X$_{15}$ is E or Q. In any of the aforementioned embodiments, X$_{16}$ is H, P, or R. In any of the aforementioned embodiments, X$_{17}$ is D or E. In any of the aforementioned embodiments, X$_{18}$ is S, L, T, or G. In any of the aforementioned embodiments, X$_{19}$ is K or R. In any of the aforementioned embodiments, X$_{20}$ is E or N. In any of the aforementioned embodiments, X$_{21}$ is S or P. In any of the aforementioned embodiments, X$_{22}$ is S or R. In any of the aforementioned embodiments, X$_{23}$ is S or G. In any of the aforementioned embodiments, X$_{24}$ is N, A, C, D, E, F, G, H, I, K, L, M, P, Q, R, S, T, V, W, or Y. In any of the aforementioned embodiments, X$_{25}$ is P, A, C, D, E, F, G, H, I, K, L, M, N, Q, R, S, T, V, W, or Y. In any of the aforementioned embodiments, X$_{26}$ is V or I. In any of the aforementioned embodiments, X$_{27}$ is F, L, V. In any of the aforementioned embodiments, X$_{28}$ is D or absent. In any of the aforementioned embodiments, X$_{29}$ is T or V. In any of the aforementioned embodiments, X$_{30}$ is F or V. In any of the aforementioned embodiments, X$_{31}$ is A or G.

In some embodiments, the polypeptide of this aspect of the disclosure includes no more than ten amino acid substitutions relative to the wild-type SIRPα D1 domain having the sequence of SEQ ID NO: 1 or 2. In some embodiments, the polypeptide of this aspect of the disclosure includes no more than seven amino acid substitutions relative to the wild-type SIRPα D1 domain having the sequence of SEQ ID NO: 1 or 2.

In some embodiments, the polypeptide binds CD47 with at least 10-fold greater binding affinity than the wild-type SIRPα D1 domain having the sequence of SEQ ID NO: 1 or 2. In some embodiments, the polypeptide binds CD47 with at least 100-fold greater binding affinity than the wild-type SIRPα D1 domain having the sequence of SEQ ID NO: 1 or 2. In some embodiments, the polypeptide binds CD47 with at least 1000-fold greater binding affinity than the wild-type SIRPα D1 domain having the sequence of SEQ ID NO: 1 or 2. In some embodiments, a SIRPα D1 domain variant polypeptide or fragment thereof binds to CD47 with a K$_D$ less than $1\times10^{-8}$M, less than $5\times10^{-9}$M, less than $1\times10^{-9}$M, less 5×10⁻¹⁰ M, less than 1×10⁻¹⁰ M or less than 1×10⁻¹¹ M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide includes a SIRPα D1 domain variant having a sequence of: EEELQX$_1$IQPDKSVX$_2$VAAGEX$_3$AX$_4$LX$_5$CTX$_6$TSLX$_7$PVGPIQWFRGAGPX$_8$RX$_9$LIYNQX$_{10}$X$_{11}$GX$_{12}$FPRVTTVSX$_{13}$X$_{14}$TKRX$_{15}$NMDFSIX$_{16}$IX$_{17}$X$_{18}$ITPADAGTYYCX$_{19}$KFRKGX$_{20}$X$_{21}$X$_{22}$DX$_{23}$EFKSGAGTELSVRAKPS (SEQ ID NO: 48), wherein X$_1$ is V or I; X$_2$ is L or S; X$_3$ is T or S; X$_4$ is T or I; X$_5$ is R or H; X$_6$ is A, V, or I; X$_7$ is I, R, Y, K or F; X$_8$ is G or A; X$_9$ is E or V; X$_{10}$ is K or R; X$_{11}$ is E, D or Q; X$_{12}$ is H or P; X$_{13}$ is D or E; X$_{14}$ is S, L or T; X$_{15}$ is N or E; X$_{16}$ is R or S; X$_{17}$ is G or S; X$_{18}$ is N or A; X$_{19}$ is V or I; X$_{20}$ is S, I or M; X$_{21}$ is P or absent; X$_{22}$ is D or P; and X$_{23}$ is V or T, or a fragment thereof.

In another aspect, the disclosure features a polypeptide including a SIRPα D1 domain variant having a sequence of: EEELQX$_1$IQPDKSVLVAAGETATLRCTX$_2$TSLX$_3$PVGPIQWFRGAGPGRX$_4$LIYNQX$_5$X$_6$GX$_7$FPRVTTVSDX$_8$TKRNNMDFSIRIGX$_9$ITPADAGTYYCX$_{10}$KFRKGSPDDVEFKSGAGTELSV RAKPS (SEQ ID NO: 49), wherein X$_1$ is V, L, or I; X$_2$ is A, I, V, or L; X$_3$ is I, F, S, or T; X$_4$ is E, V, or L; X$_5$ is K or R; X$_6$ is E or Q; X$_7$ is H, P, or R; X$_8$ is L, T, S, or G; X$_9$ is A; and X$_{10}$ is V or I; and wherein the variant comprises at least one amino acid substitution relative to a wild-type SIRPα D1 domain having the sequence of SEQ ID NO: 1.

In some embodiments, the polypeptide comprises the sequence of SEQ ID NO: 49, wherein X$_1$ is V, L or I. In any of the aforementioned embodiments in this aspect of the disclosure, X$_2$ is A, I, V, or L. In any of the aforementioned embodiments, X$_3$ is I, F, S, or T. In any of the aforementioned embodiments, X$_4$ is E, V, or L. In any of the aforementioned embodiments, X$_5$ is K or R. In any of the aforementioned embodiments, X$_6$ is E or Q. In any of the aforementioned embodiments, X$_7$ is H, P, or R. In any of the aforementioned embodiments, X$_8$ is L, T, S or G. In any of the aforementioned embodiments, X$_9$ is A. In any of the aforementioned embodiments, X$_{10}$ is V or I.

In some embodiments, the polypeptide comprises a SIRPα D1 domain that comprises at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NO: 49, wherein each of X$_1$, X$_2$, X$_3$, X$_4$, X$_5$, X$_6$, X$_7$, X$_8$, X$_9$, and X$_{10}$ are not a wild-type amino acid.

In some embodiments, the polypeptide of this aspect of the disclosure includes no more than ten amino acid substitutions relative to the wild-type SIRPα D1 domain having the sequence of any one of SEQ ID NO: 1. In some embodiments, the polypeptide of this aspect of the disclosure includes no more than seven amino acid substitutions relative to the wild-type SIRPα D1 domain having the sequence of any one of SEQ ID NO: 1.

In some embodiments, the polypeptide binds CD47 with at least 10-fold greater binding affinity than the wild-type SIRPα D1 domain having the sequence of SEQ ID NO: 1. In some embodiments, the polypeptide binds CD47 with at least 100-fold greater binding affinity than the wild-type SIRPα D1 domain having the sequence of SEQ ID NO: 1. In some embodiments, the polypeptide binds CD47 with at least 1000-fold greater binding affinity than the wild-type SIRPα D1 domain having the sequence of SEQ ID NO: 1. In some embodiments, a SIRPα D1 domain variant polypeptide or fragment thereof binds to CD47 with a $K_D$ less than 1×10⁻⁸M, less than 5×10⁻⁹M, less than 1×10⁻⁹M, less 5×10⁻¹⁰ M, less than 1×10⁻¹⁰ M or less than 1×10⁻¹¹M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In another aspect, the disclosure features a polypeptide including a SIRPα D1 domain variant having a sequence of: EEELQX$_1$IQPDKSVSVAAGESAILHCTX$_2$TSLX$_3$PVGPIQWFRGAGPARX$_4$LIYNQX$_5$X$_6$GX$_7$FPRVTTVSEX$_8$TKRENMDFSISIS X$_9$ITPADAGTYYCX$_{10}$KFRKGSPDTEFKSGAGTELSVR AKPS, (SEQ ID NO: 50), wherein X$_1$ is V or I; X$_2$ is V or I; X$_3$ is I or F; X$_4$ is E or V; X$_5$ is K or R; X$_6$ is E or Q; X$_7$ is H or P; X$_8$ is S or T; X$_9$ is N or A; and X$_{10}$ V or I; and wherein the variant comprises at least one amino acid substitution relative to a wild-type SIRPα D1 domain having the sequence of SEQ ID NO: 2.

In some embodiments, the polypeptide comprises the sequence of SEQ ID NO: 50, wherein X$_1$ is V or I. In any of the aforementioned embodiments in this aspect of the disclosure, X$_2$ is V or I. In any of the aforementioned embodiments, X$_3$ is I or F. In any of the aforementioned embodiments, X$_4$ is E or V. In any of the aforementioned embodiments, X$_5$ is K or R. In any of the aforementioned embodiments, X$_6$ is E or Q. In any of the aforementioned embodiments, X$_7$ is H or P. In any of the aforementioned embodiments, X$_8$ is S or R. In any of the aforementioned embodiments, X$_9$ is N or A. In any of the aforementioned embodiments, X$_{10}$, is V or I.

In some embodiments, the polypeptide comprises a SIRPα D1 domain that comprises at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NO: 50, wherein each of X$_1$, X$_2$, X$_3$, X$_4$, X$_5$, X$_6$, X$_7$, X$_8$, X$_9$, and X$_{10}$ is not a wild-type amino acid.

In some embodiments, the polypeptide of this aspect of the disclosure includes no more than ten amino acid substitutions relative to the wild-type SIRPα D1 domain having the sequence of SEQ ID NO: 2. In some embodiments, the polypeptide of this aspect of the disclosure includes no more than seven amino acid substitutions relative to the wild-type SIRPα D1 domain having the sequence of SEQ ID NO: 2.

In some embodiments, the polypeptide binds CD47 with at least 10-fold greater binding affinity than the wild-type SIRPα D1 domain having the sequence of SEQ ID NO: 2. In some embodiments, the polypeptide binds CD47 with at least 100-fold greater binding affinity than the wild-type SIRPα D1 domain having the sequence of SEQ ID NO: 2. In some embodiments, the polypeptide binds CD47 with at least 1000-fold greater binding affinity than the wild-type SIRPα D1 domain having the sequence of SEQ ID NO: 2. In some embodiments, a SIRPα D1 domain variant polypeptide or fragment thereof binds to CD47 with a $K_D$ less than 1×10⁻⁸M, less than 5×10⁻⁹M, less than 1×10⁻⁹M, less 5×10⁻¹⁰ M, less than 1×10⁻¹⁰ M or less than 1×10⁻¹¹M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In another aspect, the disclosure features a polypeptide including a SIRPα D1 domain variant having a sequence of: EEELQX$_1$IQPDKSVLVAAGETATLRCTX$_2$TSLX$_3$PVGP-IQWFRGAGPGRX$_4$LIYNQX$_5$EGX$_6$FPRVTTVSDX$_7$TK-RNNMDFSIRIGX$_8$ITPADAGTYYCX$_9$KFRKGSPDDVE-FKSGAGTELSV RAKPS (SEQ ID NO: 51), wherein X$_1$ is V or I; X$_2$ is A or I; X$_3$ is I or F; X$_4$ is E or V; X$_5$ is K or R; X$_6$ is H or P; X$_7$ is L or T; X$_8$ is N or A; and X$_9$ is V or I; and wherein the variant comprises at least one amino acid substitution relative to a wild-type SIRPα D1 domain having the sequence of SEQ ID NO: 1.

In some embodiments, the polypeptide comprises the sequence of SEQ ID NO: 51, wherein X$_1$ is V or I. In any of the aforementioned embodiments in this aspect of the disclosure, X$_2$ is A or I. In any of the aforementioned embodiments, X$_3$ is I or F. In any of the aforementioned embodiments, X$_4$ is E or V. In any of the aforementioned embodiments, X$_5$ is K or R. In any of the aforementioned embodiments, X$_6$ is H or P. In any of the aforementioned embodiments, X$_7$ is L or T. In any of the aforementioned embodiments, X$_8$ is N or A. In any of the aforementioned embodiments, X$_9$ is V or I. In some embodiments, X$_4$ is not V.

In some embodiments, the polypeptide comprises the sequence of SEQ ID NO: 51, wherein X$_8$ is A. In any of the aforementioned embodiments in this aspect of the disclosure, X$_8$ is A and X$_1$ is V or I. In any of the aforementioned embodiments in this aspect of the disclosure, X$_8$ is A and X$_2$ is A or I. In any of the aforementioned embodiments, X$_8$ is A and X$_3$ is I or F. In any of the aforementioned embodiments, X$_8$ is A and X$_4$ is E or V. In some embodiments, X$_4$ is not V. In any of the aforementioned embodiments, X$_8$ is A and X$_5$ is K or R. In any of the aforementioned embodiments, X$_8$ is A and X$_6$ is H or P. In any of the aforementioned embodiments, X$_8$ is A and X$_7$ is A or V. In any of the aforementioned embodiments, X$_8$ is A and X$_9$ is V or I.

In some embodiments, the polypeptide comprises the sequence of SEQ ID NO: 51, wherein X$_8$ is A. In any of the aforementioned embodiments in this aspect of the disclosure, X$_8$ is A and X$_1$ is I. In any of the aforementioned embodiments in this aspect of the disclosure, X$_8$ is A and X$_2$ is I. In any of the aforementioned embodiments, X$_8$ is A and X$_3$ is F. In any of the aforementioned embodiments, X$_8$ is A and X$_4$ is V. In any of the aforementioned embodiments, X$_8$ is A and X$_5$ is R. In any of the aforementioned embodiments, X$_8$ is A and X$_6$ is P. In any of the aforementioned embodiments, X$_8$ is A and X$_7$ is T. In any of the aforementioned embodiments, X$_8$ is A and X$_9$ is I.

In some embodiments, the polypeptide comprises a SIRPα D1 domain variant that comprises at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NO: 51, wherein each of X$_1$, X$_2$, X$_3$, X$_4$, X$_5$, X$_6$, X$_7$, X$_8$, and X$_9$ is not a wild-type amino acid.

In some embodiments, the polypeptide of this aspect of the disclosure comprises no more than ten amino acid substitutions relative to the wild-type SIRPα D1 domain having the sequence of SEQ ID NO: 1. In some embodiments, the polypeptide of this aspect of the disclosure comprises no more than seven amino acid substitutions relative to the wild-type SIRPα D1 domain having the sequence of SEQ ID NO: 1.

In some embodiments, the polypeptide binds CD47 with at least 10-fold greater binding affinity than the wild-type SIRPα D1 domain having the sequence of SEQ ID NO: 1. In some embodiments, the polypeptide binds CD47 with at least 100-fold greater binding affinity than the wild-type SIRPα D1 domain having the sequence of SEQ ID NOs: 1. In some embodiments, the polypeptide binds CD47 with at least 1000-fold greater binding affinity than the wild-type SIRPα D1 domain having the sequence of SEQ ID NO: 1. In some embodiments, a SIRPα D1 domain variant polypeptide or fragment thereof binds to CD47 with a $K_D$ less than $1\times10^{-8}$M, less than $5\times10^{-9}$M, less than $1\times10^{-9}$M, less $5\times10^{-10}$ M, less than $1\times10^{-10}$ M or less than $1\times10^{-11}$M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In another aspect, the disclosure features a polypeptide including a SIRPα D1 domain variant having a sequence of: EEELQX$_1$IQPDKSVLVAAGETATLRCTX$_2$TSLX$_3$PVGP-IQWFRGAGPGRELIYNQX$_4$EGX$_5$F PRVTTVSDX$_6$TKRNNMDFSIRIGX$_7$ITPADAGTYYCV-KFRKGSPDDVEFKSGAGTELSVR AKPS (SEQ ID NO: 222), wherein X$_1$ is V, L, or I; X$_2$ is A, I, or L; X$_3$ is I, T, S, or F; X$_4$ is K or R; X$_5$ is H or P; X$_6$ is L, T, or G; X$_7$ is N or A; and wherein the variant comprises at least one amino acid substitution relative to a wild-type SIRPα D1 domain having a sequence according to SEQ ID NO: 1.

In some embodiments, the polypeptide comprises the sequence of SEQ ID NO: 222, wherein X$_1$ is V, L, or I. In any of the aforementioned embodiments in this aspect of the disclosure, X$_2$ is A, I, or L. In any of the aforementioned embodiments, X$_3$ is I, T, S, or F. In any of the aforementioned embodiments, X$_4$ is K or R. In any of the aforementioned embodiments, X$_5$ is H or P. In any of the aforementioned embodiments, X$_6$ is L, T, or G. In any of the aforementioned embodiments, X$_7$ is N or A.

In some embodiments, the polypeptide comprises the sequence of SEQ ID NO: 222, wherein X$_1$ is V or I. In any of the aforementioned embodiments in this aspect of the disclosure, X$_2$ is A or I. In any of the aforementioned embodiments, X$_3$ is I or F. In any of the aforementioned embodiments, X$_4$ is K or R. In any of the aforementioned embodiments, X$_5$ is H or P. In any of the aforementioned embodiments, X$_6$ is L or T. In any of the aforementioned embodiments, X$_7$ is N or A.

In some embodiments, the polypeptide comprises the sequence of SEQ ID NO: 222, wherein X$_7$ is A. In any of the aforementioned embodiments in this aspect of the disclosure, X$_7$ is A and X$_1$ is V or I. In any of the aforementioned embodiments in this aspect of the disclosure, X$_7$ is A and X$_2$ is A or I. In any of the aforementioned embodiments, X$_7$ is A and X$_3$ is I or F. In any of the aforementioned embodiments, X$_7$ is A and X$_4$ is K or R. In any of the aforementioned embodiments, X$_7$ is A and X$_5$ is H or P. In any of the aforementioned embodiments, X$_7$ is A and X$_6$ is L or T.

In some embodiments, the polypeptide comprises the sequence of SEQ ID NO: 222, wherein X$_7$ is A. In any of the aforementioned embodiments in this aspect of the disclosure, X$_7$ is A and X$_1$ is I. In any of the aforementioned embodiments in this aspect of the disclosure, X$_7$ is A and X$_2$ is I. In any of the aforementioned embodiments, $X_7$ is A and $X_3$ is F. In any of the aforementioned embodiments, $X_7$ is A and $X_4$ is R. In any of the aforementioned embodiments, $X_7$ is A and $X_5$ is P. In any of the aforementioned embodiments, $X_7$ is A and $X_6$ is T.

In some embodiments, the polypeptide comprises a SIRPα D1 domain that comprises at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NO: 222, wherein each of $X_1$, $X_2$, $X_3$, $X_4$, $X_5$, $X_6$, and $X_7$ is not a wild-type amino acid.

In some embodiments, the polypeptide of this aspect of the disclosure includes no more than ten amino acid substitutions relative to the wild-type SIRPα D1 domain having the sequence of SEQ ID NO: 1. In some embodiments, the polypeptide of this aspect of the disclosure includes no more than seven amino acid substitutions relative to the wild-type SIRPα D1 domain having the sequence of SEQ ID NO: 1.

In some embodiments, the polypeptide binds CD47 with at least 10-fold greater binding affinity than the wild-type SIRPα D1 domain having the sequence of SEQ ID NO: 1. In some embodiments, the polypeptide binds CD47 with at least 100-fold greater binding affinity than the wild-type SIRPα D1 domain having the sequence of SEQ ID NO: 1. In some embodiments, the polypeptide binds CD47 with at least 1000-fold greater binding affinity than the wild-type SIRPα D1 domain having the sequence of SEQ ID NO: 1. In some embodiments, fragments include polypeptides of less than 10 amino acids in length, about 10 amino acids in length, about 20 amino acids in length, about 30 amino acids in length, about 40 amino acids in length, about 50 amino acids in length, about 60 amino acids in length, about 70 amino acids in length, about 80 amino acids in length, about 90 amino acids in length, about 100 amino acids in length, or more than about 100 amino acids in length. Fragments retain the ability to bind to CD47. Preferably, SIRPα D1 domain variant polypeptides and fragments thereof bind to CD47 with a higher affinity than a SIRPα polypeptide binds to CD47. For example, in some embodiments, a SIRPα D1 domain variant polypeptide or fragment thereof binds to CD47 with a $K_D$ less than $1\times10^{-8}$M, less than $5\times10^{-9}$M, less than $1\times10^{-9}$M, less $5\times10^{-10}$ M, less than $1\times10^{-10}$ M or less than $1\times10^{-11}$ M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In another aspect, the disclosure features a polypeptide including a SIRPα D1 domain variant having a sequence of: EEELQX$_1$IQPDKSVSVAAGESAILHCTX$_2$T SLX$_3$PVGPIQWFRGAGPARELIYNQX$_4$EGX$_5$FP RVTTVSEX$_6$TKRENMDFSISISX$_7$ITPADAGTYYCVK-FRKGSPDTEFKSGAGTEL SVRAKP S (SEQ ID NO: 212), wherein $X_1$ is V, L, or I; $X_2$ is V, I, or L; $X_3$ is I, T, S, or F; $X_4$ is K or R; $X_5$ is H, P, or R; $X_6$ is S, T, or G; $X_7$ is N or A; and wherein the variant comprises at least one amino acid substitution relative to a wild-type SIRPα D1 domain having the sequence of SEQ ID NO: 2.

In some embodiments, the polypeptide comprises the sequence of SEQ ID NO: 212, wherein $X_1$ is V, L, or I. In any of the aforementioned embodiments in this aspect of the disclosure, $X_2$ is V, I, or L. In any of the aforementioned embodiments, $X_3$ is I, T, S, or F. In any of the aforementioned embodiments, $X_4$ is K or R. In any of the aforementioned embodiments, $X_5$ is H or P. In any of the aforementioned embodiments, $X_6$ is S, T, or G. In any of the aforementioned embodiments, $X_7$ is N or A.

In some embodiments, the polypeptide comprises the sequence of SEQ ID NO: 212, wherein $X_1$ is V or I. In any of the aforementioned embodiments in this aspect of the disclosure, $X_2$ is V or I. In any of the aforementioned embodiments, $X_3$ is I or F. In any of the aforementioned embodiments, $X_4$ is K or R. In any of the aforementioned embodiments, $X_5$ is H or P. In any of the aforementioned embodiments, $X_6$ is S or T. In any of the aforementioned embodiments, $X_7$ is N or A.

In some embodiments, the polypeptide comprises the sequence of SEQ ID NO: 212, wherein $X_7$ is A. In any of the aforementioned embodiments in this aspect of the disclosure, $X_7$ is A and $X_1$ is V or I. In any of the aforementioned embodiments in this aspect of the disclosure, $X_7$ is A and $X_2$ is V or I. In any of the aforementioned embodiments, $X_7$ is A and $X_3$ is I or F. In any of the aforementioned embodiments, $X_7$ is A and $X_4$ is K or R. In any of the aforementioned embodiments, $X_7$ is A and $X_5$ is H or P. In any of the aforementioned embodiments, $X_7$ is A and $X_6$ is S or T.

In some embodiments, the polypeptide comprises the sequence of SEQ ID NO: 212, wherein $X_7$ is A. In any of the aforementioned embodiments in this aspect of the disclosure, $X_7$ is A and $X_1$ is I. In any of the aforementioned embodiments in this aspect of the disclosure, $X_7$ is A and $X_2$ is I. In any of the aforementioned embodiments, $X_7$ is A and $X_3$ is F. In any of the aforementioned embodiments, $X_7$ is A and $X_4$ is R. In any of the aforementioned embodiments, $X_7$ is A and $X_5$ is P. In any of the aforementioned embodiments, $X_7$ is A and $X_6$ is T.

In some embodiments, the polypeptide comprises a SIRPα D1 domain having at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NO: 212, wherein each of $X_1$, $X_2$, $X_3$, $X_4$, $X_5$, $X_6$, and $X_7$ is not a wild-type amino acid.

In some embodiments, the polypeptide of this aspect of the disclosure includes no more than ten amino acid substitutions relative to the wild-type SIRPα D1 domain having the sequence of SEQ ID NO: 2. In some embodiments, the polypeptide of this aspect of the disclosure includes no more than seven amino acid substitutions relative to the wild-type SIRPα D1 domain having the sequence of SEQ ID NO: 2.

In some embodiments, the polypeptide binds CD47 with at least 10-fold greater binding affinity than the wild-type SIRPα D1 domain having the sequence of SEQ ID NO: 2. In some embodiments, the polypeptide binds CD47 with at least 100-fold greater binding affinity than the wild-type SIRPα D1 domain having the sequence of SEQ ID NO: 2. In some embodiments, the polypeptide binds CD47 with at least 1000-fold greater binding affinity than the wild-type SIRPα D1 domain having the sequence of SEQ ID NO: 2. In some embodiments, fragments include polypeptides of less than 10 amino acids in length, about 10 amino acids in length, about 20 amino acids in length, about 30 amino acids in length, about 40 amino acids in length, about 50 amino acids in length, about 60 amino acids in length, about 70 amino acids in length, about 80 amino acids in length, about 90 amino acids in length, about 100 amino acids in length, or more than about 100 amino acids in length. Fragments retain the ability to bind to CD47. Preferably, SIRPα D1 domain variant polypeptides and fragments thereof bind to CD47 with a higher affinity than a SIRPα polypeptide binds to CD47. For example, in some embodiments, a SIRPα D1 domain variant polypeptide or fragment thereof binds to CD47 with a $K_D$ less than $1\times10^{-8}$M, less than $5\times10^{-9}$M, less than $1\times10^{-9}$M, less $5\times10^{-10}$ M, less than $1\times10^{-10}$ M or less than $1\times10^{-11}$ M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

Described herein, in some embodiments, is a polypeptide comprising a SIRPα D1 domain variant having a sequence according to: EEELQX$_1$IQPDKSVLVAAGETATLRCTX$_2$-TSLX$_3$PVGPIQWFRGAGPGRX$_4$LIYNQX$_5$X$_6$GX$_7$FPR-VTTVSDX$_8$TKRNNMDFSIRIGX$_9$X$_{10}$X$_{11}$X$_{12}$ADAGTY-YCX$_{13}$KFRKGSPDDVEFKSGAG TELSVRAKPS (SEQ ID NO: 218), wherein X$_1$ is V, L, or I; X$_2$ is A, V, L, or I; X$_3$ is I, S, T, or F; X$_4$ is E, L, or V; X$_5$ is K or R; X$_6$ is E or Q; X$_7$ is H, R, or P; X$_8$ is S, G, L, or T; X$_9$ is any amino acid; X$_{10}$ is any amino acid; X$_{11}$ is any amino acid; X$_{12}$ is any amino acid; and X$_{13}$ is V or I; and wherein the SIRPα D1 domain variant comprises at least two amino acid substitutions relative to a wild-type SIRPα D1 domain having a sequence according to SEQ ID NO: 1.

In some embodiments, the polypeptide comprises the sequence of SEQ ID NO: 212, wherein X$_1$, wherein X$_9$ is A. In any of the aforementioned embodiments in this aspect of the disclosure, X$_9$ is N. In any of the aforementioned embodiments in this aspect of the disclosure X$_{10}$ is I. In any of the aforementioned embodiments in this aspect of the disclosure X$_9$ is N and X$_{10}$ is P. In any of the aforementioned embodiments in this aspect of the disclosure X$_9$ is N and X$_{11}$ is any amino acid other than S, T, or C. In any of the aforementioned embodiments in this aspect of the disclosure X$_{11}$ is T. In any of the aforementioned embodiments in this aspect of the disclosure X$_{11}$ is an amino acid other than T. In any of the aforementioned embodiments in this aspect of the disclosure X$_{12}$ is P. In any of the aforementioned embodiments in this aspect of the disclosure X$_9$ is N and X$_{12}$ is any amino acid other than P.

Described herein, in some embodiments, is a polypeptide comprising a SIRPα D1 domain variant having a sequence according to: EEELQX$_1$IQPDKSVLVAAGETATLRCTX$_2$TSLX$_3$PVGP-IQWFRGAGPGRX$_4$LIYNQX$_5$X$_6$GX$_7$FPRVTTVSDX$_8$T-KRNNMDFSIRIGX$_9$ITX$_{10}$ADAGTYYCX$_{11}$KFRKGSP-DDVEFKSGAGTEL SVRAKPS (SEQ ID NO: 219), wherein X$_1$ is V, L, or I; X$_2$ is A, V, L, or I; X$_3$ is I, S, T, or F; X$_4$ is E, L, or V; X$_5$ is K or R; X$_6$ is E or Q; X$_7$ is H, R, or P; X$_8$ is S, G, L, or T; X$_9$ is N; X$_{10}$ is any amino acid other than P; and X$_{11}$ is V or I; and wherein the SIRPα D1 domain variant comprises at least two amino acid substitutions relative to a wild-type SIRPα D1 domain having a sequence according to SEQ ID NO: 1.

In another aspect of the disclosure, compositions are disclosed herein which include a SIRPα D1 domain variant polypeptide having the amino acid sequence of SEQ ID NO: 48, or a fragment thereof. In some embodiments, the SIRPα D1 domain variant polypeptide or fragment thereof binds to CD47 with a higher affinity compared to the affinity that a SIRPα polypeptide binds to the CD47. In some embodiments, the SIRPα D1 domain variant polypeptide binds to CD47 with a $K_D$ less than $1\times10^{-8}$M, or less than $1\times10^{-9}$M, less than $1\times10^{-10}$ M or less than $1\times10^{-11}$M. In some embodiments, the above-mentioned SIRPα D1 domain variant polypeptides are attached or fused to a second polypeptide. In some embodiments, the second polypeptide includes, without limitation, an Fc polypeptide, an Fc variant or a fragment of the foregoing.

Without limiting the foregoing, in some embodiments, a SIRPα D1 domain variant polypeptide is selected from any one of SEQ ID NOs: 53-87 and 213 shown in Table 6.

TABLE 6

SIRPα Variant Polypeptides

| SEQ ID NO: | Amino Acid Sequence |
|---|---|
| 53 | EEELQIIQPDKSVSVAAGESAILHCTITSLFPVGPIQWFRGAGPARVLIYNQRQGPFPRVTTVSETTKRENMDFSISISNITPADAGTYYCIKFRKGSPDTEFKSGAGTELSVRAKPS |
| 54 | EEELQVIQPDKSVSVAAGESAILHCTVTSLFPVGPIQWFRGAGPARELIYNQRQGPFPRVTTVSESTKRENMDFSISISNITPADAGTYYCVKFRKGSPDTEFKSGAGTELSVRAKPS |
| 55 | EEELQVIQPDKSVSVAAGESAILHCTITSLFPVGPIQWFRGAGPARVLIYNQRQGPFPRVTTVSETTKRENMDFSISISNITPADAGTYYCIKFRKGSPDTEFKSGAGTELSVRAKPS |
| 56 | EEELQIIQPDKSVSVAAGESAILHCTVTSLFPVGPIQWFRGAGPARVLIYNQRQGPFPRVTTVSETTKRENMDFSISISNITPADAGTYYCIKFRKGSPDTEFKSGAGTELSVRAKPS |
| 57 | EEELQIIQPDKSVSVAAGESAILHCTITSLIPVGPIQWFRGAGPARVLIYNQRQGPFPRVTTVSETTKRENMDFSISISNITPADAGTYYCIKFRKGSPDTEFKSGAGTELSVRAKPS |
| 58 | EEELQIIQPDKSVSVAAGESAILHCTITSLFPVGPIQWFRGAGPARELIYNQRQGPFPRVTTVSETTKRENMDFSISISNITPADAGTYYCIKFRKGSPDTEFKSGAGTELSVRAKPS |
| 59 | EEELQIIQPDKSVSVAAGESAILHCTITSLFPVGPIQWFRGAGPARVLIYNQKQGPFPRVTTVSETTKRENMDFSISISNITPADAGTYYCIKFRKGSPDTEFKSGAGTELSVRAKPS |

TABLE 6-continued

SIRPα Variant Polypeptides

| SEQ ID NO: | Amino Acid Sequence |
|---|---|
| 60 | EEELQIIQPDKSVSVAAGESAILHCTITSLFPVGPIQWFRGAGPARVLIYNQRE<br>GPFPRVTTVSETTKRENMDFSISISNITPADAGTYYCIKFRKGSPDTEFKSGAG<br>TELSVRAKPS |
| 61 | EEELQIIQPDKSVSVAAGESAILHCTITSLFPVGPIQWFRGAGPARVLIYNQRQ<br>GHFPRVTTVSETTKRENMDFSISISNITPADAGTYYCIKFRKGSPDTEFKSGA<br>GTELSVRAKPS |
| 62 | EEELQIIQPDKSVSVAAGESAILHCTITSLFPVGPIQWFRGAGPARVLIYNQRQ<br>GPFPRVTTVSESTKRENMDFSISISNITPADAGTYYCIKFRKGSPDTEFKSGAG<br>TELSVRAKPS |
| 63 | EEELQIIQPDKSVSVAAGESAILHCTITSLFPVGPIQWFRGAGPARVLIYNQRQ<br>GPFPRVTTVSETTKRENMDFSISISNITPADAGTYYCVKFRKGSPDTEFKSGA<br>GTELSVRAKPS |
| 64 | EEELQVIQPDKSVSVAAGESAILHCTVTSLIPVGPIQWFRGAGPARELIYNQR<br>EGPFPRVTTVSESTKRENMDFSISISNITPADAGTYYCVKFRKGSPDTEFKSG<br>AGTELSVRAKPS |
| 65 | EEELQVIQPDKSVSVAAGESAILHCTVTSLFPVGPIQWFRGAGPARELIYNQR<br>EGPFPRVTTVSESTKRENMDFSISISNITPADAGTYYCVKFRKGSPDTEFKSG<br>AGTELSVRAKPS |
| 66 | EEELQVIQPDKSVSVAAGESAILHCTITSLFPVGPIQWFRGAGPARELIYNQR<br>EGPFPRVTTVSESTKRENMDFSISISNITPADAGTYYCVKFRKGSPDTEFKSG<br>AGTELSVRAKPS |
| 67 | EEELQVIQPDKSVSVAAGESAILHCTITSLFPVGPIQWFRGAGPARELIYNQR<br>EGPFPRVTTVSETTKRENMDFSISISNITPADAGTYYCVKFRKGSPDTEFKSG<br>AGTELSVRAKPS |
| 68 | EEELQIIQPDKSVSVAAGESAILHCTITSLFPVGPIQWFRGAGPARELIYNQRE<br>GPFPRVTTVSESTKRENMDFSISISNITPADAGTYYCVKFRKGSPDTEFKSGA<br>GTELSVRAKPS |
| 69 | EEELQVIQPDKSVSVAAGESAILHCTITSLIPVGPIQWFRGAGPARELIYNQRE<br>GPFPRVTTVSESTKRENMDFSISISNITPADAGTYYCVKFRKGSPDTEFKSGA<br>GTELSVRAKPS |
| 70 | EEELQIIQPDKSVSVAAGESAILHCTITSLFPVGPIQWFRGAGPARELIYNQRE<br>GPFPRVTTVSETTKRENMDFSISISNITPADAGTYYCVKFRKGSPDTEFKSGA<br>GTELSVRAKPS |
| 71 | EEELQVIQPDKSVLVAAGETATLRCTATSLFPVGPIQWFRGAGPGRELIYNQ<br>RQGPFPRVTTVSDLTKRNNMDFSIRIGNITPADAGTYYCVKFRKGSPDDVEF<br>KSGAGTELSVRAKPS |
| 72 | EEELQIIQPDKSVLVAAGETATLRCTITSLFPVGPIQWFRGAGPGRELIYNQRE<br>GPFPRVTTVSDLTKRNNMDFSIRIGNITPADAGTYYCVKFRKGSPDDVEFKS<br>GAGTELSVRAKPS |
| 73 | EEELQVIQPDKSVLVAAGETATLRCTITSLFPVGPIQWFRGAGPGRELIYNQR<br>EGPFPRVTTVSDTTKRNNMDFSIRIGNITPADAGTYYCVKFRKGSPDDVEFK<br>SGAGTELSVRAKPS |
| 74 | EEELQIIQPDKSVLVAAGETATLRCTITSLFPVGPIQWFRGAGPGRELIYNQRE<br>GPFPRVTTVSDTTKRNNMDFSIRIGNITPADAGTYYCVKFRKGSPDDVEFKS<br>GAGTELSVRAKPS |
| 75 | EEELQVIQPDKSVLVAAGETATLRCTITSLFPVGPIQWFRGAGPGRELIYNQR<br>EGPFPRVTTVSDLTKRNNMDFSIRIGNITPADAGTYYCVKFRKGSPDDVEFK<br>SGAGTELSVRAKPS |
| 76 | EEELQVIQPDKSVLVAAGETATLRCTATSLFPVGPIQWFRGAGPGRELIYNQ<br>REGPFPRVTTVSDLTKRNNMDFSIRIGNITPADAGTYYCVKFRKGSPDDVEF<br>KSGAGTELSVRAKPS |
| 77 | EEELQIIQPDKSVLVAAGETATLRCTITSLFPVGPIQWFRGAGPGRVLIYNQR<br>QGPFPRVTTVSDTTKRNNMDFSIRIGNITPADAGTYYCIKFRKGSPDDVEFKS<br>GAGTELSVRAKPS |
| 78 | EEELQIIQPDKSVLVAAGETATLRCTITSLFPVGPIQWFRGAGPGRVLIYNQR<br>QGPFPRVTTVSDTTKRNNMDFSIRIGAITPADAGTYYCIKFRKGSPDDVEFKS<br>GAGTELSVRAKPS |

TABLE 6-continued

SIRPα Variant Polypeptides

| SEQ ID NO: | Amino Acid Sequence |
|---|---|
| 79 | EEELQVIQPDKSVLVAAGETATLRCTATSLFPVGPIQWFRGAGPGRELIYNQ RQGPFPRVTTVSDLTKRNNMDFSIRIGAITPADAGTYYCVKFRKGSPDDVEF KSGAGTELSVRAKPS |
| 80 | EEELQIIQPDKSVLVAAGETATLRCTITSLFPVGPIQWFRGAGPGRVLIYNQR EGPFPRVTTVSDTTKRNNMDFSIRIGAITPADAGTYYCIKFRKGSPDDVEFKS GAGTELSVRAKPS |
| 81 | EEELQVIQPDKSVLVAAGETATLRCTATSLFPVGPIQWFRGAGPGRELIYNQ REGPFPRVTTVSDLTKRNNMDFSIRIGAITPADAGTYYCVKFRKGSPDDVEF KSGAGTELSVRAKPS |
| 82 | EEELQVIQPDKSVLVAAGETATLRCTITSLFPVGPIQWFRGAGPGRELIYNQR EGPFPRVTTVSDLTKRNNMDFSIRIGAITPADAGTYYCVKFRKGSPDDVEFK SGAGTELSVRAKPS |
| 83 | EEELQIIQPDKSVLVAAGETATLRCTITSLFPVGPIQWFRGAGPGRELIYNQRE GPFPRVTTVSDLTKRNNMDFSIRIGAITPADAGTYYCVKFRKGSPDDVEFKS GAGTELSVRAKPS |
| 84 | EEELQVIQPDKSVLVAAGETATLRCTITSLFPVGPIQWFRGAGPGRELIYNQR EGPFPRVTTVSDTTKRNNMDFSIRIGAITPADAGTYYCVKFRKGSPDDVEFK SGAGTELSVRAKPS |
| 85 | EEELQIIQPDKSVLVAAGETATLRCTITSLFPVGPIQWFRGAGPGRELIYNQRE GPFPRVTTVSDTTKRNNMDFSIRIGAITPADAGTYYCVKFRKGSPDDVEFKS GAGTELSVRAKPS |
| 86 | EEELQIIQPDKSVLVAAGETATLRCTITSLFPVGPIQWFRGAGPGRVLIYNQR QGPFPRVTTVSDTTKRNNMDFSIRIGNITPADAGTYYCIKFRKGSPDDVEFKS GAGTELSVRAKPS |
| 87 | EEELQVIQPDKSVLVAAGETATLRCTATSLIPVGPIQWFRGAGPGRELIYNQK EGHFPRVTTVSDLTKRNNMDFSIRIGNITPADAGTYYCVKFRKGSPDDVEFK SGAGTELSVRAKPS |
| 195 | EEELQIIQPDKSVLVAAGETATLRCTMTSLFPVGPIQWFRGAGPGRELIYNQR EGPFPRVTTVSDTTKRNNMDFSIRIGAITPADAGTYYCVKFRKGSPDDVEFK SGAGTELSVRAKPS |
| 196 | EEELQIIQPDKSVLVAAGETATLRCTITSLKPVGPIQWFRGAGPGRELIYNQR EGPFPRVTTVSDTTKRNNMDFSIRIGAITPADAGTYYCVKFRKGSPDDVEFK SGAGTELSVRAKPS |
| 197 | EEELQIIQPDKSVLVAAGETATLRCTITSLRPVGPIQWFRGAGPGRELIYNQR EGPFPRVTTVSDTTKRNNMDFSIRIGAITPADAGTYYCVKFRKGSPDDVEFK SGAGTELSVRAKPS |
| 198 | EEELQIIQPDKSVLVAAGETATLRCTITSLYPVGPIQWFRGAGPGRELIYNQR EGPFPRVTTVSDTTKRNNMDFSIRIGAITPADAGTYYCVKFRKGSPDDVEFK SGAGTELSVRAKPS |
| 199 | EEELQIIQPDKSVLVAAGETATLRCTITSLFPVGPIQWFRGAGPGRELIYNQR DGPFPRVTTVSDTTKRNNMDFSIRIGAITPADAGTYYCVKFRKGSPDDVEFK SGAGTELSVRAKPS |
| 200 | EEELQIIQPDKSVLVAAGETATLRCTITSLFPVGPIQWFRGAGPGRELIYNQRE GPFPRVTTVSDTTKRNNMDFSIRIGAITPADAGTYYCVKFRKGIPDDVEFKSG AGTELSVRAKPS |
| 201 | EEELQIIQPDKSVLVAAGETATLRCTITSLFPVGPIQWFRGAGPGRELIYNQRE GPFPRVTTVSDTTKRNNMDFSIRIGAITPADAGTYYCVKFRKGMPDDVEFKS GAGTELSVRAKPS |
| 202 | EEELQIIQPDKSVLVAAGETATLRCTITSLFPVGPIQWFRGAGPGRELIYNQRE GPFPRVTTVSDTTKRNNMDFSIRIGAITPADAGTYYCVKFRKGSPDVEFKSG AGTELSVRAKPS |
| 203 | EEELQIIQPDKSVLVAAGETATLRCTITSLFPVGPIQWFRGAGPGRELIYNQRE GPFPRVTTVSDTTKRNNMDFSIRIGAITPADAGTYYCVKFRKGSSEPDVEFKS GAGTELSVRAKPS |
| 204 | EEELQIIQPDKSVLVAAGETATLRCTITSLRPVGPIQWFRGAGPGRELIYNQR DGPFPRVTTVSDTTKRNNMDFSIRIGAITPADAGTYYCVKFRKGSPDDVEFK SGAGTELSVRAKPS |

TABLE 6-continued

SIRPα Variant Polypeptides

SEQ ID NO: Amino Acid Sequence

205 EEELQIIQPDKSVLVAAGETATLRCTITSLRPVGPIQWFRGAGPGRELIYNQR
EGPFPRVTTVSDTTKRNNMDFSIRIGAITPADAGTYYCVKFRKGIPDDVEFKS
GAGTELSVRAKPS

206 EEELQIIQPDKSVLVAAGETATLRCTITSLRPVGPIQWFRGAGPGRELIYNQR
DGPFPRVTTVSDTTKRNNMDFSIRIGAITPADAGTYYCVKFRKGIPDDVEFKS
GAGTELSVRAKPS

207 EEELQIIQPDKSVLVAAGETATLRCTITSLYPVGPIQWFRGAGPGRELIYNQR
DGPFPRVTTVSDTTKRNNMDFSIRIGAITPADAGTYYCVKFRKGSPDDVEFK
SGAGTELSVRAKPS

208 EEELQIIQPDKSVLVAAGETATLRCTITSLYPVGPIQWFRGAGPGRELIYNQR
EGPFPRVTTVSDTTKRNNMDFSIRIGAITPADAGTYYCVKFRKGIPDDVEFKS
GAGTELSVRAKPS

209 EEELQIIQPDKSVLVAAGETATLRCTITSLYPVGPIQWFRGAGPGRELIYNQR
DGPFPRVTTVSDTTKRNNMDFSIRIGAITPADAGTYYCVKFRKGIPDDVEFKS
GAGTELSVRAKPS

210 EEELQIIQPDKSVLVAAGETATLRCTITSLFPVGPIQWFRGAGPGRELIYNQR
DGPFPRVTTVSDTTKRNNMDFSIRIGAITPADAGTYYCVKFRKGIPDDVEFKS
GAGTELSVRAKPS

213 EEELQVIQPDKSVLVAAGETATLRCTATSLFPVGPIQWFRGAGPGRELIYNQ
RQGPFPRVTTVSDLTKRNNMDFSIRIGNITVADAGTYYCVKFRKGSPDDVEF
KSGAGTELSVRAKPS

In some embodiments, the polypeptide comprises a SIRPα D1 domain variant that has at least 85% sequence identity (e.g., at least 86%, 87%, 88%, 89%, 90%, 91%, 92%, 93%, 94%, 95%, 96%, 97%, 98%, 99%, or 100% sequence identity) to any variant provided in Table 6.

In some embodiments, the polypeptide comprises a SIRPα D1 domain that has at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NOs: 80, 81, or 85 in Table 6.

Fc Domain Variants and Fusion Polypeptides Comprising Same

Disclosed herein, in some embodiments, are polypeptides comprising a signal-regulatory protein α (SIRP-α) D1 variant comprising a SIRPα D1 domain, or a fragment thereof, having an amino acid mutation at residue 80 relative to a wild-type SIRPα D1 domain (e.g., a wild-type SIRPα D1 domain set forth in SEQ ID NO: 1 or 2); and at least one additional amino acid mutation relative to a wild-type SIRPα D1 domain (e.g., a wild-type SIRPα D1 domain set forth in SEQ ID NO: 1 or 2) at a residue selected from the group consisting of: residue 6, residue 27, residue 31, residue 47, residue 53, residue 54, residue 56, residue 66, and residue 92.

Also disclosed herein, in some embodiments, are Fc domain variant dimers, wherein the Fc domain variant dimer comprises two Fc domain variants, wherein each Fc domain variant independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

Antibodies that target cell surface antigens can trigger immunostimulatory and effector functions that are associated with Fc receptor (FcR) engagement on immune cells. There are a number of Fc receptors that are specific for particular classes of antibodies, including IgG (gamma receptors), IgE (eta receptors), IgA (alpha receptors) and IgM (mu receptors). Binding of the Fc region to Fc receptors on cell surfaces can trigger a number of biological responses including phagocytosis of antibody-coated particles (antibody-dependent cell-mediated phagocytosis, or ADCP), clearance of immune complexes, lysis of antibody-coated cells by killer cells (antibody-dependent cell-mediated cytotoxicity, or ADCC) and, release of inflammatory mediators, placental transfer, and control of immunoglobulin production. Additionally, binding of the C1 component of complement to antibodies can activate the complement system. Activation of complement can be important for the lysis of cellular pathogens. However, the activation of complement can also stimulate the inflammatory response and can also be involved in autoimmune hypersensitivity or other immunological disorders. Variant Fc regions with reduced or ablated ability to bind certain Fc receptors are useful for developing therapeutic antibodies and Fc-fusion polypeptide constructs which act by targeting, activating, or neutralizing ligand functions while not damaging or destroying local cells or tissues.

In some embodiments, a SIRPα D1 polypeptide construct comprises a non-naturally occurring SIRPα D1 domain variant linked to an Fc domain variant which forms an Fc domain having ablated or reduced effector function.

In some embodiments, a Fc domain variant refers to a polypeptide chain that includes second and third antibody constant domains (e.g., CH2 and CH3). In some embodiments, an Fc domain variant also includes a hinge domain. In some embodiments, the Fc domain variant is of any immunoglobulin antibody isotype, including IgG, IgE, IgM, IgA, and IgD. Additionally, in some embodiments, an Fc domain variant is of any IgG subtype (e.g., IgG1, IgG2, IgG2a, IgG2b, IgG2c, IgG3, and IgG4). In some embodiments, an Fc domain variant comprises as many as ten amino acid modifications (e.g., insertions, deletions and/or substitutions) relative to a wild-type Fc domain monomer sequence (e.g., 1-10, 1-8, 1-6, 1-4 amino acid substitutions, additions or insertions, deletions, or combinations thereof) that alter the interaction between an Fc domain and an Fc receptor.

As used herein, the term "Fc domain dimer" refers to a dimer of two Fc domains. In a wild-type Fc domain dimer, two wild-type Fc domains dimerize by the interaction between the two CH3 antibody constant domains, as well as one or more disulfide bonds that form between the hinge domains of the two dimerized Fc domains.

As used herein, the term "Fc domain dimer variant" comprises at least one Fc domain variant. In some embodiments, an Fc domain dimer variant comprises Fc domain variants that are mutated to lack effector functions, for example a "dead Fc domain dimer variant." In some embodiments, each of the Fc domains in an Fc domain dimer variant includes amino acid substitutions in the CH2 antibody constant domain to reduce the interaction or binding between the Fc domain dimer variant and an Fc receptor, such as an Fcγ receptor (FcγR), an Fcα receptor (FcαR), or an Fcε (FcεR).

In some embodiments, a SIRPα D1 domain variant (e.g., any of the variants described in Tables 2, 5, and 6) is fused to an Fc domain variant of an immunoglobulin or a fragment of an Fc domain variant. In some embodiments, an Fc domain variant of an immunoglobulin or a fragment of an Fc domain variant is capable of forming an Fc domain dimer with another Fc domain variant. In some embodiments, an Fc domain variant of an immunoglobulin or a fragment of an Fc domain variant is not capable of forming an Fc domain dimer with another Fc domain variant. In some embodiments, an Fc domain variant or a fragment of an Fc domain variant is fused to a polypeptide of the disclosure to increase serum half-life of the polypeptide. In some embodiments, an Fc domain variant or a fragment of an Fc domain variant fused to a polypeptide of the disclosure dimerizes with a second Fc domain variant to form an Fc domain dimer variant which binds an Fc receptor, or alternatively, an Fc domain variant binds to an Fc receptor. In some embodiments, an Fc domain variant or a fragment of the Fc domain variant fused to a polypeptide to increase serum half-life of the polypeptide does not induce any immune system-related response.

In some embodiments, a SIRPα polypeptide or construct provided herein includes a SIRPα D1 domain or variant thereof joined to a first Fc domain variant and an antibody variable domain joined to a second Fc domain variant, in which the first and second Fc domain variants combine to form an Fc domain dimer variant (e.g., a heterodimeric Fc domain dimer variant). An Fc domain dimer is the protein structure that is found at the C-terminus of an immunoglobulin. An Fc domain dimer includes two Fc domains that are dimerized by the interaction between the CH3 antibody constant domains. A wild-type Fc domain dimer forms the minimum structure that binds to an Fc receptor, e.g., FcγRI, FcγRIIa, FcγRIIb, FcγRIIIa, FcγRIIIb, and FcγRIV.

The Fc domain dimer is not involved directly in binding an antibody to its target, but can be involved in various effector functions, such as participation of the antibody in antibody-dependent cellular toxicity. In some embodiments, the Fc domain in a SIRPα polypeptide or construct of the disclosure comprises amino acid substitutions, additions or insertions, deletions, or any combinations thereof that lead to decreased effector function such as decreased antibody-dependent cell-mediated cytotoxicity (ADCC), decreased complement-dependent cytolysis (CDC), decreased antibody-dependent cell-mediated phagocytosis (ADCP), or any combinations thereof. In some embodiments, the SIRPα polypeptides or constructs of the disclosure are characterized by decreased binding (e.g., minimal binding or absence of binding) to a human Fc receptor and decreased binding (e.g., minimal binding or absence of binding) to complement protein C1q. In some embodiments, the SIRPα constructs of the disclosure are characterized by decreased binding (e.g., minimal binding or absence of binding) to human FcγRI, FcγRIIA, FcγRIIB, FcγRIIIB, or any combinations thereof, and C1q. To alter or reduce an antibody-dependent effector function, such as ADCC, CDC, ADCP, or any combinations thereof, in some embodiments, the Fc domains in SIRPα constructs of the disclosure are of the IgG class and comprise one or more amino acid substitutions at E233, L234, L235, G236, G237, D265, D270, N297, E318, K320, K322, A327, A330, P331, or P329 (numbering according to the EU index of Kabat (Sequences of Proteins of Immunological Interest, 5th Ed. Public Health Service, National Institutes of Health, Bethesda, MD (1991))).

In some embodiments, polypeptide constructs comprising a non-native Fc region described herein exhibit reduced or ablated binding to at least one of Fcγ receptors CD16a, CD32a, CD32b, CD32c, and CD64 as compared to a polypeptide construct comprising a native Fc region. In some cases, the polypeptide constructs described herein exhibit reduced or ablated binding to CD16a, CD32a, CD32b, CD32c, and CD64 Fcγ receptors.

CDC refers to a form of cytotoxicity in which the complement cascade is activated by the complement component C1q binding to antibody Fc domains. In some embodiments, polypeptide constructs comprising a non-native Fc region described herein exhibit at least a 5%, 10%, 15%, 20%, 30%, 40%, 50%, 60%, 70%, 80%, 90% or greater reduction in C1q binding compared to a polypeptide construct comprising a wild-type Fc region. In some cases, polypeptide constructs comprising a non-native Fc region as described herein exhibit reduced CDC as compared to a polypeptide construct comprising a wild-type Fc region. In some embodiments, polypeptide constructs comprising a non-native Fc region as described herein exhibit at least a 5%, 10%, 15%, 20%, 30%, 40%, 50%, 60%, 70%, 80%, 90% or greater reduction in CDC compared to a polypeptide construct comprising a wild-type Fc region. In some cases, polypeptide constructs comprising a non-natural Fc domain variants or Fc domain dimer variants as described herein exhibit negligible CDC as compared to a polypeptide construct comprising a wild-type Fc region.

In some embodiments, the Fc domain variants or Fc domain dimer variants described herein are minimally glycosylated or have reduced glycosylation relative to a wild-type sequence. In some embodiments, deglycosylation is accomplished with a mutation of N297A, or by mutating N297 to any amino acid which is not N. In some embodiments, deglycosylation is accomplished by disrupting the motif N-Xaa1-Xaa2-Xaa3, wherein N=asparagine; Xaa1=any amino acid except P (proline); Xaa2=T (threonine), S (serine) or C (cysteine); and Xaa3=any amino acid except P (proline). In one embodiment, the N-Xaa1-Xaa2-Xaa3 motif refers to residues 297-300 as designated according to Kabat et al., 1991. In some embodiments, a mutation to any one or more of N, Xaa1, Xaa2, or Xaa3 results in deglycosylation of the Fc domain variant or Fc domain dimer variant.

In some embodiments, variants of antibody IgG constant regions (e.g., Fc domain variants or Fc domain dimer variants) possess a reduced capacity to specifically bind Fcγ receptors or have a reduced capacity to induce phagocytosis. In some embodiments, variants of antibody IgG constant regions (e.g., Fc domain variants or Fc domain dimer variants) possess a reduced capacity to specifically bind Fcγ receptors and have a reduced capacity to induce phagocytosis. For example, in some embodiments, an Fc domain variant is mutated to lack effector functions, typical of a "dead" Fc domain variant. For example, in some embodiments, an Fc domain variant includes specific amino acid substitutions that are known to minimize the interaction between the Fc domain dimer and an Fcγ receptor. In some embodiments, an Fc domain variant is from an IgG1 antibody and includes one or more of amino acid substitutions L234A, L235A, G237A, and N297A (as designated according to the EU numbering system per Kabat et al., 1991). In some embodiments, one or more additional mutations are included in such IgG1 Fc domain variant. Non-limiting examples of such additional mutations for human IgG1 Fc domain variants include E318A and K322A. In some instances, a human IgG1 Fc domain variant has up to 12, 11, 10, 9, 8, 7, 6, 5 or 4 or fewer mutations in total as compared to wild-type human IgG1 sequence. In some embodiments, one or more additional deletions are included in such IgG1 Fc domain variant. For example, in some embodiments, the C-terminal lysine of the Fc domain IgG1 heavy chain constant region provided in SEQ ID NO: 88 in Table 7 is deleted, for example to increase the homogeneity of the polypeptide when the polypeptide is produced in bacterial or mammalian cells. In some instances, a human IgG1 Fc domain variant has up to 12, 11, 10, 9, 8, 7, 6, 5 or 4 or fewer deletions in total as compared to wild-type human IgG1 sequence (see, e.g., SEQ ID NO: 161 below). In some embodiments, a IgG1 Fc domain variant has a sequence according to any one of SEQ ID NO: 135, SEQ ID NO: 136 or SEQ ID NO: 137.

SEQ ID NO: 161:
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSR

WQQGNVFSCSVMHEALHNHYTQKSLSLSPG

In some embodiments, an Fc domain variant is from an IgG2 or IgG4 antibody and includes amino acid substitutions A330S, P331S, or both A330S and P331S. The aforementioned amino acid positions are defined according to Kabat, et al. (1991). The Kabat numbering of amino acid residues can be determined for a given antibody by alignment at regions of homology of the sequence of the antibody with a "standard" Kabat numbered sequence. In some embodiments, the Fc domain variant comprises a human IgG2 Fc domain sequence comprising one or more of A330S, P331S and N297A amino acid substitutions (as designated according to the EU numbering system per Kabat, et al. (1991). In some embodiments, one or more additional mutations are included in such IgG2 Fc domain variants. Non-limiting examples of such additional mutations for human IgG2 Fc domain variant include V234A, G237A, P238S, V309L and H268A (as designated according to the EU numbering system per Kabat et al. (1991)). In some instances, a human IgG2 Fc domain variant has up to 12, 11, 10, 9, 8, 7, 6, 5, 4, 3 or fewer mutations in total as compared to wild-type human IgG2 sequence. In some embodiments, one or more additional deletions are included in such IgG2 Fc domain variant. For example, in some embodiments, the C-terminal lysine of the Fc domain IgG2 heavy chain constant region provided in SEQ ID NO: 89 in Table 7 is deleted, for example to increase the homogeneity of the polypeptide when the polypeptide is produced in bacterial or mammalian cells. In some instances, a human IgG2 Fc domain variant has up to 12, 11, 10, 9, 8, 7, 6, 5 or 4 or fewer deletions in total as compared to wild-type human IgG2 sequence (see, e.g., SEQ ID NO: 162 below).

SEQ ID NO: 162:
ERKCCVECPPCPAPPVAGPSVFLFPPKPKDTLMISRTPEVTCVVVDVSH

EDPEVQFNWYVDGVEVHNAKTKPREEQFNSTFRVVSVLTVVHQDWLNGK

EYKCKVSNKGLPAPIEKTISKTKGQPREPQVYTLPPSREEMTKNQVSLT

CLVKGFYPSDIAVEWESNGQPENNYKTTPPMLDSDGSFFLYSKLTVDKS

RWQQGNVFSCSVMHEALHNHYTQKSLSLSPG

When the Fc domain variant is an IgG4 Fc domain variant, in some embodiments, such Fc domain variant comprises a S228P mutation (as designated according to Kabat, et al. (1991)). In some instances, a human IgG4 Fc domain variant has up to 12, 11, 10, 9, 8, 7, 6, 5, 4, 3, 2 or 1 mutation(s) in total as compared to wild-type human IgG4 sequence. In some embodiments, the Fc domain variant comprises a human IgG4 Fc sequence comprising one or more of S228P, E233P, F234V, L235A, and delG236 amino acid substitutions (as designated according to the EU numbering system per Kabat, et al. (1991). In some embodiments, the Fc domain variant comprises a human IgG4 Fc sequence comprising one or more of S228P, E233P, F234V, L235A, delG236, and N297A amino acid substitutions (as designated according to the EU numbering system per Kabat, et al. (1991).

In some embodiments, the Fc domain variant includes at least one of the mutations L234A, L235A, G237A or N297A of an IgG1 Fc region or at least one of the mutations A330S, P331S or N297A of an IgG2 Fc region. In some embodiments, the Fc domain variant includes at least two of the mutations L234A, L235A, G237A or N297A of an IgG1 Fc region or at least two of the mutations A330S, P331S or N297A of an IgG2 Fc region. In some embodiments, the Fc domain variant includes at least three of the mutations L234A, L235A, G237A or N297A of an IgG1 Fc region or consists of the mutations A330S, P331S and N297A of an IgG2 Fc region. In some embodiments, the Fc domain variant consists of the mutations L234A, L235A, G237A and N297A.

In some embodiments, the Fc domain variant exhibits reduced binding to an Fc receptor of the subject compared to the wild-type human IgG Fc region. In some embodiments, the Fc domain variant exhibits ablated binding to an Fc receptor of the subject compared to the wild-type human IgG Fc region. In some embodiments, the Fc domain variant exhibits a reduction of phagocytosis compared to the wild-type human IgG Fc region. In some embodiments, the Fc domain variant exhibits ablated phagocytosis compared to the wild-type human IgG Fc region.

SEQ ID NO: 88 and SEQ ID NO: 89 provide amino acid sequences of Fc domain IgG1 and IgG2 heavy chain constant regions. In some embodiments, an Fc domain variant is any variant of SEQ ID NOs: 90-95 as shown in Table 7.

TABLE 7

Amino Acid Sequences of Fc Domain Variants

| SEQ ID NO: | AMINO ACID SEQUENCE |
|---|---|
| 88 | EPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNG KEYKCKVSNKALPAPIEKTISKAKGQPREPQVYTLPPSREEMTKNQVSLTCL VKGFYPSDIAVEWESNGQPENNYKTTPPVLDSDGSFFLYSKLTVDKSRWQQ GNVFSCSVMHEALHNHYTQKSLSLSPGK |
| 89 | STKGPSVFPLAPCSRSTSESTAALGCLVKDYFPEPVTVSWNSGALTSGVHTF PAVLQSSGLYSLSSVVTVPSSSLGTQTYTCNVDHKPSNTKVDKTVERKCCV ECPPCPAPPVAGPSVFLFPPKPKDTLMISRTPEVTCVVVDVSHEDPEVQFNW YVDGVEVHNAKTKPREEQFNSTFRVVSVLTVVHQDWLNGKEYKCKVSNK GLPAPIEKTISKTKGQPREPQVYTLPPSREEMTKNQVSLTCLVKGFYPSDIAV EWESNGQPENNYKTTPPMLDSDGSFFLYSKLTVDKSRWQQGNVFSCSVMH EALHNHYTQKSLSLSPGK |
| 90 | DKTHTCPPCPAPEAAGAPSVFLFPPKPKDTLMISRTPEVTCVVVDVSHEDPE VKFNWYVDGVEVHNAKTKPREEQYASTYRVVSVLTVLHQDWLNGKEYK CKVSNKALPAPIEKTISKAKGQPREPQVYTLPPSREEMTKNQVSLTCLVKGF YPSDIAVEWESNGQPENNYKTTPPVLDSDGSFFLYSKLTVDKSRWQQGNVF SCSVMHEALHNHYTQKSLSLSPGK |
| 91 | DKTHTCPPCPAPEAAGAPSVFLFPPKPKDTLMISRTPEVTCVVVDVSHEDPE VKFNWYVDGVEVHNAKTKPREEQYASTYRVVSVLTVLHQDWLNGKEYK CKVSNKALPAPIEKTISKAKGQPREPQVYTLPPSREEMTKNQVSLTCLVKGF YPSDIAVEWESNGQPENNYKTTPPVLDSDGSFFLYSKLTVDKSRWQQGNVF SCSVMHEALHNHYTQKSLSLSPG |
| 92 | VECPPCPAPPVAGPSVFLFPPKPKDTLMISRTPEVTCVVVDVSHEDPEVQFN WYVDGVEVHNAKTKPREEQFASTFRVVSVLTVVHQDWLNGKEYKCKVSN KGLPSSIEKTISKTKGQPREPQVYTLPPSREEMTKNQVSLTCLVKGFYPSDIA VEWESNGQPENNYKTTPPMLDSDGSFFLYSKLTVDKSRWQQGNVFSCSVM HEALHNHYTQKSLSLSPGK |
| 93 | VECPPCPAPPVAGPSVFLFPPKPKDTLMISRTPEVTCVVVDVSHEDPEVQFN WYVDGVEVHNAKTKPREEQFASTFRVVSVLTVVHQDWLNGKEYKCKVSN KGLPSSIEKTISKTKGQPREPQVYTLPPSREEMTKNQVSLTCLVKGFYPSDIA VEWESNGQPENNYKTTPPMLDSDGSFFLYSKLTVDKSRWQQGNVFSCSVM HEALHNHYTQKSLSLSPG |
| 94 | ERKSSVECPPCPAPPVAGPSVFLFPPKPKDTLMISRTPEVTCVVVDVSHEDP EVQFNWYVDGVEVHNAKTKPREEQFASTFRVVSVLTVVHQDWLNGKEYK CKVSNKGLPSSIEKTISKTKGQPREPQVYTLPPSREEMTKNQVSLTCLVKGF YPSDIAVEWESNGQPENNYKTTPPMLDSDGSFFLYSKLTVDKSRWQQGNV FSCSVMHEALHNHYTQKSLSLSPGK |
| 95 | ERKSSVECPPCPAPPVAGPSVFLFPPKPKDTLMISRTPEVTCVVVDVSHEDP EVQFNWYVDGVEVHNAKTKPREEQFASTFRVVSVLTVVHQDWLNGKEYK CKVSNKGLPSSIEKTISKTKGQPREPQVYTLPPSREEMTKNQVSLTCLVKGF YPSDIAVEWESNGQPENNYKTTPPMLDSDGSFFLYSKLTVDKSRWQQGNV FSCSVMHEALHNHYTQKSLSLSPG |

Antibody-dependent cell-mediated cytotoxicity, which is also referred to herein as ADCC, refers to a form of cytotoxicity in which secreted Ig bound onto Fc receptors (FcRs) present on certain cytotoxic cells (e.g., Natural Killer (NK) cells and neutrophils) enabling these cytotoxic effector cells to bind specifically to an antigen-bearing target cell and subsequently kill the target cell. Antibody-dependent cell-mediated phagocytosis, which is also referred to herein as ADCP, refers to a form of cytotoxicity in which secreted Ig bound onto Fc receptors (FcRs) present on certain phagocytic cells (e.g., macrophages) enabling these phagocytic effector cells to bind specifically to an antigen-bearing target cell and subsequently engulf and digest the target cell. Ligand-specific high-affinity IgG antibodies directed to the surface of target cells can stimulate the cytotoxic or phagocytic cells and can be used for such killing. In some embodiments, polypeptide constructs comprising an Fc domain variant or Fc domain dimer variant as described herein exhibit reduced ADCC or ADCP as compared to a polypeptide construct comprising a wild-type Fc region. In some embodiments, polypeptide constructs comprising an Fc domain variant or Fc domain dimer variant as described herein exhibit at least a 5%, 10%, 15%, 20%, 30%, 40%, 50%, 60%, 70%, 80%, 90% or greater reduction in ADCC or ADCP compared to a polypeptide construct comprising a wild-type Fc region. In some embodiments, polypeptide constructs comprising an Fc domain variant or Fc domain dimer variant as described herein exhibit ablated ADCC or ADCP as compared to a polypeptide construct comprising a wild-type Fc region.

Complement-directed cytotoxicity, which is also referred to herein as CDC, refers to a form of cytotoxicity in which the complement cascade is activated by the complement component C1q binding to antibody Fc domains. In some embodiments, polypeptide constructs comprising an Fc domain variant or Fc domain dimer variant as described herein exhibit at least a 5%, 10%, 15%, 20%, 30%, 40%, 50%, 60%, 70%, 80%, 90% or greater reduction in C1q binding compared to a polypeptide construct comprising a wild-type Fc region. In some cases, polypeptide constructs comprising an Fc domain variant or Fc domain dimer variant as described herein exhibit reduced CDC as compared to a polypeptide construct comprising a wild-type Fc region. In some embodiments, polypeptide constructs comprising an Fc domain variant or Fc domain dimer variant as described herein exhibit at least a 5%, 10%, 15%, 20%, 30%, 40%, 50%, 60%, 70%, 80%, 90% or greater reduction in CDC compared to a polypeptide construct comprising a wild-type Fc region. In some cases, polypeptide constructs comprising an Fc domain variant or Fc domain dimer variant as described herein exhibit negligible CDC as compared to a polypeptide construct comprising a wild-type Fc region.

Fc domain variants or Fc domain dimer variants herein include those that exhibit reduced binding to an Fcγ receptor compared to the wild-type human IgG Fc region. For example, in some embodiments, an Fc domain variant or Fc domain dimer variant exhibits binding to an Fcγ receptor that is less than the binding exhibited by a wild-type human IgG Fc region to an Fcγ receptor, as described in the Examples. In some instances, an Fc domain variant or Fc domain dimer variant has reduced binding to an Fcγ receptor by a factor of 10%, 20% 30%, 40%, 50%, 60%, 70%, 80%, 90%, 95%, 96%, 97%, 98%, 99% or 100% (fully ablated effector function). In some embodiments, the reduced binding is for any one or more Fcγ receptor, e.g., CD16a, CD32a, CD32b, CD32c, or CD64.

In some instances, the Fc domain variants or Fc domain dimer variants disclosed herein exhibit a reduction of phagocytosis compared to its wild-type human IgG Fc region. Such Fc domain variants or Fc domain dimer variants exhibit a reduction in phagocytosis compared to its wild-type human IgG Fc region, wherein the reduction of phagocytosis activity is e.g., by a factor of 10%, 20%, 30%, 40%, 50%, 60%, 70%, 80%, 90%, 95%, 96%, 97%, 98%, 99% or 100%. In some instances, an Fc domain variant or Fc domain dimer variant exhibits ablated phagocytosis compared to its wild-type human IgG Fc region.

In some embodiments, the Fc domain variants or Fc domain dimer variants disclosed herein are coupled to one or more fusion partners. In some cases the fusion partner is a therapeutic moiety. In some cases, the fusion partner is selected to enable targeting of an expressed protein, purification, screening, display, and the like. In some embodiments, the fusion partner also affects the degree of binding to Fc receptors or the degree of phagocytosis reduction. As described herein, in some embodiments, when an Fc domain variant or Fc domain dimer variant is coupled to a fusion partner, it forms a polypeptide construct as described below.

In some embodiments, fusion partners are linked to the Fc domain variant or Fc domain dimer variant sequence via a linker sequence. In some embodiments, the linker sequence generally comprises a small number of amino acids, such as less than ten amino acids, although longer linkers are also utilized. In some cases, the linker has a length less than 10, 9, 8, 7, 6, or 5 amino acids or shorter. In some cases, the linker has a length of at least 10, 11, 12, 13, 14, 15, 20, 25, 30, or 35 amino acids or longer. Optionally, in some embodiments, a cleavable linker is employed.

In some embodiments, a fusion partner is a targeting or signal sequence that directs an Fc domain variant or Fc domain dimer variant protein and any associated fusion partners to a desired cellular location or to the extracellular media. In some embodiments, certain signaling sequences target a protein to be either secreted into the growth media, or into the periplasmic space, located between the inner and outer membrane of the cell. In some embodiments, a fusion partner is a sequence that encodes a peptide or protein that enables purification or screening. Such fusion partners include, but are not limited to, polyhistidine tags (His-tags) (for example His6 (SEQ ID NO: 223) and His10 (SEQ ID NO: 224)) or other tags for use with Immobilized Metal Affinity Chromatography (IMAC) systems (e.g., Ni+2 affinity columns), GST fusions, MBP fusions, Strep-tag, the BSP biotinylation target sequence of the bacterial enzyme BirA, and epitope tags which are targeted by antibodies (for example c-myc tags, flag-tags, and the like).

In some embodiments, such tags are useful for purification, for screening, or both. For example, in some embodiments, an Fc domain variant or Fc domain dimer variant is purified using a His-tag by immobilizing it to a Ni+2 affinity column, and then after purification the same His-tag is used to immobilize the antibody to a Ni+2 coated plate to perform an ELISA or other binding assay as described elsewhere herein. In some embodiments, a fusion partner enables the use of a selection method to screen Fc domain variants or Fc domain dimer variants as described herein.

Various fusion partners that enable a variety of selection methods are available. For example, by fusing the members of an Fc domain variant or Fc domain dimer variant library to the gene III protein, phage display can be employed. In some embodiments, fusion partners Fc domain variants or Fc domain dimer variants to be labeled. Alternatively, in some embodiments, a fusion partner binds to a specific sequence on the expression vector, enabling the fusion partner and associated Fc domain variant or Fc domain dimer variant to be linked covalently or noncovalently with the nucleic acid that encodes them.

In some embodiments, when a fusion partner is a therapeutic moiety, the therapeutic moiety is, e.g., a peptide, a protein, an antibody, a siRNA, or a small molecule. Non-limiting examples of therapeutic antibodies that are coupled to the Fc domain variants or Fc domain dimer variants of the present disclosure include, but are not limited to antibodies that recognize CD47. Non-limiting examples of therapeutic polypeptides that are coupled to the Fc domain variants or Fc domain dimer variants of the present disclosure include, but are not limited to, CD47 binding polypeptides, including SIRPα polypeptides. In such instances, the CD47 binding polypeptide is attached or fused to an Fc domain variant or Fc domain dimer variant of the disclosure. Examples of CD47 binding polypeptides include, but are not limited to, anti-CD47 antibodies or fragments thereof, and ligands of CD47 such as SIRPα or a fragment thereof. Additional examples of CD47 binding polypeptides include, but are not limited to naturally-occurring forms of SIRPα as well as mutants thereof.

In some embodiments, disclosed herein is a polypeptide comprising an Fc domain dimer variant, wherein the Fc domain dimer variant comprises two Fc domain variants, wherein each Fc domain variant independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A. In some embodiments, the Fc domain variants are identical (i.e., homodimer). In some embodiments, the Fc domain variants are different (i.e., heterodimer). In some embodiments, at least one of the Fc domain variant in an Fc domain dimer is a human IgG1 Fc region consisting of mutations L234A, L235A, G237A, and N297A. In some embodiments, at least one of the Fc domain variants in an Fc domain dimer is a human IgG2 Fc region consisting of mutations A330S, P331S and N297A. In some embodiments, the Fc domain dimer variant exhibits ablated or reduced binding to an Fcγ receptor compared to the wild-type version of the human IgG Fc region. In some embodiments, the Fc domain dimer variant exhibits ablated or reduced binding to CD16a, CD32a, CD32b, CD32c, and CD64 Fcγ receptors compared to the wild-type version of the human IgG Fc region. In some embodiments, the Fc domain dimer variant exhibits ablated or reduced binding to C1q compared to the wild-type version of the human IgG Fc fusion. In some embodiments, at least one of the Fc domain variants in an Fc domain dimer variant is a human IgG4 Fc region comprising mutations S228P, E233P, F234V, L235A, delG236, and N297A. In some embodiments, the Fc domain dimer variant exhibits ablated or reduced binding to an Fcγ receptor compared to the wild-type human IgG4 Fc region. In some embodiments, the Fc domain dimer variant exhibits ablated or reduced binding to CD16a and CD32b Fcγ receptors compared to the wild-type version of its human IgG4 Fc region. In some embodiments, the Fc domain dimer variant binds to an Fcγ receptor with a KD greater than about $5 \times 10^{-6}$ M.

In some embodiments, the Fc domain dimer variant further comprises a CD47 binding polypeptide. In some embodiments, the Fc domain dimer variant exhibits ablated or reduced binding to an Fcγ receptor compared to a wild-type version of a human IgG Fc region. In some embodiments, the CD47 binding polypeptide does not cause acute anemia in rodents and non-human primates. In some embodiments, the CD47 binding polypeptide does not cause acute anemia in humans.

In some embodiments, the CD47 binding polypeptide is a signal-regulatory protein α (SIRP-α) polypeptide or a fragment thereof. In some embodiments, the SIRPα polypeptide comprises a SIRPα D1 domain variant comprising the amino acid sequence, EEELQX$_1$IQPDKSVLVAAGETATLRCTX$_2$TSLX$_3$PVGP-IQWFRGAGPGRX$_4$LIYNQX$_5$EGX$_6$ FPRVTTVSDX$_7$TKRNNMDFSIRIGX$_8$ITPADAGTYYC-X$_9$KFRKGSPDDVEFKSGAGTELSV RAKPS (SEQ ID NO: 221), wherein X$_1$ is V or I; X$_2$ is A or I; X$_3$ is I or F; X$_4$ is E or V; X$_5$ is K or R; X$_6$ is H or P; X$_7$ is L or T; X$_8$ is any amino acid other than N; and X$_9$ is V or I. In some embodiments, the SIRPα polypeptide comprises a SIRPα D1 domain variant wherein X$_1$ is V or I; X$_2$ is A or I; X$_3$ is I or F; X$_4$ is E; X$_5$ is K or R; X$_6$ is H or P; X$_7$ is L or T; X$_8$ is not N; and X$_9$ is V.

In some embodiments, disclosed herein, is a polypeptide comprising: a SIRPα D1 domain variant, wherein the SIRPα D1 domain variant is a non-naturally occurring high affinity SIRPα D1 domain, wherein the SIRPα D1 domain variant binds to human CD47 with an affinity that is at least 10-fold greater than the affinity of a naturally occurring D1 domain; and an Fc domain variant, wherein the Fc domain variant is linked to a second polypeptide comprising a second Fc domain variant to form an Fc domain dimer variant, wherein the Fc domain dimer variant has ablated or reduced effector function. In some embodiments, the non-naturally occurring high affinity SIRPα D1 domain comprises an amino acid mutation at residue 80.

In some embodiments, disclosed herein, is a SIRPα D1 domain variant, wherein the SIRPα D1 domain variant binds CD47 from a first species with a K$_D$ less than 250 nM; and wherein the SIRPα D1 domain variant binds CD47 from a second species with a K$_D$ less than 250 nM; and the K$_D$ for CD47 from the first species and the K$_D$ for CD47 from the second species are within 100 fold of each other; wherein the first species and the second species are selected from the group consisting of: human, rodent, and non-human primate. In some embodiments, the SIRPα D1 domain variant binds CD47 from at least 3 different species. In some embodiments, the non-human primate is cynomolgus monkey.

In some embodiments, disclosed herein, is a polypeptide comprising (a) a SIRPα D1 domain that binds human CD47 with a KD less than 250 nM; and (b) an Fc domain or variant thereof linked to the N-terminus or the C-terminus of the SIRPα D1 domain, wherein the polypeptide does not cause acute anemia in rodents and non-human primates. In some embodiments, the polypeptide is a non-naturally occurring variant of a human SIRP-α. In some embodiments, administration of the polypeptide in vivo results in hemoglobin reduction by less than 50% during the first week after administration. In some embodiments, administration of the polypeptide in humans results in hemoglobin reduction by less than 50% during the first week after administration. In some embodiments, the polypeptide further comprises at least one Fc domain dimer variant, wherein the Fc domain dimer variant comprises an Fc domain variant selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A. In some embodiments, the Fc domain variant is a human IgG1 Fc region consisting of mutations L234A, L235A, G237A, and N297A. In some embodiments, the Fc domain variant is a human IgG2 Fc region consisting of mutations A330S, P331S and N297A.

The SIRPα constructs of the disclosure include a SIRPα domain or variant thereof that has its C-terminus joined to the N-terminus of an Fc domain or variant thereof by way of a linker using conventional genetic or chemical means, e.g., chemical conjugation. In some embodiments, a linker (e.g., a spacer) is inserted between the polypeptide and the Fc domain or variant thereof. In some embodiments, a polypeptide of the disclosure including a SIRPα D1 domain variant is fused to an Fc domain variant that is incapable of forming a dimer. In some embodiments, a polypeptide of the disclosure is fused to an Fc domain or variant thereof that is capable of forming a dimer, e.g., a heterodimer, with another Fc domain or variant thereof. In some embodiments, a polypeptide of the invention is fused to an Fc domain or variant thereof and this fusion protein forms a homodimer. In some embodiments, a polypeptide of the disclosure is fused to a first Fc domain or variant thereof and a different protein or peptide (e.g., an antibody variable region) is fused to a second Fc domain or variant thereof. In some embodiments, a SIRPα D1 domain or variant thereof is joined to a first Fc domain or variant thereof and a therapeutic protein (e.g., a cytokine, an interleukin, an antigen, a steroid, an anti-inflammatory agent, or an immunomodulatory agent) is joined to a second Fc domain or variant thereof. In some embodiments, the first and second Fc domains or variants thereof form a heterodimer.

Without the limiting the foregoing, in some embodiments, a SIRPα D1 domain variant polypeptide (e.g., any of the variants described in Tables 2, 5, and 6) is fused to an Fc polypeptide or Fc variant polypeptide, such as an Fc domain or variant thereof. Examples of polypeptides comprising a SIRPα D1 domain variant polypeptide and a fused Fc domain variant polypeptide include, but are not limited to, SEQ ID NOS: 96-137, 214, and 216 shown in Table 8.

TABLE 8

Polypeptides Comprising SIRPα D1 Domain Variants Fused to Fc Domain Variants

| SEQ ID NO: | Amino Acid Sequence |
|---|---|
| 96 | EEELQIIQPDKSVLVAAGETATLRCTITSLFPVGPIQWFRGAGPGRVLIYNQR<br>QGPFPRVTTVSDTTKRNNMDFSIRIGNITPADAGTYYCIKFRKGSPDDVEFKS<br>GAGTELSVRAKPSDKTHTCPPCPAPEAAGAPSVFLFPPKPKDTLMISRTPEVT<br>CVVVDVSHEDPEVKFNWYVDGVEVHNAKTKPREEQYASTYRVVSVLTVL<br>HQDWLNGKEYKCKVSNKALPAPIEKTISKAKGQPREPQVYTLPPSREEMTK<br>NQVSLTCLVKGFYPSDIAVEWESNGQPENNYKTTPPVLDSDGSFFLYSKLTV<br>DKSRWQQGNVFSCSVMHEALHNHYTQKSLSLSPGK |
| 97 | EEELQVIQPDKSVLVAAGETATLRCTATSLFPVGPIQWFRGAGPGRELIYNQ<br>RQGPFPRVTTVSDLTKRNNMDFSIRIGNITPADAGTYYCVKFRKGSPDDVEF<br>KSGAGTELSVRAKPSDKTHTCPPCPAPEAAGAPSVFLFPPKPKDTLMISRTPE<br>VTCVVVDVSHEDPEVKFNWYVDGVEVHNAKTKPREEQYASTYRVVSVLT<br>VLHQDWLNGKEYKCKVSNKALPAPIEKTISKAKGQPREPQVYTLPPSREEM<br>TKNQVSLTCLVKGFYPSDIAVEWESNGQPENNYKTTPPVLDSDGSFFLYSKL<br>TVDKSRWQQGNVFSCSVMHEALHNHYTQKSLSLSPGK |
| 98 | EEELQIIQPDKSVLVAAGETATLRCTITSLFPVGPIQWFRGAGPGRVLIYNQR<br>QGPFPRVTTVSDTTKRNNMDFSIRIGAITPADAGTYYCIKFRKGSPDDVEFKS<br>GAGTELSVRAKPSDKTHTCPPCPAPEAAGAPSVFLFPPKPKDTLMISRTPEVT<br>CVVVDVSHEDPEVKFNWYVDGVEVHNAKTKPREEQYASTYRVVSVLTVL<br>HQDWLNGKEYKCKVSNKALPAPIEKTISKAKGQPREPQVYTLPPSREEMTK<br>NQVSLTCLVKGFYPSDIAVEWESNGQPENNYKTTPPVLDSDGSFFLYSKLTV<br>DKSRWQQGNVFSCSVMHEALHNHYTQKSLSLSPGK |
| 99 | EEELQVIQPDKSVLVAAGETATLRCTATSLFPVGPIQWFRGAGPGRELIYNQ<br>RQGPFPRVTTVSDLTKRNNMDFSIRIGAITPADAGTYYCVKFRKGSPDDVEF<br>KSGAGTELSVRAKPSDKTHTCPPCPAPEAAGAPSVFLFPPKPKDTLMISRTPE<br>VTCVVVDVSHEDPEVKFNWYVDGVEVHNAKTKPREEQYASTYRVVSVLT<br>VLHQDWLNGKEYKCKVSNKALPAPIEKTISKAKGQPREPQVYTLPPSREEM<br>TKNQVSLTCLVKGFYPSDIAVEWESNGQPENNYKTTPPVLDSDGSFFLYSKL<br>TVDKSRWQQGNVFSCSVMHEALHNHYTQKSLSLSPGK |
| 100 | EEELQVIQPDKSVLVAAGETATLRCTATSLFPVGPIQWFRGAGPGRELIYNQ<br>REGPFPRVTTVSDLTKRNNMDFSIRIGAITPADAGTYYCVKFRKGSPDDVEF<br>KSGAGTELSVRAKPSDKTHTCPPCPAPEAAGAPSVFLFPPKPKDTLMISRTPE<br>VTCVVVDVSHEDPEVKFNWYVDGVEVHNAKTKPREEQYASTYRVVSVLT<br>VLHQDWLNGKEYKCKVSNKALPAPIEKTISKAKGQPREPQVYTLPPSREEM<br>TKNQVSLTCLVKGFYPSDIAVEWESNGQPENNYKTTPPVLDSDGSFFLYSKL<br>TVDKSRWQQGNVFSCSVMHEALHNHYTQKSLSLSPGK |
| 101 | EEELQVIQPDKSVLVAAGETATLRCTITSLFPVGPIQWFRGAGPGRELIYNQR<br>EGPFPRVTTVSDLTKRNNMDFSIRIGAITPADAGTYYCVKFRKGSPDDVEFK<br>SGAGTELSVRAKPSDKTHTCPPCPAPEAAGAPSVFLFPPKPKDTLMISRTPEV<br>TCVVVDVSHEDPEVKFNWYVDGVEVHNAKTKPREEQYASTYRVVSVLTVL<br>HQDWLNGKEYKCKVSNKALPAPIEKTISKAKGQPREPQVYTLPPSREEMTK<br>NQVSLTCLVKGFYPSDIAVEWESNGQPENNYKTTPPVLDSDGSFFLYSKLTV<br>DKSRWQQGNVFSCSVMHEALHNHYTQKSLSLSPGK |
| 102 | EEELQIIQPDKSVLVAAGETATLRCTITSLFPVGPIQWFRGAGPGRELIYNQRE<br>GPFPRVTTVSDLTKRNNMDFSIRIGAITPADAGTYYCVKFRKGSPDDVEFKS<br>GAGTELSVRAKPSDKTHTCPPCPAPEAAGAPSVFLFPPKPKDTLMISRTPEVT<br>CVVVDVSHEDPEVKFNWYVDGVEVHNAKTKPREEQYASTYRVVSVLTVL<br>HQDWLNGKEYKCKVSNKALPAPIEKTISKAKGQPREPQVYTLPPSREEMTK<br>NQVSLTCLVKGFYPSDIAVEWESNGQPENNYKTTPPVLDSDGSFFLYSKLTV<br>DKSRWQQGNVFSCSVMHEALHNHYTQKSLSLSPGK |
| 103 | EEELQVIQPDKSVLVAAGETATLRCTITSLFPVGPIQWFRGAGPGRELIYNQR<br>EGPFPRVTTVSDTTKRNNMDFSIRIGAITPADAGTYYCVKFRKGSPDDVEFK<br>SGAGTELSVRAKPSDKTHTCPPCPAPEAAGAPSVFLFPPKPKDTLMISRTPEV<br>TCVVVDVSHEDPEVKFNWYVDGVEVHNAKTKPREEQYASTYRVVSVLTVL<br>HQDWLNGKEYKCKVSNKALPAPIEKTISKAKGQPREPQVYTLPPSREEMTK<br>NQVSLTCLVKGFYPSDIAVEWESNGQPENNYKTTPPVLDSDGSFFLYSKLTV<br>DKSRWQQGNVFSCSVMHEALHNHYTQKSLSLSPGK |
| 104 | EEELQIIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKS<br>GAGTELSVRAKPSDKTHTCPPCPAPEAAGAPSVFLFPPKPKDTLMISRTPEVT<br>CVVVDVSHEDPEVKFNWYVDGVEVHNAKTKPREEQYASTYRVVSVLTVL<br>HQDWLNGKEYKCKVSNKALPAPIEKTISKAKGQPREPQVYTLPPSREEMTK<br>NQVSLTCLVKGFYPSDIAVEWESNGQPENNYKTTPPVLDSDGSFFLYSKLTV<br>DKSRWQQGNVFSCSVMHEALHNHYTQKSLSLSPGK |
| 105 | EEELQIIQPDKSVLVAAGETATLRCTITSLFPVGPIQWFRGAGPGRVLIYNQR<br>QGPFPRVTTVSDTTKRNNMDFSIRIGNITPADAGTYYCIKFRKGSPDDVEFKS<br>GAGTELSVRAKPSVECPPCPAPPVAGPSVFLFPPKPKDTLMISRTPEVTCVVV<br>DVSHEDPEVQFNWYVDGVEVHNAKTKPREEQFASTFRVVSVLTVVHQDWL |

TABLE 8-continued

Polypeptides Comprising SIRPα D1 Domain Variants Fused to Fc Domain Variants

| SEQ ID NO: | Amino Acid Sequence |
|---|---|
|  | NGKEYKCKVSNKGLPSSIEKTISKTKGQPREPQVYTLPPSREEMTKNQVSLT
CLVKGFYPSDIAVEWESNGQPENNYKTTPPMLDSDGSFFLYSKLTVDKSRW
QQGNVFSCSVMHEALHNHYTQKSLSLSPGK |
| 106 | EEELQVIQPDKSVLVAAGETATLRCTATSLFPVGPIQWFRGAGPGRELIYNQ
RQGPFPRVTTVSDLTKRNNMDFSIRIGNITPADAGTYYCVKFRKGSPDDVEF
KSGAGTELSVRAKPSVECPPCPAPPVAGPSVFLFPPKPKDTLMISRTPEVTCV
VVDVSHEDPEVQFNWYVDGVEVHNAKTKPREEQFASTFRVVSVLTVVHQD
WLNGKEYKCKVSNKGLPSSIEKTISKTKGQPREPQVYTLPPSREEMTKNQVS
LTCLVKGFYPSDIAVEWESNGQPENNYKTTPPMLDSDGSFFLYSKLTVDKSR
WQQGNVFSCSVMHEALHNHYTQKSLSLSPGK |
| 107 | EEELQIIQPDKSVLVAAGETATLRCTITSLFPVGPIQWFRGAGPGRVLIYNQR
QGPFPRVTTVSDTTKRNNMDFSIRIGAITPADAGTYYCIKFRKGSPDDVEFKS
GAGTELSVRAKPSVECPPCPAPPVAGPSVFLFPPKPKDTLMISRTPEVTCVVV
DVSHEDPEVQFNWYVDGVEVHNAKTKPREEQFASTFRVVSVLTVVHQDWL
NGKEYKCKVSNKGLPSSIEKTISKTKGQPREPQVYTLPPSREEMTKNQVSLT
CLVKGFYPSDIAVEWESNGQPENNYKTTPPMLDSDGSFFLYSKLTVDKSRW
QQGNVFSCSVMHEALHNHYTQKSLSLSPGK |
| 108 | EEELQVIQPDKSVLVAAGETATLRCTATSLFPVGPIQWFRGAGPGRELIYNQ
RQGPFPRVTTVSDLTKRNNMDFSIRIGAITPADAGTYYCVKFRKGSPDDVEF
KSGAGTELSVRAKPSVECPPCPAPPVAGPSVFLFPPKPKDTLMISRTPEVTCV
VVDVSHEDPEVQFNWYVDGVEVHNAKTKPREEQFASTFRVVSVLTVVHQD
WLNGKEYKCKVSNKGLPSSIEKTISKTKGQPREPQVYTLPPSREEMTKNQVS
LTCLVKGFYPSDIAVEWESNGQPENNYKTTPPMLDSDGSFFLYSKLTVDKSR
WQQGNVFSCSVMHEALHNHYTQKSLSLSPGK |
| 109 | EEELQVIQPDKSVLVAAGETATLRCTATSLFPVGPIQWFRGAGPGRELIYNQ
REGPFPRVTTVSDLTKRNNMDFSIRIGAITPADAGTYYCVKFRKGSPDDVEF
KSGAGTELSVRAKPSVECPPCPAPPVAGPSVFLFPPKPKDTLMISRTPEVTCV
VVDVSHEDPEVQFNWYVDGVEVHNAKTKPREEQFASTFRVVSVLTVVHQD
WLNGKEYKCKVSNKGLPSSIEKTISKTKGQPREPQVYTLPPSREEMTKNQVS
LTCLVKGFYPSDIAVEWESNGQPENNYKTTPPMLDSDGSFFLYSKLTVDKSR
WQQGNVFSCSVMHEALHNHYTQKSLSLSPGK |
| 110 | EEELQVIQPDKSVLVAAGETATLRCTITSLFPVGPIQWFRGAGPGRELIYNQR
EGPFPRVTTVSDLTKRNNMDFSIRIGAITPADAGTYYCVKFRKGSPDDVEFK
SGAGTELSVRAKPSVECPPCPAPPVAGPSVFLFPPKPKDTLMISRTPEVTCVV
VDVSHEDPEVQFNWYVDGVEVHNAKTKPREEQFASTFRVVSVLTVVHQD
WLNGKEYKCKVSNKGLPSSIEKTISKTKGQPREPQVYTLPPSREEMTKNQVS
LTCLVKGFYPSDIAVEWESNGQPENNYKTTPPMLDSDGSFFLYSKLTVDKSR
WQQGNVFSCSVMHEALHNHYTQKSLSLSPGK |
| 111 | EEELQIIQPDKSVLVAAGETATLRCTITSLFPVGPIQWFRGAGPGRELIYNQRE
GPFPRVTTVSDLTKRNNMDFSIRIGAITPADAGTYYCVKFRKGSPDDVEFKS
GAGTELSVRAKPSVECPPCPAPPVAGPSVFLFPPKPKDTLMISRTPEVTCVVV
DVSHEDPEVQFNWYVDGVEVHNAKTKPREEQFASTFRVVSVLTVVHQDWL
NGKEYKCKVSNKGLPSSIEKTISKTKGQPREPQVYTLPPSREEMTKNQVSLT
CLVKGFYPSDIAVEWESNGQPENNYKTTPPMLDSDGSFFLYSKLTVDKSRW
QQGNVFSCSVMHEALHNHYTQKSLSLSPGK |
| 112 | EEELQVIQPDKSVLVAAGETATLRCTITSLFPVGPIQWFRGAGPGRELIYNQR
EGPFPRVTTVSDTTKRNNMDFSIRIGAITPADAGTYYCVKFRKGSPDDVEFK
SGAGTELSVRAKPSVECPPCPAPPVAGPSVFLFPPKPKDTLMISRTPEVTCVV
VDVSHEDPEVQFNWYVDGVEVHNAKTKPREEQFASTFRVVSVLTVVHQD
WLNGKEYKCKVSNKGLPSSIEKTISKTKGQPREPQVYTLPPSREEMTKNQVS
LTCLVKGFYPSDIAVEWESNGQPENNYKTTPPMLDSDGSFFLYSKLTVDKSR
WQQGNVFSCSVMHEALHNHYTQKSLSLSPGK |
| 113 | EEELQIIQPDKSVLVAAGETATLRCTITSLFPVGPIQWFRGAGPGRELIYNQRE
GPFPRVTTVSDTTKRNNMDFSIRIGAITPADAGTYYCVKFRKGSPDDVEFKS
GAGTELSVRAKPSVECPPCPAPPVAGPSVFLFPPKPKDTLMISRTPEVTCVVV
DVSHEDPEVQFNWYVDGVEVHNAKTKPREEQFASTFRVVSVLTVVHQDWL
NGKEYKCKVSNKGLPSSIEKTISKTKGQPREPQVYTLPPSREEMTKNQVSLT
CLVKGFYPSDIAVEWESNGQPENNYKTTPPMLDSDGSFFLYSKLTVDKSRW
QQGNVFSCSVMHEALHNHYTQKSLSLSPGK |
| 114 | EEELQIIQPDKSVLVAAGETATLRCTITSLFPVGPIQWFRGAGPGRVLIYNQR
QGPFPRVTTVSDTTKRNNMDFSIRIGNITPADAGTYYCIKFRKGSPDDVEFKS
GAGTELSVRAKPSERKSSVECPPCPAPPVAGPSVFLFPPKPKDTLMISRTPEV
TCVVVDVSHEDPEVQFNWYVDGVEVHNAKTKPREEQFASTFRVVSVLTVV
HQDWLNGKEYKCKVSNKGLPSSIEKTISKTKGQPREPQVYTLPPSREEMTKN
QVSLTCLVKGFYPSDIAVEWESNGQPENNYKTTPPMLDSDGSFFLYSKLTVD
KSRWQQGNVFSCSVMHEALHNHYTQKSLSLSPGK |

TABLE 8-continued

Polypeptides Comprising SIRPα D1 Domain Variants Fused to Fc Domain Variants

| SEQ ID NO: | Amino Acid Sequence |
|---|---|
| 115 | EEELQVIQPDKSVLVAAGETATLRCTATSLFPVGPIQWFRGAGPGRELIYNQ<br>RQGPFPRVTTVSDLTKRNNMDFSIRIGNITPADAGTYYCVKFRKGSPDDVEF<br>KSGAGTELSVRAKPSERKSSVECPPCPAPPVAGPSVFLFPPKPKDTLMISRTP<br>EVTCVVVDVSHEDPEVQFNWYVDGVEVHNAKTKPREEQFASTFRVVSVLT<br>VVHQDWLNGKEYKCKVSNKGLPSSIEKTISKTKGQPREPQVYTLPPSREEMT<br>KNQVSLTCLVKGFYPSDIAVEWESNGQPENNYKTTPPMLDSDGSFFLYSKLT<br>VDKSRWQQGNVFSCSVMHEALHNHYTQKSLSLSPGK |
| 116 | EEELQIIQPDKSVLVAAGETATLRCTITSLFPVGPIQWFRGAGPGRVLIYNQR<br>QGPFPRVTTVSDTTKRNNMDFSIRIGAITPADAGTYYCIKFRKGSPDDVEFKS<br>GAGTELSVRAKPSERKSSVECPPCPAPPVAGPSVFLFPPKPKDTLMISRTPEV<br>TCVVVDVSHEDPEVQFNWYVDGVEVHNAKTKPREEQFASTFRVVSVLTVV<br>HQDWLNGKEYKCKVSNKGLPSSIEKTISKTKGQPREPQVYTLPPSREEMTKN<br>QVSLTCLVKGFYPSDIAVEWESNGQPENNYKTTPPMLDSDGSFFLYSKLTVD<br>KSRWQQGNVFSCSVMHEALHNHYTQKSLSLSPGK |
| 117 | EEELQVIQPDKSVLVAAGETATLRCTATSLFPVGPIQWFRGAGPGRELIYNQ<br>RQGPFPRVTTVSDLTKRNNMDFSIRIGAITPADAGTYYCVKFRKGSPDDVEF<br>KSGAGTELSVRAKPSERKSSVECPPCPAPPVAGPSVFLFPPKPKDTLMISRTP<br>EVTCVVVDVSHEDPEVQFNWYVDGVEVHNAKTKPREEQFASTFRVVSVLT<br>VVHQDWLNGKEYKCKVSNKGLPSSIEKTISKTKGQPREPQVYTLPPSREEMT<br>KNQVSLTCLVKGFYPSDIAVEWESNGQPENNYKTTPPMLDSDGSFFLYSKLT<br>VDKSRWQQGNVFSCSVMHEALHNHYTQKSLSLSPGK |
| 118 | EEELQVIQPDKSVLVAAGETATLRCTATSLFPVGPIQWFRGAGPGRELIYNQ<br>REGPFPRVTTVSDLTKRNNMDFSIRIGAITPADAGTYYCVKFRKGSPDDVEF<br>KSGAGTELSVRAKPSERKSSVECPPCPAPPVAGPSVFLFPPKPKDTLMISRTP<br>EVTCVVVDVSHEDPEVQFNWYVDGVEVHNAKTKPREEQFASTFRVVSVLT<br>VVHQDWLNGKEYKCKVSNKGLPSSIEKTISKTKGQPREPQVYTLPPSREEMT<br>KNQVSLTCLVKGFYPSDIAVEWESNGQPENNYKTTPPMLDSDGSFFLYSKLT<br>VDKSRWQQGNVFSCSVMHEALHNHYTQKSLSLSPGK |
| 119 | EEELQVIQPDKSVLVAAGETATLRCTITSLFPVGPIQWFRGAGPGRELIYNQR<br>EGPFPRVTTVSDLTKRNNMDFSIRIGAITPADAGTYYCVKFRKGSPDDVEFK<br>SGAGTELSVRAKPSERKSSVECPPCPAPPVAGPSVFLFPPKPKDTLMISRTPE<br>VTCVVVDVSHEDPEVQFNWYVDGVEVHNAKTKPREEQFASTFRVVSVLTV<br>VHQDWLNGKEYKCKVSNKGLPSSIEKTISKTKGQPREPQVYTLPPSREEMTK<br>NQVSLTCLVKGFYPSDIAVEWESNGQPENNYKTTPPMLDSDGSFFLYSKLTV<br>DKSRWQQGNVFSCSVMHEALHNHYTQKSLSLSPGK |
| 120 | EEELQIIQPDKSVLVAAGETATLRCTITSLFPVGPIQWFRGAGPGRELIYNQRE<br>GPFPRVTTVSDLTKRNNMDFSIRIGAITPADAGTYYCVKFRKGSPDDVEFKS<br>GAGTELSVRAKPSERKSSVECPPCPAPPVAGPSVFLFPPKPKDTLMISRTPEV<br>TCVVVDVSHEDPEVQFNWYVDGVEVHNAKTKPREEQFASTFRVVSVLTVV<br>HQDWLNGKEYKCKVSNKGLPSSIEKTISKTKGQPREPQVYTLPPSREEMTKN<br>QVSLTCLVKGFYPSDIAVEWESNGQPENNYKTTPPMLDSDGSFFLYSKLTVD<br>KSRWQQGNVFSCSVMHEALHNHYTQKSLSLSPGK |
| 121 | EEELQVIQPDKSVLVAAGETATLRCTITSLFPVGPIQWFRGAGPGRELIYNQR<br>EGPFPRVTTVSDTTKRNNMDFSIRIGAITPADAGTYYCVKFRKGSPDDVEFK<br>SGAGTELSVRAKPSERKSSVECPPCPAPPVAGPSVFLFPPKPKDTLMISRTPE<br>VTCVVVDVSHEDPEVQFNWYVDGVEVHNAKTKPREEQFASTFRVVSVLTV<br>VHQDWLNGKEYKCKVSNKGLPSSIEKTISKTKGQPREPQVYTLPPSREEMTK<br>NQVSLTCLVKGFYPSDIAVEWESNGQPENNYKTTPPMLDSDGSFFLYSKLTV<br>DKSRWQQGNVFSCSVMHEALHNHYTQKSLSLSPGK |
| 122 | EEELQIIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKS<br>GAGTELSVRAKPSERKSSVECPPCPAPPVAGPSVFLFPPKPKDTLMISRTPEV<br>TCVVVDVSHEDPEVQFNWYVDGVEVHNAKTKPREEQFASTFRVVSVLTVV<br>HQDWLNGKEYKCKVSNKGLPSSIEKTISKTKGQPREPQVYTLPPSREEMTKN<br>QVSLTCLVKGFYPSDIAVEWESNGQPENNYKTTPPMLDSDGSFFLYSKLTVD<br>KSRWQQGNVFSCSVMHEALHNHYTQKSLSLSPGK |
| 123 | EEELQIIQPDKSVLVAAGETATLRCTITSLFPVGPIQWFRGAGPGRVLIYNQR<br>QGPFPRVTTVSDTTKRNNMDFSIRIGNITPADAGTYYCIKFRKGSPDDVEFKS<br>GAGTELSVRAKPSDKTHTCPPCPAPELLGGPSVFLFPPKPKDTLMISRTPEVT<br>CVVVDVSHEDPEVKFNWYVDGVEVHNAKTKPREEQYNSTYRVVSVLTVL<br>HQDWLNGKEYKCKVSNKALPAPIEKTISKAKGQPREPQVYTLPPSREEMTK<br>NQVSLTCLVKGFYPSDIAVEWESNGQPENNYKTTPPVLDSDGSFFLYSKLTV<br>DKSRWQQGNVFSCSVMHEALHNHYTQKSLSLSPGK |
| 124 | EEELQIIQPDKSVLVAAGETATLRCTITSLFPVGPIQWFRGAGPGRVLIYNQR<br>QGPFPRVTTVSDTTKRNNMDFSIRIGNITPADAGTYYCIKFRKGSPDDVEFKS<br>GAGTELSVRAKPSDKTHTCPPCPAPEAAGAPSVFLFPPKPKDTLMISRTPEVT<br>CVVVDVSHEDPEVKFNWYVDGVEVHNAKTKPREEQYNSTYRVVSVLTVL |

TABLE 8-continued

Polypeptides Comprising SIRPα D1 Domain Variants Fused to Fc Domain Variants

| SEQ ID NO: | Amino Acid Sequence |
|---|---|
| | HQDWLNGKEYKCKVSNKALPAPIEKTISKAKGQPREPQVYTLPPSREEMTK<br>NQVSLTCLVKGFYPSDIAVEWESNGQPENNYKTTPPVLDSDGSFFLYSKLTV<br>DKSRWQQGNVFSCSVMHEALHNHYTQKSLSLSPGK |
| 125 | EEELQIIQPDKSVLVAAGETATLRCTITSLFPVGPIQWFRGAGPGRVLIYNQR<br>QGPFPRVTTVSDTTKRNNMDFSIRIGNITPADAGTYYCIKFRKGSPDDVEFKS<br>GAGTELSVRAKPSDKTHTCPPCPAPELLGGPSVFLFPPKPKDTLMISRTPEVT<br>CVVVDVSHEDPEVKFNWYVDGVEVHNAKTKPREEQYASTYRVVSVLTVL<br>HQDWLNGKEYKCKVSNKALPAPIEKTISKAKGQPREPQVYTLPPSREEMTK<br>NQVSLTCLVKGFYPSDIAVEWESNGQPENNYKTTPPVLDSDGSFFLYSKLTV<br>DKSRWQQGNVFSCSVMHEALHNHYTQKSLSLSPGK |
| 126 | EEELQIIQPDKSVLVAAGETATLRCTITSLFPVGPIQWFRGAGPGRVLIYNQR<br>QGPFPRVTTVSDTTKRNNMDFSIRIGNITPADAGTYYCIKFRKGSPDDVEFKS<br>GAGTELSVRAKPSERKCCVECPPCPAPPVAGPSVFLFPPKPKDTLMISRTPEV<br>TCVVVDVSHEDPEVQFNWYVDGVEVHNAKTKPREEQFNSTFRVVSVLTVV<br>HQDWLNGKEYKCKVSNKGLPAPIEKTISKTKGQPREPQVYTLPPSREEMTK<br>NQVSLTCLVKGFYPSDIAVEWESNGQPENNYKTTPPMLDSDGSFFLYSKLTV<br>DKSRWQQGNVFSCSVMHEALHNHYTQKSLSLSPGK |
| 127 | EEELQIIQPDKSVLVAAGETATLRCTITSLFPVGPIQWFRGAGPGRVLIYNQR<br>QGPFPRVTTVSDTTKRNNMDFSIRIGNITPADAGTYYCIKFRKGSPDDVEFKS<br>GAGTELSVRAKPSERKCCVECPPCPAPPVAGPSVFLFPPKPKDTLMISRTPEV<br>TCVVVDVSHEDPEVQFNWYVDGVEVHNAKTKPREEQFNSTFRVVSVLTVV<br>HQDWLNGKEYKCKVSNKGLPSSIEKTISKTKGQPREPQVYTLPPSREEMTKN<br>QVSLTCLVKGFYPSDIAVEWESNGQPENNYKTTPPMLDSDGSFFLYSKLTVD<br>KSRWQQGNVFSCSVMHEALHNHYTQKSLSLSPGK |
| 128 | EEELQIIQPDKSVLVAAGETATLRCTITSLFPVGPIQWFRGAGPGRVLIYNQR<br>QGPFPRVTTVSDTTKRNNMDFSIRIGNITPADAGTYYCIKFRKGSPDDVEFKS<br>GAGTELSVRAKPSERKCCVECPPCPAPPVAGPSVFLFPPKPKDTLMISRTPEV<br>TCVVVDVSHEDPEVQFNWYVDGVEVHNAKTKPREEQFASTFRVVSVLTVV<br>HQDWLNGKEYKCKVSNKGLPAPIEKTISKTKGQPREPQVYTLPPSREEMTK<br>NQVSLTCLVKGFYPSDIAVEWESNGQPENNYKTTPPMLDSDGSFFLYSKLTV<br>DKSRWQQGNVFSCSVMHEALHNHYTQKSLSLSPGK |
| 129 | EEELQIIQPDKSVLVAAGETATLRCTITSLFPVGPIQWFRGAGPGRVLIYNQR<br>QGPFPRVTTVSDTTKRNNMDFSIRIGNITPADAGTYYCIKFRKGSPDDVEFKS<br>GAGTELSVRAKPSERKCCVECPPCPAPPVAGPSVFLFPPKPKDTLMISRTPEV<br>TCVVVDVSHEDPEVQFNWYVDGVEVHNAKTKPREEQFASTFRVVSVLTVV<br>HQDWLNGKEYKCKVSNKGLPSSIEKTISKTKGQPREPQVYTLPPSREEMTKN<br>QVSLTCLVKGFYPSDIAVEWESNGQPENNYKTTPPMLDSDGSFFLYSKLTVD<br>KSRWQQGNVFSCSVMHEALHNHYTQKSLSLSPGK |
| 130 | EEELQVIQPDKSVSVAAGESAILHCTVTSLIPVGPIQWFRGAGPARELIYNQK<br>EGHFPRVTTVSESTKRENMDFSISISNITPADAGTYYCVKFRKGSPDTEFKSG<br>AGTELSVRAKPSESKYGPPCPSCPAPEFLGGPSVFLFPPKPKDTLMISRTPEVT<br>CVVVDVSQEDPEVQFNWYVDGVEVHNAKTKPREEQFNSTYRVVSVLTVLH<br>QDWLNGKEYKCKVSNKGLPSSIEKTISKAKGQPREPQVYTLPPSQEEMTKN<br>QVSLTCLVKGFYPSDIAVEWESNGQPENNYKTTPPVLDSDGSFFLYSRLTVD<br>KSRWQEGNVFSCSVMHEALHNHYTQKSLSLSLGK |
| 131 | EEELQIIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKS<br>GAGTELSVRAKPSESKYGPPCPPCPAPEFLGGPSVFLFPPKPKDTLMISRTPEV<br>TCVVVDVSQEDPEVQFNWYVDGVEVHNAKTKPREEQFNSTYRVVSVLTVL<br>HQDWLNGKEYKCKVSNKGLPSSIEKTISKAKGQPREPQVYTLPPSQEEMTK<br>NQVSLTCLVKGFYPSDIAVEWESNGQPENNYKTTPPVLDSDGSFFLYSRLTV<br>DKSRWQEGNVFSCSVMHEALHNHYTQKSLSLSLGK |
| 132 | EEELQIIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKS<br>GAGTELSVRAKPSESKYGPPCPPCPAPEFEGGPSVFLFPPKPKDTLMISRTPEV<br>TCVVVDVSQEDPEVQFNWYVDGVEVHNAKTKPREEQFNSTYRVVSVLTVL<br>HQDWLNGKEYKCKVSNKGLPSSIEKTISKAKGQPREPQVYTLPPSQEEMTK<br>NQVSLTCLVKGFYPSDIAVEWESNGQPENNYKTTPPVLDSDGSFFLYSRLTV<br>DKSRWQEGNVFSCSVMHEALHNHYTQKSLSLSLGK |
| 133 | EEELQIIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKS<br>GAGTELSVRAKPSESKYGPPCPPCPAPPVAGPSVFLFPPKPKDTLMISRTPEV<br>TCVVVDVSQEDPEVQFNWYVDGVEVHNAKTKPREEQFNSTYRVVSVLTVL<br>HQDWLNGKEYKCKVSNKGLPSSIEKTISKAKGQPREPQVYTLPPSQEEMTK<br>NQVSLTCLVKGFYPSDIAVEWESNGQPENNYKTTPPVLDSDGSFFLYSRLTV<br>DKSRWQEGNVFSCSVMHEALHNHYTQKSLSLSLGK |

TABLE 8-continued

Polypeptides Comprising SIRPα D1 Domain Variants Fused to Fc Domain Variants

| SEQ ID NO: | Amino Acid Sequence |
|---|---|
| 134 | EEELQIIQPDKSVLVAAGETATLRCTITSLFPVGPIQWFRGAGPGRVLIYNQR<br>QGPFPRVTTVSDTTKRNNMDFSIRIGNITPADAGTYYCIKFRKGSPDDVEFKS<br>GAGTELSVRAKPSAAAPPCPPCPAPEFLGGPSVFLFPPKPKDTLMISRTPEVT<br>CVVVDVSQEDPEVQFNWYVDGVEVHNAKTKPREEQFNSTYRVVSVLTVLH<br>QDWLNGKEYKCKVSNKGLPSSIEKTISKAKGQPREPQVYTLPPSQEEMTKN<br>QVSLTCLVKGFYPSDIAVEWESNGQPENNYKTTPPVLDSDGSFFLYSRLTVD<br>KSRWQEGNVFSCSVMHEALHNHYTQKSLSLSPGK |
| 135 | EEELQVIQPDKSVLVAAGETATLRCTATSLFPVGPIQWFRGAGPGRELIYNQ<br>REGPFPRVTTVSDLTKRNNMDFSIRIGAITPADAGTYYCVKFRKGSPDDVEF<br>KSGAGTELSVRAKPSDKTHTCPPCPAPEAAGAPSVFLFPPKPKDTLMISRTPE<br>VTCVVVDVSHEDPEVKFNWYVDGVEVHNAKTKPREEQYASTYRVVSVLT<br>VLHQDWLNGKEYKCKVSNKALPAPIEKTISKAKGQPREPQVYTLPPSREEM<br>TKNQVSLTCLVKGFYPSDIAVEWESNGQPENNYKTTPPVLDSDGSFFLYSKL<br>TVDKSRWQQGNVFSCSVMHEALHNHYTQKSLSLSPG |
| 136 | EEELQIIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKS<br>GAGTELSVRAKPSDKTHTCPPCPAPEAAGAPSVFLFPPKPKDTLMISRTPEVT<br>CVVVDVSHEDPEVKFNWYVDGVEVHNAKTKPREEQYASTYRVVSVLTVL<br>HQDWLNGKEYKCKVSNKALPAPIEKTISKAKGQPREPQVYTLPPSREEMTK<br>NQVSLTCLVKGFYPSDIAVEWESNGQPENNYKTTPPVLDSDGSFFLYSKLTV<br>DKSRWQQGNVFSCSVMHEALHNHYTQKSLSLSPG |
| 137 | EEELQIIQPDKSVLVAAGETATLRCTITSLFPVGPIQWFRGAGPGRVLIYNQR<br>EGPFPRVTTVSDTTKRNNMDFSIRIGAITPADAGTYYCIKFRKGSPDDVEFKS<br>GAGTELSVRAKPSDKTHTCPPCPAPEAAGAPSVFLFPPKPKDTLMISRTPEVT<br>CVVVDVSHEDPEVKFNWYVDGVEVHNAKTKPREEQYASTYRVVSVLTVL<br>HQDWLNGKEYKCKVSNKALPAPIEKTISKAKGQPREPQVYTLPPSREEMTK<br>NQVSLTCLVKGFYPSDIAVEWESNGQPENNYKTTPPVLDSDGSFFLYSKLTV<br>DKSRWQQGNVFSCSVMHEALHNHYTQKSLSLSPG |
| 211 | EEELQIIQPDKSVLVAAGETATLRCTITSLRPVGPIQWFRGAGPGRELIYNQR<br>DGPFPRVTTVSDTTKRNNMDFSIRIGAITPADAGTYYCVKFRKGIPDDVEFKS<br>GAGTELSVRAKPSDKTHTCPPCPAPEAAGAPSVFLFPPKPKDTLMISRTPEVT<br>CVVVDVSHEDPEVKFNWYVDGVEVHNAKTKPREEQYASTYRVVSVLTVL<br>HQDWLNGKEYKCKVSNKALPAPIEKTISKAKGQPREPQVYTLPPSREEMTK<br>NQVSLTCLVKGFYPSDIAVEWESNGQPENNYKTTPPVLDSDGSFFLYSKLTV<br>DKSRWQQGNVFSCSVMHEALHNHYTQKSLSLSPG |
| 214 | EEELQVIQPDKSVLVAAGETATLRCTATSLFPVGPIQWFRGAGPGRELIYNQ<br>REGPFPRVTTVSDLTKRNNMDFSIRIGAITPADAGTYYCVKFRKGSPDDVEF<br>KSGAGTELSVRAKPSERKSSVECPPCPAPPVAGPSVFLFPPKPKDTLMISRTP<br>EVTCVVVDVSHEDPEVQFNWYVDGVEVHNAKTKPREEQFASTFRVVSVLT<br>VVHQDWLNGKEYKCKVSNKGLPSSIEKTISKTKGQPREPQVYTLPPSREEMT<br>KNQVSLTCLVKGFYPSDIAVEWESNGQPENNYKTTPPMLDSDGSFFLYSKLT<br>VDKSRWQQGNVFSCSVMHEALHNHYTQKSLSLSPG |
| 216 | EEELQIIQPDKSVLVAAGETATLRCTITSLFPVGPIQWFRGAGPGRVLIYNQR<br>QGPFPRVTTVSDTTKRNNMDFSIRIGNITPADAGTYYCIKFRKGSPDDVEFKS<br>GAGTELSVRAKPSDKTHTCPPCPAPELLGGPSVFLFPPKPKDTLMISRTPEVT<br>CVVVDVSHEDPEVKFNWYVDGVEVHNAKTKPREEQYNSTYRVVSVLTVL<br>HQDWLNGKEYKCKVSNKALPAPIEKTISKAKGQPREPQVYTLPPSREEMTK<br>NQVSLTCLVKGFYPSDIAVEWESNGQPENNYKTTPPVLDSDGSFFLYSKLTV<br>DKSRWQQGNVFSCSVMHEALHNHYTQKSLSLSPGK |
| 217 | EEELQIIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKS<br>GAGTELSVRAKPSEKTHTCPECPAPEAAGAPSVFLFPPKPKDTLMISRTPEVT<br>CVVVDVSHEDPEVKFNWYVDGVEVHNAKTKPREEQYASTYRVVSVLTVL<br>HQDWLNGKEYKCKVSNKALPAPIEKTISKAKGQPREPQVYTLPPSREEMTK<br>NQVSLTCEVKGFYPSDIAVEWESNGQPENNYKTTPPVLDSDGSFFLYSKLTV<br>DKSRWQQGNVFSCSVMHEALHNHYTQKSLSLSPGK |

In some embodiments, the polypeptide comprises a SIRPα D1 variant domain that has at least 85% sequence identity (e.g., at least 86%, 87%, 88%, 89%, 90%, 91%, 92%, 93%, 94%, 95%, 96%, 97%, 98%, 99%, or 100% sequence identity) to any variant provided in Table 8.

In some embodiments, the polypeptide comprises a SIRPα D1 domain variant that has at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NOs: 98-104, 107-113, 116-122, or 135-137 in Table 8.

In some embodiments, the polypeptide comprises (a) a signal-regulatory protein α (SIRP-α) D1 variant, wherein the SIRPα D1 domain variant comprises the amino acid sequence, EEX$_1$X$_2$QX$_3$IQPDKX$_4$VX$_5$VAAGEX$_6$X$_7$X$_8$LX$_9$CTX$_{10}$T-SLX$_{11}$PVGPIQWFRGAGPX$_{12}$RX$_{13}$LIY $NQX_{14}X_{15}GX_{16}FPRVTTVSX_{17}X_{18}TX_{19}RX_{20}NMDFX_{21}$-$IX_{22}IX_{23}X_{24}ITX_{25}ADAGTYYCX_{26}KX_{27}$ $RKGSPDX_{28}X_{29}EX_{30}KSGAGTELSVRX_{31}KPS$ (SEQ ID NO: 47), wherein $X_1$ is E, or G; $X_2$ is L, I, or V; $X_3$ is V, L, or I; $X_4$ is S, or F; $X_5$ is L, or S; $X_6$ is S, or T; $X_7$ is A, or V; $X_8$ is I, or T; $X_9$ is H, R, or L; $X_{10}$ is A, V, I, or L; $X_{11}$ is I, T, S, or F; $X_{12}$ is A, or G; $X_{13}$ is E, V, or L; $X_{14}$ is K, or R; $X_{15}$ is E, or Q; $X_{16}$ is H, P, or R; $X_{17}$ is D, or E; $X_{18}$ is S, L, T, or G; $X_{19}$ is K, or R; $X_{20}$ is E, or N; $X_{21}$ is S, or P; $X_{22}$ is S, or R; $X_{23}$ is S, or G; $X_{24}$ is any amino acid; $X_{25}$ is any amino acid; $X_{26}$ is V, or I; $X_{27}$ is F, L, or V; $X_{28}$ is D or absent; $X_{29}$ is T, or V; $X_{30}$ is F, or V; and $X_{31}$ is A, or G; and wherein the SIRPα D1 domain variant comprises at least two amino acid substitutions relative to a wild-type SIRPα D1 domain having a sequence according to any one of SEQ ID NOs: 1 to 10; and (b) an Fc domain dimer variant having two Fc domain variants, wherein each Fc domain variant independently is (i) a human IgG1 Fc region comprising a N297A mutation; (ii) a human IgG1 Fc region comprising L234A, L235A, and G237A mutations; (iii) a human IgG1 Fc region comprising L234A, L235A, G237A, and N297A mutations; (iv) a human IgG2 Fc region comprising a N297A mutation; (v) a human IgG2 Fc region comprising A330S and P331S mutations; (vi) a human IgG2 Fc region comprising A330S, P331S, and N297A mutations; (vii) a human IgG4 Fc region comprising S228P, E233P, F234V, L235A, and delG236 mutations; or (viii) a human IgG4 Fc region comprising S228P, E233P, F234V, L235A, delG236, and N297A mutations.

In some embodiments, the polypeptide comprises a SIRPα D1 domain variant wherein the SIRPα D1 domain variant comprises an amino acid sequence according to SEQ ID NO: 47; an Fc domain dimer having two Fc domains, wherein one of the Fc domains is an Fc domain variant comprising a human IgG1 Fc region comprising L234A, L235A, G237A, and N297A mutations.

Dimerization of Fc Domains

In some embodiments, a SIRPα D1 domain variant polypeptide (e.g., any of the variants described in Tables 2, 5, and 6) is fused to a first Fc domain (e.g., an Fc domain variant) either at the N-terminus or at the C-terminus. In some embodiments, the first Fc domain is a variant that is incapable of forming an dimer. In some embodiments, the first Fc domain forms a dimer with a second Fc domain. In some embodiments, the first and second Fc domains comprise amino acid substitutions that promote heterodimerization between the first and second domain Fc domains.

In some embodiments, each of the two Fc domains in an Fc domain dimer includes amino acid substitutions that promote the heterodimerization of the two monomers. In some embodiments, a SIRPα construct is formed, for example, from a first subunit including a SIRPα D1 domain variant polypeptide fused to a first Fc domain and a second subunit including a second Fc domain (e.g., without a SIRPα D1 domain variant polypeptide or any other polypeptide). In some embodiments, a construct has a single SIRPα D1 domain variant polypeptide linked to an Fc domain dimer (e.g., single arm). In some embodiments, a construct has two SIRPα D1 domain variant polypeptides linked to an Fc domain dimer (e.g., double arm). In some embodiments, a SIRPα D1 domain variant having a $K_D$ of about 500 nM is particularly useful in a double arm construct. In some embodiments, a SIRPα D1 domain variant having a KD of about 50 nM is particularly useful in a double arm construct. In some embodiments, a SIRPα D1 domain variant having a KD of about 5 nM is useful in a double arm construct and a single arm construct. In some embodiments, a SIRPα D1 domain variant having a $K_D$ of about 500 pM is useful in a double arm construct and a single arm construct. In some embodiments, a SIRPα D1 domain variant having a $K_D$ of about 100 pM is useful in a double arm construct and a single arm construct. In some embodiments, a SIRPα D1 domain variant having a $K_D$ of about 50 pM is useful in a double arm construct and a single arm construct. In some embodiments, a SIRPα D1 domain variant having a $K_D$ of about 10 pM is useful in a double arm construct and a single arm construct.

In some embodiments, heterodimerization of Fc domains is promoted by introducing different, but compatible, substitutions in the two Fc domains, such as "knob-into-hole" residue pairs and charge residue pairs. The knob and hole interaction favors heterodimer formation, whereas the knob-knob and the hole-hole interaction hinder homodimer formation due to steric clash and deletion of favorable interactions. A hole refers to a void that is created when an original amino acid in a protein is replaced with a different amino acid having a smaller side-chain volume. A knob refers to a bump that is created when an original amino acid in a protein is replaced with a different amino acid having a larger side-chain volume. For example, in some embodiments, an amino acid being replaced is in the CH3 antibody constant domain of an Fc domain and involved in the dimerization of two Fc domains. In some embodiments, a hole in one CH3 antibody constant domain is created to accommodate a knob in another CH3 antibody constant domain, such that the knob and hole amino acids act to promote or favor the heterodimerization of the two Fc domains. In some embodiments, a hole in one CH3 antibody constant domain is created to better accommodate an original amino acid in another CH3 antibody constant domain. In some embodiments, a knob in one CH3 antibody constant domain is created to form additional interactions with original amino acids in another CH3 antibody constant domain.

In some embodiments, a hole is constructed by replacing amino acids having larger side chains such as tyrosine or tryptophan with amino acids having smaller side chains such as alanine, valine, or threonine, for example a Y407V mutation in the CH3 antibody constant domain. Similarly, in some embodiments, a knob is constructed by replacing amino acids having smaller side chains with amino acids having larger side chains, for example a T366W mutation in the CH3 antibody constant domain. In some embodiments, one Fc domain includes the knob mutation T366W and the other Fc domain includes hole mutations T366S, L358A, and Y407V. In some embodiments, a polypeptide of the disclosure including a SIRPα D1 domain variant is fused to an Fc domain including the knob mutation T366W to limit unwanted knob-knob homodimer formation. Examples of knob-into-hole amino acid pairs are included, without limitation, in Table 9 and examples of knob-into-hole Fc domain variants and SIRPα-Fc fusions are provided in Table 10.

TABLE 9

Knob-Into-Hole Amino Acid Pairs

| First Fc Domain | Y407T | Y407A | F405A | T394S | T366S L358A Y407V | T394W Y407T | T394W Y407A | T366W T394S |
|---|---|---|---|---|---|---|---|---|
| Second Fc Domain | T366Y | T366W | T394W | F405W | T366W | T366Y F405A | T366W F405W | F405W Y407A |

TABLE 10

Exemplary Fc Domain Variants and SIRPα D1 Domain Variant - Fc Domain Variant Fusion Polypeptides

| SEQ ID NO: | Amino Acid Sequence |
|---|---|
| 138 | EEELQIIQPDKSVLVAAGETATLRCTITSLFPVGPIQWFRGAGPGRVLIYNQR QGPFPRVTTVSDTTKRNNMDFSIRIGAITPADAGTYYCIKFRKGSPDDVEFK SGAGTELSVRAKPSDKTHTCPPCPAPEAAGAPSVFLFPPKPKDTLMISRTPE VTCVVVDVSHEDPEVKFNWYVDGVEVHNAKTKPREEQYASTYRVVSVLT VLHQDWLNGKEYKCKVSNKALPAPIEKTISKAKGQPREPQVYTLPPSREEM TKNQVSLWCLVKGFYPSDIAVEWESNGQPENNYKTTPPVLDSDGSFFLYSK LTVDKSRWQQGNVFSCSVMHEALHNHYTQKSLSLSPGK |
| 139 | DKTHTCPPCPAPEAAGAPSVFLFPPKPKDTLMISRTPEVTCVVVDVSHEDPE VKFNWYVDGVEVHNAKTKPREEQYASTYRVVSVLTVLHQDWLNGKEYK CKVSNKALPAPIEKTISKAKGQPREPQVYTLPPSREEMTKNQVSLSCAVKGF YPSDIAVEWESNGQPENNYKTTPPVLDSDGSFFLVSKLTVDKSRWQQGNVF SCSVMHEALHNHYTQKSLSLSPGK |
| 140 | EEELQIIQPDKSVLVAAGETATLRCTITSLFPVGPIQWFRGAGPGRVLIYNQR QGPFPRVTTVSDTTKRNNMDFSIRIGAITPADAGTYYCIKFRKGSPDDVEFK SGAGTELSVRAKPSDKTHTCPPCPAPEAAGAPSVFLFPPKPKDTLMISRTPE VTCVVVDVSHEDPEVKFNWYVDGVEVHNAKTKPREEQYASTYRVVSVLT VLHQDWLNGKEYKCKVSNKALPAPIEKTISKAKGQPREPQVYTLPPSREEM TKNQVSLSCAVKGFYPSDIAVEWESNGQPENNYKTTPPVLDSDGSFFLVSK LTVDKSRWQQGNVFSCSVMHEALHNHYTQKSLSLSPGK |
| 141 | DKTHTCPPCPAPEAAGAPSVFLFPPKPKDTLMISRTPEVTCVVVDVSHEDPE VKFNWYVDGVEVHNAKTKPREEQYASTYRVVSVLTVLHQDWLNGKEYK CKVSNKALPAPIEKTISKAKGQPREPQVYTLPPSREEMTKNQVSLWCLVKG FYPSDIAVEWESNGQPENNYKTTPPVLDSDGSFFLYSKLTVDKSRWQQGNV FSCSVMHEALHNHYTQKSLSLSPGK |
| 142 | EEELQIIQPDKSVLVAAGETATLRCTITSLFPVGPIQWFRGAGPGRELIYNQR EGPFPRVTTVSDTTKRNNMDFSIRIGAITPADAGTYYCVKFRKGSPDDVEFK SGAGTELSVRAKPSDKTHTCPPCPAPEAAGAPSVFLFPPKPKDTLMISRTPE VTCVVVDVSHEDPEVKFNWYVDGVEVHNAKTKPREEQYASTYRVVSVLT VLHQDWLNGKEYKCKVSNKALPAPIEKTISKAKGQPREPQVYTLPPSREEM TKNQVSLWCLVKGFYPSDIAVEWESNGQPENNYKTTPPVLDSDGSFFLYSK LTVDKSRWQQGNVFSCSVMHEALHNHYTQKSLSLSPGK |
| 143 | EEELQIIQPDKSVLVAAGETATLRCTITSLFPVGPIQWFRGAGPGRELIYNQR EGPFPRVTTVSDTTKRNNMDFSIRIGAITPADAGTYYCVKFRKGSPDDVEFK SGAGTELSVRAKPSDKTHTCPPCPAPEAAGAPSVFLFPPKPKDTLMISRTPE VTCVVVDVSHEDPEVKFNWYVDGVEVHNAKTKPREEQYASTYRVVSVLT VLHQDWLNGKEYKCKVSNKALPAPIEKTISKAKGQPREPQVYTLPPSREEM TKNQVSLSCAVKGFYPSDIAVEWESNGQPENNYKTTPPVLDSDGSFFLVSK LTVDKSRWQQGNVFSCSVMHEALHNHYTQKSLSLSPGK |
| 144 | QVQLKQSGPGLVQPSQSLSITCTVSGFSLTNYGVHWVRQSPGKGLEWLGVI WSGGNTDYNTPFTSRLSINKDNSKSQVFFKMNSLQSNDTAIYYCARALTYY DYEFAYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNVN HKPSNTKVDKKVEPKSCRKTHTCPRCPAPELLGGPSVFLFPPKPKDTLMISR TPEVTCVVVDVSHEDPEVKFNWYVDGVEVHNAKTKPREEQYASTYRVVS VLTVLHQDWLNGKEYKCKVSNKALPAPIEKTISKAKGQPREPQVYTLPPSR EEMTKNQVSLTCLVKGFYPSDIAVEWESNGQPENNYKTTPPVLDSDGSFFL YSRLTVDKSRWQQGNVFSCSVMHEALHNHYTQKSLSLSPGK |
| 145 | EEELQIIQPDKSVLVAAGETATLRCTITSLFPVGPIQWFRGAGPGRELIYNQR EGPFPRVTTVSDTTKRNNMDFSIRIGAITPADAGTYYCVKFRKGSPDDVEFK SGAGTELSVRAKPSEKTHTCPECPAPEAAGAPSVFLFPPKPKDTLMISRTPEV TCVVVDVSHEDPEVKFNWYVDGVEVHNAKTKPREEQYASTYRVVSVLTV LHQDWLNGKEYKCKVSNKALPAPIEKTISKAKGQPREPQVYTLPPSREEMT KNQVSLTCEVKGFYPSDIAVEWESNGQPENNYKTTPPVLDSDGSFFLYSKL TVDKSRWQQGNVFSCSVMHEALHNHYTQKSLSLSPGK |

TABLE 10-continued

Exemplary Fc Domain Variants and SIRPα D1 Domain Variant - Fc Domain Variant Fusion Polypeptides

| SEQ ID NO: | Amino Acid Sequence |
|---|---|
| 146 | EEELQVIQPDKSVLVAAGETATLRCTATSLFPVGPIQWFRGAGPGRELIYNQ<br>RQGPFPRVTTVSDLTKRNNMDFSIRIGNITPADAGTYYCVKFRKGSPDDVEF<br>KSGAGTELSVRAKPSDKTHTCPPCPAPEAAGAPSVFLFPPKPKDTLMISRTP<br>EVTCVVVDVSHEDPEVKFNWYVDGVEVHNAKTKPREEQYNSTYRVVSVL<br>TVLHQDWLNGKEYKCKVSNKALPAPIEKTISKAKGQPREPQVYTLPPSREE<br>MTKNQVSLWCLVKGFYPSDIAVEWESNGQPENNYKTTPPVLDSDGSFFLYS<br>KLTVDKSRWQQGNVFSCSVMHEALHNHYTQKSLSLSPGK |
| 147 | DKTHTCPPCPAPEAAGAPSVFLFPPKPKDTLMISRTPEVTCVVVDVSHEDPE<br>VKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLSCAVKGF<br>YPSDIAVEWESNGQPENNYKTTPPVLDSDGSFFLVSKLTVDKSRWQQGNVF<br>SCSVMHEALHNHYTQKSLSLSPGK |
| 148 | EEELQVIQPDKSVLVAAGETATLRCTATSLFPVGPIQWFRGAGPGRELIYNQ<br>RQGPFPRVTTVSDLTKRNNMDFSIRIGNITPADAGTYYCVKFRKGSPDDVEF<br>KSGAGTELSVRAKPSDKTHTCPPCPAPEAAGAPSVFLFPPKPKDTLMISRTP<br>EVTCVVVDVSHEDPEVKFNWYVDGVEVHNAKTKPREEQYNSTYRVVSVL<br>TVLHQDWLNGKEYKCKVSNKALPAPIEKTISKAKGQPREPQVYTLPPSREE<br>MTKNQVSLSCAVKGFYPSDIAVEWESNGQPENNYKTTPPVLDSDGSFFLVS<br>KLTVDKSRWQQGNVFSCSVMHEALHNHYTQKSLSLSPGK |
| 149 | DKTHTCPPCPAPEAAGAPSVFLFPPKPKDTLMISRTPEVTCVVVDVSHEDPE<br>VKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLWCLVKG<br>FYPSDIAVEWESNGQPENNYKTTPPVLDSDGSFFLYSKLTVDKSRWQQGNV<br>FSCSVMHEALHNHYTQKSLSLSPGK |

In addition to the knob-into-hole strategy, in some embodiments, electrostatic steering is also used to control the dimerization of Fc domains. Electrostatic steering refers to the utilization of favorable electrostatic interactions between oppositely charged amino acids in peptides, protein domains, and proteins to control the formation of higher ordered protein molecules. In particular, to control the dimerization of Fc domains using electrostatic steering, one or more amino acid residues that make up the CH3-CH3 interface are replaced with positively- or negatively-charged amino acid residues such that the interaction becomes electrostatically favorable or unfavorable depending on the specific charged amino acids introduced. In some embodiments, a positively-charged amino acid in the interface, such as lysine, arginine, or histidine, is replaced with a negatively-charged amino acid such as aspartic acid or glutamic acid. In some embodiments, a negatively-charged amino acid in the interface is replaced with a positively-charged amino acid. In some embodiments, the charged amino acids are introduced to one of the interacting CH3 antibody constant domains, or both. In some embodiments, introducing charged amino acids to the interacting CH3 antibody constant domains of the two Fc domains promotes the selective formation of heterodimers of Fc domains as controlled by the electrostatic steering effects resulting from the interaction between charged amino acids. Examples of electrostatic steering amino acid pairs are included, without limitation, in Table 11.

TABLE 11

| Electrostatic Steering Amino Acid Pairs | | | | | | | | | |
|---|---|---|---|---|---|---|---|---|---|
| Fc domain monomer 1 | K409D | K409D | K409E | K409E | K392D | K392D | K392E | K392E | K409D K392D | K370E K409D K439E |
| Fc domain monomer 2 | D399K | D399R | D399K | D399R | D399K | D399R | D399K | D399R | D399K D356K | D356K E357K D399K |

Other methods used to control the heterodimerization of Fc domains, especially in the context of constructing a bispecific antibody, are available.

In some embodiments, a first Fc domain and a second Fc domain each includes one or more of the following amino acid substitutions: T366W, T366S, L368A, Y407V, T366Y, T394W, F405W, Y349T, Y349E, Y349V, L351T, L351H, L351N, L351K, P353S, S354D, D356K, D356R, D356S, E357K, E357R, E357Q, S364A, T366E, L368T, L368Y, L368E, K370E, K370D, K370Q, K392E, K392D, T394N, P395N, P396T, V397T, V397Q, L398T, D399K, D399R, D399N, F405T, F405H, F405R, Y407T, Y407H, Y407I, K409E, K409D, K409T, and K409I, relative to the sequence of human IgG1.

In some embodiments an Fc domain comprises: (a) one of the following amino acid substitutions relative to wild type human IgG1: T366W, T366S, L368A, Y407V, T366Y, T394W, F405W, Y349T, Y349E, Y349V, L351T, L351H, L351N, L351K, P353S, S354D, D356K, D356R, D356S, E357K, E357R, E357Q, S364A, T366E, L368T, L368Y, L368E, K370E, K370D, K370Q, K392E, K392D, T394N, P395N, P396T, V397T, V397Q, L398T, D399K, D399R, D399N, F405T, F405H, F405R, Y407T, Y407H, Y407I, K409E, K409D, K409T, or K409I; or (b) (i) a N297A mutation relative to a human IgG1 Fc region; (ii) a L234A, L235A, and G237A mutation relative to a human IgG1 Fc region; (iii) a L234A, L235A, G237A, and N297A mutation relative to a human IgG1 Fc region; (iv) a N297A mutation relative to a human IgG2 Fc region; (v) a A330S and P331S mutation relative to a human IgG2 Fc region; (vi) a A330S, P331S, and N297A mutation relative to a human IgG2 Fc region; (vii) a S228P, E233P, F234V, L235A, and delG236 mutation relative to a human IgG4 Fc region; or (viii) a S228P, E233P, F234V, L235A, delG236, and N297A mutation relative to a human IgG4 Fc region. In some embodiments an Fc domain variant comprises: (a) one of the following amino acid substitutions relative to wild type human IgG1: T366W, T366S, L368A, Y407V, T366Y, T394W, F405W, Y349T, Y349E, Y349V, L351T, L351H, L351N, L351K, P353S, S354D, D356K, D356R, D356S, E357K, E357R, E357Q, S364A, T366E, L368T, L368Y, L368E, K370E, K370D, K370Q, K392E, K392D, T394N, P395N, P396T, V397T, V397Q, L398T, D399K, D399R, D399N, F405T, F405H, F405R, Y407T, Y407H, Y407I, K409E, K409D, K409T, or K409I; and (b) further comprises (i) a N297A mutation relative to a human IgG1 Fc region; (ii) a L234A, L235A, and G237A mutation relative to a human IgG1 Fc region; (iii) a L234A, L235A, G237A, and N297A mutation relative to a human IgG1 Fc region; (iv) a N297A mutation relative to a human IgG2 Fc region; (v) a A330S and P331S mutation relative to a human IgG2 Fc region; (vi) a A330S, P331S, and N297A mutation relative to a human IgG2 Fc region; (vii) a S228P, E233P, F234V, L235A, and delG236 mutation relative to a human IgG4 Fc region; or (viii) a S228P, E233P, F234V, L235A, delG236, and N297A mutation relative to a human IgG4 Fc region.

In some embodiments, the first and second Fc domains include different amino acid substitutions. In some embodiments, the first Fc domain includes T366W. In some embodiments, the second Fc domain includes T366S, L368A, and Y407V. In some embodiments, the first Fc domain includes D399K. In some embodiments, the second Fc domain includes K409D.

Linkers

Disclosed herein, in some embodiments, are polypeptides comprising a signal-regulatory protein α (SIRP-α) D1 variant comprising a SIRPα D1 domain, or a fragment thereof, having an amino acid mutation at residue 80 relative to a wild-type SIRPα D1 domain; and at least one additional amino acid mutation relative to a wild-type SIRPα D1 domain at a residue selected from the group consisting of: residue 6, residue 27, residue 31, residue 47, residue 53, residue 54, residue 56, residue 66, and residue 92.

Also disclosed herein, in some embodiments, are polypeptides comprising an Fc variant, wherein the Fc variant comprises an Fc domain dimer comprising two Fc domain variants, wherein each Fc domain variant independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

In the present disclosure, a linker is used to describe a linkage or connection between polypeptides or protein domains or associated non-protein moieties. In some embodiments, a linker is a linkage or connection between an Fc domain (or variant thereof) and a SIRPα D1 domain variant. In some embodiments, the linker connects the C-terminus of the SIRPα D1 domain variant and the N-terminus of the Fc domain variant, such that the two polypeptides are joined to each other in tandem series.

In some embodiments, a linker is a simple covalent bond, e.g., a peptide bond, a synthetic polymer, or any kind of bond created from a chemical reaction, e.g. chemical conjugation. When a linker is a peptide bond, in some embodiments, the carboxylic acid group at the C-terminus of one protein domain reacts with the amino group at the N-terminus of another protein domain in a condensation reaction to form a peptide bond. In some embodiments, the peptide bond is formed from synthetic means through a conventional organic chemistry reaction, or by natural production from a host cell, wherein a nucleic acid molecule encoding the DNA sequences of both proteins (e.g., an Fc domain variant and a SIRPα D1 domain variant) in tandem series can be directly transcribed and translated into a contiguous polypeptide encoding both proteins by the necessary molecular machineries (e.g., DNA polymerase and ribosome) in the host cell.

When a linker is a synthetic polymer, in some embodiments, the polymer is functionalized with reactive chemical functional groups at each end to react with the terminal amino acids at the connecting ends of two proteins.

When a linker (except peptide bond mentioned above) is made from a chemical reaction, in some embodiments, chemical functional groups (e.g., amine, carboxylic acid, ester, azide, or other functional groups), are attached synthetically to the C-terminus of one protein and the N-terminus of another protein, respectively. In some embodiments, the two functional groups then react through synthetic chemistry means to form a chemical bond, thus connecting the two proteins together.

Spacers

In the present disclosure, in some embodiments, a linker between an Fc domain monomer and a SIRPα D1 variant polypeptide of the disclosure, is an amino acid spacer including about 1-200 amino acids. Suitable peptide spacers include peptide linkers containing flexible amino acid residues such as glycine and serine. Examples of linker sequences are provided in Table 12. In some embodiments, a spacer contains motifs, e.g., multiple or repeating motifs, of GS, GG, GGS, GGG, GGGGS (SEQ ID NO: 163), GGSG (SEQ ID NO: 164), or SGGG (SEQ ID NO: 165). In some embodiments, a spacer contains 2 to 12 amino acids including motifs of GS, e.g., GS, GSGS (SEQ ID NO: 166), GSGSGS (SEQ ID NO: 167), GSGSGSGS (SEQ ID NO: 168), GSGSGSGSGS (SEQ ID NO: 169), or GSGSGSGSGSGS (SEQ ID NO: 170). In some embodiments, a spacer contains 3 to 12 amino acids including motifs of GGS, e.g., GGS, GGSGGS (SEQ ID NO: 171), GGSGGSGGS (SEQ ID NO: 172), and GGSGGSGGSGGS (SEQ ID NO: 173). In some embodiments, a spacer contains 4 to 12 amino acids including motifs of GGSG (SEQ ID NO: 164), e.g., GGSG (SEQ ID NO: 164), GGSGGGSG (SEQ ID NO: 174), or GGSGGGSGGGSG (SEQ ID NO: 175). In some embodiments, a spacer contains motifs of GGGGS (SEQ ID NO: 163), e.g., GGGGSGGGGSGGGGS (SEQ ID NO: 176). In some embodiments, a spacer contains amino acids other than glycine and serine, e.g., AAS (SEQ ID NO: 177), AAAL (SEQ ID NO: 178), AAAK (SEQ ID NO: 179), AAAR (SEQ ID NO: 180), EGKSSGSGSESKST (SEQ ID NO: 181), GSAGSAAGSGEF (SEQ ID NO: 182), AEAAAKEAAAKA (SEQ ID NO: 183), KESGSVSSE- QLAQFRSLD (SEQ ID NO: 184), GGGGAGGGG (SEQ ID NO: 185), GENLYFQSGG (SEQ ID NO: 186), SACYCELS (SEQ ID NO: 187), RSIAT (SEQ ID NO: 188), RPACKIPNDLKQKVMNH (SEQ ID NO: 189), GGSAGGSGSGSSGGSSGASGTGTAGGTGSGSGTGSG (SEQ ID NO: 190), AAANSSIDLISVPVDSR (SEQ ID NO: 191), or GGSGGGSEGGGSEGGGSEGGGSEGGGSEGGGSGGGS (SEQ ID NO: 192).

In some embodiments, a spacer contains motifs, e.g., multiple or repeating motifs, of EAAAK (SEQ ID NO: 193). In some embodiments, a spacer contains motifs, e.g., multiple or repeating motifs, of proline-rich sequences such as (XP)n, in which X is any amino acid (e.g., A, K, or E) and n is from 1-5, and PAPAP(SEQ ID NO: 194).

TABLE 12

Linker Sequences

| SEQ ID NO: | AMINO ACID SEQUENCE |
|---|---|
| 163 | GGGGS |
| 164 | GGSG |
| 165 | SGGG |
| 166 | GSGS |
| 167 | GSGSGS |
| 168 | GSGSGSGS |
| 169 | GSGSGSGSGS |
| 170 | GSGSGSGSGSGS |
| 171 | GGSGGS |
| 172 | GGSGGSGGS |
| 173 | GGSGGSGGSGGS |
| 174 | GGSGGGSG |
| 175 | GGSGGGSGGGSG |
| 176 | GGGGSGGGGSGGGGS |
| 177 | AAS |
| 178 | AAAL |
| 179 | AAAK |
| 180 | AAAR |
| 181 | EGKSSGSGSESKST |
| 182 | GSAGSAAGSGEF |
| 183 | AEAAAKEAAAKA |
| 184 | KESGSVSSEQLAQFRSLD |
| 185 | GGGGAGGGG |
| 186 | GENLYFQSGG |
| 187 | SACYCELS |
| 188 | RSIAT |
| 189 | RPACKIPNDLKQKVMNH |
| 190 | GGSAGGSGSGSSGGSSGASGTGTAGGTGSGSGTGSG |

TABLE 12-continued

Linker Sequences

| SEQ ID NO: | AMINO ACID SEQUENCE |
|---|---|
| 191 | AAANSSIDLISVPVDSR |
| 192 | GGSGGGSEGGGSEGGGSEGGGSEGGGSEGGGSGGGS |
| 193 | EAAAK |
| 194 | PAPAP |

In some embodiments, the length of the peptide spacer and the amino acids used is adjusted depending on the two proteins involved and the degree of flexibility desired in the final protein fusion polypeptide. In some embodiments, the length of the spacer is adjusted to ensure proper protein folding and avoid aggregate formation. In some embodiments, a spacer is A or AAAL (SEQ ID NO: 178).

Vectors, Host Cells, and Protein Production

Disclosed herein, in some embodiments, are polypeptides comprising a signal-regulatory protein α (SIRP-α) D1 variant comprising a SIRPα D1 domain, or a fragment thereof, having an amino acid mutation at residue 80 relative to a wild-type SIRPα D1 domain; and at least one additional amino acid mutation relative to a wild-type SIRPα D1 domain at a residue selected from the group consisting of: residue 6, residue 27, residue 31, residue 47, residue 53, residue 54, residue 56, residue 66, and residue 92.

Also disclosed herein, in some embodiments, are polypeptides comprising an Fc variant, wherein the Fc variant comprises an Fc domain dimer having two Fc domain monomers, wherein each Fc domain monomer independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

In some embodiments, the polypeptides of the disclosure are produced from a host cell. A host cell refers to a vehicle that includes the necessary cellular components, e.g., organelles, needed to express the polypeptides and fusion polypeptides described herein from their corresponding nucleic acids. In some embodiments, the nucleic acids are included in nucleic acid vectors introduced into the host cell by transformation, transfection, electroporation, calcium phosphate precipitation, direct microinjection, infection, etc. In some embodiments, the choice of nucleic acid vector depends on the host cell to be used. In some embodiments, host cells are of either prokaryotic (e.g., bacterial) or eukaryotic (e.g., mammalian) origin.

In some embodiments, a polypeptide, for example a polypeptide construct comprising a SIRPα D1 domain variant (e.g., any variant provided in Tables 2, 5, and 6) and a fusion partner such as an Fc variant are produced by culturing a host cell transformed with a nucleic acid, preferably an expression vector, containing a nucleic acid encoding the polypeptide construct (e.g., Fc variant, linker, and fusion partner) under the appropriate conditions to induce or cause expression of the polypeptide construct. In some embodiments, the conditions appropriate for expression varies with the expression vector and the host cell chosen. In some embodiments, a wide variety of appropriate host cells are used, including, but not limited to, mammalian cells, bacteria, insect cells, and yeast. For example, a variety of cell lines that find use in the present disclosure are described in the ATCC® cell line catalog, available from the American Type Culture Collection. In some embodiments, Fc domain variants of this disclosure are expressed in a cell that is optimized not to glycosylate proteins that are expressed by such cell, either by genetic engineering of the cell line or modifications of cell culture conditions such as addition of kifunensine or by using a naturally non-glycosylating host such as a prokaryote (*E. coli*, etc.), and in some cases, modification of the glycosylation sequence in the Fc is not be needed.

Nucleic Acid Vector Construction and Host Cells

A nucleic acid sequence encoding the amino acid sequence of a polypeptide of the disclosure can be prepared by a variety of methods. These methods include, but are not limited to, oligonucleotide-mediated (or site-directed) mutagenesis and PCR mutagenesis. In some embodiments, a nucleic acid molecule encoding a polypeptide of the disclosure is obtained using standard techniques, e.g., gene synthesis. Alternatively, a nucleic acid molecule encoding a wild-type SIRPα D1 domain is mutated to include specific amino acid substitutions using standard techniques, e.g., QuikChange™ mutagenesis. In some cases, nucleic acid molecules are synthesized using a nucleotide synthesizer or PCR techniques.

In some embodiments, the nucleic acids that encode a polypeptide construct, for example a polypeptide construct comprising a SIRPα D1 domain variant (e.g., any variant provided in Tables 2, 5, and 6) and a fusion partner such as an Fc variant are incorporated into an expression vector in order to express the protein. A variety of expression vectors can be utilized for protein expression. Expression vectors can comprise self-replicating, extra-chromosomal vectors or vectors which integrate into a host genome. A vector can also include various components or elements. For example, in some embodiments, the vector components include, but are not limited to, transcriptional and translational regulatory sequences such as a promoter sequence, a ribosomal binding site, a signal sequence, transcriptional start and stop sequences, translational start and stop sequences, 3' and 5' untranslated regions (UTRs), and enhancer or activator sequences; an origin of replication; a selection marker gene; and the nucleic acid sequence encoding the polypeptide of interest, and a transcription termination sequence. In some embodiments, expression vectors comprise a protein operably linked with control or regulatory sequences, selectable markers, any fusion partners, additional elements, or any combinations thereof. The term "operably linked" means that the nucleic acid is placed into a functional relationship with another nucleic acid sequence. Generally, these expression vectors include transcriptional and translational regulatory nucleic acid operably linked to the nucleic acid encoding the Fc variant, and are typically appropriate to the host cell used to express the protein. A selection gene or marker, such as, but not limited to, an antibiotic resistance gene or fluorescent protein gene, can be used to select for host cells containing the expression vector, for example by antibiotic or fluorescence expression. Various selection genes are available.

In some embodiments, the components or elements of a vector are optimized such that expression vectors are compatible with the host cell type. Expression vectors which find use in the present disclosure include, but are not limited to, those which enable protein expression in mammalian cells, bacteria, insect cells, yeast, and in in vitro systems.

In some embodiments, mammalian cells are used as host cells to produce polypeptides of the disclosure. Examples of mammalian cell types include, but are not limited to, human embryonic kidney (HEK) (e.g., HEK293, HEK 293F), Chinese hamster ovary (CHO), HeLa, COS, PC3, Vero, MC3T3, NSO, Sp2/0, VERY, BHK, MDCK, W138, BT483, Hs578T, HTB2, BT20, T47D, NSO (a murine myeloma cell line that does not endogenously produce any immunoglobulin chains), CRL7O3O, and HsS78Bst cells. In some embodiments, *E. coli* cells are used as host cells to produce polypeptides of the disclosure. Examples of *E. coli* strains include, but are not limited to, *E. coli* 294 (ATCC® 31,446), *E. coli* λ, 1776 (ATCC® 31,537, *E. coli* BL21 (DE3) (ATCC® BAA-1025), and *E. coli* RV308 (ATCC® 31,608).

Different host cells have characteristic and specific mechanisms for the posttranslational processing and modification of protein products (e.g., glycosylation). In some embodiments, appropriate cell lines or host systems are chosen to ensure the correct modification and processing of the polypeptide expressed. Once the vectors are introduced into host cells for protein production, host cells are cultured in conventional nutrient media modified as appropriate for inducing promoters, selecting transformants, or amplifying the genes encoding the desired sequences.

In some embodiments, a polypeptide construct, for example a polypeptide construct comprising a SIRPα D1 domain variant (e.g., any variant provided in Tables 2, 5, and 6) and a fusion partner such as an Fc variant are expressed in mammalian expression systems, including systems in which the expression constructs are introduced into the mammalian cells using virus such as retrovirus or adenovirus. In some embodiments, human, mouse, rat, hamster, or primate cells are utilized. Suitable cells also include known research cells, including but not limited to Jurkat T cells, NIH3T3, CHO, COS, and 293 cells. Alternately, in some embodiments, proteins are expressed in bacterial cells. Bacterial expression systems are well known in the art, and include *Escherichia coli* (*E. coli*), *Bacillus subtilis*, *Streptococcus cremoris*, and *Streptococcus lividans*. In some cases, polypeptide constructs comprising Fc domain variants are produced in insect cells such as but not limited to Sf9 and Sf21 cells or yeast cells such as but not limited to organisms from the genera *Saccharomyces, Pichia, Kluyveromyces, Hansenula* and *Yarrowia*. In some cases, polypeptide constructs comprising Fc domain variants are expressed in vitro using cell free translation systems. In vitro translation systems derived from both prokaryotic (e.g., *E. coli*) and eukaryotic (e.g., wheat germ, rabbit reticulocytes) cells are available and, in some embodiments, chosen based on the expression levels and functional properties of the protein of interest. For example, as appreciated by those skilled in the art, in vitro translation is required for some display technologies, for example ribosome display. In addition, in some embodiments, the Fc domain variants are produced by chemical synthesis methods such as, but not limited to, liquid-phase peptide synthesis and solid-phase peptide synthesis. In the case of in vitro transcription using a non-glycosylating system such as bacterial extracts, the Fc will not be glycosylated even in presence of the natural glycosylation site and therefore inactivation of the Fc will be equivalently obtained.

In some embodiments, a polypeptide construct includes non-natural amino acids, amino acid analogues, amino acid mimetics, or any combinations thereof that function in a manner similar to the naturally occurring amino acids. Naturally encoded amino acids generally refer to the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs refers to compounds that have the same basic chemical structure as a naturally occurring amino acid, e.g., a carbon that is bound to a hydrogen, a carboxyl group, an amino group, and an R group, such as, homoserine, norleucine, methionine sulfoxide, methionine methyl sulfonium. In some embodiments, such analogs have modified R groups (such as, norleucine) or modified peptide backbones, but generally retain the same basic chemical structure as a naturally occurring amino acid.

Protein Production, Recovery, and Purification

In some embodiments, host cells used to produce polypeptides of the disclosure are grown in media suitable for culturing of the selected host cells. Examples of suitable media for mammalian host cells include Minimal Essential Medium (MEM), Dulbecco's Modified Eagle's Medium (DMEM), Expi293™ Expression Medium, DMEM with supplemented fetal bovine serum (FBS), and RPMI-1640. Examples of suitable media for bacterial host cells include Luria broth (LB) plus necessary supplements, such as a selection agent, e.g., ampicillin. In some embodiments, host cells are cultured at suitable temperatures, such as from about 20° C. to about 39° C., e.g., from about 25° C. to about 37° C., preferably 37° C., and $CO_2$ levels, such as about 5% to 10%. In some embodiments, the pH of the medium is from about pH 6.8 to pH 7.4, e.g., pH 7.0, depending mainly on the host organism. If an inducible promoter is used in the expression vector, protein expression can be induced under conditions suitable for the activation of the promoter.

In some embodiments, protein recovery involves disrupting the host cell, for example by osmotic shock, sonication, or lysis. Once the cells are disrupted, cell debris is removed by centrifugation or filtration. The proteins can then be further purified. In some embodiments, a polypeptide of the disclosure is purified by various methods of protein purification, for example, by chromatography (e.g., ion exchange chromatography, affinity chromatography, and size-exclusion column chromatography), centrifugation, differential solubility, or by any other standard technique for the purification of proteins. For example, in some embodiments, the protein is isolated and purified by appropriately selecting and combining affinity columns such as Protein A column (e.g., POROS Protein A chromatography) with chromatography columns (e.g., POROS HS-50 cation exchange chromatography), filtration, ultra-filtration, de-salting and dialysis procedures. In some embodiments, a polypeptide is conjugated to marker sequences, such as a peptide to facilitate purification. An example of a marker amino acid sequence is a hexa-histidine peptide (His6-tag (SEQ ID NO: 223)), which can bind to a nickel-functionalized agarose affinity column with micromolar affinity. As an alternative, a hemagglutinin "HA" tag, which corresponds to an epitope derived from the influenza hemagglutinin protein can be used.

In some embodiments, polypeptides of the disclosure, for example a polypeptide construct comprising a SIRPα D1 domain variant (e.g., any variant provided in Tables 2, 5, and 6) and a fusion partner such as an Fc variant are produced by the cells of a subject (e.g., a human), e.g., in the context of gene therapy, by administrating a vector such as a viral vector (e.g., a retroviral vector, adenoviral vector, poxviral vector (e.g., vaccinia viral vector, such as Modified Vaccinia Ankara (MVA)), adeno-associated viral vector, and alphaviral vector) containing a nucleic acid molecule encoding a polypeptide of the disclosure. The vector, once inside a cell of the subject (e.g., by transformation, transfection, electroporation, calcium phosphate precipitation, direct microinjection, infection, etc.) can be used for the expression of a polypeptide disclosed herein. In some cases, the polypeptide is secreted from the cell. In some embodiments, if treatment of a disease or disorder is the desired outcome, no further action is required. In some embodiments, if collection of the protein is desired, blood is collected from the subject and the protein purified from the blood by various methods.

Methods of Treating Cancer

Provided herein are methods of treating cancer in an individual (e.g., a human individual) that comprises administering to the individual an effective amount of (a) a polypeptide comprising a SIRPα D1 domain variant (e.g., a SIRPα D1 domain variant described herein) and an Fc domain variant (e.g., an Fc domain variant described herein) and (b) a chemotherapy agent (e.g., at least one chemotherapy agent, such as at least two, at least three, or at least four chemotherapy agents). In some embodiments the method further comprises administering to the individual an effective amount of a therapeutic antibody (e.g., at least one therapeutic antibody, such as at least two, at least three, or at least four therapeutic antibodies). Additionally or alternatively, in some embodiments the method further comprises administering to the individual an effective amount of an immunotherapeutic agent (e.g., at least one immunotherapeutic agent, such as at least two, at least three, or at least four immunotherapeutic agents). Additionally or alternatively, in some embodiments, the method comprises administering the polypeptide and the chemotherapy agent in combination with one or more additional modes of therapy, including, but not limited to, e.g., radiation therapy, surgery, cryoablation, and bone marrow transplant.

Combination Therapies Comprising Chemotherapy Agents, and Exemplary Chemotherapy Agents Exemplary chemotherapy agent(s) that can be used in a method of treating cancer described herein include, without limitation, e.g., methotrexate (RHEUMATREX®, Amethopterin), cyclophosphamide (CYTOXAN®), abiraterone, abemaciclib, altretamine, thalidomide (THALIDOMID®), acridine carboxamide, Actimid®, actinomycin, actinomycin-D, afatinib, 17-N-allylamino-17-demethoxygeldanamycin, alectinib, alpelisib, aminopterin, amsacrine, anlotinib, anthracycline, antineoplastic, antineoplaston, apartinib, 5-azacitidine, 6-mercaptopurine, 6-thioguanine, arabinosylcytosine, axitinib, azacitidine, azathioprine, BL22, bendamustine, binimetinib, biricodar, bleomycin, bortezomib, bosutinib, brigatinib, bryostatin, busulfan, cabozantinib, calyculin, camptothecin, capecitabine, carboplatin, carmustine, ceritinib, chlorambucil, cisplatin, cladribine, clofarabine, cobimetinib, crizotinib, cytarabine, dabrafenib, dacarbazine, dacomitinib, dasatinib, daunorubicin, dexamethasone, dichloroacetic acid, discodermolide, docetaxel, doxorubicin, encorafenib, epirubicin, entrectinib, enzalutamide, epothilone, erdafitinib, eribulin, erlotinib, estramustine, etoposide, everolimus, exatecan, exisulind, ferruginol, floxuridine, fludarabine, fluorouracil (such as 5-fluorouracil), folinic acid, fosfestrol, fotemustine, fruquintinib, ganciclovir, gefitinib, gemcitabine, gilteritinib, goserelin, hexamethylmelamine, hydroxycarbamide, hydroxyurea, IT-101, ibrutinib, icotinib, idarubicin, idelalisib, ifosfamide, imatinib, irinoimiquimod, irinotecan, irofulven, ivosidenib, ixabepilone, laniquidar, lapatinib, larotrectinib, lenalidomide, lenvatinib, lorlatinib, lomustine, lurtotecan, mafosfamide, masoprocol, mechlorethamine, melphalan, mercaptopurine, methotrexate, methylprednisolone, mitomycin, mitotane, mitoxantrone, nelarabine, neratinib, niraparib, nilotinib, nintedanib, oblimersen, olaparib, osimertinib, oxaliplatin, nedaplatin, phenanthriplatin, picoplatin, PAC-1, paclitaxel, palbociclib, pazopanib, pemetrexed, pegfilgrastim, pentostatin, pipobroman, pixantrone, plicamycin, prednisone, ponatinib, procarbazine, proteasome inhibitors (e.g., bortezomib), pyrotinib, raltitrexed, rebeccamycin, Revlimid®, regorafenib, ribociclib, rubitecan, rucaparib, ruxolitinib, SN-38, salinosporamide A, satraplatin, sirolimus, sonidegib, sorafenib, streptozocin, streptozotocin, sunitinib, swainsonine, talazoparib, tariquidar, taxane, tegafur-uracil, temsirolimus, teniposide, temozolomide, testolactone, thioTEPA, tioguanine, topotecan, trabectedin, trametinib, tretinoin, trifluridine, triplatin tetranitrate, tris(2-chloroethyl)amine, troxacitabine, uracil mustard, valrubicin, vandetanib, vemurafenib, venetoclax (ABT-199), navitoclax (ABT-263), vinblastine, vincristine, vinorelbine, vismodegib, vorinostat, ziv-aflibercept (ZALTRAP®), zosuquidar, or the like.

In some embodiments, the method of treating cancer comprises administering an agent that blocks the interaction between CD47 (e.g., hCD47) and SIRPα (e.g., hSIRPα) in combination with chemotherapeutic agent(s)s of a particular class. In some embodiments, the agent that blocks the interaction between CD47 and SIRPα is a polypeptide described herein (e.g., a fusion polypeptide comprising a SIRPα d1 domain variant and an Fc variant; a fusion polypeptide comprising a SIRPγ variant, a SIRPβ1 variant, or a SIRPβ2 variant and an Fc variant). For example, in some embodiments, the method of treating cancer comprises administering a polypeptide (e.g. fusion polypeptide) described herein in combination with an adrenal inhibitor (including, but not limited to adrenal inhibitors described herein). For example, in some embodiments, the method of treating cancer comprises administering a polypeptide described herein in combination with an anthracycline (including, but not limited to anthracyclines described herein). In some embodiments, the method of treating cancer comprises administering a polypeptide described herein in combination with an alkylating agent (including, but not limited to alkylating agents described herein). In some embodiments, the method of treating cancer comprises administering a polypeptide described herein in combination with an androgen inhibitor (including, but not limited to androgen inhibitors described herein). In some embodiments, the method of treating cancer comprises administering a polypeptide described herein in combination with an antimetabolite, e.g., a purine analog, (including, but not limited to antimetabolites, e.g., purine analogs, described herein). In some embodiments, the method of treating cancer comprises administering a polypeptide described herein in combination with an antitumor antibiotic (including, but not limited to antitumor antibiotics described herein. In some embodiments, the method of treating cancer comprises administering a polypeptide described herein in combination with a BLC-2 inhibitor (including, but not limited to BLC-2 inhibitors described herein). In some embodiments, the method of treating cancer comprises administering a polypeptide described herein in combination with a BTK inhibitor (including, but not limited to BTK inhibitors described herein. In some embodiments, the method of treating cancer comprises administering a polypeptide described herein in combination with a CDK 4/6 inhibitor (including, but not limited to CDK 4/6 inhibitors described herein). In some embodiments, the method of treating cancer comprises administering a polypeptide described herein in combination with a colony stimulating factor (including, but not limited to colony stimulating factors described herein). In some embodiments, the method of treating cancer comprises administering a polypeptide described herein in combination with a corticosteroid (including, but not limited to corticosteroids described herein). In some embodiments, the method of treating cancer comprises administering a polypeptide described herein in combination with an EGFR inhibitor (including, but not limited to EGFR inhibitors described herein). In some embodiments, the method of treating cancer comprises administering a polypeptide described herein in combination with a gonadotropin releasing hormone (GnRH) agonist (including, but not limited to GnRH agonists described herein). In some embodiments, the method of treating cancer comprises administering a polypeptide described herein in combination with a mitotic inhibitor/microtubule inhibitor (including, but not limited to mitotic inhibitors/microtubule inhibitors described herein). In some embodiments, the method of treating cancer comprises administering a polypeptide described herein in combination with an mTOR kinase inhibitor (including, but not limited to mTOR kinase inhibitors described herein). In some embodiments, the method of treating cancer comprises administering a polypeptide described herein in combination with a proteasome inhibitor (including, but not limited to proteasome inhibitors described herein). In some embodiments, the method of treating cancer comprises administering a polypeptide described herein in combination with a signal transduction inhibitor, e.g., a protein-tyrosine kinase inhibitor, a PAK4 inhibitor, a PI3K inhibitor, (including, but not limited to signal transduction inhibitors described herein). In some embodiments, the method of treating cancer comprises administering a polypeptide described herein in combination with a topoisomerase inhibitor, (including, but not limited to topoisomerase inhibitors described herein). In some embodiments, the method of treating cancer comprises administering a polypeptide described herein in combination with a tyrosine kinase inhibitor, (including, but not limited to tyrosine kinase inhibitors described herein). In some embodiments, the method of treating cancer comprises administering a polypeptide described herein in combination with a VEGF inhibitor, such as a VEGF1 inhibitor, a VEGF2 inhibitor, and/or a VEGF3 inhibitor (including, but not limited to VEGF inhibitors described herein. In some embodiments, the method of treating cancer comprises administering a polypeptide described herein in combination with an agent that modulates apoptosis, e.g., by modulating the activity of Bcl-2, Mcl1, Bcl-1x, etc., (including, but not limited to agents that modulate apoptosis, e.g., by modulating the activity of Bcl-2, Mcl1, Bcl-1x, etc., described herein). In some embodiments, the method of treating cancer comprises administering a polypeptide described herein in combination with a platinum-based agent, (including, but not limited to platinum-based agents described herein). In some embodiments, the method of treating cancer comprises administering a polypeptide described herein in combination with an inhibitor of NTRK1, NTRK2, and/or NTRK3, an ALK inhibitor, a ROS inhibitor, a FLT3 inhibitor, a BRAF inhibitor, an inhibitor of MEK1 and/or MEK2, an inhibitor of HER2, HER3, and/or HER 4, an inhibitor of RET/PTC, an inhibitor of BCR-ABL, a c-KIT inhibitor, an inhibitor of PDGFR-alpha and/or PDGFR-beta, an inhibitor of FGFR1, FGFR2, FGFR3, and/or FGFR4, an Smoothened inhibitor and/or an inhibitor of PARP1, PARP2, and/or PARP3 (including, but not limited to inhibitors described herein). In some embodiments, the inhibitor is an antisense polynucleotide (such as an siRNA or an RNAi). In some embodiments, the inhibitor is a small molecule inhibitor, as described in further detail below.

In some embodiments the chemotherapeutic agent is a small molecule anti-cancer agent (such as a small molecule inhibitor In some embodiments, the method of treating cancer comprises administering a polypeptide described herein in combination with a small molecule inhibitor of VEGFR and/or PDGFR, a small molecule EGFR inhibitor, a small molecule ALK inhibitor, a small molecule CDK4/6 inhibitor, a small molecule PARP inhibitor, a small molecule PAK4 inhibitor, a small molecule mTOR inhibitor, a small molecule KRAS inhibitor, a small molecule TRK inhibitor, a small molecule BCL2 inhibitor, a small molecule B-raf inhibitor, a small molecule IDH inhibitor, a small molecule PI3K inhibitor, a small molecule DDR (DNA damage response) inhibitor, or a small molecule hypomethylation agent. In other cases, the targeted small molecule modulates a cellular signaling pathway of the cell expressing CD47, e.g., an IDO/TDO inhibitor, AhR inhibitor, arginase inhibitor, A2a R inhibitor, TLR agonists, STING agonist, or Rig-1 agonist.

In some embodiments, the method of treating cancer comprises administering a polypeptide described herein (e.g., a fusion polypeptide comprising a SIRPα d1 domain variant and an Fc variant) in combination with at least one, at least two, at least three, or at least four chemotherapeutic agents. In some embodiments where two or more chemotherapeutic agents are administered, the two or more chemotherapeutic agents are from different classes (as described above) and/or exert their anti-cancer effects via different mechanisms of action.

Further details regarding exemplary pharmaceutical compositions and preparations, exemplary dosages, and exemplary routes of administration for the fusion polypeptides described herein are provided in WO 2017/027422 and U.S. Pat. No. 10,259,859, the contents of each of which are incorporated by reference entireties.

Combination Therapies Comprising Therapeutic Antibodies, and Exemplary Therapeutic Antibodies In some embodiments a method of treating cancer provided herein comprises administering to the individual an effective amount of a therapeutic antibody (e.g., at least one therapeutic antibody, such as at least two, at least three, or at least four therapeutic antibodies), i.e., in combination with agent that blocks the interaction between CD47 (e.g., hCD47) and SIRPα (e.g., a fusion polypeptide described herein) and a chemotherapeutic agent described herein (e.g., at least one chemotherapeutic agent, such as at least two, at least three, or at least four chemotherapeutic agents). In some embodiments, the therapeutic antibody is conjugated to a drug (i.e., an antibody-drug conjugate, or "ADC").

Exemplary therapeutic antibodies (e.g., therapeutic monoclonal antibodies) for use in a method herein include, but are not limited to, e.g., 3F8, 8H9, Abagovomab, Abciximab, Abituzumab, Abrilumab, Actoxumab, Adalimumab, Adecatumumab, Aducanumab, Afelimomab, Afutuzumab, Alacizumab pegol, ALD518, Alemtuzumab, Alirocumab, Altumomab pentetate, Amatuximab, Anatumomab mafenatox, Anetumab ravtansine, Anifrolumab, Anrukinzumab (IMA-638), Apolizumab, Arcitumomab, Ascrinvacumab, Aselizumab, Atezolizumab, Atinumab, Atlizumab (tocilizumab), Atorolimumab, Avelumab, Bapineuzumab, Basiliximab, Bavituximab, Bectumomab, Begelomab, Belimumab, Benralizumab, Bertilimumab, Besilesomab, Bevacizumab, Bezlotoxumab, Biciromab, Bimagrumab, Bimekizumab, Bivatuzumab mertansine, Blinatumomab, Blosozumab, Bococizumab, Brentuximab vedotin, Briakinumab, Brodalumab, Brolucizumab, Brontictuzumab, Cabiralizumab (FPA008), Camrelizumab, Canakinumab, Cantuzumab mertansine, Cantuzumab ravtansine, Caplacizumab, Capromab pendetide, Carlumab, Catumaxomab, cBR96-doxorubicin immunoconjugate, CC49, Cedelizumab, Certolizumab pegol, Cetuximab, Ch.14.18, Citatuzumab bogatox, Cixutumumab, Clazakizumab, Clenoliximab, Clivatuzumab tetraxetan, Codrituzumab, Coltuximab ravtansine, Conatumumab, Concizumab, Crenezumab, CR6261, Dacetuzumab, Daclizumab, Dalotuzumab, Dapirolizumab pegol, Daratumumab, Dectrekumab, Demcizumab, Denintuzumab mafodotin, Denosumab, Derlotuximab biotin, Detumomab, Dinutuximab, Diridavumab, Dorlimomab aritox, Drozitumab, Duligotumab, Dupilumab, Durvalumab, Dusigitumab, Ecromeximab, Eculizumab, Edobacomab, Edrecolomab, Efalizumab, Efungumab, Eldelumab, Elgemtumab, Elotuzumab, Elsilimomab, Emactuzumab (RG7155), Emibetuzumab, Enavatuzumab, Enfortumab vedotin, Enlimomab pegol, Enoblituzumab, Enokizumab, Enoticumab, Ensituximab, Epitumomab cituxetan, Epratuzumab, Erlizumab, Ertumaxomab, Etaracizumab, Etrolizumab, Evinacumab, Evolocumab, Exbivirumab, Fanolesomab, Faralimomab, Farletuzumab, Fasinumab, FBTA05, Felvizumab, Fezakinumab, Ficlatuzumab, Figitumumab, Firivumab, Flanvotumab, Fletikumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Idarucizumab, Igovomab, IMAB362, Imalumab, Imciromab, Imgatuzumab, Inclacumab, Indatuximab ravtansine, Indusatumab vedotin, Infliximab, Intetumumab, Inolimomab, Inotuzumab ozogamicin, Ipilimumab, Iratumumab, Isatuximab, Itolizumab, Ixekizumab, Keliximab, Labetuzumab, Lambrolizumab, Lampalizumab, Lebrikizumab, Lemalesomab, Lenzilumab, Lerdelimumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, MSB0010718C (avelumab), Mapatumumab, Margetuximab, Maslimomab, Mavrilimumab, Matuzumab, MEDI6469, MEDI0680, MEDI6383, Mepolizumab, Metelimumab, Milatuzumab, Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Narnatumab, Natalizumab, Nebacumab, Necitumumab, Nemolizumab, Nerelimomab, Nesvacumab, Nimotuzumab, Nivolumab, Nofetumomab merpentan, Obiltoxaximab, Obinutuzumab, Ocaratuzumab, Ocrelizumab, Odulimomab, Ofatumumab, Olaratumab, Olokizumab, Omalizumab, Onartuzumab, Ontuxizumab, Opicinumab, Oportuzumab monatox, Oregovomab, Orticumab, Otelixizumab, Otlertuzumab, Oxelumab, Ozanezumab, Ozoralizumab, Pagibaximab, Palivizumab, Panitumumab, Pankomab, Panobacumab, Parsatuzumab, Pascolizumab, Pasotuxizumab, Pateclizumab, Patritumab, Pembrolizumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, PRO 140, Quilizumab, Racotumomab, Radretumab, Rafivirumab, Ralpancizumab, Ramucirumab, Ranibizumab, Raxibacumab, Refanezumab, Regavirumab, Reslizumab, Rilotumumab, Rinucumab, Rituximab, Robatumumab, Roledumab, Romosozumab, Rontalizumab, Rovelizumab, Ruplizumab, Sacituzumab govitecan, Samalizumab, SAR650984 (Isatuximab) Sarilumab, Satumomab pendetide, Secukinumab, Seribantumab, Setoxaximab, Sevirumab, Sibrotuzumab, SGN-CD19A, SGN-CD33A, Sifalimumab, Siltuximab, Simtuzumab, Sintilimab, Siplizumab, Sirukumab, Sofituzumab vedotin, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tarextumab, Tefibazumab, Telimomab aritox, Tenatumomab, Teneliximab, Teplizumab, Teprotumumab, Tesidolumab, TGN1412, Ticilimumab (tremelimumab), Tildrakizumab, Tigatuzumab, TNX-650, Tocilizumab (atlizumab), Toralizumab, Toripalimab, Tosatoxumab, Tositumomab, Tovetumab, Tralokinumab, Trastuzumab, trastuzumab-emtansine, TRBS07, Tregalizumab, Tremelimumab, Tucotuzumab celmoleukin, Tuvirumab, Ublituximab, Ulocuplumab, Urelumab, Urtoxazumab, Ustekinumab, Utomilumab (PF-05082566), Vandortuzumab vedotin, Vantictumab, Vanucizumab, Vapaliximab, Varlilumab, Vatelizumab, Vedolizumab, Veltuzumab, Vepalimomab, Vesencumab, Visilizumab, Volociximab, Vonlerolizumab (RG7888), Vorsetuzumab mafodotin, Votumumab, Zalutumumab, Zanolimumab, Zatuximab, Ziralimumab, or Zolimomab aritox, including biosimilars of any of the preceding therapeutic antibodies.

Other exemplary therapeutic antibodies (e.g., therapeutic monoclonal antibodies) that can be used in a method herein is an antibody include, but are not limited to, e.g., an anti-CD20 antibody, an anti-EGFR antibody, an anti-Her2/Neu (ERBB2) antibody, an anti-EPCAM antibody, an anti-GL2 antibody, anti-GD2, anti-GD3, anti-CD2, anti-CD3, anti-CD4, anti-CD8, anti-CD I 9, anti-CD22, anti-CD30, anti-CD33, anti-CD39, anti-CD45, anti-CD47, anti-CD52, anti-CD56, anti-CD70, anti-CD73, anti-CD117, an anti-SIRPα antibody, an anti-LILRB1, an anti-LILRB2, an anti-LILRB4 antibody, an anti-PD-1 antibody (e.g., an anti PD-1 antagonist antibody), an anti-PD-L1 antibody (e.g., an anti PD-L1 antagonist antibody), an anti-PD-L2 antibody, or any antibody designed to bind to a tumor cell, a virally- or bacterially-infected cell, immune cell, or healthy normal cell, or to a cytokine, chemokine, or hormone of any kind.

In some embodiments, the therapeutic antibody used in a method herein is an antibody that binds to, e.g., CS1/SLAMF7, Trop-2, VWF, vimentin, VEGFR2, VEGFR-1, VEGF, VEGF-A, TYRP1 (glycoprotein 75), TWEAK receptor, tumor specific glycosylation of MUC1, tumor antigen CTAA16.88, TRAIL-R2, TRAIL-R1, TNF-alpha, TGF-beta, TGF beta 2, TGF beta 1, TFPI, tenascin C, TEM1, TAG-72, T-cell receptor, STEAP1, sphingosine-1-phosphate, SOST, SLAMF7, BCL-2, selectin P, SDC1, sclerostin, RTN4, RON, Rhesus factor, RHD, respiratory syncytial virus, RANKL, rabies virus glycoprotein, platelet-derived growth factor receptor beta, phosphatidylserine, phosphate-sodium co-transporter, PDGF-R alpha, PDCD1, PD-1, PD-L1, PCSK9, oxLDL, OX-40, NRP1, Notch receptor 4, Notch receptor 3, Notch receptor 2, Notch receptor 1, NOGO-A, NGF, neural apoptosis-regulated proteinase 1, NCA-90 (granulocyte antigen), NARP-1, N-glycolylneuraminic acid, myostatin, myelin-associated glycoprotein, mucin CanAg, MUC1, MSLN, MS4A1, MIF, mesothelin, MCP-1, LTA, LOXL2, lipoteichoic acid, LINGO-1, LFA-1 (CD11a), Lewis-Y antigen, L-selectin (CD62L), KIR2D, ITGB2 (CD18), ITGA2, interferon alpha/beta receptor, interferon receptor, interferon gamma-induced protein, integrin αvβ3, integrin αIIβ3, integrin α7β7, integrin α5β1, integrin α4β7, integrin α4, insulin-like growth factor I receptor, Influenza A hemagglutinin, ILGF2, IL9, IL6, IL4, IL3 IRA, IL23, ILI 7A, IL-6 receptor, IL-6, IL-S, IL-4, IL-23, IL-22, IL-I, IL-I 7A, IL-I 7, IL-13, IL-I 2, IL-I, IL 20, IGHE, IgG4, IGF-I, IGF-I receptor, IgE Fc region, IFN-gamma, IFN-alpha, ICAM-1 (CD54), human TNF, human scatter factor receptor kinase, Hsp90, HNGF, HLA-DR, HIV-1, histone complex, HHGFR, HGF, HER3, HER2, HER2/neu, HER1, hepatitis B surface antigen, hemagglutinin, GUCY2C, GPNMB, GMCSF receptor alpha-chain, glypican 3, GD3 ganglioside, GD2, ganglioside GD2, Frizzled receptor, folate receptor 1, folate hydrolase, fibronectin extra domain-B, fibrin II, beta chain, FAP, F protein of respiratory syncytial virus, ERBB3, episialin, EpCAM, endotoxin, EGFR, EGFL7, *E. coli* shiga toxin type-2, *E. coli* shiga toxin type-I, DRS, DPP4, DLL4, dabigatran, cytomegalovirus glycoprotein B, CTLA-4, CSF2, CSF1R, clumping factor A, CLDN18.2, ch4DS, CFD, CEA-related antigen, CEA, CD80, CD79B, CD74, CD73, CD70, CD6, CD56, CD52, CD51, CD5, CD44 v6, CD41, CD40 ligand, CD40, CD4, CD39, CD38, CD37, CD33, CD30 (TNFRSF8), CD123, CD138, CD3 epsilon, CD3, CD28, CD274, CD27, CD2S (a chain of IL-2 receptor), CD23 (IgE receptor), CD221, CD22, CD200, CD20, CD2, CD19, CD137, CD154, CD152, CD15, CD147 (basigin), CD140a, CD125, CD11, CD-18, CCR5, CCR4, CCL11 (eotaxin-I), cardiac myosin, carbonic anhydrase 9 (CA-IX), *Canis lupus familiaris* IL31, CA-125, C5, C242 antigen, C—X—C chemokine receptor type 4, beta-amyloid, BAFF, B7-H3, B-lymphoma cell, AOC3 (VAP-I), anthrax toxin, protective antigen, angiopoietin 3, angiopoietin 2, alpha-fetoprotein, AGS-22M6, adenocarcinoma antigen, ACVR2B, activin receptor-like kinase I, 5T4, SAC, 4-IBB or 1-40-beta-amyloid.

In some embodiments, the therapeutic antibody used in a method herein binds to an antigen expressed by a cancer cell (e.g., expressed on the surface of a cancer cell). Exemplary antigens expressed by cancers are known in the art and include, without limitation, e.g., CD19, CD20, CD22, CD30, CD33, CD38, CD52, CD56, CD70, CD74, CD79b, CD123, CD138, CS1/SLAMF7, Trop-2, 5T4, BCMA, Mucin 1, Mucin 16, PTK7, PD-L1, STEAP1, Endothelin B Receptor, mesothelin, EGFRvIII, ENPP3, SLC44A4, GNMB, nectin 4, NaPi2b, LIV-1A, Guanylyl cyclase C, DLL3, EGFR, HER2, VEGF, VEGFR, integrin αVβ3, integrin α5β1, MET, IGF1R, TRAILR1, TRAILR2, RANKL, FAP, Tenascin, Le$^y$, EpCAM, CEA, gpA33, PSMA, TAG72, a mucin, CAIX, EPHA3, folate receptor α, GD2, GD3, and an MHC/peptide complex comprising a peptide from NY-ESO-1/LAGE, SSX-2, a MAGE family protein, MAGE-A3, gp100/pmel17, Melan-A/MART1, gp75/TRP1, tyrosinase, TRP2, CEA, PSA, TAG-72, immature laminin receptor, MOK/RAGE-1, WT-1, SAP-1, BING-4, EpCAM, MUC1, PRAME, survivin, BRCA1, BRCA2, CDK4, CML66, MART-2, p53, Ras, β-catenin, HPV E6, or HPV E7. For example, in some embodiments, an polypeptide described herein is administered in combination with a chemotherapeutic agent (e.g., at least one chemotherapeutic agent) and a monoclonal antibody that binds CD123 (also known as IL-3 receptor alpha), such as talacotuzumab (also known as CSL362 and JNJ-56022473).

In some embodiments, the therapeutic antibody (e.g., therapeutic monoclonal antibody) used in a method herein is an antibody that binds an antigen expressed by an NK cell. Exemplary antigens expressed by an NK cell include, without limitation, NKR-P1A (KLRB1), CD94 (NKG2A), KLRG1, KIR2DL5A, KIR2DL5B, KIR2DL1, KIR2DL2, KIR2DL3, KIR2DS2, KIR2DS3, KIR2DS4, KIR2DS5, KIR3DS1, KIR2DS1, CD94 (NKG2C/E), NKG2D, CD160 (BY55), CD16 (FcγRIIIA), NKp46 (NCR1), NKp30 (NCR3), NKp44 (NCR2), DNAM1 (CD226), CRTAM, CD27, NTB-A (SLAMF6), PSGL1, CD96 (Tactile), CD100

(SEMA4D), NKp80 (KLRF1, CLECSC), SLAMF7 (CRACC, CS1, CD319), and CD244 (2B4, SLAMF4).

Combination Therapies Comprising Immunotherapeutic Agents, and Exemplary Immunotherapeutic Agents In some embodiments a method of treating cancer provided herein comprises administering to the individual an effective amount of an immunotherapeutic agent (e.g., at least one immunotherapeutic agent, such as at least two, at least three, or at least four immunotherapeutic agents), i.e., in combination with an agent that blocks the interaction between CD47 (e.g., hCD47) and SIRPα (e.g., a polypeptide described herein) and a chemotherapeutic agent described herein (e.g., at least one chemotherapeutic agent, such as at least two, at least three, or at least four chemotherapeutic agents).

In some embodiments, an immunotherapeutic agent refers to any therapeutic that targets the immune system and promotes a therapeutic redirection of the immune system, such as a modulator of a costimulatory pathway, cancer vaccine, recombinantly modified immune cell, etc. Exemplary and non-limiting immunotherapeutic agents are described infra. In some embodiments, the immunotherapeutic agent is or comprises an antibody. Exemplary targets of immunotherapeutic antibodies are known in the art and include, without limitation, BDCA2, BDCA4, ILT7, LILRB1, LILRB2, LILRB3, LILRB4, LILRB5, Siglec-3, Siglec-7, Siglec-9, Siglec-10, Siglec-15, FGL-1, CD200, CD200R, CSF-1R, CD24, CD40, CD40L, CD163, CD206, DEC205, CD47, CD123, arginase, IDO, TDO, AhR, EP2, COX-2, CCR2, CCR-7, CXCR1, CX3CR1, CXCR2, CXCR3, CXCR4, CXCR7, TGF-β RI, TGF-β MI, c-Kit, CD244, L-selectin/CD62L, CD11b, CD11c, CD68, 41BB, CTLA4, PD1, PD-L1, PD-L2, TIM-3, BTLA, VISTA, LAG-3, CD28, OX40, GITR, CD137, CD27, HVEM, CCR4, CD25, CD103, KIrg1, Nrp1, CD278, Gpr83, TIGIT, CD154, CD160, TNFR2, PVRIG, DNAM, and ICOS.

Immunotherapeutic agents that are approved or in late-stage clinical testing include, without limitation, ipilimumab, pembrolizumab, nivolumab, atezolizumab, avelumab, durvalumab, and the like. In certain embodiments, the agent that blocks the interaction between CD47 and SIRPα (such as a polypeptide described herein) is administered in combination with an inhibitor of the PD-L1/PD-1 pathway, e.g., an antibody, a small molecule, or polypeptide that blocks the interaction between PD-L1 and PD-1 (e.g., by binding to PD-1 or PD-L1). In some embodiments, the inhibitor of the PD-L1/PD-1 pathway is an antisense polynucleotide. In some embodiments, the inhibitor of the PD-L1/PD-1 pathway is an anti-PD-L1 or anti-PD-1 antagonist antibody (e.g., an anti-PD-1 or anti-PD-L1 antagonist antibody described elsewhere herein). As demonstrated herein, combined administration of an agent that blocks the interaction between CD47 and SIRPα (such as a polypeptide described herein) and an inhibitor of the PD-L1/PD-1 pathway can result in synergistic anti-tumor activity. In some embodiments, the immunotherapeutic agent is or comprises a vaccine, oncolytic virus, adoptive cell therapy, cytokine, or small molecule immunotherapeutic agent. Examples of such immunotherapeutic agents are known in the art. For example, adoptive cell therapies and therapeutics can include without limitation chimeric antigen receptor T-cell therapy (CAR-T), tumor infiltrating lymphocytes (TILs), TCR engineered T cells, TCR engineered NK cell, and macrophage cell products. Vaccines can include without limitation polynucleotide vaccines, polypeptide vaccines, or cell-based (e.g., tumor or dendritic cell-based) vaccines. Various cytokines useful for the treatment of cancer are known and include without limitation IL-2, IL-15, IL-7, IL-10, IL-12, IL21, TNFa, IFNs, GM-CSF, and engineered cytokine mutants. Small molecule immunotherapeutic agents can include without limitation IDO/TDO inhibitors, AhR inhibitors, arginase inhibitors, A2a R inhibitors, TLR agonists, STING agonists, and Rig-1 agonists.

In some embodiments where the agent that blocks the interaction between CD47 and SIRPα (such as a polypeptide described herein) and the chemotherapeutic agent (e.g., at least one chemotherapeutic agent) are administered in combination with further agent(s) described herein (e.g., therapeutic antibodies, small molecule inhibitors, immunotherapeutic agents, etc.), the further agent(s) are from different classes and/or exert their anti-cancer effects via different mechanisms of action. For example, in some embodiments, the method of treating cancer comprises administering an agent that blocks the interaction between CD47 and SIRPα (such as a polypeptide described herein) in combination with a chemotherapeutic agent (including, but not limited to those described herein) and a therapeutic antibody (including, but not limited to those described herein, e.g., an anti-HER2 antibody). In some embodiments, the agent that blocks the interaction between CD47 and SIRPα (such as a polypeptide described herein) is administered in combination with a chemotherapeutic agent (including, but not limited to those described herein) and a small molecule inhibitor (including, but not limited to those described herein). Other combinations are also contemplated.

In some embodiments, the agent that blocks the interaction between CD47 and SIRPα (such as a polypeptide described herein) is administered in combination with one or more agents including, without limitation, e.g., anti-diarrheal agents, anti-emetic agents, analgesics, opioids and/or non-steroidal anti-inflammatory agent.

Combination Therapies That Comprise Additional Mode(s) of Therapy

In some embodiments, the agent that blocks the interaction between CD47 and SIRPα (such as a polypeptide described herein) is administered in combination with at least one chemotherapy agent and one or more additional modes of therapy. In some embodiments, the one or more additional modes therapy comprises radiotherapy (e.g., gamma-rays, X-rays, and/or the directed delivery of radioisotopes to tumor cells, microwaves, UV radiation, or gene therapy. For example, therapeutic genes for gene therapy include, but are not limited to, an antisense version of an inducer of cellular proliferation (oncogene), an inhibitor of cellular proliferation (tumor suppressor), or an inducer of programmed cell death (pro-apoptotic gene). In some embodiments, any one or more of the combination therapies described herein are administered in conjunction with a surgery (e.g., resection).

Exemplary Therapeutic Combinations

In some embodiments, the method of treating cancer comprises administering to an individual in need thereof an agent that blocks the interaction between CD47 (e.g., hCD47) and SIRPα (e.g., hSIRPα) in combination with trastuzumab and one or agents selected from: lenalidomide, ibrutinib, palbociclib, enzalutamide, pemetrexed, nilotinib, abiraterone, imatinib, palbociclib, erlotinib, bortezomib, enzalutamide, cyclophosphamide, carboplatin, cisplatin, oxaliplatin, 5-fluorouracil, 6-mercaptopurine, cytarabine, gemcitabine, methotrexate, bleomycin, daunorubicin, doxorubicin, docetaxel, estramustine, paclitaxel, vinblastine, etoposide, irinotecan, teniposide, topotecan, prednisone, methylprednisolone, and dexamethasone. In some embodiments, the agent that blocks the interaction between CD47 and SIRPα is a polypeptide described herein (e.g., a fusion polypeptide comprising a SIRPα D1 domain variant and an Fc variant).

In some embodiments, the method of treating cancer comprises administering an agent that blocks the interaction between CD47 (e.g., hCD47) and SIRPα (e.g., hSIRPα) in combination with trastuzumab, ramucirumab, and paclitaxel. In some embodiments, the agent that blocks the interaction between CD47 and SIRPα is a polypeptide described herein (e.g., a fusion polypeptide comprising a SIRPα D1 domain variant and an Fc variant).

In some embodiments, provided is a method of treating cancer in an individual, comprising administering to the individual an effective amount of: (a) a polypeptide comprising a SIRPα D1 domain variant and an Fc domain variant, (b) an anti-HER2 antibody, (c) an anti-VEGF2 antibody, and (d) paclitaxel; wherein the SIRPα D1 domain variant comprises the amino acid sequence of SEQ ID NO: 81 or SEQ ID NO: 85; wherein the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat, wherein the cancer is gastric cancer or gastroesophageal junction (GEJ) cancer, and wherein the individual has received at least one prior therapy for the gastric or the GEJ cancer. In some embodiments, the polypeptide (e.g., fusion polypeptide comprises the amino acid sequence of SEQ ID NO: 136 or SEQ ID NO: 135. In some embodiments, the polypeptide (e.g., fusion polypeptide) forms a dimer (e.g., homodimer). In some embodiments, the gastric cancer or GEJ cancer is a HER2-overexpressing (e.g., HER2$^+$) gastric cancer or a HER2-overexpressing GEJ cancer. In some embodiments, the individual has received prior therapy with an anti-HER2 antibody, with an anti-HER2 antibody and a fluoropyrimidine, or with an anti HER2 antibody and a platinum-based chemotherapy agent. In some embodiments, the individual progressed (e.g., experienced disease progression) during or after prior therapy with trastuzumab and fluoropyrimidine-containing chemotherapy (e.g., fluorouracil). In some embodiments, the individual progressed (e.g., experienced disease progression) during or after prior therapy with trastuzumab and platinum-containing chemotherapy. In some embodiments, the individual progressed (e.g., experienced disease progression) during or after prior therapy with trastuzumab, fluoropyrimidine-containing chemotherapy (e.g., fluorouracil), and platinum-containing chemotherapy. In some embodiments, the individual has not received prior therapy with an anti-CD47 agent or an anti-SIRPα agent. In some embodiments, the anti-HER2 antibody is trastuzumab. In some embodiments, the anti-VEGF antibody is ramucirumab. In some embodiments, the polypeptide comprising a SIRPα D1 domain variant and an Fc domain variant is administered to the individual at a dosage and frequency described below. In some embodiments, the anti-HER2 antibody (e.g., trastuzumab) is administered to the individual at a dosage and frequency described below. In some embodiments the anti-HER2 antibody (e.g., trastuzumab) is administered to the individual according to the dosage and frequency indicated in the prescribing label. For example, for the United States, details regarding the dosage and frequency of administration for trastuzumab can be found at www(dot)accessdata(dot)fda(dot)gov/drugsatfda_docs/label/2010/103792 s52501b1(dot)pdf.

In some embodiments, provided is a method of treating cancer in an individual, comprising administering to the individual a polypeptide comprising a SIRPα D1 domain variant and an Fc domain variant administered at a dose of about 10 to about 60 mg/kg once a week (qw). In some embodiments, the polypeptide comprising the SIRPα D1 domain variant and the Fc domain variant is administered at a dose of about 10 to about 60 mg/kg once every two weeks (q2w). In some embodiments, the polypeptide comprising the SIRPα D1 domain variant and the Fc domain variant is administered at a dose of 10 mg/kg once every week. In some embodiments, the polypeptide comprising the SIRPα D1 domain variant and the Fc domain variant is administered at a dose of 15 mg/kg once every week. In some embodiments, the polypeptide comprising the SIRPα D1 domain variant and the Fc domain variant is administered at a dose of 20 mg/kg once every week. In some embodiments, the polypeptide comprising the SIRPα D1 domain variant and the Fc domain variant is administered at a dose of 30 mg/kg once every week. In some embodiments, the polypeptide comprising the SIRPα D1 domain variant and the Fc domain variant is administered at a dose of 40 mg/kg once every week. In some embodiments, the polypeptide comprising the SIRPα D1 domain variant and the Fc domain variant is administered at a dose of 50 mg/kg once every week. In some embodiments, the polypeptide comprising the SIRPα D1 domain variant and the Fc domain variant is administered at a dose of 60 mg/kg once every week. In some embodiments, the polypeptide comprising the SIRPα D1 domain variant and the Fc domain variant is administered at a dose of 10 mg/kg once every 2 weeks (q2w). In some embodiments, the polypeptide comprising the SIRPα D1 domain variant and the Fc domain variant is administered at a dose of 15 mg/kg once every 2 weeks (q2w). In some embodiments, the polypeptide comprising the SIRPα D1 domain variant and the Fc domain variant is administered at a dose of 20 mg/kg once every 2 weeks (q2w). In some embodiments, the polypeptide comprising the SIRPα D1 domain variant and the Fc domain variant is administered at a dose of 30 mg/kg once every 2 weeks (q2w). In some embodiments, the polypeptide comprising the SIRPα D1 domain variant and the Fc domain variant is administered at a dose of 40 mg/kg once every 2 weeks (q2w). In some embodiments, the polypeptide comprising the SIRPα D1 domain variant and the Fc domain variant is administered at a dose of 50 mg/kg once every 2 weeks (q2w). In some embodiments, the polypeptide comprising the SIRPα D1 domain variant and the Fc domain variant is administered at a dose of 60 mg/kg once every 2 weeks (q2w). In some embodiments, the polypeptide comprising a SIRPα D1 domain variant and an Fc domain variant comprises a SIRPα variant that comprises SEQ ID NO: 81 or SEQ ID NO: 85 and an the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat. In some embodiments, the polypeptide (e.g., fusion polypeptide comprises the amino acid sequence of SEQ ID NO: 136 or SEQ ID NO: 135. In some embodiments, the polypeptide (e.g., fusion polypeptide) forms a dimer (e.g., homodimer). In some embodiments, the polypeptide comprising a SIRPα D1 domain variant and an Fc domain variant is administered to the individual in combination with (a) an anti-HER2 antibody, (b) an anti-VEGF2 antibody, and (c) paclitaxel. In some embodiments, the cancer is gastric cancer or gastroesophageal junction (GEJ) cancer. In some embodiments, the individual has received at least one prior therapy for the gastric or the GEJ cancer. In some embodiments, the gastric cancer or GEJ cancer is a HER2-overexpressing (e.g., HER2$^+$) gastric cancer or a HER2-overexpressing GEJ cancer. In some embodiments, the individual has received prior therapy with an anti-HER2 antibody, with an anti-HER2 antibody and a fluoropyrimidine, or with an anti HER2 antibody and a platinum-based chemotherapy agent. In some embodiments, the individual progressed (e.g., experienced disease progression) during or after prior therapy with an anti-HER2 antibody (e.g., trastuzumab) and fluoropyrimidine-containing chemotherapy (e.g., fluorouracil). In some embodiments, the individual progressed (e.g., experienced disease progression) during or after prior therapy with an anti-HER2 antibody (e.g., trastuzumab) and platinum-containing chemotherapy. In some embodiments, the individual progressed (e.g., experienced disease progression) during or after prior therapy with an anti-HER2 antibody (e.g., trastuzumab), fluoropyrimidine-containing chemotherapy (e.g., fluorouracil), and platinum-containing chemotherapy. In some embodiments, the individual has not received prior therapy with an anti-CD47 agent or an anti-SIRPα agent. In some embodiments, the anti-HER2 antibody is trastuzumab. In some embodiments, the anti-VEGF antibody is ramucirumab. In some embodiments the anti-VEGFR-2 antibody (e.g., ramucirumab) is administered to the individual according to the dosage and frequency indicated in the prescribing label. For example, for the United States, details regarding the dosage and frequency of administration for ramucirumab can be found at www(dot)accessdata(dot)fda(dot)gov/drugsatfda_docs/label/2020/125477 s0341b1(dot)pdf. In some embodiments, the anti-HER2 antibody (e.g., trastuzumab) is administered to the individual at a dosage and frequency described below. In some embodiments the anti-HER2 antibody (e.g., trastuzumab) is administered to the individual according to the dosage and frequency indicated in the prescribing label. For example, for the United States, details regarding the dosage and frequency of administration for trastuzumab can be found at www(dot)accessdata(dot)fda(dot)gov/drugsatfda_docs/label/2010/103792 s52501b1(dot)pdf.

In some embodiments, provided is a method of treating cancer in an individual, comprising administering to the individual a polypeptide comprising a SIRPα D1 domain variant and an Fc domain variant administered at a dose of 10 mg/kg once every week in combination with trastuzumab at an initial dose of 8 mg/kg followed by 6 mg/kg once every three weeks (e.g., an initial dose of 8 mg/kg during week 1 followed by a 6 mg/kg dose given during week two, and a 6 mg/kg dose once every three weeks after the first 6 mg/kg dose). In some embodiments, provided is a method of treating cancer in an individual, comprising administering to the individual a polypeptide comprising a SIRPα D1 domain variant and an Fc domain variant administered at a dose of 10 mg/kg once every week in combination with trastuzumab at an initial dose of 8 mg/kg followed by 6 mg/kg once every three weeks and ramucirumab at a dose of 8 mg/kg once every other week (e.g., on Days 1 and 15 during each 28 day cycle). In some embodiments, provided is a method of treating cancer in an individual, comprising administering to the individual a polypeptide comprising a SIRPα D1 domain variant and an Fc domain variant administered at a dose of 10 mg/kg once every week in combination with trastuzumab at an initial dose of 8 mg/kg followed by 6 mg/kg once every three weeks, ramucirumab at a dose of 8 mg/kg once every other week (e.g., on Days 1 and 15 during each 28 day cycle), and paclitaxel at a dose of 80 mg/m$^2$ once a week for three weeks during every 4 week cycle (e.g., on Days 1, 8, and 15 during every 28 day cycle). In some embodiments, the polypeptide comprising a SIRPα D1 domain variant and an Fc domain variant comprises a SIRPα variant that comprises SEQ ID NO: 81 or SEQ ID NO: 85 and an the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat. In some embodiments, the polypeptide (e.g., fusion polypeptide comprises the amino acid sequence of SEQ ID NO: 136 or SEQ ID NO: 135. In some embodiments, the polypeptide (e.g., fusion polypeptide) forms a dimer (e.g., homodimer). In some embodiments, the cancer is gastric cancer or gastroesophageal junction (GEJ) cancer. In some embodiments, the individual has received at least one prior therapy for the gastric or the GEJ cancer. In some embodiments, the gastric cancer or GEJ cancer is a HER2-overexpressing (e.g., HER2$^+$) gastric cancer or a HER2-overexpressing GEJ cancer. In some embodiments, the individual has received prior therapy with an anti-HER2 antibody, with an anti-HER2 antibody and a fluoropyrimidine, or with an anti HER2 antibody and a platinum-based chemotherapy agent. In some embodiments, the individual progressed (e.g., experienced disease progression) during or after prior therapy with an anti-HER2 antibody (e.g., trastuzumab) and fluoropyrimidine-containing chemotherapy (e.g., fluorouracil). In some embodiments, the individual progressed (e.g., experienced disease progression) during or after prior therapy with an anti-HER2 antibody (e.g., trastuzumab) and platinum-containing chemotherapy. In some embodiments, the individual progressed (e.g., experienced disease progression) during or after prior therapy with an anti-HER2 antibody (e.g., trastuzumab), fluoropyrimidine-containing chemotherapy (e.g., fluorouracil), and platinum-containing chemotherapy. In some embodiments, the individual has not received prior therapy with an anti-CD47 agent or an anti-SIRPα agent.

In some embodiments, provided is a method of treating cancer in an individual, comprising administering to the individual a polypeptide comprising a SIRPα D1 domain variant and an Fc domain variant administered at a dose of 15 mg/kg once every week in combination with trastuzumab at an initial dose of 8 mg/kg followed by 6 mg/kg once every three weeks (e.g., an initial dose of 8 mg/kg during week 1 followed by a 6 mg/kg dose given during week two, and a 6 mg/kg dose once every three weeks after the first 6 mg/kg dose). In some embodiments, provided is a method of treating cancer in an individual, comprising administering to the individual a polypeptide comprising a SIRPα D1 domain variant and an Fc domain variant administered at a dose of 15 mg/kg once every week in combination with trastuzumab at an initial dose of 8 mg/kg followed by 6 mg/kg once every three weeks and ramucirumab at a dose of 8 mg/kg once every other week (e.g., on Days 1 and 15 during each 28 day cycle). In some embodiments, provided is a method of treating cancer in an individual, comprising administering to the individual a polypeptide comprising a SIRPα D1 domain variant and an Fc domain variant administered at a dose of 15 mg/kg once every week in combination with trastuzumab at an initial dose of 8 mg/kg followed by 6 mg/kg once every three weeks, ramucirumab at a dose of 8 mg/kg once every other week (e.g., on Days 1 and 15 during each 28 day cycle), and paclitaxel at a dose of 80 mg/m² once a week for three weeks during every 4 week cycle (e.g., on Days 1, 8, and 15 during every 28 day cycle). In some embodiments, the polypeptide comprising a SIRPα D1 domain variant and an Fc domain variant comprises a SIRPα variant that comprises SEQ ID NO: 81 or SEQ ID NO: 85 and an the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat. In some embodiments, the polypeptide (e.g., fusion polypeptide comprises the amino acid sequence of SEQ ID NO: 136 or SEQ ID NO: 135. In some embodiments, the polypeptide (e.g., fusion polypeptide) forms a dimer (e.g., homodimer). In some embodiments, the cancer is gastric cancer or gastroesophageal junction (GEJ) cancer. In some embodiments, the individual has received at least one prior therapy for the gastric or the GEJ cancer. In some embodiments, the gastric cancer or GEJ cancer is a HER2-overexpressing (e.g., HER2$^+$) gastric cancer or a HER2-overexpressing GEJ cancer. In some embodiments, the individual has received prior therapy with an anti-HER2 antibody, with an anti-HER2 antibody and a fluoropyrimidine, or with an anti HER2 antibody and a platinum-based chemotherapy agent. In some embodiments, the individual progressed (e.g., experienced disease progression) during or after prior therapy an anti-HER2 antibody (e.g., trastuzumab) and fluoropyrimidine-containing chemotherapy (e.g., fluorouracil). In some embodiments, the individual progressed (e.g., experienced disease progression) during or after prior therapy with an anti-HER2 antibody (e.g., trastuzumab) and platinum-containing chemotherapy. In some embodiments, the individual progressed (e.g., experienced disease progression) during or after prior therapy with an anti-HER2 antibody (e.g., trastuzumab), fluoropyrimidine-containing chemotherapy (e.g., fluorouracil), and platinum-containing chemotherapy. In some embodiments, the individual has not received prior therapy with an anti-CD47 agent or an anti-SIRPα agent.

In some embodiments, provided is a method of treating cancer in an individual, comprising administering to the individual a polypeptide comprising a SIRPα D1 domain variant and an Fc domain variant administered at a dose of 30 mg/kg once every two weeks in combination with trastuzumab at an initial dose of 6 mg/kg followed by 4 mg/kg once every two weeks (e.g., an initial dose of 6 mg/kg, followed by a 4 mg/kg dose two weeks after the initial 6 mg/kg dose, followed by a 4 mg/kg dose every two weeks after the first 4 mg/kg dose). In some embodiments, provided is a method of treating cancer in an individual, comprising administering to the individual a polypeptide comprising a SIRPα D1 domain variant and an Fc domain variant administered at a dose of 30 mg/kg once every two weeks in combination with trastuzumab at an initial dose of 6 mg/kg followed by 4 mg/kg once every two weeks (e.g., as described elsewhere herein) and ramucirumab at a dose of 8 mg/kg once every two weeks (e.g., on Days 1 and 15 of every 28 day cycle). In some embodiments, provided is a method of treating cancer in an individual, comprising administering to the individual a polypeptide comprising a SIRPα D1 domain variant and an Fc domain variant administered at a dose of 30 mg/kg once every two weeks in combination with trastuzumab at an initial dose of 6 mg/kg followed by 4 mg/kg once every two weeks (e.g., as described elsewhere herein) and ramucirumab at a dose of 8 mg/kg once every two weeks (e.g., on Days 1 and 15 of every 28 day cycle), and paclitaxel at a dose of 80 mg/m2 once a week for three weeks of every 4 week cycle (e.g., on Days 1, 8 and 15 of a 28-day cycle). In some embodiments, the polypeptide comprising a SIRPα D1 domain variant and an Fc domain variant comprises a SIRPα variant that comprises SEQ ID NO: 81 or SEQ ID NO: 85 and an the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat. In some embodiments, the polypeptide (e.g., fusion polypeptide comprises the amino acid sequence of SEQ ID NO: 136 or SEQ ID NO: 135. In some embodiments, the polypeptide (e.g., fusion polypeptide) forms a dimer (e.g., homodimer). In some embodiments, the cancer is gastric cancer or gastroesophageal junction (GEJ) cancer. In some embodiments, the individual has received at least one prior therapy for the gastric or the GEJ cancer. In some embodiments, the gastric cancer or GEJ cancer is a HER2-overexpressing (e.g., HER2$^+$) gastric cancer or a HER2-overexpressing GEJ cancer. In some embodiments, the individual has received prior therapy with an anti-HER2 antibody, with an anti-HER2 antibody and a fluoropyrimidine, or with an anti HER2 antibody and a platinum-based chemotherapy agent. In some embodiments, the individual progressed (e.g., experienced disease progression) during or after prior therapy an anti-HER2 antibody (e.g., trastuzumab) and fluoropyrimidine-containing chemotherapy (e.g., fluorouracil). In some embodiments, the individual progressed (e.g., experienced disease progression) during or after prior therapy with an anti-HER2 antibody (e.g., trastuzumab) and platinum-containing chemotherapy. In some embodiments, the individual progressed (e.g., experienced disease progression) during or after prior therapy with an anti-HER2 antibody (e.g., trastuzumab), fluoropyrimidine-containing chemotherapy (e.g., fluorouracil), and platinum-containing chemotherapy. In some embodiments, the individual has not received prior therapy with an anti-CD47 agent or an anti-SIRPα agent.

Exemplary Cancers

In some embodiments, the cancer treated by a method provided herein is breast cancer, lung cancer, adenocarcinoma of the lung, squamous cell lung cancer, small cell lung cancer (SCLC), non-small cell lung cancer (NSCLC), head and neck cancer, mesothelioma, brain cancer, brain tumor, abdominal cancer, colon cancer, colorectal cancer, esophageal cancer, parapharyngeal cancer, gastrointestinal cancer, glioma, liver cancer, gastric cancer, oral cancer, tongue cancer, neuroblastoma, osteosarcoma, ovarian cancer, renal cancer, urinary bladder cancer, urinary tract cancer, pancreatic cancer, retinoblastoma, cervical cancer, uterine cancer, Wilm's tumor, multiple myeloma, skin cancer, lymphoma, leukemia, blood cancer, thyroid cancer, bone cancer, adenocystic tumor, chondrosar-coma, pancreatic islet cell tumor, neuroendocrine tumor, prostate cancer, glioblastoma, endometrial carcinoma, endometrial cancer, leiomyosarcoma, gall bladder cancer, hepatocellular cancer, a melanoma, or a solid tumor.

In some embodiments, the cancer treated by a method provided herein is gastric cancer. In some embodiments, the cancer treated by a method provided herein is gastric adenocarcimoa. In some embodiments, the cancer treated by a method provided herein is gastroesophogeal junction adenocarcinoma. In some embodiments, the cancer treated by a method provided herein is HER2-overexpressing gastroesophogeal junction adenocarcinoma.

Methods of Treating Solid Tumor

In some embodiments, provided is a method of treating solid tumor in an individual (e.g., a human individual) that comprises administering to the individual an effective amount of (a) an agent that blocks the interaction between CD47 (e.g., hCD47) and SIRPα (e.g., hSIRPα) and (b) a platinum-based chemotherapy agent. In some embodiments, the solid tumor is colon cancer (e.g., colon carcinoma), lung cancer, head and neck cancer, esophageal cancer, breast cancer, bladder cancer, ovarian cancer, cervical cancer, testicular cancer, brain tumor, mesothelioma, or neuroblastoma. In some embodiments, the platinum-based chemotherapy agent is carboplatin, cisplatin, oxaliplatin, nedaplatin, triplatin tetranitrate, phenanthriplatin, picoplatin, and/or satraplatin. In some embodiments, the platinum-based chemotherapy agent is cisplatin. In some embodiments, the agent is a polypeptide (e.g., fusion polypeptide) comprising a SIRPα D1 domain variant (e.g., a SIRPα D1 domain variant described herein) and an Fc domain variant (e.g., an Fc domain variant described herein). In some embodiments, the polypeptide (e.g., fusion polypeptide) comprises a SIRPα D1 domain variant that comprises the amino acid sequence of SEQ ID NO: 81 or SEQ ID NO: 85. In some embodiments, the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat. In some embodiments, the polypeptide (e.g., fusion polypeptide) administered to the individual comprises the amino acid sequence of SEQ ID NO: 136 or SEQ ID NO: 135. In some embodiments, the polypeptide (e.g., fusion polypeptide) forms a homodimer. In some embodiments, the polypeptide (e.g., fusion polypeptide) and the platinum-based chemotherapy agent (e.g., cisplatin) are administered simultaneously, concurrently, or sequentially.

Platinum agents (such as carboplatin, cisplatin, oxaliplatin, nedaplatin, triplatin tetranitrate, phenanthriplatin, picoplatin, and satraplatin) are widely used antitumor drugs that cause crosslinking of DNA as monoadduct, interstrand crosslinks, intrastrand crosslinks or DNA protein crosslinks. Platinum agents typically act on the adjacent N-7 position of guanine, forming a 1, 2 intrastrand crosslink (Poklar et al. (1996). Proc. Natl. Acad. Sci. U.S.A. 93 (15): 7606-11; Rudd et al. (1995). Cancer Chemother. Pharmacol. 35 (4): 323-6). The resultant crosslinking inhibits DNA repair and/or DNA synthesis in cancer cells.

Cisplatin is an exemplary platinum coordination compound used in the methods described herein. The chemical name for cisplatin is dichloroplatinum diammoniate, and cisplatin has the following structural formula:

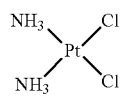

Cisplatin is an inorganic and water-soluble platinum complex with the molecular formula of $Pt(NH_3)_2Cl_2$ and a molecular weight of 300.046. After undergoing hydrolysis, it reacts with DNA to produce both intra and interstrand crosslinks. These crosslinks appear to impair replication and transcription of DNA. The cytotoxicity of cisplatin correlates with cellular arrest in the G2 phase of the cell cycle. Cisplatin, which has been assigned the CAS Registry No. 15663-27-1, is commercially available as PLATINOL®, PLATINOL®-AQ, CDDP, CISPLAN, CISPLAT, PLATIKEM, PLATIONCO, PRACTICIS, PLATICIS, BLASTOLEM, CISMAX, CISPLAN, CISPLATINUM, CISTEEN, DUPLAT, KEMOPLAT, ONCOPLATIN-AQ, PLATINEX, PLATIN, TEVAPLATIN, and others. Complete information about cisplatin preparation, dispensing, dosage, and administration schedule can be found in local package insert (for the United States, see, e.g., www(dot)accessdata(dot)fda(dot)gov/drugsatfda_docs/label/2011/018057 s0801b1(dot)pdf and www(dot)accessdata(dot)fda(dot)gov/drugsatfda_docs/label/2015/018057 s0831b1(dot)pdf). In some embodiments, the cisplatin is administered in accordance with the dosing and frequency recommended in the local package insert.

Carboplatin is another exemplary platinum coordination compound used in the methods described herein. The chemical name for carboplatin is platinum, diammine [1,1cyclobutane-dicarboxylato(2-)-0,0]-,(SP-4-2), and carboplatin has the following structural formula:

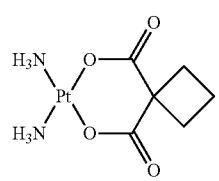

Carboplatin is a water-soluble platinum complex with the molecular formula of $C_6H_{12}N_2O_4Pt$ and a molecular weight of 373.26. Carboplatin has been assigned the CAS Registration Number 41575-94-4, and its mechanism of action is similar to that of cisplatin. Carboplatin is typically prescribed more commonly than cisplatin. Carboplatin is commercially available as PARAPLATIN®, BLASTOCARB®, BLASTOPLATIN®, CARBOKEM®, CARBOMAX®, PARAPLATIN®, CARBOPA®, KARPLAT®, and others.

Complete information about carboplatin preparation, dispensing, dosage, and administration schedule can be found in local package insert (for the United States, see, e.g., www(dot)accessdata(dot)fda(dot)gov/drugsatfda_docs/label/2010/020452 s0051b1(dot)pdf and www(dot)accessdata.fda(dot)gov/drugsatfda_docs/label/2012/0771390rig1s0161b1(dot)pdf). In some embodiments, the carboplatin is administered in accordance with the dosing and frequency recommended in the local package insert.

In some embodiments, provided is a method of treating solid tumor in an individual (e.g., a human individual) that comprises administering to the individual an effective amount of (a) an agent that blocks the interaction between CD47 (e.g., hCD47) and SIRPα (e.g., hSIRPα), (b) an anti-HER 2 antibody, and (c) an anti-PD-L1 antibody. In some embodiments the anti-HER2 antibody is trastuzumab (CAS Registry No. 180288-69-1). In some embodiments the anti-PD-L1 antibody is atezolizumab (CAS Registry No. 1380723-44-3), avelumab (CAS Registry No. 1537032-82-8), or durvalumab (CAS Registry No. 1428935-60-7). In some embodiments, the agent is a polypeptide (e.g., fusion polypeptide) comprising a SIRPα D1 domain variant (e.g., a SIRPα D1 domain variant described herein) and an Fc domain variant (e.g., an Fc domain variant described herein). In some embodiments, the polypeptide (e.g., fusion polypeptide) comprises a SIRPα D1 domain variant that comprises the amino acid sequence of SEQ ID NO: 81 or SEQ ID NO: 85. In some embodiments, the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat. In some embodiments, the polypeptide (e.g., fusion polypeptide) administered to the individual comprises the amino acid sequence of SEQ ID NO: 136 or SEQ ID NO: 135. In some embodiments, the polypeptide (e.g., fusion polypeptide) forms a homodimer. In some embodiments, the polypeptide (e.g., fusion polypeptide), the anti-HER2 antibody, the anti-PD-L1 antibody (e.g., an anti PD-L1 antagonist antibody) are administered simultaneously, concurrently, or sequentially. In some embodiments, the solid tumor is colon cancer, lung cancer, head and neck cancer, esophageal cancer, breast cancer, bladder cancer, ovarian cancer, cervical cancer, testicular cancer, endometrial cancer, liver cancer, gastric cancer, gastroesophageal junction cancer, brain tumor, mesothelioma, or neuroblastoma. In some embodiments, the solid tumor is HER2$^+$ solid tumor. In some embodiments, the solid tumor is colon cancer (e.g., HER2$^+$ colon cancer).

Methods of Treating Gastric Cancer (GC) or Gastroesophageal Junction (GEJ) Cancer In some embodiments, provided is a method of treating gastric cancer or gastroesophageal junction (GEJ) cancer in an individual (e.g., a human individual) that comprises administering to the individual an effective amount of (a) an agent that blocks the interaction between CD47 (e.g., hCD47) and SIRPα (e.g., hSIRPα), (b) an anti-HER 2 antibody, (c) an anti-VEGFR2 antibody, and (d) paclitaxel. In some embodiments the anti-HER2 antibody is trastuzumab (CAS Registry No. 180288-69-1). In some embodiments the anti-VEGFR2 antibody is ramucirumab (CAS Registry No. 947687-13-0). In some embodiments, the agent is a polypeptide (e.g., fusion polypeptide) comprising a SIRPα D1 domain variant (e.g., a SIRPα D1 domain variant described herein) and an Fc domain variant (e.g., an Fc domain variant described herein). In some embodiments, the polypeptide (e.g., fusion polypeptide) comprises a SIRPα D1 domain variant that comprises the amino acid sequence of SEQ ID NO: 81 or SEQ ID NO: 85. In some embodiments, the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat. In some embodiments, the polypeptide (e.g., fusion polypeptide) administered to the individual comprises the amino acid sequence of SEQ ID NO: 136 or SEQ ID NO: 135. In some embodiments, the polypeptide (e.g., fusion polypeptide) forms a dimer (e.g., homodimer). In some embodiments, the polypeptide (e.g., fusion polypeptide), the anti-HER2 antibody, the anti-VEGFR2 antibody, and the paclitaxel are administered simultaneously, concurrently, or sequentially. In some embodiments, the polypeptide (e.g. fusion polypeptide) is administered to the individual at a dose of 10 mg/kg once a week or 15 mg/kg once a week or 30 mg/kg once every two weeks. In some embodiments, the individual receiving treatment has gastric or GEJ adenocarcinoma. In some embodiments, the individual receiving treatment has HER2$^+$ gastric cancer or HER2$^+$ GEJ cancer (e.g., a HER2-overexpessing gastric or GEJ cancer). In some embodiments, the HER2$^+$ gastric cancer or HER2$^+$ GEJ cancer is advanced and/or metastatic. In some embodiments, the individual receiving treatment has gastric or GEJ cancer that has progressed during or after prior treatment(s) comprising anti-HER2 antibody (e.g., trastuzumab). In some embodiments, the individual receiving treatment has gastric or GEJ cancer that has progressed during or after prior treatment(s) comprising anti-HER2 antibody (e.g., trastuzumab) and a fluoropyrimidine (e.g., fluorouracil, also known as 5-fluorouracil). In some embodiments, the individual receiving treatment has gastric or GEJ cancer that has progressed during or after prior treatment(s) comprising a fluoropyrimidine (e.g., fluorouracil). In some embodiments, the individual receiving treatment has gastric or GEJ cancer that has progressed during or after prior treatment(s) comprising a platinum-based chemotherapeutic agent (e.g., carboplatin or cisplatin). In some embodiments, the individual receiving treatment has gastric or GEJ cancer that has progressed during or after prior treatments(s) comprising anti-HER2 antibody (e.g., trastuzumab) and a platinum-based chemotherapeutic agent (e.g., carboplatin or cisplatin). In some embodiments, the individual receiving treatment has gastric or GEJ cancer (e.g., HER2$^+$ gastric cancer or GEJ cancer) that has progressed during or after prior treatment(s) comprising anti-HER2 antibody (e.g., trastuzumab) and/or a fluoropyrimidine (e.g., fluorouracil), and/or a platinum-based chemotherapeutic agent (e.g., carboplatin or cisplatin). In some embodiments, the individual receiving treatment has gastric or GEJ cancer (e.g., HER2$^+$ gastric cancer or GEJ cancer) that has progressed during or after prior treatment(s) comprising anti-HER2 antibody (e.g., trastuzumab) and/or a fluoropyrimidine (e.g., fluorouracil). In some embodiments, the individual receiving treatment has gastric or GEJ cancer (e.g., HER2⁺ gastric cancer or GEJ cancer) that has progressed during or after prior treatment(s) with a platinum-based chemotherapeutic agent (e.g., carboplatin or cisplatin). In some embodiments, the individual failed (e.g., relapsed after or did not respond to) prior therapy with an anti-HER2 antibody, with an anti-HER2 antibody and a fluoropyrimidine (e.g., fluorouracil), with an anti-HER2 antibody and a platinum-based chemotherapy agent (e.g., carboplatin or cisplatin), or with a platinum-based chemotherapy agent (e.g., carboplatin or cisplatin). In some embodiments, the fluoropyrimidine was fluorouracil (also known as 5-fluorouracil). In some embodiments, the the individual receiving treatment has undergone a prior anti-VEGFR2 antibody-containing therapy for gastric or GEJ cancer. In some embodiments, the prior anti-VEGFR2 antibody-containing therapy was a therapy comprising ramucirumab. In some embodiments, the the individual receiving treatment has not undergone a prior anti-VEGFR2 antibody-containing therapy (e.g., therapy comprising ramucirumab) for gastric or GEJ cancer. In some embodiments, the the individual receiving treatment has undergone at least one, at least two, at least three, or at least four prior therapies for gastric or GEJ cancer. In some embodiments, treatment with the polypeptide, the anti-HER2 antibody, the anti-VEGFR2 antibody, and the paclitaxel does not result in adverse effects. In some embodiments, treatment with the polypeptide, the anti-HER2 antibody, the anti-VEGFR2 antibody, and the paclitaxel results in only low grade adverse effects.

In some embodiments, provided is a method of treating gastric cancer or gastroesophageal junction (GEJ) cancer in an individual (e.g., a human individual) that comprises administering to the individual an effective amount of (a) an agent that blocks the interaction between CD47 (e.g., hCD47) and SIRPα (e.g., hSIRPα), (b) an anti-PD-1 antibody (e.g., an anti-PD-1 antagonist antibody), (c) an anti-HER2 antibody, (d) 5-fluorouracil and (e) a platinum-based chemotherapeutic agent. In some embodiments, provided is a method of treating gastric cancer or gastroesophageal junction (GEJ) cancer in an individual (e.g., a human individual) that comprises administering to the individual an effective amount of (a) an agent that blocks the interaction between CD47 (e.g., hCD47) and SIRPα (e.g., hSIRPα), (b) an anti-PD-1 antibody (e.g., an anti-PD-1 antagonist antibody), (c) an anti-HER2 antibody, (d) capecitabine, and (e) a platinum-based chemotherapeutic agent. In some embodiments the anti-PD-1 antibody is pembrolizumab (CAS Registry No. 1374853-91-4). In some embodiments the anti-HER2 antibody is trastuzumab (CAS Registry No. 180288-69-1). In some embodiments, the platinum-based chemotherapeutic agent is cisplatin. In some embodiments, the agent is a polypeptide (e.g., fusion polypeptide) comprising a SIRPα D1 domain variant (e.g., a SIRPα D1 domain variant described herein) and an Fc domain variant (e.g., an Fc domain variant described herein). In some embodiments, the polypeptide (e.g., fusion polypeptide) comprises a SIRPα D1 domain variant that comprises the amino acid sequence of SEQ ID NO: 81 or SEQ ID NO: 85. In some embodiments, the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat. In some embodiments, the polypeptide (e.g., fusion polypeptide) administered to the individual comprises the amino acid sequence of SEQ ID NO: 136 or SEQ ID NO: 135. In some embodiments, the polypeptide (e.g., fusion polypeptide) forms a dimer (e.g., a homodimer). In some embodiments, the polypeptide (e.g., fusion polypeptide), the anti-PD-1 antibody, the anti-HER2 antibody, the 5-fluorouracil, and the platinum-based chemotherapeutic agent are administered simultaneously, concurrently, or sequentially. In some embodiments, the polypeptide (e.g., fusion polypeptide), the anti-PD-1 antibody, the anti-HER2 antibody, the capecitabine, and the platinum-based chemotherapeutic agent are administered simultaneously, concurrently, or sequentially. In some embodiments, the individual receiving treatment has HER2-overexpressing gastric cancer or HER2-overexpressing GEJ cancer. In some embodiments, the gastric cancer or the GEJ cancer is advanced and/or metastatic. In some embodiments, the individual has not received prior treatment for gastric cancer or the GEJ cancer.

In some embodiments, provided is a method of treating gastric cancer in an individual, comprising administering to the individual a polypeptide comprising a SIRPα D1 domain variant and an Fc domain variant administered at a dose between about 10 to about 60 mg/kg once a week (qw). In some embodiments, the polypeptide comprising the SIRPα D1 domain variant and the Fc domain variant is administered at a dose between about 10 to about 60 mg/kg once every two weeks (q2w). In some embodiments, the polypeptide comprising the SIRPα D1 domain variant and the Fc domain variant is administered at a dose of 10 mg/kg once every week. In some embodiments, the polypeptide comprising the SIRPα D1 domain variant and the Fc domain variant is administered at a dose of 15 mg/kg once every week. In some embodiments, the polypeptide comprising the SIRPα D1 domain variant and the Fc domain variant is administered at a dose of 20 mg/kg once every week. In some embodiments, the polypeptide comprising the SIRPα D1 domain variant and the Fc domain variant is administered at a dose of 30 mg/kg once every week. In some embodiments, the polypeptide comprising the SIRPα D1 domain variant and the Fc domain variant is administered at a dose of 40 mg/kg once every week. In some embodiments, the polypeptide comprising the SIRPα D1 domain variant and the Fc domain variant is administered at a dose of 45 mg/kg once every week. In some embodiments, the polypeptide comprising the SIRPα D1 domain variant and the Fc domain variant is administered at a dose of 50 mg/kg once every week. In some embodiments, the polypeptide comprising the SIRPα D1 domain variant and the Fc domain variant is administered at a dose of 60 mg/kg once every week. In some embodiments, the polypeptide comprising the SIRPα D1 domain variant and the Fc domain variant is administered at a dose of 10 mg/kg once every 2 weeks (q2w). In some embodiments, the polypeptide comprising the SIRPα D1 domain variant and the Fc domain variant is administered at a dose of 15 mg/kg once every 2 weeks (q2w). In some embodiments, the polypeptide comprising the SIRPα D1 domain variant and the Fc domain variant is administered at a dose of 20 mg/kg once every 2 weeks (q2w). In some embodiments, the polypeptide comprising the SIRPα D1 domain variant and the Fc domain variant is administered at a dose of 30 mg/kg once every 2 weeks (q2w). In some embodiments, the polypeptide comprising the SIRPα D1 domain variant and the Fc domain variant is administered at a dose of 40 mg/kg once every 2 weeks (q2w). In some embodiments, the polypeptide comprising the SIRPα D1 domain variant and the Fc domain variant is administered at a dose of 45 mg/kg once every 2 weeks (q2w). In some embodiments, the polypeptide comprising the SIRPα D1 domain variant and the Fc domain variant is administered at a dose of 50 mg/kg once every 2 weeks (q2w). In some embodiments, the polypeptide comprising the SIRPα D1 domain variant and the Fc domain variant is administered at a dose of 60 mg/kg once every 2 weeks (q2w). In some embodiments, the polypeptide comprising the SIRPα D1 domain variant and the Fc domain variant is administered, e.g., at any of the doses and administration frequencies described herein, in combination with trastuzumab at an initial dose of 6 mg/kg followed by 4 mg/kg once every two weeks (e.g., as described elsewhere herein) and ramucirumab at a dose of 8 mg/kg once every two weeks, and paclitaxel at a dose of 80 mg/m2 on days 1, 8 and 15 of a 28-day cycle.

In some embodiments, provided is a method of treating cancer in an individual, comprising administering to the individual a polypeptide polypeptide comprising a SIRPα D1 domain variant and an Fc domain variant administered at a dose of 10 mg/kg once every week in combination with trastuzumab at an initial dose of 8 mg/kg followed by 6 mg/kg once every three weeks (e.g., an initial dose of 8 mg/kg during week 1 followed by a 6 mg/kg dose given during week two, and a 6 mg/kg dose once every three weeks after the first 6 mg/kg dose). In some embodiments, provided is a method of treating cancer in an individual, comprising administering to the individual a polypeptide polypeptide comprising a SIRPα D1 domain variant and an Fc domain variant administered at a dose of 10 mg/kg once every week in combination with trastuzumab at an initial dose of 8 mg/kg followed by 6 mg/kg once every three weeks and ramucirumab at a dose of 8 mg/kg on days 1 and 15 every four weeks. In some embodiments, provided is a method of treating cancer in an individual, comprising administering to the individual a polypeptide polypeptide comprising a SIRPα D1 domain variant and an Fc domain variant administered at a dose of 10 mg/kg once every week in combination with trastuzumab at an initial dose of 8 mg/kg followed by 6 mg/kg once every three weeks, ramucirumab at a dose of 8 mg/kg on days 1 and 15 every four weeks and paclitaxel at a dose of 80 mg/m2 on days 1, 8, and 15 every four weeks.

In some embodiments, provided is a method of treating gastric cancer in an individual, comprising administering to the individual a polypeptide polypeptide comprising a SIRPα D1 domain variant and an Fc domain variant administered at a dose of 15 mg/kg once every week in combination with trastuzumab at an initial dose of 8 mg/kg followed by 6 mg/kg once every three weeks. In some embodiments, provided is a method of treating cancer in an individual, comprising administering to the individual a polypeptide polypeptide comprising a SIRPα D1 domain variant and an Fc domain variant administered at a dose of 15 mg/kg once every week in combination with trastuzumab at an initial dose of 8 mg/kg followed by 6 mg/kg once every three weeks and ramucirumab at a dose of 8 mg/kg on days 1 and 15 every four weeks. In some embodiments, provided is a method of treating cancer in an individual, comprising administering to the individual a polypeptide polypeptide comprising a SIRPα D1 domain variant and an Fc domain variant administered at a dose of 15 mg/kg once every week in combination with trastuzumab at an initial dose of 8 mg/kg followed by 6 mg/kg once every three weeks, ramucirumab at a dose of 8 mg/kg on days 1 and 15 every four weeks and paclitaxel at a dose of 80 mg/m2 on days 1, 8, and 15 every four weeks.

In some embodiments, provided is a method of treating gastric cancer in an individual, comprising administering to the individual a polypeptide comprising a SIRPα D1 domain variant and an Fc domain variant administered at a dose of 30 mg/kg once every two weeks in combination with trastuzumab at an initial dose of 6 mg/kg followed by 4 mg/kg once every two weeks (e.g., an initial dose of 6 mg/kg, followed by a 4 mg/kg dose two weeks after the initial 6 mg/kg dose, followed by a 4 mg/kg dose every two weeks after the first 4 mg/kg dose) and ramucirumab at a dose of 8 mg/kg once every two weeks, and paclitaxel at a dose of 80 mg/m2 on days 1, 8 and 15 of a 28-day cycle. In some embodiments, provided is a method of treating gastric adenocarcinoma in an individual, comprising administering to the individual a polypeptide comprising a SIRPα D1 domain variant and an Fc domain variant administered at a dose of 30 mg/kg once every two weeks in combination with trastuzumab at an initial dose of 6 mg/kg followed by 4 mg/kg once every two weeks and ramucirumab at a dose of 8 mg/kg once every two weeks, and paclitaxel at a dose of 80 mg/m2 on days 1, 8 and 15 of a 28-day cycle. In some embodiments, provided is a method of treating gastric esophogeal junction adenocarcinoma in an individual, comprising administering to the individual a polypeptide comprising a SIRPα D1 domain variant and an Fc domain variant administered at a dose of 30 mg/kg once every two weeks in combination with trastuzumab at an initial dose of 6 mg/kg followed by 4 mg/kg once every two weeks and ramucirumab at a dose of 8 mg/kg once every two weeks, and paclitaxel at a dose of 80 mg/m2 on days 1, 8 and 15 of a 28-day cycle.

In some embodiments, provided is a method of treating gastroesophogeal junction cancer in an individual, comprising administering to the individual a polypeptide comprising a SIRPα D1 domain variant and an Fc domain variant administered at a dose of about 10 to about 60 mg/kg once a week (qw). In some embodiments, the polypeptide comprising the SIRPα D1 domain variant and the Fc domain variant is administered at a dose of about 10 to about 60 mg/kg once every two weeks (q2w). In some embodiments, the polypeptide comprising the SIRPα D1 domain variant and the Fc domain variant is administered at a dose of 10 mg/kg once every week. In some embodiments, the polypeptide comprising the SIRPα D1 domain variant and the Fc domain variant is administered at a dose of 15 mg/kg once every week. In some embodiments, the polypeptide comprising the SIRPα D1 domain variant and the Fc domain variant is administered at a dose of 20 mg/kg once every week. In some embodiments, the polypeptide comprising the SIRPα D1 domain variant and the Fc domain variant is administered at a dose of 30 mg/kg once every week. In some embodiments, the polypeptide comprising the SIRPα D1 domain variant and the Fc domain variant is administered at a dose of 40 mg/kg once every week. In some embodiments, the polypeptide comprising the SIRPα D1 domain variant and the Fc domain variant is administered at a dose of 45 mg/kg once every week. In some embodiments, the polypeptide comprising the SIRPα D1 domain variant and the Fc domain variant is administered at a dose of 50 mg/kg once every week. In some embodiments, the polypeptide comprising the SIRPα D1 domain variant and the Fc domain variant is administered at a dose of 60 mg/kg once every week. In some embodiments, the polypeptide comprising the SIRPα D1 domain variant and the Fc domain variant is administered at a dose of 10 mg/kg once every 2 weeks (q2w). In some embodiments, the polypeptide comprising the SIRPα D1 domain variant and the Fc domain variant is administered at a dose of 15 mg/kg once every 2 weeks (q2w). In some embodiments, the polypeptide comprising the SIRPα D1 domain variant and the Fc domain variant is administered at a dose of 20 mg/kg once every 2 weeks (q2w). In some embodiments, the polypeptide comprising the SIRPα D1 domain variant and the Fc domain variant is administered at a dose of 30 mg/kg once every 2 weeks (q2w). In some embodiments, the polypeptide comprising the SIRPα D1 domain variant and the Fc domain variant is administered at a dose of 40 mg/kg once every 2 weeks (q2w). In some embodiments, the polypeptide comprising the SIRPα D1 domain variant and the Fc domain variant is administered at a dose of 45 mg/kg once every two weeks. In some embodiments, the polypeptide comprising the SIRPα D1 domain variant and the Fc domain variant is administered at a dose of 50 mg/kg once every 2 weeks (q2w). In some embodiments, the polypeptide comprising the SIRPα D1 domain variant and the Fc domain variant is administered at a dose of 60 mg/kg once every 2 weeks (q2w).

In some embodiments, provided is a method of treating gastroesophogeal junction cancer in an individual, comprising administering to the individual a polypeptide polypeptide comprising a SIRPα D1 domain variant and an Fc domain variant administered at a dose of 10 mg/kg once every week in combination with trastuzumab at an initial dose of 8 mg/kg followed by 6 mg/kg once every three weeks. In some embodiments, provided is a method of treating gastroesophogeal junction cancer in an individual, comprising administering to the individual a polypeptide polypeptide comprising a SIRPα D1 domain variant and an Fc domain variant administered at a dose of 10 mg/kg once every week in combination with trastuzumab at an initial dose of 8 mg/kg followed by 6 mg/kg once every three weeks and ramucirumab at a dose of 8 mg/kg on days 1 and 15 every four weeks. In some embodiments, provided is a method of treating gastroesophogeal junction cancer in an individual, comprising administering to the individual a polypeptide polypeptide comprising a SIRPα D1 domain variant and an Fc domain variant administered at a dose of 10 mg/kg once every week in combination with trastuzumab at an initial dose of 8 mg/kg followed by 6 mg/kg once every three weeks, ramucirumab at a dose of 8 mg/kg on days 1 and 15 every four weeks and paclitaxel at a dose of 80 mg/m2 on days 1, 8, and 15 every four weeks.

In some embodiments, provided is a method of treating gastroesophogeal junction cancer in an individual, comprising administering to the individual a polypeptide polypeptide comprising a SIRPα D1 domain variant and an Fc domain variant administered at a dose of 15 mg/kg once every week in combination with trastuzumab at an initial dose of 8 mg/kg followed by 6 mg/kg once every three weeks. In some embodiments, provided is a method of treating gastroesophogeal junction cancer in an individual, comprising administering to the individual a polypeptide polypeptide comprising a SIRPα D1 domain variant and an Fc domain variant administered at a dose of 15 mg/kg once every week in combination with trastuzumab at an initial dose of 8 mg/kg followed by 6 mg/kg once every three weeks and ramucirumab at a dose of 8 mg/kg on days 1 and 15 every four weeks. In some embodiments, provided is a method of treating gastroesophogeal junction cancer in an individual, comprising administering to the individual a polypeptide polypeptide comprising a SIRPα D1 domain variant and an Fc domain variant administered at a dose of 15 mg/kg once every week in combination with trastuzumab at an initial dose of 8 mg/kg followed by 6 mg/kg once every three weeks, ramucirumab at a dose of 8 mg/kg on days 1 and 15 every four weeks and paclitaxel at a dose of 80 mg/m2 on days 1, 8, and 15 every four weeks.

In some embodiments, provided is a method of treating gastroesophogeal junction cancer in an individual, comprising administering to the individual a polypeptide comprising a SIRPα D1 domain variant and an Fc domain variant administered at a dose of 30 mg/kg once every two weeks in combination with trastuzumab at an initial dose of 6 mg/kg followed by 4 mg/kg once every two weeks and ramucirumab at a dose of 8 mg/kg once every two weeks, and paclitaxel at a dose of 80 mg/m2 on days 1, 8 and 15 of a 28-day cycle. In some embodiments, provided is a method of treating gastroesophogeal junction cancer in an individual, comprising administering to the individual a polypeptide comprising a SIRPα D1 domain variant and an Fc domain variant administered at a dose of 30 mg/kg once every two weeks in combination with trastuzumab at an initial dose of 6 mg/kg followed by 4 mg/kg once every two weeks (e.g., an initial dose of 6 mg/kg, followed by a 4 mg/kg dose two weeks after the initial 6 mg/kg dose, followed by a 4 mg/kg dose every two weeks after the first 4 mg/kg dose) and ramucirumab at a dose of 8 mg/kg once every two weeks, and paclitaxel at a dose of 80 mg/m2 on days 1, 8 and 15 of a 28-day cycle. In some embodiments, provided is a method of treating gastroesophogeal junction cancer a in an individual, comprising administering to the individual a polypeptide comprising a SIRPα D1 domain variant and an Fc domain variant administered at a dose of 30 mg/kg once every two weeks in combination with trastuzumab at an initial dose of 6 mg/kg followed by 4 mg/kg once every two weeks (e.g., an initial dose of 6 mg/kg, followed by a 4 mg/kg dose two weeks after the initial 6 mg/kg dose, followed by a 4 mg/kg dose every two weeks after the first 4 mg/kg dose) and ramucirumab at a dose of 8 mg/kg once every two weeks, and paclitaxel at a dose of 80 mg/m2 on days 1, 8 and 15 of a 28-day cycle.

In some embodiments, provided is a method of treating gastric cancer or GEJ cancer in an individual (e.g., a human individual) that comprises administering to the individual an effective amount of (a) an agent that blocks the interaction between CD47 (e.g., hCD47) and SIRPα (e.g., hSIRPα), (b) an anti-HER 2 antibody, (c) an anti-VEGFR2 antibody, and (d) paclitaxel, wherein, among a population of patients who receive treatment, the overall response rate (ORR) of the population is greater than 50%. In some embodiments, provided is a method of treating gastric cancer or gastroesophageal junction (GEJ) cancer in an individual (e.g., a human individual) that comprises administering to the individual an effective amount of (a) an agent that blocks the interaction between CD47 (e.g., hCD47) and SIRPα (e.g., hSIRPα), (b) an anti-HER 2 antibody, (c) an anti-VEGFR2 antibody, and (d) paclitaxel, wherein, among a population of patients who receive treatment, the overall response rate (ORR) of the population is greater than 55%. In some embodiments, provided is a method of treating gastric cancer or gastroesophageal junction (GEJ) cancer in an individual (e.g., a human individual) that comprises administering to the individual an effective amount of (a) an agent that blocks the interaction between CD47 (e.g., hCD47) and SIRPα (e.g., hSIRPα), (b) an anti-HER 2 antibody, (c) an anti-VEGFR2 antibody, and (d) paclitaxel, wherein, among a population of patients who receive treatment, the overall response rate (ORR) of the population is greater than 60%. In some embodiments, provided is a method of treating gastric cancer or gastroesophageal junction (GEJ) cancer in an individual (e.g., a human individual) that comprises administering to the individual an effective amount of (a) an agent that blocks the interaction between CD47 (e.g., hCD47) and SIRPα (e.g., hSIRPα), (b) an anti-HER 2 antibody, (c) an anti-VEGFR2 antibody, and (d) paclitaxel, wherein, among a population of patients who receive treatment, the overall response rate (ORR) of the population is greater than 65%. In some embodiments, provided is a method of treating gastric cancer or gastroesophageal junction (GEJ) cancer in an individual (e.g., a human individual) that comprises administering to the individual an effective amount of (a) an agent that blocks the interaction between CD47 (e.g., hCD47) and SIRPα (e.g., hSIRPα), (b) an anti-HER 2 antibody, (c) an anti-VEGFR2 antibody, and (d) paclitaxel, wherein, among a population of patients who receive treatment, the overall response rate (ORR) of the population is greater than 70%. In some embodiments, provided is a method of treating gastric cancer or gastroesophageal junction (GEJ) cancer in an individual (e.g., a human individual) that comprises administering to the individual an effective amount of (a) an agent that blocks the interaction between CD47 (e.g., hCD47) and SIRPα (e.g., hSIRPα), (b) an anti-HER 2 antibody, (c) an anti-VEGFR2 antibody, and (d) paclitaxel, wherein, among a population of patients who receive treatment, the overall response rate (ORR) of the population is greater than 75%. In some embodiments, provided is a method of treating gastric cancer or gastroesophageal junction (GEJ) cancer in an individual (e.g., a human individual) that comprises administering to the individual an effective amount of (a) an agent that blocks the interaction between CD47 (e.g., hCD47) and SIRPα (e.g., hSIRPα), (b) an anti-HER 2 antibody, (c) an anti-VEGFR2 antibody, and (d) paclitaxel, wherein, among a population of patients who receive treatment, the overall response rate (ORR) of the population is greater than 80%. In some embodiments, provided is a method of treating gastric cancer or gastroesophageal junction (GEJ) cancer in an individual (e.g., a human individual) that comprises administering to the individual an effective amount of (a) an agent that blocks the interaction between CD47 (e.g., hCD47) and SIRPα (e.g., hSIRPα), (b) an anti-HER 2 antibody, (c) an anti-VEGFR2 antibody, and (d) paclitaxel, wherein, among a population of patients who receive treatment, the overall response rate (ORR) of the population is greater than 85%. In some embodiments, provided is a method of treating gastric cancer or gastroesophageal junction (GEJ) cancer in an individual (e.g., a human individual) that comprises administering to the individual an effective amount of (a) an agent that blocks the interaction between CD47 (e.g., hCD47) and SIRPα (e.g., hSIRPα), (b) an anti-HER 2 antibody, (c) an anti-VEGFR2 antibody, and (d) paclitaxel, wherein, among a population of patients who receive treatment, the overall response rate (ORR) of the population is greater than 90%. In some embodiments, provided is a method of treating gastric cancer or gastroesophageal junction (GEJ) cancer in an individual (e.g., a human individual) that comprises administering to the individual an effective amount of (a) an agent that blocks the interaction between CD47 (e.g., hCD47) and SIRPα (e.g., hSIRPα), (b) an anti-HER 2 antibody, (c) an anti-VEGFR2 antibody, and (d) paclitaxel, wherein, among a population of patients who receive treatment, the overall response rate (ORR) of the population is greater than 95%. In some embodiments, the overall response rate (ORR) is the percent of a population of patients who achieve a partial response (PR) or a complete response (CR) to treatment. In some embodiments, PR and CR are determined according to RECIST criteria (Response Evaluation Criteria in Solid Tumors). Further details regarding RECIST are provided at e.g., https://ctep(dot)cancer(dot)gov/protocolDevelopment/docs/recist_guideline.pdf or https://recist(dot)eortc(dot)org.

Combination Cancer Therapies Comprising an anti-TROP2 Antibody

In some embodiments, provided is a method of treating cancer in an individual (e.g., a human individual) that comprises administering to the individual an effective amount of (a) an agent that blocks the interaction between CD47 (e.g., hCD47) and SIRPα (e.g., hSIRPα) and (b) an anti-TROP2 antibody. In some embodiments, the anti-TROP2 antibody is RS7, which is described in U.S. Pat. No. 10,179,171, the contents of which are incorporated herein in their entirety. In some embodiments, the anti-TROP2 antibody is conjugated to a drug (i.e., an antibody-drug conjugate or "ADC"). In some embodiments, the anti-TROP2 ADC is Sacituzumab govitecan (also known as hRS7-SN38 or IMMU-132), which is described in US 2017/0281791, the contents of which are incorporated herein by reference in their entirety. In some embodiments, the agent is a polypeptide (e.g., fusion polypeptide) comprising a SIRPα D1 domain variant (e.g., a SIRPα D1 domain variant described herein) and an Fc domain variant (e.g., an Fc domain variant described herein). In some embodiments, the polypeptide (e.g., fusion polypeptide) comprises a SIRPα D1 domain variant that comprises the amino acid sequence of SEQ ID NO: 81 or SEQ ID NO: 85. In some embodiments, the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat. In some embodiments, the polypeptide (e.g., fusion polypeptide) administered to the individual comprises the amino acid sequence of SEQ ID NO: 136 or SEQ ID NO: 135. In some embodiments, the polypeptide (e.g., fusion polypeptide) forms a homodimer. In some embodiments, the polypeptide (e.g., fusion polypeptide), and the anti-TROP2 antibody are administered simultaneously, concurrently, or sequentially. In some embodiments, the cancer is solid tumor, gastric cancer, nasopharyngeal cancer, gallbladder cancer, cervical cancer, extranodal NK/T cell lymphoma, lung cancer, laryngeal squamous cell cancer, colon cancer, Hilar Cholangiocarcinoma, pancreatic cancer, squamous cell carcinoma of the oral cavity, endometrioid endometrial carcinoma, or ovarian carcinoma. In some embodiments, the cancer is characterized by the overexpression of TROP2. In some embodiments, the cancer is not characterized by the overexpression of TROP2.

Methods of Increasing Phagocytosis of a Target Cell

In some embodiments, provided is a method of increasing phagocytosis of a target cell (e.g., a cancer cell) that comprises contacting the target cell with (a) an agent that blocks the interaction between CD47 (e.g., hCD47) and SIRPα (e.g., hSIRPα) and (b) an anti-TROP2 antibody. In some embodiments, the anti-TROP2 antibody is RS7, which is described in U.S. Pat. No. 10,179,171, the contents of which are incorporated herein in their entirety. In some embodiments, the anti-TROP2 antibody is conjugated to a drug (i.e., an antibody-drug conjugate or "ADC"). In some embodiments, the anti-TROP2 ADC is Sacituzumab govitecan (also known as hRS7-SN38 or IMMU-132), which is described in US 2017/0281791, the contents of which are incorporated herein by reference in their entirety. In some embodiments, the agent is a polypeptide (e.g., fusion polypeptide) comprising a SIRPα D1 domain variant (e.g., a SIRPα D1 domain variant described herein) and an Fc domain variant (e.g., an Fc domain variant described herein). In some embodiments, the polypeptide (e.g., fusion polypeptide) comprises a SIRPα D1 domain variant that comprises the amino acid sequence of SEQ ID NO: 81 or SEQ ID NO: 85. In some embodiments, the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat. In some embodiments, the polypeptide (e.g., fusion polypeptide) administered to the individual comprises the amino acid sequence of SEQ ID NO: 136 or SEQ ID NO: 135. In some embodiments, the polypeptide (e.g., fusion polypeptide) forms a homodimer. In some embodiments, the target cell is a cancer cell. In some embodiments, the cancer cell is a solid tumor cell, a gastric cancer cell, a nasopharyngeal cancer cell, a gallbladder cancer cell, a cervical cancer cell, an extranodal NK/T cell lymphoma cell, a lung cancer cell, a laryngeal squamous cell cancer cell, a colon cancer cell, a Hilar Cholangiocarcinoma cell, a pancreatic cancer cell, a squamous cell carcinoma cell of the oral cavity, an endometrioid endometrial carcinoma cell, or an ovarian carcinoma cell.

In some embodiments, provided is a method of increasing phagocytosis of a target cell comprising contacting the target cell with (a) an agent that blocks the interaction between CD47 (e.g., hCD47) and SIRPα (e.g., hSIRPα) and (b) a second agent that is capable of enhancing phagocytosis. In some embodiments, the agent that blocks the interaction between CD47 and SIRPα is a polypeptide (e.g., fusion polypeptide) comprising a SIRPα D1 domain variant (e.g., a SIRPα D1 domain variant described herein) and an Fc domain variant (e.g., an Fc domain variant described herein). In some embodiments, the polypeptide (e.g., fusion polypeptide) comprises a SIRPα D1 domain variant that comprises the amino acid sequence of SEQ ID NO: 81 or SEQ ID NO: 85. In some embodiments, the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat. In some embodiments, the polypeptide (e.g., fusion polypeptide) administered to the individual comprises the amino acid sequence of SEQ ID NO: 136 or SEQ ID NO: 135. In some embodiments, the polypeptide (e.g., fusion polypeptide) forms a homodimer. In some embodiments, the second agent enhances phagocytosis, e.g., by blocking "don't eat me" signals. Exemplary agents include, but are not limited to, e.g., an anti-LILRB2 antibody, an anti-LILRB1 antibody, an anti-SIGLEC-10 antibody, an anti-CD24 antibody, an anti-SIRPα antibody, an anti-PD1 antibody (e.g., an anti PD1 antagonist antibody), and an anti-PD-L1 antibody (e.g., an anti PD-L1 antagonist antibody). In some embodiments, the second agent enhances phagocytosis, e.g., by enhancing "eat me" signals. Exemplary agents include, but are not limited to, e.g., BTK activators, TLR agonists, agents that promote the interaction between Mac-1 and SLAMF7, and agents that agents that promote the interaction between calreticulin and LRP1. Additional exemplary agents that enhance phagocytosis include, but are not limited to, e.g., agents that modulate podosome adhesions, agents that modulate the expression level of lamin A, activators of the SHP-1 phosphatase activity, and activators of myosin IIa assembly. In some embodiments, the method comprises contacting the target cell with (a) the polypeptide (e.g., fusion polypeptide) comprising a SIRPα D1 domain variant (e.g., a SIRPα D1 domain variant described herein) and an Fc domain variant (e.g., an Fc domain variant described herein) and (b) an an anti-LILRB2 antibody, an anti-CD24 antibody, or an anti-SIGLEC-10 antibody. In some embodiments, the method comprise contacting the target cell with (a) the fusion polypeptide and (b) a BTK activator. In some embodiments, the method comprises contacting the target cell with (a) the fusion polypeptide and (b) a TLR agonist.

In some embodiments, the method comprises contacting the target cell with (a) the polypeptide (e.g., fusion polypeptide) comprising a SIRPα D1 domain variant (e.g., a SIRPα D1 domain variant described herein) and an Fc domain variant (e.g., an Fc domain variant described herein) and (b) two or more agents that are capable of enhancing phagocytosis (e.g., including, but not limited to, two or more agents described herein). In some embodiments, the method comprises contacting the target cell with (a) the polypeptide (e.g., fusion polypeptide) comprising a SIRPα D1 domain variant (e.g., a SIRPα D1 domain variant described herein) and an Fc domain variant (e.g., an Fc domain variant described herein), (b) and an anti-LILRB2 antibody, an anti-CD24 antibody, or an anti-SIGLEC-10 antibody, and (c) an anti-PD1 antibody (e.g., an anti-PD-1 antagonist antibody) or an anti-PD-L1 antibody (e.g., an anti-PD-L1 antagonist antibody). In some embodiments, the method comprises contacting the target cell with (a) the fusion polypeptide, (b) an anti-LILRB2 antibody, and (c) an anti-PD1 antibody (e.g., anti-PD-1 antagonist antibody). In some embodiments, the method comprises contacting the target cell with (a) the fusion polypeptide, (b) an anti-LILRB2 antibody, and (c) an anti-PD-L1 antibody (e.g. an anti-PD-L1 antagonist antibody).

In some embodiments, the contacting is performed in vitro. In some embodiments, the contacting is performed in vivo. In some embodiments, the target cell is a cancer cell. In some embodiments, contacting the target cell with (a) the polypeptide comprising a SIRPα D1 domain variant (e.g., a SIRPα D1 domain variant described herein) and an Fc domain variant (e.g., an Fc domain variant described herein) and (b) one or more agents that are capable of enhancing phagocytosis increases phagocytosis of target cells by at least any one of 5%, 10%, 15%, 20%, 25%, 30%, 35%, 40%, 45%, 50%, 55%, 60%, 65%, 70%, 75%, 80%, 85%, 90%, 95%, 99%, or more than 99% as compared contacting the target cell with one or more agents that are capable of enhancing phagocytosis (i.e., in the absence of the polypeptide comprising a SIRPα D1 domain variant (e.g., a SIRPα D1 domain variant described herein) and an Fc domain variant (e.g., an Fc domain variant described herein)).

Kits and Articles of Manufacture

In another embodiment of the invention, an article of manufacture or a kit is provided comprising a polypeptide (e.g., a fusion polypeptide described herein) comprising a SIRPα D1 domain variant and an Fc domain variant. In some embodiments, the SIRPα D1 domain variant comprises the amino acid sequence selected from the group consisting of: SEQ ID NO: 81 and SEQ ID NO: 85. In some embodiments, the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat. In some embodiments, the Fc domain variant comprises the amino acid sequence of SEQ ID NO: 91. In some embodiments the polypeptide comprises the amino acid sequence of SEQ ID NO: 135 or SEQ ID NO: 136. In some embodiments, the kit or article of manufacture is for use according to a method of treatment provided herein.

In some embodiments, the kit or article of manufacture further comprises an anti-HER2 antibody (e.g., trastuzumab), an anti-VEGFR2 antibody (e.g., ramucirumab), and paclitaxel. In some embodiments, the kit comprises a package insert or label with instructions for using the polypeptide (e.g., fusion polypeptide) in combination with the anti-HER2 antibody (e.g., trastuzumab), the anti-VEGFR2 antibody (e.g., ramucirumab), and the paclitaxel to treat or delay progression of gastric cancer or gastroesophageal junction (GEJ) cancer in an individual (such as a human individual), e.g., according to a method described herein.

In some embodiments, the polypeptide (e.g., fusion polypeptide) and the one or more additional anti-cancer agents (e.g., as outlined in the embodiments above) are provided together in the kit. In some embodiments, the polypeptide (e.g., fusion polypeptide) and the one or more additional anti-cancer agents are provided in the same container or separate containers. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, an anti-neoplastic agent, a therapeutic antibody, etc). Suitable containers for the one or more agents include, for example, bottles, vials, bags and syringes.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

EXAMPLES

The present disclosure will be more fully understood by reference to the following examples. The examples should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this application and scope of the appended claims Example 1: Anti-Tumor Activity of DRUG A in Combination with Trastuzumab and an Anti-PD-L1 Antibody in a Colon Cancer Model MC38 mouse/human HER2-expressing cells ("MC38 m/h HER2 cells") were generated by infecting MC38 murine colon adenocarcinoma cells with a lentivirus vector encoding a chimera of mouse and human HER2 transmembrane and extracellular domains. MC38 m/h HER2 cells were maintained in DMEM (Thermo Fisher Scientific 11965092) supplemented with 10% FBS, 1% Penicillin-Streptomycin, 1% GlutaMAX and 1 mM Sodium Pyruvate (Thermo Fisher Scientific 11360070) at 37° C., 5% CO2 incubator. All tissue culture was performed under aseptic conditions.

Prior to implantation, a master cell bank of each cell line was generated to assure that cells used in subsequent experiments were of the same passage number. Cells were harvested and washed two times in 50 mL cold PBS (Life Technologies 10010072). After the final wash, cells were resuspended in PBS or RPMI at $5\times10^6$ cells/mL for MC38 m/h HER2 cell line. 100 of cell suspension were subcutaneously injected into the right flank of C57BL/6 mice for MC38 m/h HER2. When tumor size reached an average of 65-69 mm$^3$ for MC38 m/h HER2 tumors, the animals were randomized into 8 groups of 10 mice. Each group was assigned to a treatment group outlined in Table A below.

TABLE A

| Treatment Groups - MC38 m/h Tumor Model | |
|---|---|
| Treatment Group | Dosing regimen |
| DRUG A (single agent) | DRUG A (IP): 30 mg/kg, 2q10d |
| anti-PD-L1 antibody (single agent) | anti-PD-L1 antibody (IP): 1 mg/kg, 3q5d |
| Trastuzumab (single agent) | trastuzumab (IP): 30 mg/kg, 3q5d |
| DRUG A + anti-PD-L1 antibody doublet | DRUG A (IP): 30 mg/kg, 2q10d<br>anti-PD-L1 antibody (IP): 1 mg/kg, 3q5d |
| DRUG A + trastuzumab doublet | DRUG A (IP): 30 mg/kg, 2q10d<br>trastuzumab (IP): 30 mg/kg, 3q5d |
| anti-PD-L1 antibody + trastuzumab doublet | anti-PD-L1 antibody (IP): 1 mg/kg, 3q5d<br>trastuzumab (IP): 30 mg/kg, 3q5d |
| DRUG A + anti-PD-L1 antibody + trastuzumab | DRUG A (IP): 30 mg/kg, 2q10d<br>anti-PD-L1 antibody (IP): 1 mg/kg, 3q5d |
| PBS (control) | |

DRUG A is an exemplary fusion protein comprising a SIRPα variant that binds hCD47 wth high affinity and an inactive Fc region (i.e., an Fc region that does not exhibit ADCC effector function).

Tumor volume (mm³) was assessed using a Mitutoyo Digital Caliper (Mitutoyo America, Aurora, Illinois). Tumor volumes and body weights were recorded two or three times per week. Mice exceeding tumor volume of 2000 mm³ or loss of 20% body weight were euthanized according to IACUC guidelines. Tumor volume was calculated as ([length×{width×width}]×0.5)=volume in mm³). Statistical analysis and p values were calculated using GraphPad Prism Software.

Chimeric mouse/human HER2, with the extracellular domain from human HER2 and intracellular domain from mouse HER2, was expressed on MC38 colon cells to permit evaluation of trastuzumab's activity against MC38 murine tumors. As shown in FIG. 1, Monotherapy with trastuzumab had no effect on tumor growth, while DRUG A monotherapy and anti-PD-L1 antibody monotherapy each had a moderate effect on tumor growth. Treatment with the DRUG A+anti-PD-L1 antibody doublet or the trastuzumab+anti-PD-L1 antibody doublet showed improved tumor growth inhibition as compared to trastuzumab monotherapy, DRUG A monotherapy, and anti-PD-L1 monotherapy. Treatment with the DRUG A+anti-PD-L1+trastuzumab triple combination showed improved tumor inhibition when compared to each doublet therapy. The effect of the triple combination in inhibiting tumor growth, as compared to the DRUG A+anti-PD-L1 antibody doublet or the trastuzumab+anti-PD-L1 antibody doublet, was most evident on days 19 and 22, which were 3-6 days post final dose. Days 19 and 22 are indicated with "*" in FIG. 1. By day 26, the triple combination was minimally better at reducing tumor growth as compared to the DRUG A+anti-PD-L1 antibody doublet or the trastuzumab+anti-PD-L1 antibody doublet. No adverse effects were observed in any of the treatment cohorts in the MC38 m/h HER2 colon tumor models.

Example 2A: Exemplary Clinical Trial to Assess the Anti-Tumor Activity of a DRUG A Combination Therapie in Human Patients DRUG A, Trastuzumab, Ramucirumab, and Paclitaxel in Gastric or Gastroesophageal Junction (GEJ) Adenocarcinoma A clinical trial was performed to assess the safety, tolerability, and efficacy of the combination of DRUG A, trastuzumab, ramucirumab, and paclitaxel in patients with HER2⁺ overexpressing advanced or metastatic gastric or GEJ adenocarcinoma that had progressed during or after prior therapy with trastuzumab and fluoropyrimidine-containing chemotherapy (e.g., fluorouracil); during or after prior therapy with trastuzumab and platinum-containing chemotherapy; or during or after prior therapy with trastuzumab, fluoropyrimidine-containing chemotherapy (e.g., fluorouracil), and platinum-containing chemotherapy. The patients enrolled in the trial were suitable for treatment with trastuzumab. The patients had not received prior therapy with an anti-CD47 agent or an anti-SIRPα agent.

Example 2B: Preliminary Safety Results from Exemplary Clinical Trials

One patient with untreated advanced head and neck squamous cell carcinoma (HNSCC) received treatment with DRUG A (10 mg/kg IV QW), pembrolizumab (200 mg IV Q3W), 5-fluorouracil (1,000 mg/m² per day on days 1, 2, 3, 4 Q3W×6), and carboplatin (AUC=5 mg/ml/min on Day 1, Q3W×6). (In expansion studies, cisplatin (100 mg/m² Q3W×6) or carboplatin (AUC=5 mg/ml/min on Day 1, Q3W×6) is administered in combination with DRUG A, pembrolizumab, and fluorouracil. Patients who received carboplatin continued to receive carboplatin for the duration of the expansion studies; patients who received cisplatin continued to receive cisplatin for the duration of the expansion studies).

Three patients with HER2-positive gastric/gastroesophageal cancer who progressed on prior treatment(s) with trastuzumab, fluorouracil, and a platinum agent received treatment with DRUG A (10 mg/kg IV QW), trastuzumab (8 mg/kg IV for the initial dose, followed by 6 mg/kg Q3W), ramucirumab (8 mg/kg on Days 1 and 15 Q4W), and paclitaxel (80 mg/m2 on Days 1, 8, and 15 Q4W).

Three additional patients with HER2-positive gastric/gastroesophageal cancer who progressed on prior treatment(s) with trastuzumab, fluorouracil, and a platinum agent received treatment with DRUG A (15 mg/kg IV QW), trastuzumab (8 mg/kg IV for the initial dose, followed by 6 mg/kg Q3W), ramucirumab (8 mg/kg on Days 1 and 15 Q4W), and paclitaxel (80 mg/m2 on Days 1, 8, and 15 Q4W).

Initial results suggest that DRUG A, when administered a dose of 10 mg/kg or 15 mg/kg QW in the combination regimens discussed above, is well tolerated with no dose-limiting toxicities to date. Three patients (50%) administered with DRUG A+trastuzumab+ramucirumab+paclitaxel and no patient (0%) administered with DRUG A+pembrolizumab+fluorouracil+carboplatin experienced treatment-related adverse events (TRAEs). There were no dose limiting toxicities in patients receiving DRUG A+pembrolizumab+fluorouracil+carboplatin or DRUG A+trastuzumab+ramucirumab+paclitaxel. There were also no treatment related adverse events (TRAE) that occurred in two or more patients in the following 3 cohorts:

> DRUG $A(10mg/kg\ QW)$+pembrolizumab+fluorouracil+carboplatin$(N=1)$
>
> DRUG $A(10mg/kg\ QW)$+trastuzumab+ramucirumab+paclitaxel$(N=3)$
>
> DRUG $A(15mg/kg\ QW)$+trastuzumab+ramucirumab+paclitaxel$(N=3)$ And finally, there were also no grade 3 or above Treatment related adverse events (TRAE≥Grade 3) reported in patients treated with DRUG A+pembrolizumab+fluorouracil+carboplatin or DRUG A+trastuzumab+ramucirumab+paclitaxel.

Example 2C: Preliminary Efficacy Results from the Exemplary Clinical Trials Described in Example 2A The patient with untreated advanced head and neck squamous cell carcinoma (HNSCC) who received treatment with DRUG A, pembrolizumab, 5-fluorouracil, and a platinum agent at the dosages and administration schedule described in Example 2B achieved partial response (PR) based on investigator-assessed response using RECIST v1.1 criteria.

Among the three patients with HER2-positive gastric/gastroesophageal cancer who received treatment with DRUG A (10 mg/kg QW), trastuzumab, ramucirumab, and paclitaxel, (see Example 2B) two were not yet evaluable. One patient achieved PR based on investigator-assessed response using RECIST v1.1 criteria.

Among the three patients with HER2-positive gastric/gastroesophageal cancer who received treatment with DRUG A (15 mg/kg QW), trastuzumab, ramucirumab, and paclitaxel, (see Example 2B) two were not yet evaluable. One patient achieved PR based on investigator-assessed response using RECIST v1.1 criteria. Low rates of cytopenias were observed.

DRUG A in combination with pembrolizumab, 5-fluorouracil, and a platinum agent showed clinical activity in the treatment of advanced 1 L HNSCC (i.e., as a first treatment in patients with advanced HNSCC who have not received prior therapy for HNSCC.) DRUG A in combination with trastuzumab, ramucirumab, and paclitaxel showed clinical activity in the treatment of advanced ≥2 L gastric/gastroesophageal cancer (i.e., as a treatment in patients who have received at least one prior therapy for gastric or GEJ cancer).

Results from pharmacodynamics analyses indicated that near complete CD47 target occupancy (also known as receptor occupancy) was maintained throughout the DRUG A dosing interval when combined with chemotherapy-containing regimens.

Example 2D: Additional Results from the Exemplary Clinical Trials Described in Example 2A CD47 is a myeloid checkpoint up-regulated by tumors to evade the anticancer immune response. DRUG A is an exemplary high affinity CD47-blocking fusion protein with an inactive Fc region designed to safely enhance anticancer therapeutics (Kauder et al. (2018) *PLoS ONE.* 13(8): e0201832; Chow et al. (2020) *Journal of Clinical Oncology.* 38:15_suppl, 3056-3056; and Lakhani et al. (2021) *Lancet Oncology.* 22(12).1740-1751). DRUG A in combination with standard chemotherapy and antibody regimens was evaluated in patients with advanced HER2-positive gastric cancer (GC) or with head and neck squamous cell carcinoma (HNSCC).

Methods

Patients with previously treated advanced HER2-positive GC received DRUG A (A) 10 mg/kg QW or 15 mg/kg QW in combination with trastuzumab (T)+ramucirumab (ram)+paclitaxel (pac) as 2nd or later-line treatment. The GC patients had progressed during or following a prior fluoropyrimidine therapy (or a fluoropyrimidine-containing therapy). GC patients who had progressed during or following a prior therapy with trastuzumab and/or a platinum-based chemotherapeutic agent were included. Patients with untreated advanced HNSCC received DRUG A (A) 10 mg/kg QW or 15 mg/kg QW in combination with pembrolizumab (P)+5FU+platinum (cisplatin or carboplatin) as 1st line therapy. The primary endpoint was dose limiting toxicity (DLT). Tumor response, pharmacokinetic (PK), and pharmacodynamic (PD) markers were assessed in all patients.

Results

Fifty-five patients were enrolled in the study. Patients' baseline characteristics are shown in Table B:

TABLE B

| Baseline Characteristics | | | |
|---|---|---|---|
| | | DRUG A + trastuzumab + chemo ≥2L GC (N = 14) | DRUG A + pembrolizumab + chemo 1L HNSCC (N = 5) |
| Median age, years (range) | | 63 (36-83) | 61 (45-63) |
| Sex, n | M | 10 | 4 |
| | F | 4 | 1 |

TABLE B-continued

| Baseline Characteristics | | | |
|---|---|---|---|
| | | DRUG A + trastuzumab + chemo ≥2L GC (N = 14) | DRUG A + pembrolizumab + chemo 1L HNSCC (N = 5) |
| Race, n | Asian | 11 | 4 |
| | White | 3 | 1 |
| | Other | — | — |
| ECOG PS, n | 0 | 5 | 4 |
| | 1 | 9 | 1 |
| Progressed upon prior anti-HER2 Therapy, n (%) | | 13 (93) | N/A |
| Progressed upon ≥2 prior anti-HER2 therapy n (%) | | 1 (7.1) | N/A |
| Progressed upon prior CPI Therapy, n (%) | | 1 (7.1) | 0 (0) |
| Visceral distant metastasis, n (%) | | 13 (93) | 1 (20) |

1 patients with ≥2 L GC received A+T+ram+pac and were evaluated for safety. No dose-limiting toxicities (DLTs) were reported, and the DRUG A maximum administered dose was 15 mg/kg QW. Of the 9 patients who experienced any adverse event, 8 patients reported treatment-related adverse events (TRAE). The most common TRAEs were low grade diarrhea, fatigue, pruritus/urticaria and rash (each n=21%). TRAEs≥Grade 3 severity were of low frequency. There were no treatment related SAEs reported amongst GC patients treated with A+T+ram+pac. Among the 11 GC patients who received DRUG A at 15 mg/kg qw+trastuzumab+ramucirumab+paclitaxel, 7 demonstrated partial response, 3 demonstrated stable disease, and 1 demonstrated progressive disease. Among the 3 patients who received DRUG A at 10 mg/kg qw+trastuzumab+ramucirumab+paclitaxel, 2 demonstrated partial response, and one demonstrated stable disease.

Three patients with previously untreated HNSCC were administered A+P+5FU+platinum, as described above. No DLTs were reported. Three pts experienced any adverse events (AE), none were treatment-related. The HNSCC patient who received DRUG A at 15 mg/kg qw+pembrolizumab+5-fluorouracil+a platinum-based chemotherapeutic agent was CPI naïve and demonstrated partial response. Of the three patients who received DRUG A at 10 mg/kg qw+pembrolizumab+5-fluorouracil+a platinum-based chemotherapeutic agent, all were CPI naïve. One patient demonstrated complete response, one patient demonstrated partial response, and one demonstrated progressive disease.

The clinical activity of DRUG A chemotherapy combinations in response evaluable patients are summarized in Table C below:

TABLE C

| Responses to DRUG A Chemotherapy Combinations | | | |
|---|---|---|---|
| Patient/Treatment | N | ORR (95% CI) | Median Follow-up* (95% CI) |
| ≥2L Gastric Cancer/ DRUG A + trastuzumab + ramucirumab + paclitaxel | 14 | 64.3% [38.8%; 83.7%] | 5.3 [2.8; 6.7] |
| DRUG A (15 mg/kg qw) | 11 | 63.6% [35.4%; 84.8%] | 4.2 [2.4; 6.2] |
| DRUG A (10 mg/kg qw) | 3 | 66.7% [20.8%; 93.9%] | 8.9 [5.1; 9.6] |

TABLE C-continued

Responses to DRUG A Chemotherapy Combinations

| Patient/Treatment | N | ORR (95% CI) | Median Follow-up* (95% CI) |
|---|---|---|---|
| 1L HNSCC/ DRUG A + pembrolizumab + 5FU + platinum | 4 | 75% [30.0%; 95.0%] | 5.0 [1.3; 8.8] |
| DRUG A (15 mg/kg qw) | 1 | 100% [20.5; 100%] | 1.6 [1.3; 1.9] |
| DRUG A (10 mg/kg qw) | 3 | 66.7% [20.8%; 93.9%] | 5.3 [5.0; 8.8] |

Initial DRUG A combination PK and CD47 target occupancy are similar to that of single agent administration. Near complete (80%-100%) CD47 target occupancy is maintained throughout DRUG A dosing interval when combined with chemotherapy-containing regimens. Circulating immune cell profiles (CD4+ T cells, CD8+ T cells, CD19+ B cells, and CD16+CD56+ NK cells) are generally unchanged following DRUG A combined with chemotherapy-containing regimens. DRUG A PK following combination therapies with pembrolizumab or trastuzumab is comparable, with and without chemotherapy.

Conclusions

Preliminary data indicated that DRUG A is well tolerated and can be safety combined with the anticancer antibody+ multi-agent chemotherapy regimens studied with no maximum tolerated dose reached. The maximum administered dose of DRUG A in combination was 15 mg/kg QW.

DRUG A demonstrates initial ORR of 64% in patients with ≥2 L HER2 positive GC in combination with trastuzumab and ramucirumab+paclitaxel that compares favorably with the clinical experience of ramucirumab+ paclitaxel in patients whose disease has progressed upon prior trastuzumab-containing regimens.

DRUG A demonstrates initial anti-cancer activity including complete and partial objective responses in combination with pembrolizumab+5FU+platinum in patients who have not received prior treatment for their advanced HNSCC.

Preliminary pharmacokinetics and pharmacodynamic analysis demonstrates no impact of the combination partners upon DRUG A exposure levels with full CD47 receptor occupancy.

Example 2E: A Phase 1 Study of DRUG A, an Agent that Blocks the Interaction Between CD47 and SIRPα, in Combination with Trastuzumab, Ramucirumab, and Paclitaxel in Patients with 2$^{nd}$ Line HER2-Positive Advanced Gastric or Gastroesophageal (GC) Cancer Data provided herein further supports use of DRUG A as a single agent and in combination with established anticancer agents, namely, the anti-HER2 antibody trastuzumab, the anti-VEGFR2 antibody ramucirumab, and paclitaxel. DRUG A was administered at a dose of 10 mg/kg (mpk) QW or 15 mg/kg (mpk) QW in combination with traztuzumab, ramucirumab, and paclitaxel to patients with HER2-overexpressing advanced or metastatic gastric cancer (GC) or gastroesophageal junction (GEJ) adenocarcinoma that has progressed on or after treatment with a prior HER2-directed agent and fluoropyrimidine-containing therapy or with a prior platinum-containing chemotherapy. The patients had receieve one or two prior treatments for GC or GEJ adenocarcinoma. The maximum administered dose of DRUG A in combination was 15 mg/kg QW. There were no dose limiting toxicities on study deaths, or DRUG A-related serious adverse events (SAEs) in patients receiveing the DRUG A+trastuzumab+ramucirumab+paclitaxel combination treatment.

Figure 2A:
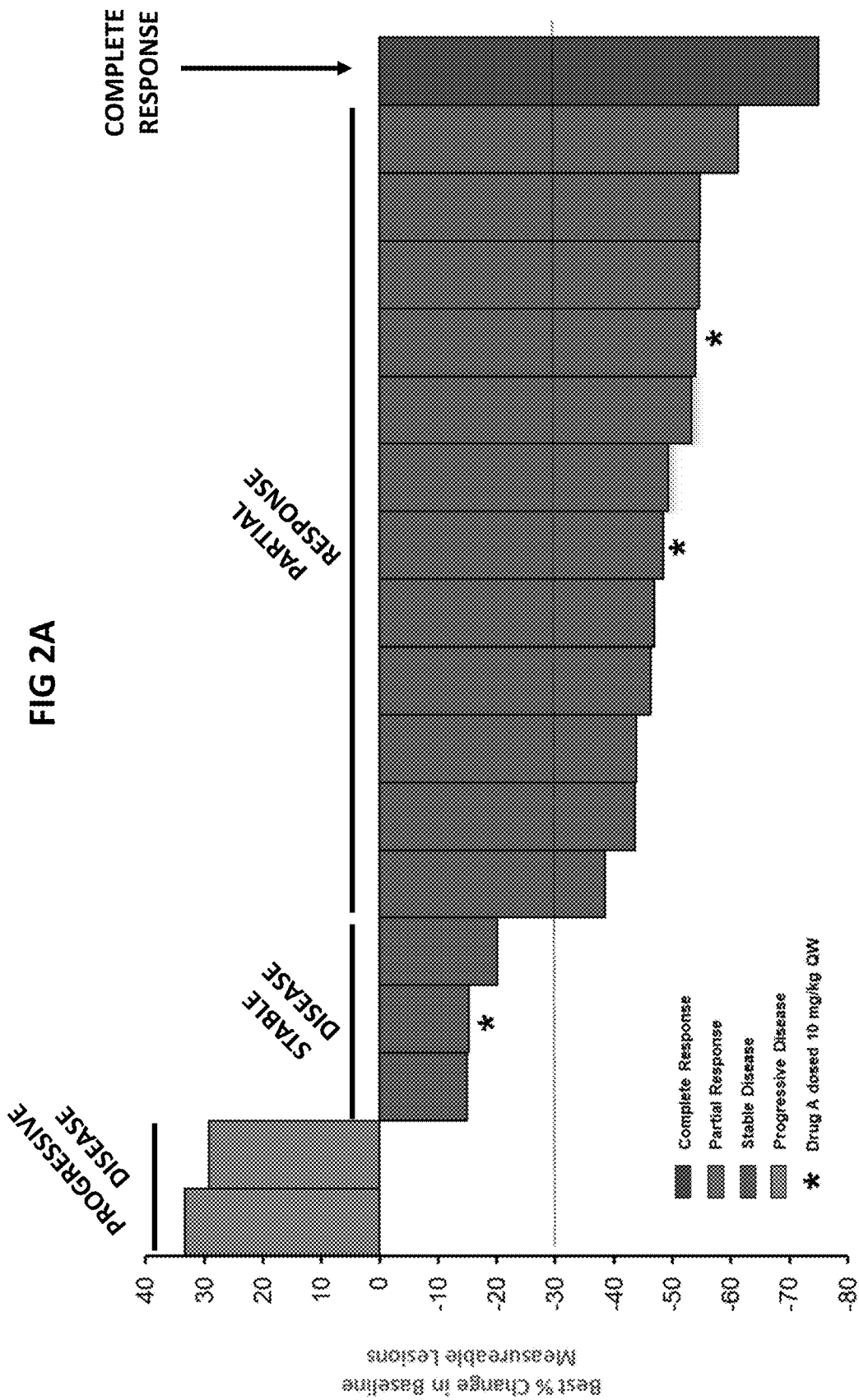
FIG. 2A provides a graph of the best % change in baseline measurable lesions in each patient in the study described in Example 2E.
Figure 2B:
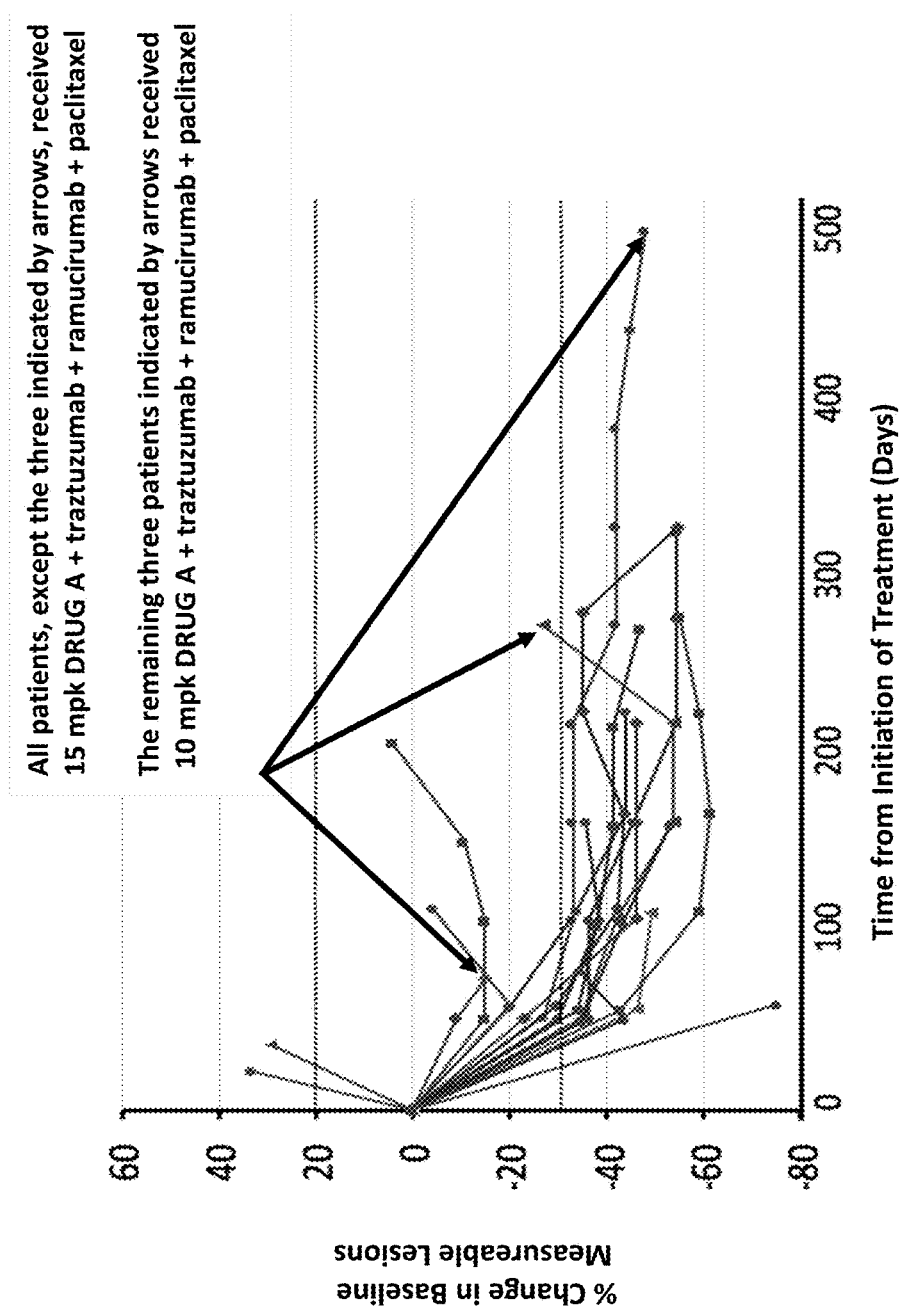
FIG. 2B provides a graph showing the % change in baseline measurable lesions in each patient in the study described in Example 2E as a function of time.

Briefly, FIGS. 2A and 2B provide the results of phase 1 clinical study of combination therapy of DRUG A in combination with (a) an anti-HER2 antibody (trastuzumab), (b) an anti VEGFR antibody (ramucirumab), and (c) paclitaxel. FIG. 2A, provides a graph of the best % change in baseline measurable lesions in each study participant. 3/18 patients achieved stable disease (SD), 12/18 achieved partial response (PR), and one patient achieved complete response (CR). FIG. 2B provides a graph showing the % change in baseline measurable lesions in each study participant as a function of time.

Table D below shows further analyses of the clinical activity of DRUG A combinations in response evaluable patients with ≥2 L HER2 positive GC or GEJ adenocarcinoma. The table shows the overall response rate (ORR) among patients receiving treatment with DRUG A+trastuzumab+ramucirumab+paclitaxel was about 72%.

TABLE D

Overall Response Rate (ORR), Duration of Response (DOR), Progression Free Survival (PFS) Rates and Overall Survival (OS) Rates among Gastric/Gastresophageal Cancer Patients treated wth DRUG A + Tastuzumab + Ramucirumab + Paclitaxel

| Population | N (eval) | ORR (%) [95% CI] | DOR (months) [95% CI] | PFS (months) [95% CI] | PFS rate at 6 months [95% CI] | OS (months) [95% CI] | OS rate at 12 months [95% CI] | Follow up (months) [95% CI] |
|---|---|---|---|---|---|---|---|---|
| ≥2L Gastric/GEJ trastuzumab + ramucirumab + paclitaxel + 10 mg/kg DRUG A or 15 mg/kg DRUG A | 18 | 72.2 [49.1%; 87.5%] | NR | 9.1 [3.8; NR] | 74.5% | NR | 75.8% | 10.5 [4.8; 12.5] |
| ≥2L Gastric/GEJ trastuzumab + ramucirumab + paclitaxel + 10 mg/kg DRUG A | 3 | 66.7 [20.8%; 93.9%] | NR | NR | 100% | NR | 66.7% | 14.3 [12.0; NR] |
| ≥2L Gastric/GEJ trastuzumab + ramucirumab + paclitaxel + 15 mg/kg DRUG A | 15 | 73.3 [48.1%; 89.1%] | NR | NR | 68.3% | NR | 80.8% | 9.4 [4.2; 12.5] |

TABLE D-continued

Overall Response Rate (ORR), Duration of Response (DOR), Progression Free Survival (PFS) Rates and Overall Survival (OS)
Rates among Gastric/Gastresophageal Cancer Patients treated wth DRUG A + Tastuzumab + Ramucirumab + Paclitaxel

| Population | N (eval) | ORR (%) [95% CI] | DOR (months) [95% CI] | PFS (months) [95% CI] | PFS rate at 6 months [95% CI] | OS (months) [95% CI] | OS rate at 12 months [95% CI] | Follow up (months) [95% CI] |
|---|---|---|---|---|---|---|---|---|
| ≥2L Gastric/GEJ trastuzumab + 10 mg/kg DRUG A | 19* | 21.1 [8.5%; 43.3%] | 8.7 [5.6; NR] | 2.2 [1.9; 5.5] | 16.7% | 8.1 [3.4; 12.6] | 38.2% | 27.0 [NR] |

NR = Not reached
*One patient discontinued prior to fist imaging assessment with symptoms consisted with progression and was not evaluable for response, per protocol Preliminary data suggest that DRUG A can be safely combined with trastuzumab, ramucirumab and paclitaxel with no maximum tolerated dose reached.

Preliminary PK/PD analysis demonstrate no impact of the combination partners upon DRUG A exposure levels with full CD47 receptor occupancy.

DRUG A in combination with trastuzumab, ramucirumab and paclitaxel demonstrates an initial ORR of 72.2% and estimated overall survival (OS) at 12 months of 75.8% in patients with ≥2 L HER2 positive GC or GEJ adenocarcinoma that has progressed after a prior trastuzumab-containing regimen. This compares favorably with both RAINBOW (See Wilke et al., Lancet October 2014) and DESTINY-01 (See Enhertu package insert, and Shitara et al., NEJM Jun. 18, 2020) clinical trial historical controls.

Updated data from patients receiving DRUG A+trastuzumab after their tumors have progressed upon prior trastuzumab therapy suggests clinical activity beyond that expected from either trastuzumab or chemotherapy alone.

Example 3: A Phase 2/3 Study of DRUG A in Patients With Advanced HER2-Overexpressing Gastric/Gastroesophageal Junction Adenocarcinoma The data described herein supports further trials to test efficacy of the combination therapies described herein. This is a randomized phase 2 (open-label)/3 (double-blind), international, multi-center study of patients with metastatic HER2-overexpressing gastric/GEJ adenocarcinoma that has progressed on or after prior HER2-directed therapy and fluoropyrimidine- or platinum-containing chemotherapy and are suitable for chemotherapy (2nd-line or 3rd-line). Approximately 450 adult patients are expected to be enrolled in the study across both phases.

Conditions: Gastric Cancer; Gastroesophageal Junction Adenocarcinoma; Gastric Adenocarcinoma Experimental: Phase 2—Arm A: DRUG A—30 mg/kg Q2W IV, trastuzumab (initial dose of 6 mg/kg followed by 4 mg/kg) Q2W IV, ramucirumab 8 mg/kg Q2W IV, and paclitaxel 80 mg/m2 IV Days 1, 8, and 15 of a 28-day cycle. Active Comparator: Phase 2—Arm B Trastuzumab (initial dose of 6 mg/kg followed by 4 mg/kg) Q2W IV, ramucirumab 8 mg/kg Q2W IV, and paclitaxel 80 mg/m2 IV Days 1, 8, and 15 of a 28-day cycle.

Experimental: Phase 3—Arm A: DRUG A 30 mg/kg Q2W IV, trastuzumab (initial dose of 6 mg/kg followed by 4 mg/kg) Q2W IV, ramucirumab 8 mg/kg Q2W IV, and paclitaxel 80 mg/m2 IV Days 1, 8, and 15 of a 28-day cycle. Active Comparator: Phase 3—Arm B Ramucirumab 8 mg/kg Q2W IV and paclitaxel 80 mg/m2 IV Days 1, 8, and 15 of a 28-day cycle.

Outcome Measures: Primary Outcome Measures include for Phase 2 an objective response rate per RECIST 1.1 and for Phase 3 an overall survival.

The following are eligibility criteria for the study: Eligibility Minimum Age: 18 Years; Maximum Age: none. Sex: All; Accepts Healthy Volunteers: No.

Inclusion Criteria: HER2-overexpressing advanced or metastatic gastric or gastroesophageal junction (GEJ) adenocarcinoma that has progressed on or after a prior HER2-directed agent and fluoropyrimidine- or platinum-containing chemotherapy (2nd-line or 3rd-line); Adequate Bone Marrow Function; Adequate Renal & Liver Function; Adequate Performance Status.

Exclusion Criteria: Patients with known symptomatic CNS metastases or leptomeningeal disease requiring steroids, Prior treatment with any anti-CD47 or anti-SIRPα agent, Prior treatment with ramucirumab.

Example 4: Effects of DRUG B in Combination with Anti-Mouse VEGFR-2, Paclitaxel and Trastuzumab in a Syngeneic Murine Model of HER2+ Colorectal Carcinoma Overview DRUG B, a murine surrogate for DRUG A, comprises a SIRPα variant that exhibits high affinity for murine CD47 ("mCD47") and an inactive Fc domain (i.e., an Fc domain that does not exhibit effector function). DRUG B, was evaluated in a quadruplet combination treatment with with trastuzumab (i.e., an anti-human HER2 antibody), anti-mouse VEGFR-2 (i.e., a murine ramucirumab surrogate), and paclitaxel in a chimeric mouse/human HER2 CT26 (CT26 m:h HER2), murine colorectal carcinoma model expressing mouse and human HER2. The triplet treatment of trastuzumab, paclitaxel, and anti-mouse VEGFR-2, exhibited marginal tumor growth inhibition. However, the addition of DRUG B to the triplet regimen significantly enhanced tumor growth inhibition and prolonged survival.

The therapeutic effect of DRUG B in the absence of trastuzumab was also evaluated. The combination of DRUG B with paclitaxel and anti-mouse VEGFR-2 doublet therapy in CT26 murine colorectal carcinoma model did not show enhanced anti-tumor activity as compared to paclitaxel and anti-mouse VEGFR-2 therapy.

These data demonstrate that inhibiting the CD47-SIRPα axis with DRUG B potentiates the anti-tumor efficacy of trastuzumab, anti-mouse VEGFR-2 and paclitaxel treatments in a HER2 expressing tumor model. In the absence of trastuzumab, DRUG B does not enhance anti-tumor activity of paclitaxel and anti-mouse VEGFR-2 doublet therapy.

DRUG A was shown to bridge innate and adaptive immunity to reduce immune suppression and activate the adaptive immune response in an antigen-specific manner. DRUG A treatment resulted in an increased anti-tumor response, significant tumor growth inhibition and prolonged survival in combination with anti-PD-1 and anti-PD-L1 antibodies in both checkpoint inhibitor sensitive syngeneic murine models of cancer (i.e., using the murine CT26 colon carcinoma cell line and the murine MC38 colon adenocarcinoma cell line) and a checkpoint inhibitor resistant syngeneic murine model of cancer (i.e., using the murine 4T1 mammary cancer cell line). See Kauder et al. (2018) PLoS One. 2018; 13(8):e0201832.

In HER2 positive gastric/gastroesophageal junction (G/GEJ) cancer, the necessary pro-phagocytic signal is provided by using trastuzumab to specifically target the HER2 antigen while engaging FcγR on macrophages with its active Fc IgG1 domain. This selective pro-phagocytic signal in combination DRUG A's blockade of the anti-phagocytic myeloid checkpoint signal maximizes the macrophage's G/GEJ cancer specific ADCP activity. By providing blockade of the anti-phagocytic CD47-SIRPα interaction in conjunction with the tumor targeting and macrophage FcγR engagement provided by trastuzumab, DRUG A in combination, is able to deliver anti-tumor activity even in clinical settings where trastuzumab has been shown to have minimal activity, such as in the treatment of HER2-positive gastric cancer with trastuzumab and paclitaxel in the second line setting in disease that has progressed upon trastuzumab (T-ACT trial; Makiyama et al. (2020) Clin Oncol. 8(17): 1919-1927).

Study Objectives

The experiments in this Example were performed to characterize the in vivo anti-tumor activity for DRUG B, a murine surrogate for DRUG A, in combination with paclitaxel and anti-mouse VEGFR-2, in the presence or absence of trastuzumab in a syngeneic murine colorectal carcinoma model.

Materials and Methods

Reagents used in this Example include those listed in Table E below:

TABLE E

| Reagents | | | |
|---|---|---|---|
| Reagent | Source | Lot | Isotype |
| DRUG B | ALX Oncology | ES20201005 | Mouse IgG1 N297A AAA |
| Anti-mouse VEGFR-2 clone DC101 (Ramucirumab surrogate) | BioXell | 796321M1 | Rat IgG1, k |
| Anti-HER2 (Trastuzumab) | Genentech | 3094840 | Human IgG1 |
| Paclitaxel | Med Chem Express | CS-1145 | NA |

Animals for In Vivo Studies

BALB/c were purchased from Charles River Laboratories International (Hollister, CA). All animals were housed in pathogen free facility in accordance with IACUC guidelines. Animals used for all studies were 6-8 weeks old.

Cell Lines

CT26 m:h HER2 was generated by the transduction of CT26 (ATCC CRL-2638) with lentivirus expressing murine HER2 engrafted with the extracellular domain of trastuzumab epitope.

CT26 and CT26 m:h HER2 were cultured in complete RPMI-1640 medium consisting of RPMI-1640 (Thermo Fisher Scientific 11875119) medium supplemented with 10% fetal bovine serum (FBS) (Millipore TMS-013B), 1% Penicillin-Streptomycin (Thermo Fisher Scientific 15140163) and 1% GlutaMAX (Thermo Fisher Scientific 35050061) at 37° C., 5% CO2 incubator.

Subcutaneous Tumor Models in Mice

All tissue culture was performed under aseptic conditions. CT26 and CT26 m:h HER2 cells were harvested and washed two times in 50 mL cold PBS (Thermo Fisher Scientific 10010072). After the final wash, cells were resuspended in serum free RPMI-1640 at $20 \times 10^6$ cells/mL of CT26 or CT26 m:h HER2. 100 mL of cell suspension were subcutaneously injected into the right flank of BALB/c mice.

In the CT26 tumor model, when tumors reached an average of 47-85 mm$^3$, the animals were randomized into groups of eight mice and dosing was initiated. All treatment agents were administered intraperitoneally (IP). Paclitaxel was administrated one day prior to rest of the regimen at 20 mg/kg for a total of three doses every five days. DRUG B was administered five times five days apart at 30 mg/kg. Anti-mouse VEGFR-2 was administered five times every 2-3 days at 40 mg/kg.

In the CT26 m:h HER2 tumor model, when tumors reached an average of 45-73 mm$^3$, the animals were randomized into groups of 10 mice and dosing was initiated. All treatment agents were administered IP. Paclitaxel was administrated one day prior to rest of the regimen at 20 mg/kg for a total of three doses every three days. DRUG B was administered four times five days apart at 30 mg/kg. Anti-mouse VEGFR-2 was administered five times four days apart at 40 mg/kg. Trastuzumab was administered four times five days apart at 30 mg/kg.

Tumor volumes (mm$^3$) were assessed using a Mitutoyo Digital Caliper (Mitutoyo America, Aurora, Illinois). Tumor volumes and body weights were recorded 1-3 times per week. Tumor volume is calculated as ([length× {width× width}]×0.5)=volume in mm$^3$). P-values were calculated using student's t-test for tumor volume and survival was calculated using Log-rank (Mantel-Cox) test using Prism 9 software (GraphPad). Mice exceeding tumor volume of 2000 mm$^3$ and loss of 20% body weight were euthanized in accordance with the IACUC guidelines.

Results and Discussion

Figure 3:
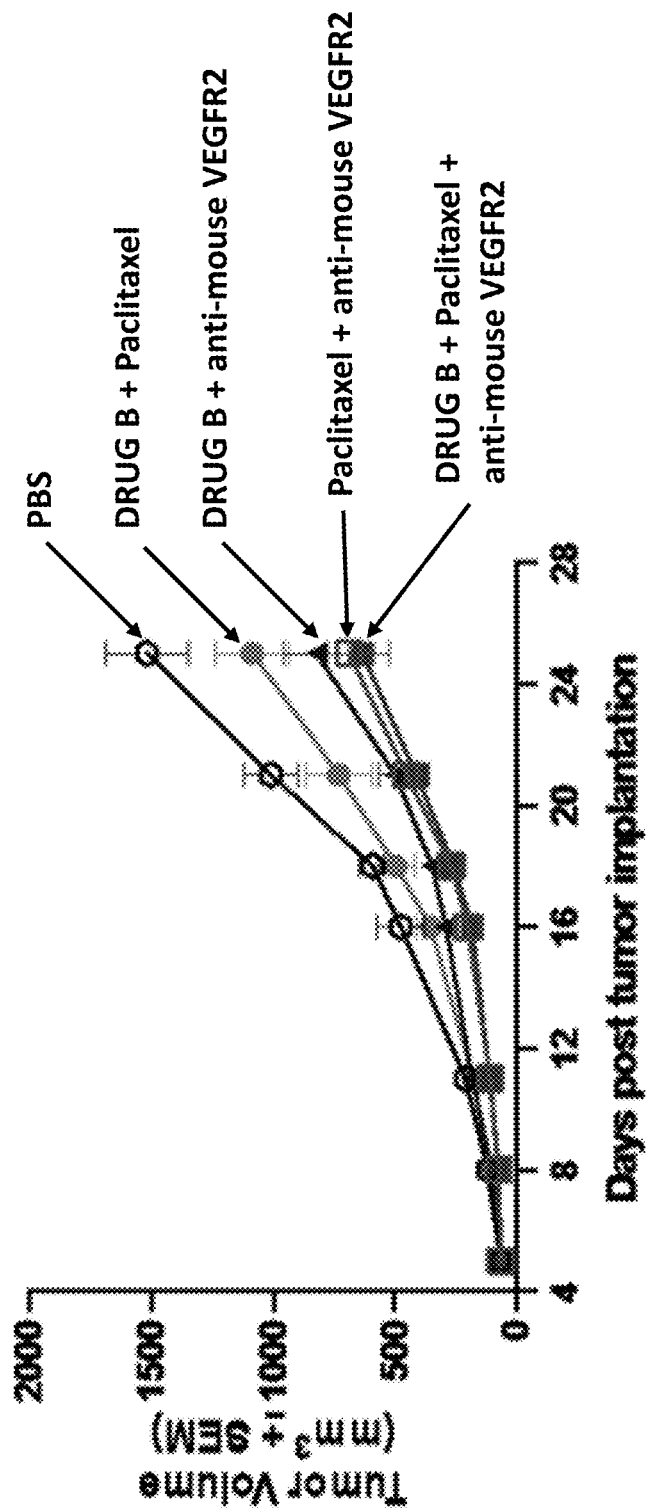
FIG. 3 shows the results of experiments that were performed to assess whether DRUG B enhances the anti-tumor activity of anti-mouse VEGFR-2+paclitaxel doublet therapy in a CT26 syngeneic mouse tumor model.

DRUG B does not Enhance Anti-Tumor Activity in Combination with Anti-Mouse VEGFR-2 and Paclitaxel Compared to Anti-Mouse VEGFR-2$^+$ Paclitaxel Doublet in a CT26 Syngeneic Tumor Model In a CT26 colon carcinoma tumor model, animals treated with the doublet regimen of 20 mh/kg paclitaxel and 40 mg/kg anti-mouse VEGFR-2 exhibited sub-optimal tumor growth inhibition. As shown in FIG. 3, a triplet combination comprising 20 mg/kg paclitaxel, 40 mg/kg anti-mouse VEGFR-2, and 30 mg/kg DRUG B did not inhibit tumor growth compared to the doublet regimen of paclitaxel, and anti-mouse VEGFR-2 alone.

Figure 4A:
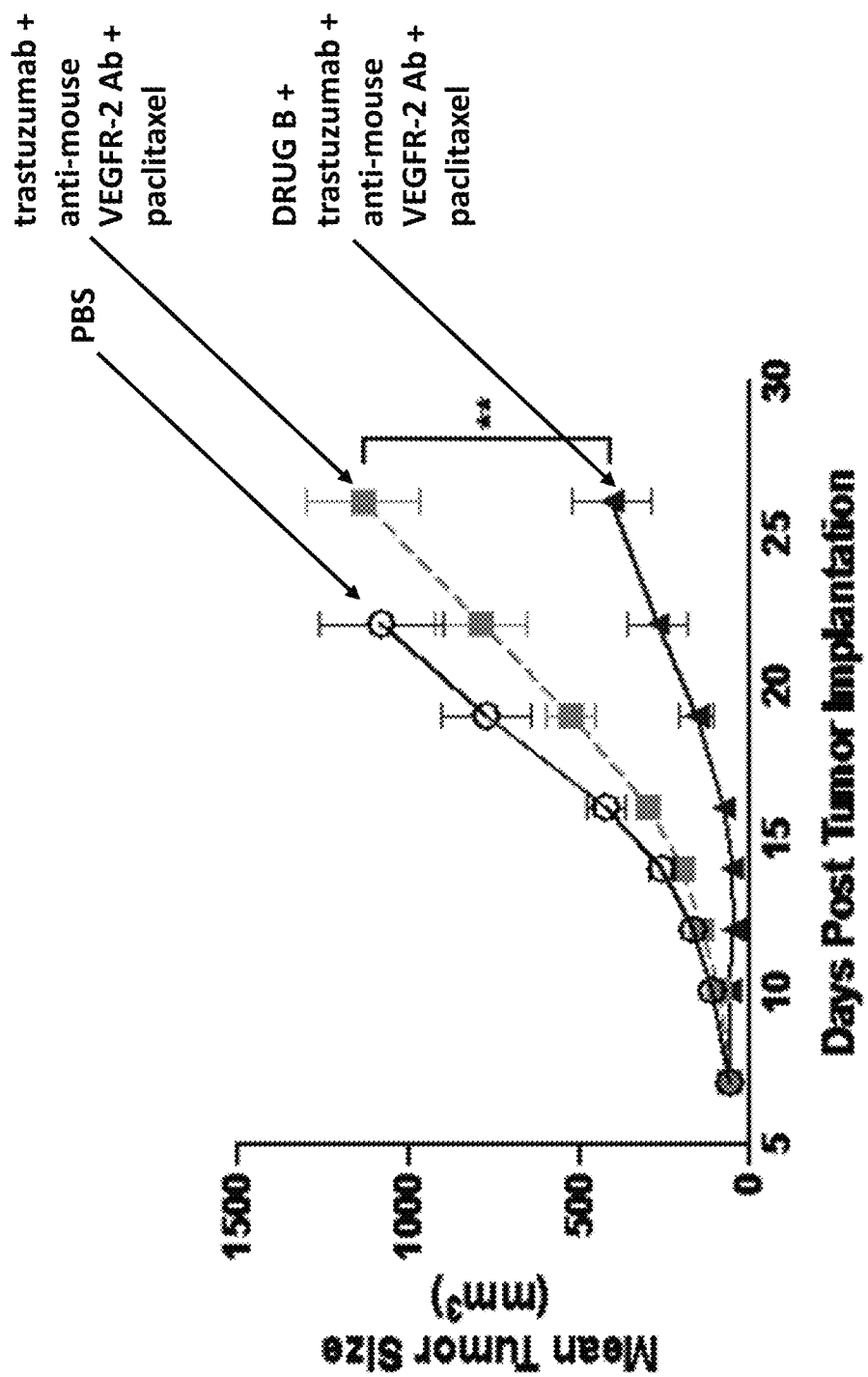
FIG. 4A shows the results of experiments that were performed to assess whether DRUG B enhances the anti-tumor activity of trastuzumab+anti-mouse VEGFR-2+paclitaxel triplet therapy in a CT26 m:h HER2-expression chimeric tumor model in mice.

Addition of DRUG B to Trastuzumab, Anti-Mouse VEGFR-2, and Paclitaxel Triplet Enhances Anti-Tumor Response Compared to Triplet in a CT26 m: h HER2-Expressing Colon Carcinoma Tumor Model In a CT26 m:h HER2-expressing colon carcinoma tumor model, animals treated with the triplet regimen of 30 mg/kg trastuzumab, 20 mg/kg paclitaxel, and 40 mg/kg anti-mouse VEGFR-2 exhibited marginal tumor growth inhibition. The addition of 30 mg/kg DRUG B to the trastuzumab+paclitaxel+anti-mouse VEGFR-2 triplet significantly enhanced tumor growth inhibition as compared to the triplet in the absence of DRUG B (day 26 unpaired t-test, p<0.0022). On day 26, the quadruplet cohort had three out of ten animals with complete tumor eradication. No tumor eradication was observed in the triplet or PBS cohorts. See FIG. 4A, which shows tumor growth±SEM of n=10 mice per cohort. Additionally, DRUG B in combination with the trastuzumab, anti-mouse VEGFR-2, and paclitaxel triplet regimen significantly increased survival compared to the triplet or PBS cohorts alone. (Log-rank (Mantel-Cox) test, p<0.0001). See FIG. 4B.

These results demonstrate that in a CT26 m:h HER2-expressing colon carcinoma tumor model, DRUG B in combination with trastuzumab, paclitaxel, and anti-mouse VEGFR-2 significantly increased anti-tumor response, enhanced tumor growth inhibition resulting in complete tumor eradication, and prolonged survival in a subset of treated animals.

Conclusions

The anti-tumor effect of DRUG B in combination with paclitaxel and anti-mouse VEGFR2 (i.e., without trastuzumab) was evaluated in a CT26 syngeneic mouse tumor model. The DRUG B+paclitaxel, +anti-mouse VEGFR-2 triplet therapy did not show enhanced anti-tumor activity as compared to paclitaxel and anti-mouse VEGFR-2 doublet therapy.

The anti-tumor effect of DRUG B in combination with trastuzumab, paclitaxel, and anti-mouse VEGFR2 was evaluated in a CT26 m:h HER2-expressing colon carcinoma tumor model. The quadruple combination significantly increased tumor growth inhibition as compared to the trastuzumab, paclitaxel, and anti-mouse VEGFR2 triplet, resulting in complete tumor eradication and prolonged survival in a subset of treated animals. The trastuzumab, paclitaxel, and anti-mouse VEGFR-2 triplet did not show significant tumor growth inhibition as compared to PBS control.

REFERENCES FOR EXAMPLES 3 AND 4

Brown E J, Frazier W A. Integrin-associated protein (CD47) and its ligands. Trends Cell Biol. 2001 March; 11(3):130-5.

Chao M P, Alizadeh A A, Tang C, Myklebust J H, Varghese B, Gill S, et al. Anti-CD47 antibody synergizes with rituximab to promote phagocytosis and eradicate non-Hodgkin lymphoma. Cell. 2010 Sep. 3; 142(4):699-713.

Kauder S E, Kuo T C, Harrabi O, et al. ALX148 blocks CD47 and enhances innate and adaptive antitumor immunity with a favorable safety profile. PLoS One. 2018; 13(8):e0201832.

Jaiswal S, Chao M P, Mejeti R and Weissman I L. Macrophages as mediators of tumor immunosurveillance. Trends Immunol. 2010 June; 31(6): 212-219.

Makiyama A, Sukawa Y, Kashiwada T, et al. Randomized, Phase II Study of Trastuzumab Beyond Progression in Patients with HER2-Positive Advance Gastric or Gastroesophageal Junction Cancer. J Clin Oncol. 2020 Jun. 10; 38(17):1919-1927.

Weiskopf K, Ring A M, Ho C C, Volkmer J-P, Levin A M, Volkmer A K, et al. Engineered SIRPα variants as immunotherapeutic adjuvants to anticancer antibodies. Science. 2013 Jul. 5; 341(6141):88-91.

Willingham S B, Volkmer J P, Gentles A J, Sahoo D, Dalerba P, Mitra S S, et al. The CD47-signal regulatory protein alpha (SIRPα) interaction is a therapeutic target for human solid tumors. Proc Natl Acad Sci USA. 2012 Apr. 24; 109(17):6662-7.

Zhao X W, Van Beek E M, Schornagela K, Van der Maadenb H, Houdta M V; CD47—signal regulatory protein-α (SIRPα) interactions form a barrier for antibody-mediated tumor cell destruction. Proc Natl Acad Sci USA. 2011 Nov. 8; 108(45):18342-7.

The preceding Examples are offered for illustrative purposes only, and are not intended to limit the scope of the present invention in any way. Various modifications of the invention in addition to those shown and described herein will become apparent to those skilled in the art from the foregoing description and fall within the scope of the appended claims.

The invention claimed is:

1. A method of treating cancer in an individual, comprising administering to the individual an effective amount of: (a) a polypeptide comprising a SIRPα D1 domain variant and an Fc domain variant, (b) an anti-HER2 antibody, (c) an anti-VEGFR2 antibody, and (d) paclitaxel;
 wherein the SIRPα D1 domain variant comprises the amino acid sequence of SEQ ID NO: 81 or SEQ ID NO: 85;
 wherein the Fc domain variant is
 a human IgG1 Fc region comprising L234A, L235A, G237A, and N297A mutations, wherein numbering is according to the EU index of Kabat;
 wherein the cancer is gastric cancer (GC) or gastroesophageal junction (GEJ) cancer, wherein the individual has received at least one prior therapy for the gastric or the GEJ cancer; and
 wherein the polypeptide comprising a SIRPα D1 domain variant and an Fc domain variant is administered at a dose of 30 mg/kg once every two weeks, wherein the anti-HER2 antibody is trastuzumab and is administered at an initial dose of 6 mg/kg followed by 4 mg/kg once every two weeks, wherein the anti-VEGFR2 antibody is ramucirumab and is administered at a dose of 8 mg/kg once every two weeks, and wherein the paclitaxel is administered at a dose of 80 mg/m2 on Days 1, 8, and 15 of every 28-day cycle.

2. The method of claim 1, wherein the individual has received prior therapy with an anti-HER2 antibody, with an anti-HER2 antibody and a fluoropyrimidine, or with an anti-HER2 antibody and a platinum-based chemotherapy agent.

3. The method of claim 1, wherein the gastric cancer or the GEJ cancer is HER2$^+$ gastric cancer or HER2$^+$ GEJ cancer.

4. The method of claim 1, wherein the ramucirumab is administered at a dose of 8 mg/kg on Days 1 and 15 of every 28 day cycle.

5. The method of claim 1, wherein the individual is a human.

6. The method of claim 1, wherein the polypeptide comprising a SIRPα D1 domain variant and an Fc domain variant forms a homodimer.

* * * * *

UNITED STATES PATENT AND TRADEMARK OFFICE
CERTIFICATE OF CORRECTION

| | |
|---|---|
| PATENT NO. | : 12,098,214 B2 |
| APPLICATION NO. | : 17/743350 |
| DATED | : September 24, 2024 |
| INVENTOR(S) | : Hong Wan et al. |

It is certified that error appears in the above-identified patent and that said Letters Patent is hereby corrected as shown below:

On the Title Page

In item (56), page 4, Column 1, Line 18, please delete "Biochim" and insert -- Biochem --;

In item (56), page 4, Column 1, Line 45, please delete "Immunotherpay" and insert -- Immunotherapy --;

In the Drawings

Figure 4B:
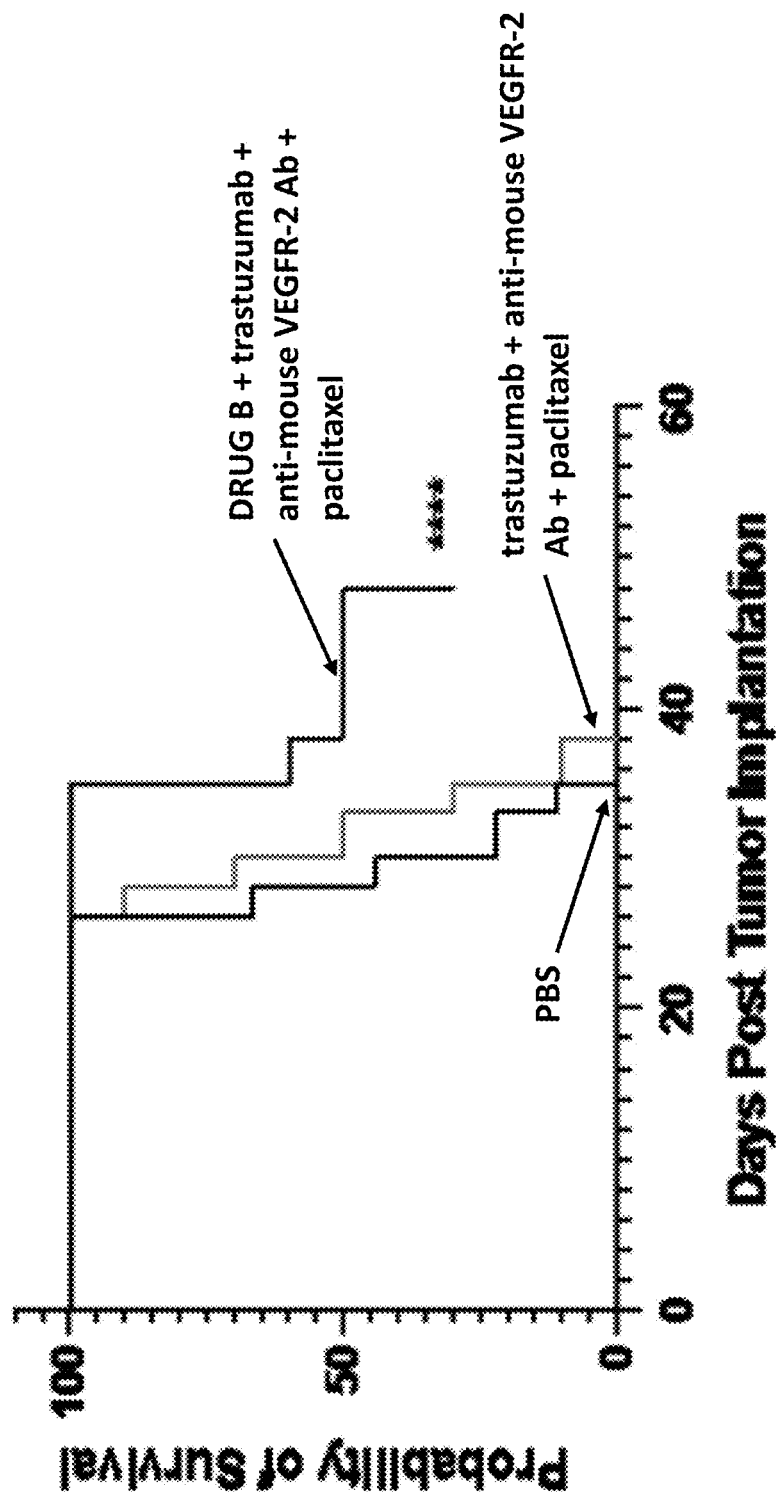
FIG. 4B shows the results of experiments that were performed to assess whether quadruplet therapy with DRUG B+trastuzumab+anti-mouse VEGFR-2+paclitaxel increases the probability of survival compared to triplet therapy with trastuzumab+anti-mouse VEGFR-2+paclitaxel in a CT26 m:h HER2-expression chimeric tumor model in mice.

On page 3 of 6, FIG 2B, Line 2, please delete "traztuzumab" and insert -- trastuzumab --;

On page 3 of 6, FIG 2B, Line 4, please delete "traztuzumab" and insert -- trastuzumab --;

On page 6 of 6, FIG 4B, Line 2 (Y-axis), please delete "Probabllity of Survlval" and insert -- Probability of Survival --;

In the Specification

At Column 6, Line number 39, please delete "pM 10" and insert -- pM, 10 --;

At Column 7, Line number 17, please delete "pM 10" and insert -- pM, 10 --;

At Column 9, Line number 23, please delete "50268" and insert -- S0268 --;

At Columns 23-24, Line number 23 (Table 5-continued), please delete "$X_3 = ,$" and insert -- $X_3 = I,$ --;

At Column 66, Line number 61, please delete "K409l," and insert -- K409I, --;

At Column 67, Line number 5, please delete "K409l," and insert -- K409I, --;

Signed and Sealed this
Twenty-second Day of April, 2025

Coke Morgan Stewart
*Acting Director of the United States Patent and Trademark Office*

At Column 67, Line number 26, please delete "K4091," and insert -- K409I, --;

At Column 72, Line number 4, please delete "NSO," and insert -- NS0, --;

At Column 72, Line number 5, please delete "NSO," and insert -- NS0, --;

At Column 72, Line number 11, please delete "λ," and insert -- λ --;

At Column 74, Line number 42, please delete "apartinib," and insert -- apatinib, --;

At Column 76, Line number 44, please delete "Bcl-1x," and insert -- Bcl-lx, --;

At Column 76, Line number 46, please delete "Bcl-1x," and insert -- Bcl-lx, --;

At Column 80, Line number 50, before "HPV" please insert -- TGF-βRII, --;

At Column 81, Line number 1, please delete "CLECSC)," and insert -- CLEC5C, --;

At Column 81, Line number 31, please delete "MI," and insert -- RII, --;

At Column 84, Line number 4, please delete "103792 s52501b1" and insert -- 103792s5250lbl --;

At Column 84, Line number 57, please delete "an the" and insert -- the --;

At Column 85, Line number 42, please delete "125477 s0341b1" and insert -- 125477s034lbl --;

At Column 85, Line number 51, please delete "103792 s52501b1" and insert -- 103792s5250lbl --;

At Column 86, Line number 15, please delete "an the" and insert -- the --;

At Column 87, Line number 19, please delete "an the" and insert -- the --;

At Column 88, Line number 24, please delete "an the" and insert -- the --;

At Column 89, Line numbers 18-19, please delete "adenocarcimoa." and insert -- adenocarcinoma. --;

At Column 89, Line number 20, please delete "gastroesophogeal" and insert -- gastroesophageal --;

At Column 89, Line numbers 22-23, please delete "gastroesophogeal" and insert -- gastroesophageal --;

At Column 90, Line numbers 38-39, please delete "018057 s0801b1" and insert -- 018057s080lbl --;

At Column 90, Line number 40, please delete "018057 s0831b1" and insert -- 018057s083lbl --;

At Column 91, Line number 5, please delete "020452 s0051b1" and insert -- 020452s005lbl --;

CERTIFICATE OF CORRECTION (continued)
U.S. Pat. No. 12,098,214 B2

At Column 93, Line number 14, please delete "the the" and insert -- the --;

At Column 93, Line number 18, please delete "the the" and insert -- the --;

At Column 93, Line number 22, please delete "the the" and insert -- the --;

At Column 95, Line number 23, please delete "polypeptide polypeptide" and insert -- polypeptide --;

At Column 95, Line numbers 32-33, please delete "polypeptide polypeptide" and insert -- polypeptide --;

At Column 95, Line number 40, please delete "polypeptide polypeptide" and insert -- polypeptide --;

At Column 95, Line number 50, please delete "polypeptide polypeptide" and insert -- polypeptide --;

At Column 95, Line number 57, please delete "polypeptide polypeptide" and insert -- polypeptide --;

At Column 95, Line number 64, please delete "polypeptide polypeptide" and insert -- polypeptide --;

At Column 96, Line number 27, please delete "esophogeal" and insert -- esophageal --;

At Column 96, Line number 37, please delete "gastroesophogeal" and insert -- gastroesophageal --;

At Column 97, Line number 26, please delete "gastroesophogeal" and insert -- gastroesophageal --;

At Column 97, Line numbers 27-28, please delete "polypeptide polypeptide" and insert -- polypeptide --;

At Column 97, Line number 33, please delete "gastroesophogeal" and insert -- gastroesophageal --;

At Column 97, Line numbers 34-35, please delete "polypeptide polypeptide" and insert -- polypeptide --;

At Column 97, Line number 41, please delete "gastroesophogeal" and insert -- gastroesophageal --;

At Column 97, Line number 43, please delete "polypeptide polypeptide" and insert -- polypeptide --;

At Column 97, Line number 51, please delete "gastroesophogeal" and insert -- gastroesophageal --;

At Column 97, Line numbers 52-53, please delete "polypeptide polypeptide" and insert -- polypeptide --;

At Column 97, Line number 58, please delete "gastroesophogeal" and insert -- gastroesophageal --;

At Column 97, Line numbers 59-60, please delete "polypeptide polypeptide" and insert -- polypeptide --;

At Column 97, Line number 66, please delete "gastroesophogeal" and insert -- gastroesophageal --;

At Column 98, Line number 1, please delete "polypeptide polypeptide" and insert -- polypeptide --;

At Column 98, Line number 9, please delete "gastroesophogeal" and insert -- gastroesophageal --;

At Column 98, Line number 18, please delete "gastroesophogeal" and insert -- gastroesophageal --;

At Column 98, Line number 30, please delete "gastroesophogeal" and insert -- gastroesophageal --;

At Column 104, Line number 38, after "100" please insert -- µL --;

At Column 104, Line number 65, please delete "wth" and insert -- with --;

At Column 107, Line number 31, please delete "22(12)." and insert -- 22(12): --;

At Column 110, Line number 13, please delete "traztuzumab," and insert -- trastuzumab, --;

At Column 110, Line number 20, please delete "receieve" and insert -- receive --;

At Column 110, Line number 24, please delete "receiveing" and insert -- receiving --;

At Columns 109-110, TABLE D, Line number 49, please delete "Gastresophageal" and insert -- Gastroesophageal --;

At Columns 109-110, TABLE D, Line number 49, please delete "wth" and insert -- with --;

At Columns 109-110, TABLE D, Line number 49, please delete "Tastuzumab" and insert -- Trastuzumab --;

At Columns 111-112, TABLE D-continued, Line number 2, please delete "Gastresophageal" and insert -- Gastroesophageal --;

At Columns 111-112, TABLE D-continued, Line number 2, please delete "wth" and insert -- with --;

At Columns 111-112, TABLE D-continued, Line number 2, please delete "Tastuzumab" and insert -- Trastuzumab --;

At Column 111, Line number 52, please delete "Adenocarcinoma" and insert -- Adenocarcinoma. --;

At Column 112, Line number 44, please delete "with with" and insert -- with --; and At Column 114, Line number 60, please delete "m: h" and insert -- m:h --.

SEQUENCE LISTING

<160> NUMBER OF SEQ ID NOS: 224

<210> SEQ ID NO 1
<211> LENGTH: 119
<212> TYPE: PRT
<213> ORGANISM: Homo sapiens

<400> SEQUENCE: 1

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95
```

```
Gly Ser Pro Asp Asp Val Glu Phe Lys Ser Gly Ala Gly Thr Glu Leu
                100                 105                 110

Ser Val Arg Ala Lys Pro Ser
        115
```

<210> SEQ ID NO 2
<211> LENGTH: 118
<212> TYPE: PRT
<213> ORGANISM: Homo sapiens

<400> SEQUENCE: 2

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser
        115
```

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = E or G
<220> FEATURE:
<221> NAME/KEY: VARIANT
<222> LOCATION: 12
<223> OTHER INFORMATION: Xaa = S or F
<220> FEATURE:
<221> NAME/KEY: VARIANT
<222> LOCATION: 14
<223> OTHER INFORMATION: Xaa = L or S
<220> FEATURE:
<221> NAME/KEY: VARIANT
<222> LOCATION: 20
<223> OTHER INFORMATION: Xaa = T or S
<220> FEATURE:
<221> NAME/KEY: VARIANT
<222> LOCATION: 22
<223> OTHER INFORMATION: Xaa = T or I
<220> FEATURE:
<221> NAME/KEY: VARIANT
<222> LOCATION: 24
<223> OTHER INFORMATION: Xaa = R, H, or L
<220> FEATURE:
<221> NAME/KEY: VARIANT
<222> LOCATION: 27
<223> OTHER INFORMATION: Xaa = A or V
<220> FEATURE:
<221> NAME/KEY: VARIANT
<222> LOCATION: 45
<223> OTHER INFORMATION: Xaa = G or A
<220> FEATURE:
<221> NAME/KEY: VARIANT
<222> LOCATION: 65
<223> OTHER INFORMATION: Xaa = D or E
<220> FEATURE:
<221> NAME/KEY: VARIANT
<222> LOCATION: 66
<223> OTHER INFORMATION: Xaa = L or S
<220> FEATURE:
<221> NAME/KEY: VARIANT
<222> LOCATION: 70
<223> OTHER INFORMATION: Xaa = N or E or D
<220> FEATURE:
<221> NAME/KEY: VARIANT
<222> LOCATION: 75
<223> OTHER INFORMATION: Xaa = S or P
<220> FEATURE:
<221> NAME/KEY: VARIANT
<222> LOCATION: 77
<223> OTHER INFORMATION: Xaa = R or S
<220> FEATURE:
<221> NAME/KEY: VARIANT
<222> LOCATION: 79
<223> OTHER INFORMATION: Xaa = G or S
<220> FEATURE:

```
<221> NAME/KEY: VARIANT
<222> LOCATION: 99
<223> OTHER INFORMATION: Xaa = P or absent
<220> FEATURE:
<221> NAME/KEY: VARIANT
<222> LOCATION: 100
<223> OTHER INFORMATION: Xaa = D or P
<220> FEATURE:
<221> NAME/KEY: VARIANT
<222> LOCATION: 102
<223> OTHER INFORMATION: Xaa = V or T
<220> FEATURE:
<221> NAME/KEY: VARIANT
<222> LOCATION: 116
<223> OTHER INFORMATION: Xaa = A or G

<400> SEQUENCE: 11

Glu Glu Xaa Leu Gln Val Ile Gln Pro Asp Lys Xaa Val Xaa Val Ala
1               5                   10                  15

Ala Gly Glu Xaa Ala Xaa Leu Xaa Cys Thr Xaa Thr Ser Leu Ile Pro
            20                  25                  30

Val Gly Pro Ile Gln Trp Phe Arg Gly Ala Gly Pro Xaa Arg Glu Leu
            35                  40                  45

Ile Tyr Asn Gln Lys Glu Gly His Phe Pro Arg Val Thr Thr Val Ser
50                  55                  60

Xaa Xaa Thr Lys Arg Xaa Asn Met Asp Phe Xaa Ile Xaa Ile Xaa Asn
65                  70                  75                  80

Ile Thr Pro Ala Asp Ala Gly Thr Tyr Tyr Cys Val Lys Phe Arg Lys
                85                  90                  95

Gly Ser Xaa Xaa Asp Xaa Glu Phe Lys Ser Gly Ala Gly Thr Glu Leu
            100                 105                 110

Ser Val Arg Xaa Lys Pro Ser
        115

<210> SEQ ID NO 12

<400> SEQUENCE: 12

000

<210> SEQ ID NO 13
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 27
<223> OTHER INFORMATION: Xaa = A, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 47
```

```
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = L, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 104
<223> OTHER INFORMATION: Xaa = F, V

<400> SEQUENCE: 13

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Xaa Arg Asn Asn Met Asp Phe Ser Ile Arg Ile Gly Asn
65                  70                  75                  80

Ile Thr Pro Ala Asp Ala Gly Thr Tyr Tyr Cys Xaa Lys Xaa Arg Lys
                85                  90                  95

Gly Ser Pro Asp Asp Val Glu Xaa Lys Ser Gly Ala Gly Thr Glu Leu
            100                 105                 110

Ser Val Arg Ala Lys Pro Ser
            115

<210> SEQ ID NO 14
<211> LENGTH: 118
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 21
<223> OTHER INFORMATION: Xaa = A, V
```

```
<220> FEATURE:
<221> NAME/KEY: VARIANT
<222> LOCATION: 27
<223> OTHER INFORMATION: Xaa = V, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = S, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 103
<223> OTHER INFORMATION: Xaa = F, V

<400> SEQUENCE: 14

Glu Glu Glu Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Xaa Arg Glu Asn Met Asp Phe Ser Ile Ser Ile Ser Asn
65                  70                  75                  80

Ile Thr Pro Ala Asp Ala Gly Thr Tyr Tyr Cys Xaa Lys Xaa Arg Lys
                85                  90                  95

Gly Ser Pro Asp Thr Glu Xaa Lys Ser Gly Ala Gly Thr Glu Leu Ser
            100                 105                 110

Val Arg Ala Lys Pro Ser
        115

<210> SEQ ID NO 15

<400> SEQUENCE: 15

000
```

```
<210> SEQ ID NO 16
<400> SEQUENCE: 16

000

<210> SEQ ID NO 17
<400> SEQUENCE: 17

000

<210> SEQ ID NO 18
<400> SEQUENCE: 18

000

<210> SEQ ID NO 19
<400> SEQUENCE: 19

000

<210> SEQ ID NO 20
<400> SEQUENCE: 20

000

<210> SEQ ID NO 21
<400> SEQUENCE: 21

000

<210> SEQ ID NO 22
<400> SEQUENCE: 22

000

<210> SEQ ID NO 23
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = E, G
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 12
<223> OTHER INFORMATION: Xaa = S, F
<220> FEATURE:
<221> NAME/KEY: VARIANT
<222> LOCATION: 14
<223> OTHER INFORMATION: Xaa = L, S
<220> FEATURE:
<221> NAME/KEY: VARIANT
<222> LOCATION: 20
<223> OTHER INFORMATION: Xaa = S, T
```

-continued

```
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 22
<223> OTHER INFORMATION: Xaa = I, T
<220> FEATURE:
<221> NAME/KEY: VARIANT
<222> LOCATION: 24
<223> OTHER INFORMATION: Xaa = H, R
<220> FEATURE:
<221> NAME/KEY: VARIANT
<222> LOCATION: 27
<223> OTHER INFORMATION: Xaa = A, V, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 45
<223> OTHER INFORMATION: Xaa = A, G
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 65
<223> OTHER INFORMATION: Xaa = D, E
<220> FEATURE:
<221> NAME/KEY: VARIANT
<222> LOCATION: 66
<223> OTHER INFORMATION: Xaa = S, L, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 70
<223> OTHER INFORMATION: Xaa = E, D
<220> FEATURE:
<221> NAME/KEY: VARIANT
<222> LOCATION: 75
<223> OTHER INFORMATION: Xaa = S, P
<220> FEATURE:
<221> NAME/KEY: VARIANT
<222> LOCATION: 77
<223> OTHER INFORMATION: Xaa = S, R
<220> FEATURE:
<221> NAME/KEY: VARIANT
<222> LOCATION: 79
<223> OTHER INFORMATION: Xaa = S, G
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 101
```

```
<223> OTHER INFORMATION: Xaa = D or absent
<220> FEATURE:
<221> NAME/KEY: VARIANT
<222> LOCATION: 102
<223> OTHER INFORMATION: Xaa = T, V
<220> FEATURE:
<221> NAME/KEY: VARIANT
<222> LOCATION: 104
<223> OTHER INFORMATION: Xaa = F, V
<220> FEATURE:
<221> NAME/KEY: VARIANT
<222> LOCATION: 116
<223> OTHER INFORMATION: Xaa = A, G

<400> SEQUENCE: 23

Glu Glu Xaa Xaa Gln Xaa Ile Gln Pro Asp Lys Xaa Val Xaa Val Ala
1               5                   10                  15

Ala Gly Glu Xaa Xaa Xaa Leu Xaa Cys Thr Xaa Thr Ser Leu Xaa Pro
            20                  25                  30

Val Gly Pro Ile Gln Trp Phe Arg Gly Ala Gly Pro Xaa Arg Xaa Leu
        35                  40                  45

Ile Tyr Asn Gln Xaa Xaa Gly Xaa Phe Pro Arg Val Thr Thr Val Ser
    50                  55                  60

Xaa Xaa Thr Xaa Arg Xaa Asn Met Asp Phe Xaa Ile Xaa Ile Xaa Asn
65              70                  75                  80

Ile Thr Pro Ala Asp Ala Gly Thr Tyr Tyr Cys Xaa Lys Xaa Arg Lys
                85                  90                  95

Gly Ser Pro Asp Xaa Xaa Glu Xaa Lys Ser Gly Ala Gly Thr Glu Leu
                100                 105                 110

Ser Val Arg Xaa Lys Pro Ser
                115

<210> SEQ ID NO 24
<211> LENGTH: 102
<212> TYPE: PRT
<213> ORGANISM: Artificial Sequence
<220> FEATURE:
<223> OTHER INFORMATION: Synthetic Construct

<400> SEQUENCE: 24

Ala Pro Val Val Ser Gly Pro Ala Ala Arg Ala Thr Pro Gln His Thr
1               5                   10                  15

Val Ser Phe Thr Cys Glu Ser His Gly Phe Ser Pro Arg Asp Ile Thr
            20                  25                  30

Leu Lys Trp Phe Lys Asn Gly Asn Glu Leu Ser Asp Phe Gln Thr Asn
        35                  40                  45

Val Asp Pro Val Gly Glu Ser Val Ser Tyr Ser Ile His Ser Thr Ala
    50                  55                  60

Lys Val Val Leu Thr Arg Glu Asp Val His Ser Gln Val Ile Cys Glu
65              70                  75                  80

Val Ala His Val Thr Leu Gln Gly Asp Pro Leu Arg Gly Thr Ala Asn
                85                  90                  95

Leu Ser Glu Thr Ile Arg
            100

<210> SEQ ID NO 25
<211> LENGTH: 99
<212> TYPE: PRT
<213> ORGANISM: Artificial Sequence
<220> FEATURE:
<223> OTHER INFORMATION: Synthetic Construct
```

-continued

<400> SEQUENCE: 25

Val Pro Pro Thr Leu Glu Val Thr Gln Gln Pro Val Arg Ala Glu Asn
1               5                   10                  15

Gln Val Asn Val Thr Cys Gln Val Arg Lys Phe Tyr Pro Gln Arg Leu
            20                  25                  30

Gln Leu Thr Trp Leu Glu Asn Gly Asn Val Ser Arg Thr Glu Thr Ala
        35                  40                  45

Ser Thr Val Thr Glu Asn Lys Asp Gly Thr Tyr Asn Trp Met Ser Trp
50                  55                  60

Leu Leu Val Asn Val Ser Ala His Arg Asp Asp Val Lys Leu Thr Cys
65                  70                  75                  80

Gln Val Glu His Asp Gly Gln Pro Ala Val Ser Lys Ser His Asp Leu
                85                  90                  95

Lys Val Ser

<210> SEQ ID NO 26
<211> LENGTH: 118
<212> TYPE: PRT
<213> ORGANISM: Artificial Sequence
<220> FEATURE:
<223> OTHER INFORMATION: Synthetic Construct

<400> SEQUENCE: 26

Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly His Phe Pro Arg Val Thr Thr Val Ser
50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
        115

<210> SEQ ID NO 27
<211> LENGTH: 118
<212> TYPE: PRT
<213> ORGANISM: Artificial Sequence
<220> FEATURE:
<223> OTHER INFORMATION: Synthetic Construct

<400> SEQUENCE: 27

Glu Glu Glu Val Gln Val Ile Gln Pro Asp Lys Ser Val Ser Val Ala
1               5                   10                  15

Ala Gly Glu Ser Ala Ile Leu His Cys Thr Leu Thr Ser Leu Ile Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly His Phe Pro Arg Val Thr Thr Val Ser
50                  55                  60

```
Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 28
<211> LENGTH: 118
<212> TYPE: PRT
<213> ORGANISM: Artificial Sequence
<220> FEATURE:
<223> OTHER INFORMATION: Synthetic Construct

<400> SEQUENCE: 28

Glu Glu Glu Val Gln Ile Ile Gln Pro Asp Lys Ser Val Ser Val Ala
1               5                   10                  15

Ala Gly Glu Ser Val Ile Leu His Cys Thr Ile Thr Ser Leu Thr Pro
            20                  25                  30

Val Gly Pro Ile Gln Trp Phe Arg Gly Ala Gly Pro Ala Arg Leu Leu
        35                  40                  45

Ile Tyr Asn Gln Arg Glu Gly Pro Phe Pro Arg Val Thr Thr Val Ser
    50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Val Lys Leu Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 29
<211> LENGTH: 118
<212> TYPE: PRT
<213> ORGANISM: Artificial Sequence
<220> FEATURE:
<223> OTHER INFORMATION: Synthetic Construct

<400> SEQUENCE: 29

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Ser Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Gly Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Leu Arg Lys
                85                  90                  95
```

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 30
<211> LENGTH: 118
<212> TYPE: PRT
<213> ORGANISM: Artificial Sequence
<220> FEATURE:
<223> OTHER INFORMATION: Synthetic Construct

<400> SEQUENCE: 30

Glu Glu Glu Ile Gln Val Ile Gln Pro Asp Lys Ser Val Ser Val Ala
1               5                   10                  15

Ala Gly Glu Ser Val Ile Ile His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Arg Phe Pro Arg Val Thr Thr Val Ser
    50                  55                  60

Glu Gly Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Val Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
        115

<210> SEQ ID NO 31
<211> LENGTH: 118
<212> TYPE: PRT
<213> ORGANISM: Artificial Sequence
<220> FEATURE:
<223> OTHER INFORMATION: Synthetic Construct

<400> SEQUENCE: 31

Glu Glu Glu Val Gln Ile Ile Gln Pro Asp Lys Ser Val Ser Val Ala
1               5                   10                  15

Ala Gly Glu Ser Ile Ile Leu His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Glu Gly Arg Phe Pro Arg Val Thr Thr Val Ser
    50                  55                  60

Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Leu Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 32
<211> LENGTH: 118
<212> TYPE: PRT

```
<213> ORGANISM: Artificial Sequence
<220> FEATURE:
<223> OTHER INFORMATION: Synthetic Construct

<400> SEQUENCE: 32

Glu Glu Glu Val Gln Leu Ile Gln Pro Asp Lys Ser Val Ser Val Ala
1               5                   10                  15

Ala Gly Glu Ser Ala Ile Leu His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Glu Gly Pro Phe Pro Arg Val Thr Thr Val Ser
50                  55                  60

Glu Gly Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
        115

<210> SEQ ID NO 33
<211> LENGTH: 119
<212> TYPE: PRT
<213> ORGANISM: Artificial Sequence
<220> FEATURE:
<223> OTHER INFORMATION: Synthetic Construct

<400> SEQUENCE: 33

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 34
<211> LENGTH: 118
<212> TYPE: PRT
<213> ORGANISM: Artificial Sequence
<220> FEATURE:
<223> OTHER INFORMATION: Synthetic Construct

<400> SEQUENCE: 34

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30
```

-continued

Val Gly Pro Ile Gln Trp Phe Arg Gly Ala Gly Pro Ala Arg Leu Leu
            35                  40                  45

Ile Tyr Asn Gln Arg Gln Gly Pro Phe Pro Arg Val Thr Thr Val Ser
        50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 35
<211> LENGTH: 118
<212> TYPE: PRT
<213> ORGANISM: Artificial Sequence
<220> FEATURE:
<223> OTHER INFORMATION: Synthetic Construct

<400> SEQUENCE: 35

Glu Glu Glu Val Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
            35                  40                  45

Ile Tyr Asn Gln Lys Gln Gly Pro Phe Pro Arg Val Thr Thr Ile Ser
        50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 36
<211> LENGTH: 118
<212> TYPE: PRT
<213> ORGANISM: Artificial Sequence
<220> FEATURE:
<223> OTHER INFORMATION: Synthetic Construct

<400> SEQUENCE: 36

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Thr Pro
            20                  25                  30

Val Gly Pro Ile Gln Trp Phe Arg Gly Ala Gly Pro Ala Arg Val Leu
            35                  40                  45

Ile Tyr Asn Gln Arg Gln Gly Pro Phe Pro Arg Val Thr Thr Val Ser
        50                  55                  60

Glu Gly Thr Arg Arg Glu Asn Met Asp Phe Ser Ile Ser Ile Ser Asn
65                  70                  75                  80

```
Ile Thr Pro Ala Asp Ala Gly Thr Tyr Tyr Cys Ile Lys Phe Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
        115

<210> SEQ ID NO 37
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 27
<223> OTHER INFORMATION: Xaa = A, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = L, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 80
<223> OTHER INFORMATION: Xaa = N, A, C, D, E, F, G, H, I, K, L,
      M, P, Q, R, S, T, V, W, Y
<220> FEATURE:
<221> NAME/KEY: VARIANT
<222> LOCATION: 83
<223> OTHER INFORMATION: Xaa = P, A, C, D, E, F, G, H, I, K, L,
      M, N, Q, R, S, T, V, W, Y
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
```

```
<220> FEATURE:
<221> NAME/KEY: VARIANT
<222> LOCATION: 104
<223> OTHER INFORMATION: Xaa = F, V

<400> SEQUENCE: 37

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Xaa Arg Asn Asn Met Asp Phe Ser Ile Arg Ile Gly Xaa
65              70                  75                  80

Ile Thr Xaa Ala Asp Ala Gly Thr Tyr Tyr Cys Xaa Lys Xaa Arg Lys
            85                  90                  95

Gly Ser Pro Asp Asp Val Glu Xaa Lys Ser Gly Ala Gly Thr Glu Leu
            100                 105                 110

Ser Val Arg Ala Lys Pro Ser
            115

<210> SEQ ID NO 38
<211> LENGTH: 118
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 27
<223> OTHER INFORMATION: Xaa = V, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = S, T, G
<220> FEATURE:
```

```
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 80
<223> OTHER INFORMATION: Xaa = N, A, C, D, E, F, G, H, I, K, L, M, P, Q,
      R, S, T, V, W, Y
<220> FEATURE:
<221> NAME/KEY: VARIANT
<222> LOCATION: 83
<223> OTHER INFORMATION: Xaa = P, A, C, D, E, F, G, H, I, K, L, M, N, Q,
      R, S, T, V, W, Y
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 103
<223> OTHER INFORMATION: Xaa = F, V

<400> SEQUENCE: 38

Glu Glu Glu Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Xaa Arg Glu Asn Met Asp Phe Ser Ile Ser Ile Ser Xaa
65              70                  75                  80

Ile Thr Xaa Ala Asp Ala Gly Thr Tyr Tyr Cys Xaa Lys Xaa Arg Lys
            85                  90                  95

Gly Ser Pro Asp Thr Glu Xaa Lys Ser Gly Ala Gly Thr Glu Leu Ser
            100                 105                 110

Val Arg Ala Lys Pro Ser
            115

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000
```

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = E, G
<220> FEATURE:
<221> NAME/KEY: VARIANT
<222> LOCATION: 4
<223> OTHER INFORMATION: Xaa = L, I, V
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 12
<223> OTHER INFORMATION: Xaa = S, F
<220> FEATURE:
<221> NAME/KEY: VARIANT
<222> LOCATION: 14
<223> OTHER INFORMATION: Xaa = L, S
<220> FEATURE:
<221> NAME/KEY: VARIANT
<222> LOCATION: 20
<223> OTHER INFORMATION: Xaa = S, T
<220> FEATURE:
<221> NAME/KEY: VARIANT
<222> LOCATION: 21
<223> OTHER INFORMATION: Xaa = A, V
<220> FEATURE:
<221> NAME/KEY: VARIANT
<222> LOCATION: 22
<223> OTHER INFORMATION: Xaa = I, T
<220> FEATURE:
<221> NAME/KEY: VARIANT
<222> LOCATION: 24
<223> OTHER INFORMATION: Xaa = H, R, L
<220> FEATURE:
<221> NAME/KEY: VARIANT
<222> LOCATION: 27
<223> OTHER INFORMATION: Xaa = A, V, I, L
<220> FEATURE:
<221> NAME/KEY: VARIANT
<222> LOCATION: 31

```
<223> OTHER INFORMATION: Xaa = I, T, S, F
<220> FEATURE:
<221> NAME/KEY: VARIANT
<222> LOCATION: 45
<223> OTHER INFORMATION: Xaa = A, G
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 65
<223> OTHER INFORMATION: Xaa = D, E
<220> FEATURE:
<221> NAME/KEY: VARIANT
<222> LOCATION: 66
<223> OTHER INFORMATION: Xaa = S, L, T, G
<220> FEATURE:
<221> NAME/KEY: VARIANT
<222> LOCATION: 68
<223> OTHER INFORMATION: Xaa = K, R
<220> FEATURE:
<221> NAME/KEY: VARIANT
<222> LOCATION: 70
<223> OTHER INFORMATION: Xaa = E, N
<220> FEATURE:
<221> NAME/KEY: VARIANT
<222> LOCATION: 75
<223> OTHER INFORMATION: Xaa = S, P
<220> FEATURE:
<221> NAME/KEY: VARIANT
<222> LOCATION: 77
<223> OTHER INFORMATION: Xaa = S, R
<220> FEATURE:
<221> NAME/KEY: VARIANT
<222> LOCATION: 79
<223> OTHER INFORMATION: Xaa = S, G
<220> FEATURE:
<221> NAME/KEY: VARIANT
<222> LOCATION: 80
<223> OTHER INFORMATION: Xaa = Any Amino Acid
<220> FEATURE:
<221> NAME/KEY: VARIANT
<222> LOCATION: 83
<223> OTHER INFORMATION: Xaa = Any Amino Acid
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 94
<223> OTHER INFORMATION: Xaa = F, L, V
<220> FEATURE:
<221> NAME/KEY: VARIANT
<222> LOCATION: 101
<223> OTHER INFORMATION: Xaa = D or absent
<220> FEATURE:
<221> NAME/KEY: VARIANT
<222> LOCATION: 102
<223> OTHER INFORMATION: Xaa = T, V
<220> FEATURE:
<221> NAME/KEY: VARIANT
<222> LOCATION: 104
<223> OTHER INFORMATION: Xaa = F, V
<220> FEATURE:
<221> NAME/KEY: VARIANT
```

<222> LOCATION: 116
<223> OTHER INFORMATION: Xaa = A, G

<400> SEQUENCE: 47

Glu Glu Xaa Xaa Gln Xaa Ile Gln Pro Asp Lys Xaa Val Xaa Val Ala
1               5                   10                  15

Ala Gly Glu Xaa Xaa Xaa Leu Xaa Cys Thr Xaa Thr Ser Leu Xaa Pro
            20                  25                  30

Val Gly Pro Ile Gln Trp Phe Arg Gly Ala Gly Pro Xaa Arg Xaa Leu
            35                  40                  45

Ile Tyr Asn Gln Xaa Xaa Gly Xaa Phe Pro Arg Val Thr Thr Val Ser
            50                  55                  60

Xaa Xaa Thr Xaa Arg Xaa Asn Met Asp Phe Xaa Ile Xaa Ile Xaa Xaa
65              70                  75                  80

Ile Thr Xaa Ala Asp Ala Gly Thr Tyr Tyr Cys Xaa Lys Xaa Arg Lys
            85                  90                  95

Gly Ser Pro Asp Xaa Xaa Glu Xaa Lys Ser Gly Ala Gly Thr Glu Leu
            100                 105                 110

Ser Val Arg Xaa Lys Pro Ser
        115

<210> SEQ ID NO 48
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V, I
<220> FEATURE:
<221> NAME/KEY: VARIANT
<222> LOCATION: 14
<223> OTHER INFORMATION: Xaa = L, S
<220> FEATURE:
<221> NAME/KEY: VARIANT
<222> LOCATION: 20
<223> OTHER INFORMATION: Xaa = T, S
<220> FEATURE:
<221> NAME/KEY: VARIANT
<222> LOCATION: 22
<223> OTHER INFORMATION: Xaa = T, I
<220> FEATURE:
<221> NAME/KEY: VARIANT
<222> LOCATION: 24
<223> OTHER INFORMATION: Xaa = R, H
<220> FEATURE:
<221> NAME/KEY: VARIANT
<222> LOCATION: 27
<223> OTHER INFORMATION: Xaa = A, V, I
<220> FEATURE:
<221> NAME/KEY: VARIANT
<222> LOCATION: 31
<223> OTHER INFORMATION: Xaa = I, R, Y, K, F
<220> FEATURE:
<221> NAME/KEY: VARIANT
<222> LOCATION: 45
<223> OTHER INFORMATION: Xaa = G, A
<220> FEATURE:
<221> NAME/KEY: VARIANT
<222> LOCATION: 47
<223> OTHER INFORMATION: Xaa = E, V
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54

<223> OTHER INFORMATION: Xaa = E, D, Q
<220> FEATURE:
<221> NAME/KEY: VARIANT
<222> LOCATION: 56
<223> OTHER INFORMATION: Xaa = H, P
<220> FEATURE:
<221> NAME/KEY: VARIANT
<222> LOCATION: 65
<223> OTHER INFORMATION: Xaa = D, E
<220> FEATURE:
<221> NAME/KEY: VARIANT
<222> LOCATION: 66
<223> OTHER INFORMATION: Xaa = S, L, T
<220> FEATURE:
<221> NAME/KEY: VARIANT
<222> LOCATION: 70
<223> OTHER INFORMATION: Xaa = N, E
<220> FEATURE:
<221> NAME/KEY: VARIANT
<222> LOCATION: 77
<223> OTHER INFORMATION: Xaa = R, S
<220> FEATURE:
<221> NAME/KEY: VARIANT
<222> LOCATION: 79
<223> OTHER INFORMATION: Xaa = G, S
<220> FEATURE:
<221> NAME/KEY: VARIANT
<222> LOCATION: 80
<223> OTHER INFORMATION: Xaa = N, A
<220> FEATURE:
<221> NAME/KEY: VARIANT
<222> LOCATION: 92
<223> OTHER INFORMATION: Xaa = V, I
<220> FEATURE:
<221> NAME/KEY: VARIANT
<222> LOCATION: 98
<223> OTHER INFORMATION: Xaa = S, I, M
<220> FEATURE:
<221> NAME/KEY: VARIANT
<222> LOCATION: 99
<223> OTHER INFORMATION: Xaa = P or absent
<220> FEATURE:
<221> NAME/KEY: VARIANT
<222> LOCATION: 100
<223> OTHER INFORMATION: Xaa = D, P
<220> FEATURE:
<221> NAME/KEY: VARIANT
<222> LOCATION: 102
<223> OTHER INFORMATION: Xaa = V, T

<400> SEQUENCE: 48

Glu Glu Glu Leu Gln Xaa Ile Gln Pro Asp Lys Ser Val Xaa Val Ala
1               5                   10                  15

Ala Gly Glu Xaa Ala Xaa Leu Xaa Cys Thr Xaa Thr Ser Leu Xaa Pro
            20                  25                  30

Val Gly Pro Ile Gln Trp Phe Arg Gly Ala Gly Pro Xaa Arg Xaa Leu
        35                  40                  45

Ile Tyr Asn Gln Xaa Xaa Gly Xaa Phe Pro Arg Val Thr Thr Val Ser
50                  55                  60

Xaa Xaa Thr Lys Arg Xaa Asn Met Asp Phe Ser Ile Xaa Ile Xaa Xaa
65                  70                  75                  80

Ile Thr Pro Ala Asp Ala Gly Thr Tyr Tyr Cys Xaa Lys Phe Arg Lys
                85                  90                  95

Gly Xaa Xaa Xaa Asp Xaa Glu Phe Lys Ser Gly Ala Gly Thr Glu Leu
            100                 105                 110

Ser Val Arg Ala Lys Pro Ser
            115

<210> SEQ ID NO 49
<211> LENGTH: 119

```
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V, I, L
<220> FEATURE:
<221> NAME/KEY: VARIANT
<222> LOCATION: 27
<223> OTHER INFORMATION: Xaa = A, I, V, L
<220> FEATURE:
<221> NAME/KEY: VARIANT
<222> LOCATION: 31
<223> OTHER INFORMATION: Xaa = I, F, S, T
<220> FEATURE:
<221> NAME/KEY: VARIANT
<222> LOCATION: 47
<223> OTHER INFORMATION: Xaa = E, V, L
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = L, T, S, G
<220> FEATURE:
<221> NAME/KEY: VARIANT
<222> LOCATION: 80
<223> OTHER INFORMATION: Xaa = A
<220> FEATURE:
<221> NAME/KEY: VARIANT
<222> LOCATION: 92
<223> OTHER INFORMATION: Xaa = V, I

<400> SEQUENCE: 49

Glu Glu Glu Leu Gln Xaa Ile Gln Pro Asp Lys Ser Val Leu Val Ala
1               5                   10                  15

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Lys Arg Asn Asn Met Asp Phe Ser Ile Arg Ile Gly Xaa
65                  70                  75                  80

Ile Thr Pro Ala Asp Ala Gly Thr Tyr Tyr Cys Xaa Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 50
<211> LENGTH: 118
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: VARIANT
<222> LOCATION: 6
<223> OTHER INFORMATION: Xaa = V, I
<220> FEATURE:
<221> NAME/KEY: VARIANT
<222> LOCATION: 27
<223> OTHER INFORMATION: Xaa = V, I
<220> FEATURE:
<221> NAME/KEY: VARIANT
<222> LOCATION: 31
<223> OTHER INFORMATION: Xaa = I, F
<220> FEATURE:
<221> NAME/KEY: VARIANT
<222> LOCATION: 47
<223> OTHER INFORMATION: Xaa = E, V
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 54
<223> OTHER INFORMATION: Xaa = E, Q
<220> FEATURE:
<221> NAME/KEY: VARIANT
<222> LOCATION: 56
<223> OTHER INFORMATION: Xaa = H, P
<220> FEATURE:
<221> NAME/KEY: VARIANT
<222> LOCATION: 66
<223> OTHER INFORMATION: Xaa = S, T
<220> FEATURE:
<221> NAME/KEY: VARIANT
<222> LOCATION: 80
<223> OTHER INFORMATION: Xaa = N, A
<220> FEATURE:
<221> NAME/KEY: VARIANT
<222> LOCATION: 92
<223> OTHER INFORMATION: Xaa = V, I

<400> SEQUENCE: 50

Glu Glu Glu Leu Gln Xaa Ile Gln Pro Asp Lys Ser Val Ser Val Ala
1               5                   10                  15

Ala Gly Glu Ser Ala Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Lys Arg Glu Asn Met Asp Phe Ser Ile Ser Ile Ser Xaa
65                  70                  75                  80

Ile Thr Pro Ala Asp Ala Gly Thr Tyr Tyr Cys Xaa Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 51
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V, I
<220> FEATURE:
<221> NAME/KEY: VARIANT
```

-continued

```
<222> LOCATION: 27
<223> OTHER INFORMATION: Xaa = A, I
<220> FEATURE:
<221> NAME/KEY: VARIANT
<222> LOCATION: 31
<223> OTHER INFORMATION: Xaa = I, F
<220> FEATURE:
<221> NAME/KEY: VARIANT
<222> LOCATION: 47
<223> OTHER INFORMATION: Xaa = E, V
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 56
<223> OTHER INFORMATION: Xaa = H, P
<220> FEATURE:
<221> NAME/KEY: VARIANT
<222> LOCATION: 66
<223> OTHER INFORMATION: Xaa = L, T
<220> FEATURE:
<221> NAME/KEY: VARIANT
<222> LOCATION: 80
<223> OTHER INFORMATION: Xaa = N, A
<220> FEATURE:
<221> NAME/KEY: VARIANT
<222> LOCATION: 92
<223> OTHER INFORMATION: Xaa = V, I

<400> SEQUENCE: 51

Glu Glu Glu Leu Gln Xaa Ile Gln Pro Asp Lys Ser Val Leu Val Ala
1               5                   10                  15

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Glu Gly Xaa Phe Pro Arg Val Thr Thr Val Ser
    50                  55                  60

Asp Xaa Thr Lys Arg Asn Asn Met Asp Phe Ser Ile Arg Ile Gly Xaa
65                  70                  75                  80

Ile Thr Pro Ala Asp Ala Gly Thr Tyr Tyr Cys Xaa Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 52
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 27
<223> OTHER INFORMATION: Xaa = A, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 53
```

<223> OTHER INFORMATION: Xaa = K, R
<220> FEATURE:
<221> NAME/KEY: VARIANT
<222> LOCATION: 56
<223> OTHER INFORMATION: Xaa = H, P, R
<220> FEATURE:
<221> NAME/KEY: VARIANT
<222> LOCATION: 66
<223> OTHER INFORMATION: Xaa = L, T, G
<220> FEATURE:
<221> NAME/KEY: VARIANT
<222> LOCATION: 80
<223> OTHER INFORMATION: Xaa = N, A

<400> SEQUENCE: 52

Glu Glu Glu Leu Gln Xaa Ile Gln Pro Asp Lys Ser Val Leu Val Ala
1               5                   10                  15

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Glu Leu
        35                  40                  45

Ile Tyr Asn Gln Xaa Glu Gly Xaa Phe Pro Arg Val Thr Thr Val Ser
    50                  55                  60

Asp Xaa Thr Lys Arg Asn Asn Met Asp Phe Ser Ile Arg Ile Gly Xaa
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 53
<211> LENGTH: 118
<212> TYPE: PRT
<213> ORGANISM: Artificial Sequence
<220> FEATURE:
<223> OTHER INFORMATION: Synthetic Construct

<400> SEQUENCE: 53

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 54
<211> LENGTH: 118
<212> TYPE: PRT
<213> ORGANISM: Artificial Sequence

```
<220> FEATURE:
<223> OTHER INFORMATION: Synthetic Construct

<400> SEQUENCE: 54

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Phe Pro
            20                  25                  30

Val Gly Pro Ile Gln Trp Phe Arg Gly Ala Gly Pro Ala Arg Glu Leu
        35                  40                  45

Ile Tyr Asn Gln Arg Gln Gly Pro Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 55
<211> LENGTH: 118
<212> TYPE: PRT
<213> ORGANISM: Artificial Sequence
<220> FEATURE:
<223> OTHER INFORMATION: Synthetic Construct

<400> SEQUENCE: 55

Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 56
<211> LENGTH: 118
<212> TYPE: PRT
<213> ORGANISM: Artificial Sequence
<220> FEATURE:
<223> OTHER INFORMATION: Synthetic Construct

<400> SEQUENCE: 56

Glu Glu Glu Leu Gln Ile Ile Gln Pro Asp Lys Ser Val Ser Val Ala
1               5                   10                  15

Ala Gly Glu Ser Ala Ile Leu His Cys Thr Val Thr Ser Leu Phe Pro
            20                  25                  30
```

```
Val Gly Pro Ile Gln Trp Phe Arg Gly Ala Gly Pro Ala Arg Val Leu
            35                  40                  45

Ile Tyr Asn Gln Arg Gln Gly Pro Phe Pro Arg Val Thr Thr Val Ser
 50                  55                  60

Glu Thr Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser
            115

<210> SEQ ID NO 57
<211> LENGTH: 118
<212> TYPE: PRT
<213> ORGANISM: Artificial Sequence
<220> FEATURE:
<223> OTHER INFORMATION: Synthetic Construct

<400> SEQUENCE: 57

Glu Glu Glu Leu Gln Ile Ile Gln Pro Asp Lys Ser Val Ser Val Ala
 1               5                  10                  15

Ala Gly Glu Ser Ala Ile Leu His Cys Thr Ile Thr Ser Leu Ile Pro
                20                  25                  30

Val Gly Pro Ile Gln Trp Phe Arg Gly Ala Gly Pro Ala Arg Val Leu
            35                  40                  45

Ile Tyr Asn Gln Arg Gln Gly Pro Phe Pro Arg Val Thr Thr Val Ser
 50                  55                  60

Glu Thr Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser
            115

<210> SEQ ID NO 58
<211> LENGTH: 118
<212> TYPE: PRT
<213> ORGANISM: Artificial Sequence
<220> FEATURE:
<223> OTHER INFORMATION: Synthetic Construct

<400> SEQUENCE: 58

Glu Glu Glu Leu Gln Ile Ile Gln Pro Asp Lys Ser Val Ser Val Ala
 1               5                  10                  15

Ala Gly Glu Ser Ala Ile Leu His Cys Thr Ile Thr Ser Leu Phe Pro
                20                  25                  30

Val Gly Pro Ile Gln Trp Phe Arg Gly Ala Gly Pro Ala Arg Glu Leu
            35                  40                  45

Ile Tyr Asn Gln Arg Gln Gly Pro Phe Pro Arg Val Thr Thr Val Ser
 50                  55                  60

Glu Thr Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Ile Lys Phe Arg Lys
                85                  90                  95
```

```
Gly Ser Pro Asp Thr Glu Phe Lys Ser Gly Ala Gly Thr Glu Leu Ser
                100                 105                 110

Val Arg Ala Lys Pro Ser
        115

<210> SEQ ID NO 59
<211> LENGTH: 118
<212> TYPE: PRT
<213> ORGANISM: Artificial Sequence
<220> FEATURE:
<223> OTHER INFORMATION: Synthetic Construct

<400> SEQUENCE: 59

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
                20                  25                  30

Val Gly Pro Ile Gln Trp Phe Arg Gly Ala Gly Pro Ala Arg Val Leu
            35                  40                  45

Ile Tyr Asn Gln Lys Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser
        115

<210> SEQ ID NO 60
<211> LENGTH: 118
<212> TYPE: PRT
<213> ORGANISM: Artificial Sequence
<220> FEATURE:
<223> OTHER INFORMATION: Synthetic Construct

<400> SEQUENCE: 60

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
                20                  25                  30

Val Gly Pro Ile Gln Trp Phe Arg Gly Ala Gly Pro Ala Arg Val Leu
            35                  40                  45

Ile Tyr Asn Gln Arg Glu Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser
        115

<210> SEQ ID NO 61
<211> LENGTH: 118
<212> TYPE: PRT
```

<213> ORGANISM: Artificial Sequence
<220> FEATURE:
<223> OTHER INFORMATION: Synthetic Construct

<400> SEQUENCE: 61

```
Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly His Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115
```

<210> SEQ ID NO 62
<211> LENGTH: 118
<212> TYPE: PRT
<213> ORGANISM: Artificial Sequence
<220> FEATURE:
<223> OTHER INFORMATION: Synthetic Construct

<400> SEQUENCE: 62

```
Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115
```

<210> SEQ ID NO 63
<211> LENGTH: 118
<212> TYPE: PRT
<213> ORGANISM: Artificial Sequence
<220> FEATURE:
<223> OTHER INFORMATION: Synthetic Construct

<400> SEQUENCE: 63

```
Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30
```

```
Val Gly Pro Ile Gln Trp Phe Arg Gly Ala Gly Pro Ala Arg Val Leu
            35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser
            115
```

<210> SEQ ID NO 64
<211> LENGTH: 118
<212> TYPE: PRT
<213> ORGANISM: Artificial Sequence
<220> FEATURE:
<223> OTHER INFORMATION: Synthetic Construct

<400> SEQUENCE: 64

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
            35                  40                  45

Ile Tyr Asn Gln Arg Glu Gly Pro Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser
            115
```

<210> SEQ ID NO 65
<211> LENGTH: 118
<212> TYPE: PRT
<213> ORGANISM: Artificial Sequence
<220> FEATURE:
<223> OTHER INFORMATION: Synthetic Construct

<400> SEQUENCE: 65

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Phe Pro
            20                  25                  30

Val Gly Pro Ile Gln Trp Phe Arg Gly Ala Gly Pro Ala Arg Glu Leu
            35                  40                  45

Ile Tyr Asn Gln Arg Glu Gly Pro Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80
```

```
Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 66
<211> LENGTH: 118
<212> TYPE: PRT
<213> ORGANISM: Artificial Sequence
<220> FEATURE:
<223> OTHER INFORMATION: Synthetic Construct

<400> SEQUENCE: 66

Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Phe Pro
                20                  25                  30

Val Gly Pro Ile Gln Trp Phe Arg Gly Ala Gly Pro Ala Arg Glu Leu
            35                  40                  45

Ile Tyr Asn Gln Arg Glu Gly Pro Phe Pro Arg Val Thr Thr Val Ser
50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 67
<211> LENGTH: 118
<212> TYPE: PRT
<213> ORGANISM: Artificial Sequence
<220> FEATURE:
<223> OTHER INFORMATION: Synthetic Construct

<400> SEQUENCE: 67

Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Phe Pro
                20                  25                  30

Val Gly Pro Ile Gln Trp Phe Arg Gly Ala Gly Pro Ala Arg Glu Leu
            35                  40                  45

Ile Tyr Asn Gln Arg Glu Gly Pro Phe Pro Arg Val Thr Thr Val Ser
50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115
```

```
<210> SEQ ID NO 68
<211> LENGTH: 118
<212> TYPE: PRT
<213> ORGANISM: Artificial Sequence
<220> FEATURE:
<223> OTHER INFORMATION: Synthetic Construct

<400> SEQUENCE: 68
```

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly Pro Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

```
<210> SEQ ID NO 69
<211> LENGTH: 118
<212> TYPE: PRT
<213> ORGANISM: Artificial Sequence
<220> FEATURE:
<223> OTHER INFORMATION: Synthetic Construct

<400> SEQUENCE: 69
```

Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly Pro Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

```
<210> SEQ ID NO 70
<211> LENGTH: 118
<212> TYPE: PRT
<213> ORGANISM: Artificial Sequence
<220> FEATURE:
<223> OTHER INFORMATION: Synthetic Construct

<400> SEQUENCE: 70
```

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 71
<211> LENGTH: 119
<212> TYPE: PRT
<213> ORGANISM: Artificial Sequence
<220> FEATURE:
<223> OTHER INFORMATION: Synthetic Construct

<400> SEQUENCE: 71

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 72
<211> LENGTH: 119
<212> TYPE: PRT
<213> ORGANISM: Artificial Sequence
<220> FEATURE:
<223> OTHER INFORMATION: Synthetic Construct

<400> SEQUENCE: 72

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 73
<211> LENGTH: 119
<212> TYPE: PRT
<213> ORGANISM: Artificial Sequence
<220> FEATURE:
<223> OTHER INFORMATION: Synthetic Construct

<400> SEQUENCE: 73

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
        50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 74
<211> LENGTH: 119
<212> TYPE: PRT
<213> ORGANISM: Artificial Sequence
<220> FEATURE:
<223> OTHER INFORMATION: Synthetic Construct

<400> SEQUENCE: 74

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
        50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

```
Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 75
<211> LENGTH: 119
<212> TYPE: PRT
<213> ORGANISM: Artificial Sequence
<220> FEATURE:
<223> OTHER INFORMATION: Synthetic Construct

<400> SEQUENCE: 75

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 76
<211> LENGTH: 119
<212> TYPE: PRT
<213> ORGANISM: Artificial Sequence
<220> FEATURE:
<223> OTHER INFORMATION: Synthetic Construct

<400> SEQUENCE: 76

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 77
<211> LENGTH: 119
<212> TYPE: PRT
```

```
<213> ORGANISM: Artificial Sequence
<220> FEATURE:
<223> OTHER INFORMATION: Synthetic Construct

<400> SEQUENCE: 77

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 78
<211> LENGTH: 119
<212> TYPE: PRT
<213> ORGANISM: Artificial Sequence
<220> FEATURE:
<223> OTHER INFORMATION: Synthetic Construct

<400> SEQUENCE: 78

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 79
<211> LENGTH: 119
<212> TYPE: PRT
<213> ORGANISM: Artificial Sequence
<220> FEATURE:
<223> OTHER INFORMATION: Synthetic Construct

<400> SEQUENCE: 79

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30
```

-continued

Val Gly Pro Ile Gln Trp Phe Arg Gly Ala Gly Pro Gly Arg Glu Leu
            35                  40                  45

Ile Tyr Asn Gln Arg Gln Gly Pro Phe Pro Arg Val Thr Thr Val Ser
 50                  55                  60

Asp Leu Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser
            115

<210> SEQ ID NO 80
<211> LENGTH: 119
<212> TYPE: PRT
<213> ORGANISM: Artificial Sequence
<220> FEATURE:
<223> OTHER INFORMATION: Synthetic Construct

<400> SEQUENCE: 80

Glu Glu Glu Leu Gln Ile Ile Gln Pro Asp Lys Ser Val Leu Val Ala
 1               5                  10                  15

Ala Gly Glu Thr Ala Thr Leu Arg Cys Thr Ile Thr Ser Leu Phe Pro
             20                  25                  30

Val Gly Pro Ile Gln Trp Phe Arg Gly Ala Gly Pro Gly Arg Val Leu
            35                  40                  45

Ile Tyr Asn Gln Arg Glu Gly Pro Phe Pro Arg Val Thr Thr Val Ser
 50                  55                  60

Asp Thr Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser
            115

<210> SEQ ID NO 81
<211> LENGTH: 119
<212> TYPE: PRT
<213> ORGANISM: Artificial Sequence
<220> FEATURE:
<223> OTHER INFORMATION: Synthetic Construct

<400> SEQUENCE: 81

Glu Glu Glu Leu Gln Val Ile Gln Pro Asp Lys Ser Val Leu Val Ala
 1               5                  10                  15

Ala Gly Glu Thr Ala Thr Leu Arg Cys Thr Ala Thr Ser Leu Phe Pro
             20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
 50                  55                  60

Asp Leu Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 82
<211> LENGTH: 119
<212> TYPE: PRT
<213> ORGANISM: Artificial Sequence
<220> FEATURE:
<223> OTHER INFORMATION: Synthetic Construct

<400> SEQUENCE: 82

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 83
<211> LENGTH: 119
<212> TYPE: PRT
<213> ORGANISM: Artificial Sequence
<220> FEATURE:
<223> OTHER INFORMATION: Synthetic Construct

<400> SEQUENCE: 83

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

-continued

```
<210> SEQ ID NO 84
<211> LENGTH: 119
<212> TYPE: PRT
<213> ORGANISM: Artificial Sequence
<220> FEATURE:
<223> OTHER INFORMATION: Synthetic Construct

<400> SEQUENCE: 84

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 85
<211> LENGTH: 119
<212> TYPE: PRT
<213> ORGANISM: Artificial Sequence
<220> FEATURE:
<223> OTHER INFORMATION: Synthetic Construct

<400> SEQUENCE: 85

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 86
<211> LENGTH: 119
<212> TYPE: PRT
<213> ORGANISM: Artificial Sequence
<220> FEATURE:
<223> OTHER INFORMATION: Synthetic Construct

<400> SEQUENCE: 86

Glu Glu Glu Leu Gln Ile Ile Gln Pro Asp Lys Ser Val Leu Val Ala
1               5                   10                  15
```

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
            85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 87
<211> LENGTH: 119
<212> TYPE: PRT
<213> ORGANISM: Artificial Sequence
<220> FEATURE:
<223> OTHER INFORMATION: Synthetic Construct

<400> SEQUENCE: 87

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
            85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 88
<211> LENGTH: 232
<212> TYPE: PRT
<213> ORGANISM: Artificial Sequence
<220> FEATURE:
<223> OTHER INFORMATION: Synthetic Construct

<400> SEQUENCE: 88

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

```
Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 89
<211> LENGTH: 325
<212> TYPE: PRT
<213> ORGANISM: Artificial Sequence
<220> FEATURE:
<223> OTHER INFORMATION: Synthetic Construct

<400> SEQUENCE: 89

Ser Thr Lys Gly Pro Ser Val Phe Pro Leu Ala Pro Cys Ser Arg Ser
  1               5                  10                  15

Thr Ser Glu Ser Thr Ala Ala Leu Gly Cys Leu Val Lys Asp Tyr Phe
             20                  25                  30

Pro Glu Pro Val Thr Val Ser Trp Asn Ser Gly Ala Leu Thr Ser Gly
         35                  40                  45

Val His Thr Phe Pro Ala Val Leu Gln Ser Ser Gly Leu Tyr Ser Leu
     50                  55                  60

Ser Ser Val Val Thr Val Pro Ser Ser Ser Leu Gly Thr Gln Thr Tyr
 65                  70                  75                  80

Thr Cys Asn Val Asp His Lys Pro Ser Asn Thr Lys Val Asp Lys Thr
                 85                  90                  95

Val Glu Arg Lys Cys Cys Val Glu Cys Pro Pro Cys Pro Ala Pro Pro
            100                 105                 110

Val Ala Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
130                 135                 140

Ser His Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Phe Arg Val Val Ser Val Leu Thr Val Val His Gln Asp Trp Leu
            180                 185                 190
```

```
Asn Gly Lys Glu Tyr Lys Cys Lys Val Ser Asn Lys Gly Leu Pro Ala
            195                 200                 205

Pro Ile Glu Lys Thr Ile Ser Lys Thr Lys Gly Gln Pro Arg Glu Pro
    210                 215                 220

Gln Val Tyr Thr Leu Pro Pro Ser Arg Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Met Leu Asp Ser Asp Gly Ser Phe Phe Leu Tyr Ser Lys Leu
        275                 280                 285

Thr Val Asp Lys Ser Arg Trp Gln Gln Gly Asn Val Phe Ser Cys Ser
    290                 295                 300

Val Met His Glu Ala Leu His Asn His Tyr Thr Gln Lys Ser Leu Ser
305                 310                 315                 320

Leu Ser Pro Gly Lys
            325

<210> SEQ ID NO 90
<211> LENGTH: 227
<212> TYPE: PRT
<213> ORGANISM: Artificial Sequence
<220> FEATURE:
<223> OTHER INFORMATION: Synthetic Construct

<400> SEQUENCE: 90

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220
```

```
Pro Gly Lys
225

<210> SEQ ID NO 91
<211> LENGTH: 226
<212> TYPE: PRT
<213> ORGANISM: Artificial Sequence
<220> FEATURE:
<223> OTHER INFORMATION: Synthetic Construct

<400> SEQUENCE: 91

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 92
<211> LENGTH: 223
<212> TYPE: PRT
<213> ORGANISM: Artificial Sequence
<220> FEATURE:
<223> OTHER INFORMATION: Synthetic Construct

<400> SEQUENCE: 92

Val Glu Cys Pro Pro Cys Pro Ala Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45
```

```
Val Gln Phe Asn Trp Tyr Val Asp Gly Val Glu Val His Asn Ala Lys
     50                  55                  60

Thr Lys Pro Arg Glu Glu Gln Phe Ala Ser Thr Phe Arg Val Val Ser
 65                  70                  75                  80

Val Leu Thr Val Val His Gln Asp Trp Leu Asn Gly Lys Glu Tyr Lys
                 85                  90                  95

Cys Lys Val Ser Asn Lys Gly Leu Pro Ser Ser Ile Glu Lys Thr Ile
                100                 105                 110

Ser Lys Thr Lys Gly Gln Pro Arg Glu Pro Gln Val Tyr Thr Leu Pro
                115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
                180                 185                 190

Trp Gln Gln Gly Asn Val Phe Ser Cys Ser Val Met His Glu Ala Leu
    195                 200                 205

His Asn His Tyr Thr Gln Lys Ser Leu Ser Leu Ser Pro Gly Lys
    210                 215                 220

<210> SEQ ID NO 93
<211> LENGTH: 222
<212> TYPE: PRT
<213> ORGANISM: Artificial Sequence
<220> FEATURE:
<223> OTHER INFORMATION: Synthetic Construct

<400> SEQUENCE: 93

Val Glu Cys Pro Pro Cys Pro Ala Pro Pro Val Ala Gly Pro Ser Val
  1               5                  10                  15

Phe Leu Phe Pro Pro Lys Pro Lys Asp Thr Leu Met Ile Ser Arg Thr
                 20                  25                  30

Pro Glu Val Thr Cys Val Val Val Asp Val Ser His Glu Asp Pro Glu
             35                  40                  45

Val Gln Phe Asn Trp Tyr Val Asp Gly Val Glu Val His Asn Ala Lys
     50                  55                  60

Thr Lys Pro Arg Glu Glu Gln Phe Ala Ser Thr Phe Arg Val Val Ser
 65                  70                  75                  80

Val Leu Thr Val Val His Gln Asp Trp Leu Asn Gly Lys Glu Tyr Lys
                 85                  90                  95

Cys Lys Val Ser Asn Lys Gly Leu Pro Ser Ser Ile Glu Lys Thr Ile
                100                 105                 110

Ser Lys Thr Lys Gly Gln Pro Arg Glu Pro Gln Val Tyr Thr Leu Pro
                115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
                180                 185                 190
```

```
Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly
    210                 215                 220

<210> SEQ ID NO 94
<211> LENGTH: 228
<212> TYPE: PRT
<213> ORGANISM: Artificial Sequence
<220> FEATURE:
<223> OTHER INFORMATION: Synthetic Construct

<400> SEQUENCE: 94

Glu Arg Lys Ser Ser Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Ala Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 95
<211> LENGTH: 227
<212> TYPE: PRT
<213> ORGANISM: Artificial Sequence
<220> FEATURE:
<223> OTHER INFORMATION: Synthetic Construct

<400> SEQUENCE: 95

Glu Arg Lys Ser Ser Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30
```

```
Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
 50                  55                  60

Val His Asn Ala Lys Thr Lys Pro Arg Glu Glu Gln Phe Ala Ser Thr
 65                  70                  75                  80

Phe Arg Val Val Ser Val Leu Thr Val Val His Gln Asp Trp Leu Asn
                 85                  90                  95

Gly Lys Glu Tyr Lys Cys Lys Val Ser Asn Lys Gly Leu Pro Ser Ser
                100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
                180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
        210                 215                 220

Ser Pro Gly
225

<210> SEQ ID NO 96
<211> LENGTH: 346
<212> TYPE: PRT
<213> ORGANISM: Artificial Sequence
<220> FEATURE:
<223> OTHER INFORMATION: Synthetic Construct

<400> SEQUENCE: 96

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
 50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser Asp Lys Thr His Thr Cys Pro Pro Cys
            115                 120                 125

Pro Ala Pro Glu Ala Ala Gly Ala Pro Ser Val Phe Leu Phe Pro Pro
        130                 135                 140

Lys Pro Lys Asp Thr Leu Met Ile Ser Arg Thr Pro Glu Val Thr Cys
145                 150                 155                 160
```

```
Val Val Val Asp Val Ser His Glu Asp Pro Glu Val Lys Phe Asn Trp
            165                 170                 175

Tyr Val Asp Gly Val Glu Val His Asn Ala Lys Thr Lys Pro Arg Glu
        180                 185                 190

Glu Gln Tyr Ala Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
                260                 265                 270

Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
                340                 345

<210> SEQ ID NO 97
<211> LENGTH: 346
<212> TYPE: PRT
<213> ORGANISM: Artificial Sequence
<220> FEATURE:
<223> OTHER INFORMATION: Synthetic Construct

<400> SEQUENCE: 97

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175
```

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 98
<211> LENGTH: 346
<212> TYPE: PRT
<213> ORGANISM: Artificial Sequence
<220> FEATURE:
<223> OTHER INFORMATION: Synthetic Construct

<400> SEQUENCE: 98

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
        290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 99
<211> LENGTH: 346
<212> TYPE: PRT
<213> ORGANISM: Artificial Sequence
<220> FEATURE:
<223> OTHER INFORMATION: Synthetic Construct

<400> SEQUENCE: 99

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

```
His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345
```

<210> SEQ ID NO 100
<211> LENGTH: 346
<212> TYPE: PRT
<213> ORGANISM: Artificial Sequence
<220> FEATURE:
<223> OTHER INFORMATION: Synthetic Construct

<400> SEQUENCE: 100

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220
```

-continued

```
Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
            245                 250                 255

Met Thr Lys Asn Gln Val Ser Leu Thr Cys Leu Val Lys Gly Phe Tyr
        260                 265                 270

Pro Ser Asp Ile Ala Val Glu Trp Glu Ser Asn Gly Gln Pro Glu Asn
    275                 280                 285

Asn Tyr Lys Thr Thr Pro Pro Val Leu Asp Ser Asp Gly Ser Phe Phe
290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 101
<211> LENGTH: 346
<212> TYPE: PRT
<213> ORGANISM: Artificial Sequence
<220> FEATURE:
<223> OTHER INFORMATION: Synthetic Construct

<400> SEQUENCE: 101

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240
```

```
Gln Pro Arg Glu Pro Gln Val Tyr Thr Leu Pro Ser Arg Glu Glu
            245                 250                 255

Met Thr Lys Asn Gln Val Ser Leu Thr Cys Leu Val Lys Gly Phe Tyr
        260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
        290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
            325                 330                 335

Gln Lys Ser Leu Ser Leu Ser Pro Gly Lys
            340                 345

<210> SEQ ID NO 102
<211> LENGTH: 346
<212> TYPE: PRT
<213> ORGANISM: Artificial Sequence
<220> FEATURE:
<223> OTHER INFORMATION: Synthetic Construct

<400> SEQUENCE: 102

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255
```

```
Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 103
<211> LENGTH: 346
<212> TYPE: PRT
<213> ORGANISM: Artificial Sequence
<220> FEATURE:
<223> OTHER INFORMATION: Synthetic Construct

<400> SEQUENCE: 103

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270
```

Pro Ser Asp Ile Ala Val Glu Trp Glu Ser Asn Gly Gln Pro Glu Asn
            275                 280                 285

Asn Tyr Lys Thr Thr Pro Val Leu Asp Ser Asp Gly Ser Phe Phe
        290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 104
<211> LENGTH: 346
<212> TYPE: PRT
<213> ORGANISM: Artificial Sequence
<220> FEATURE:
<223> OTHER INFORMATION: Synthetic Construct

<400> SEQUENCE: 104

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

```
Asn Tyr Lys Thr Thr Pro Pro Val Leu Asp Ser Asp Gly Ser Phe Phe
            290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 105
<211> LENGTH: 342
<212> TYPE: PRT
<213> ORGANISM: Artificial Sequence
<220> FEATURE:
<223> OTHER INFORMATION: Synthetic Construct

<400> SEQUENCE: 105

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300
```

```
Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 106
<211> LENGTH: 342
<212> TYPE: PRT
<213> ORGANISM: Artificial Sequence
<220> FEATURE:
<223> OTHER INFORMATION: Synthetic Construct

<400> SEQUENCE: 106

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
290                 295                 300

Leu Thr Val Asp Lys Ser Arg Trp Gln Gln Gly Asn Val Phe Ser Cys
305                 310                 315                 320
```

```
Ser Val Met His Glu Ala Leu His Asn His Tyr Thr Gln Lys Ser Leu
            325                 330                 335

Ser Leu Ser Pro Gly Lys
            340

<210> SEQ ID NO 107
<211> LENGTH: 342
<212> TYPE: PRT
<213> ORGANISM: Artificial Sequence
<220> FEATURE:
<223> OTHER INFORMATION: Synthetic Construct

<400> SEQUENCE: 107

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335
```

Ser Leu Ser Pro Gly Lys
          340

<210> SEQ ID NO 108
<211> LENGTH: 342
<212> TYPE: PRT
<213> ORGANISM: Artificial Sequence
<220> FEATURE:
<223> OTHER INFORMATION: Synthetic Construct

<400> SEQUENCE: 108

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340
```

<210> SEQ ID NO 109
<211> LENGTH: 342
<212> TYPE: PRT
<213> ORGANISM: Artificial Sequence
<220> FEATURE:
<223> OTHER INFORMATION: Synthetic Construct

<400> SEQUENCE: 109

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340
```

<210> SEQ ID NO 110

<211> LENGTH: 342
<212> TYPE: PRT
<213> ORGANISM: Artificial Sequence
<220> FEATURE:
<223> OTHER INFORMATION: Synthetic Construct

<400> SEQUENCE: 110

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 111
<211> LENGTH: 342
<212> TYPE: PRT
<213> ORGANISM: Artificial Sequence
<220> FEATURE:
<223> OTHER INFORMATION: Synthetic Construct

<400> SEQUENCE: 111

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340
```

<210> SEQ ID NO 112
<211> LENGTH: 342
<212> TYPE: PRT
<213> ORGANISM: Artificial Sequence
<220> FEATURE:
<223> OTHER INFORMATION: Synthetic Construct

<400> SEQUENCE: 112

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340
```

<210> SEQ ID NO 113
<211> LENGTH: 342
<212> TYPE: PRT
<213> ORGANISM: Artificial Sequence
<220> FEATURE:
<223> OTHER INFORMATION: Synthetic Construct

<400> SEQUENCE: 113

```
Glu Glu Glu Leu Gln Ile Ile Gln Pro Asp Lys Ser Val Leu Val Ala
1               5                   10                  15
Ala Gly Glu Thr Ala Thr Leu Arg Cys Thr Ile Thr Ser Leu Phe Pro
            20                  25                  30
Val Gly Pro Ile Gln Trp Phe Arg Gly Ala Gly Pro Gly Arg Glu Leu
        35                  40                  45
Ile Tyr Asn Gln Arg Glu Gly Pro Phe Pro Arg Val Thr Thr Val Ser
    50                  55                  60
Asp Thr Thr Lys Arg Asn Asn Met Asp Phe Ser Ile Arg Ile Gly Ala
65                  70                  75                  80
Ile Thr Pro Ala Asp Ala Gly Thr Tyr Tyr Cys Val Lys Phe Arg Lys
                85                  90                  95
Gly Ser Pro Asp Asp Val Glu Phe Lys Ser Ala Gly Thr Glu Leu
            100                 105                 110
Ser Val Arg Ala Lys Pro Ser Val Glu Cys Pro Pro Cys Pro Ala Pro
        115                 120                 125
Pro Val Ala Gly Pro Ser Val Phe Leu Phe Pro Pro Lys Pro Lys Asp
    130                 135                 140
Thr Leu Met Ile Ser Arg Thr Pro Glu Val Thr Cys Val Val Val Asp
145                 150                 155                 160
Val Ser His Glu Asp Pro Glu Val Gln Phe Asn Trp Tyr Val Asp Gly
                165                 170                 175
Val Glu Val His Asn Ala Lys Thr Lys Pro Arg Glu Glu Gln Phe Ala
            180                 185                 190
Ser Thr Phe Arg Val Val Ser Val Leu Thr Val Val His Gln Asp Trp
        195                 200                 205
Leu Asn Gly Lys Glu Tyr Lys Cys Lys Val Ser Asn Lys Gly Leu Pro
    210                 215                 220
Ser Ser Ile Glu Lys Thr Ile Ser Lys Thr Lys Gly Gln Pro Arg Glu
225                 230                 235                 240
Pro Gln Val Tyr Thr Leu Pro Pro Ser Arg Glu Glu Met Thr Lys Asn
                245                 250                 255
Gln Val Ser Leu Thr Cys Leu Val Lys Gly Phe Tyr Pro Ser Asp Ile
            260                 265                 270
Ala Val Glu Trp Glu Ser Asn Gly Gln Pro Glu Asn Asn Tyr Lys Thr
        275                 280                 285
Thr Pro Pro Met Leu Asp Ser Asp Gly Ser Phe Phe Leu Tyr Ser Lys
    290                 295                 300
Leu Thr Val Asp Lys Ser Arg Trp Gln Gln Gly Asn Val Phe Ser Cys
305                 310                 315                 320
Ser Val Met His Glu Ala Leu His Asn His Tyr Thr Gln Lys Ser Leu
                325                 330                 335
Ser Leu Ser Pro Gly Lys
            340
```

<210> SEQ ID NO 114
<211> LENGTH: 347
<212> TYPE: PRT
<213> ORGANISM: Artificial Sequence
<220> FEATURE:
<223> OTHER INFORMATION: Synthetic Construct

<400> SEQUENCE: 114

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 115
<211> LENGTH: 347
<212> TYPE: PRT
<213> ORGANISM: Artificial Sequence
<220> FEATURE:
<223> OTHER INFORMATION: Synthetic Construct

<400> SEQUENCE: 115

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Val Ala Gly Pro Ser Val Phe Leu Phe Pro
130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 116
<211> LENGTH: 347
<212> TYPE: PRT
<213> ORGANISM: Artificial Sequence
<220> FEATURE:
<223> OTHER INFORMATION: Synthetic Construct

<400> SEQUENCE: 116

| | | | | | | | | | | | | | | |
|---|---|---|---|---|---|---|---|---|---|---|---|---|---|---|
|Glu|Glu|Glu|Leu|Gln|Ile|Ile|Gln|Pro|Asp|Lys|Ser|Val|Leu|Val|Ala|
|1| | |  |5| | | | |10| | | | |15| |

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Val Leu
            35                  40                  45

Ile Tyr Asn Gln Arg Gln Gly Pro Phe Pro Arg Val Thr Thr Val Ser
        50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 117
<211> LENGTH: 347
<212> TYPE: PRT
<213> ORGANISM: Artificial Sequence
<220> FEATURE:
<223> OTHER INFORMATION: Synthetic Construct

<400> SEQUENCE: 117

```
Glu Glu Glu Leu Gln Val Ile Gln Pro Asp Lys Ser Val Leu Val Ala
1               5                   10                  15
Ala Gly Glu Thr Ala Thr Leu Arg Cys Thr Ala Thr Ser Leu Phe Pro
            20                  25                  30
Val Gly Pro Ile Gln Trp Phe Arg Gly Ala Gly Pro Gly Arg Glu Leu
        35                  40                  45
Ile Tyr Asn Gln Arg Gln Gly Pro Phe Pro Arg Val Thr Thr Val Ser
    50                  55                  60
Asp Leu Thr Lys Arg Asn Asn Met Asp Phe Ser Ile Arg Ile Gly Ala
65                  70                  75                  80
Ile Thr Pro Ala Asp Ala Gly Thr Tyr Tyr Cys Val Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Glu Arg Lys Ser Ser Val Glu Cys Pro
        115                 120                 125
Pro Cys Pro Ala Pro Pro Val Ala Gly Pro Ser Val Phe Leu Phe Pro
    130                 135                 140
Pro Lys Pro Lys Asp Thr Leu Met Ile Ser Arg Thr Pro Glu Val Thr
145                 150                 155                 160
Cys Val Val Val Asp Val Ser His Glu Asp Pro Glu Val Gln Phe Asn
                165                 170                 175
Trp Tyr Val Asp Gly Val Glu Val His Asn Ala Lys Thr Lys Pro Arg
            180                 185                 190
Glu Glu Gln Phe Ala Ser Thr Phe Arg Val Val Ser Val Leu Thr Val
        195                 200                 205
Val His Gln Asp Trp Leu Asn Gly Lys Glu Tyr Lys Cys Lys Val Ser
    210                 215                 220
Asn Lys Gly Leu Pro Ser Ser Ile Glu Lys Thr Ile Ser Lys Thr Lys
225                 230                 235                 240
Gly Gln Pro Arg Glu Pro Gln Val Tyr Thr Leu Pro Pro Ser Arg Glu
                245                 250                 255
Glu Met Thr Lys Asn Gln Val Ser Leu Thr Cys Leu Val Lys Gly Phe
            260                 265                 270
Tyr Pro Ser Asp Ile Ala Val Glu Trp Glu Ser Asn Gly Gln Pro Glu
        275                 280                 285
Asn Asn Tyr Lys Thr Thr Pro Pro Met Leu Asp Ser Asp Gly Ser Phe
    290                 295                 300
Phe Leu Tyr Ser Lys Leu Thr Val Asp Lys Ser Arg Trp Gln Gln Gly
305                 310                 315                 320
Asn Val Phe Ser Cys Ser Val Met His Glu Ala Leu His Asn His Tyr
                325                 330                 335
Thr Gln Lys Ser Leu Ser Leu Ser Pro Gly Lys
            340                 345
```

<210> SEQ ID NO 118
<211> LENGTH: 347
<212> TYPE: PRT
<213> ORGANISM: Artificial Sequence
<220> FEATURE:
<223> OTHER INFORMATION: Synthetic Construct

<400> SEQUENCE: 118

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345
```

<210> SEQ ID NO 119
<211> LENGTH: 347
<212> TYPE: PRT
<213> ORGANISM: Artificial Sequence
<220> FEATURE:
<223> OTHER INFORMATION: Synthetic Construct

<400> SEQUENCE: 119

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 120
<211> LENGTH: 347
<212> TYPE: PRT
<213> ORGANISM: Artificial Sequence
<220> FEATURE:
<223> OTHER INFORMATION: Synthetic Construct

<400> SEQUENCE: 120

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 121
<211> LENGTH: 347
<212> TYPE: PRT
<213> ORGANISM: Artificial Sequence
<220> FEATURE:
<223> OTHER INFORMATION: Synthetic Construct

<400> SEQUENCE: 121

```
Glu Glu Glu Leu Gln Val Ile Gln Pro Asp Lys Ser Val Leu Val Ala
1               5                   10                  15
Ala Gly Glu Thr Ala Thr Leu Arg Cys Thr Ile Thr Ser Leu Phe Pro
            20                  25                  30
Val Gly Pro Ile Gln Trp Phe Arg Gly Ala Gly Pro Gly Arg Glu Leu
        35                  40                  45
Ile Tyr Asn Gln Arg Glu Gly Pro Phe Pro Arg Val Thr Thr Val Ser
    50                  55                  60
Asp Thr Thr Lys Arg Asn Asn Met Asp Phe Ser Ile Arg Ile Gly Ala
65                  70                  75                  80
Ile Thr Pro Ala Asp Ala Gly Thr Tyr Tyr Cys Val Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Glu Arg Lys Ser Ser Val Glu Cys Pro
        115                 120                 125
Pro Cys Pro Ala Pro Val Ala Gly Pro Ser Val Phe Leu Phe Pro
    130                 135                 140
Pro Lys Pro Lys Asp Thr Leu Met Ile Ser Arg Thr Pro Glu Val Thr
145                 150                 155                 160
Cys Val Val Val Asp Val Ser His Glu Asp Pro Glu Val Gln Phe Asn
                165                 170                 175
Trp Tyr Val Asp Gly Val Glu Val His Asn Ala Lys Thr Lys Pro Arg
            180                 185                 190
Glu Glu Gln Phe Ala Ser Thr Phe Arg Val Val Ser Val Leu Thr Val
        195                 200                 205
Val His Gln Asp Trp Leu Asn Gly Lys Glu Tyr Lys Cys Lys Val Ser
    210                 215                 220
Asn Lys Gly Leu Pro Ser Ser Ile Glu Lys Thr Ile Ser Lys Thr Lys
225                 230                 235                 240
Gly Gln Pro Arg Glu Pro Gln Val Tyr Thr Leu Pro Pro Ser Arg Glu
                245                 250                 255
Glu Met Thr Lys Asn Gln Val Ser Leu Thr Cys Leu Val Lys Gly Phe
            260                 265                 270
Tyr Pro Ser Asp Ile Ala Val Glu Trp Glu Ser Asn Gly Gln Pro Glu
        275                 280                 285
Asn Asn Tyr Lys Thr Thr Pro Pro Met Leu Asp Ser Asp Gly Ser Phe
    290                 295                 300
Phe Leu Tyr Ser Lys Leu Thr Val Asp Lys Ser Arg Trp Gln Gln Gly
305                 310                 315                 320
Asn Val Phe Ser Cys Ser Val Met His Glu Ala Leu His Asn His Tyr
                325                 330                 335
Thr Gln Lys Ser Leu Ser Leu Ser Pro Gly Lys
            340                 345
```

<210> SEQ ID NO 122
<211> LENGTH: 347
<212> TYPE: PRT
<213> ORGANISM: Artificial Sequence
<220> FEATURE:
<223> OTHER INFORMATION: Synthetic Construct

<400> SEQUENCE: 122

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
            115                 120                 125

Pro Cys Pro Ala Pro Val Ala Gly Pro Ser Val Phe Leu Phe Pro
        130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
            195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 123
<211> LENGTH: 346
<212> TYPE: PRT
<213> ORGANISM: Artificial Sequence
<220> FEATURE:
<223> OTHER INFORMATION: Synthetic Construct

<400> SEQUENCE: 123

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Leu Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 124
<211> LENGTH: 346
<212> TYPE: PRT
<213> ORGANISM: Artificial Sequence
<220> FEATURE:
<223> OTHER INFORMATION: Synthetic Construct

<400> SEQUENCE: 124

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 125
<211> LENGTH: 346
<212> TYPE: PRT
<213> ORGANISM: Artificial Sequence
<220> FEATURE:
<223> OTHER INFORMATION: Synthetic Construct

<400> SEQUENCE: 125

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Leu Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 126
<211> LENGTH: 347
<212> TYPE: PRT
<213> ORGANISM: Artificial Sequence
<220> FEATURE:
<223> OTHER INFORMATION: Synthetic Construct

<400> SEQUENCE: 126

```
Glu Glu Glu Leu Gln Ile Ile Gln Pro Asp Lys Ser Val Leu Val Ala
1               5                   10                  15
Ala Gly Glu Thr Ala Thr Leu Arg Cys Thr Ile Thr Ser Leu Phe Pro
            20                  25                  30
Val Gly Pro Ile Gln Trp Phe Arg Gly Ala Gly Pro Gly Arg Val Leu
        35                  40                  45
Ile Tyr Asn Gln Arg Gln Gly Pro Phe Pro Arg Val Thr Thr Val Ser
    50                  55                  60
Asp Thr Thr Lys Arg Asn Asn Met Asp Phe Ser Ile Arg Ile Gly Asn
65                  70                  75                  80
Ile Thr Pro Ala Asp Ala Gly Thr Tyr Tyr Cys Ile Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Glu Arg Lys Cys Cys Val Glu Cys Pro
        115                 120                 125
Pro Cys Pro Ala Pro Pro Val Ala Gly Pro Ser Val Phe Leu Phe Pro
    130                 135                 140
Pro Lys Pro Lys Asp Thr Leu Met Ile Ser Arg Thr Pro Glu Val Thr
145                 150                 155                 160
Cys Val Val Val Asp Val Ser His Glu Asp Pro Glu Val Gln Phe Asn
                165                 170                 175
Trp Tyr Val Asp Gly Val Glu Val His Asn Ala Lys Thr Lys Pro Arg
            180                 185                 190
Glu Glu Gln Phe Asn Ser Thr Phe Arg Val Val Ser Val Leu Thr Val
        195                 200                 205
Val His Gln Asp Trp Leu Asn Gly Lys Glu Tyr Lys Cys Lys Val Ser
    210                 215                 220
Asn Lys Gly Leu Pro Ala Pro Ile Glu Lys Thr Ile Ser Lys Thr Lys
225                 230                 235                 240
Gly Gln Pro Arg Glu Pro Gln Val Tyr Thr Leu Pro Pro Ser Arg Glu
                245                 250                 255
Glu Met Thr Lys Asn Gln Val Ser Leu Thr Cys Leu Val Lys Gly Phe
            260                 265                 270
Tyr Pro Ser Asp Ile Ala Val Glu Trp Glu Ser Asn Gly Gln Pro Glu
        275                 280                 285
Asn Asn Tyr Lys Thr Thr Pro Pro Met Leu Asp Ser Asp Gly Ser Phe
    290                 295                 300
Phe Leu Tyr Ser Lys Leu Thr Val Asp Lys Ser Arg Trp Gln Gln Gly
305                 310                 315                 320
Asn Val Phe Ser Cys Ser Val Met His Glu Ala Leu His Asn His Tyr
                325                 330                 335
Thr Gln Lys Ser Leu Ser Leu Ser Pro Gly Lys
            340                 345
```

<210> SEQ ID NO 127
<211> LENGTH: 347
<212> TYPE: PRT
<213> ORGANISM: Artificial Sequence
<220> FEATURE:
<223> OTHER INFORMATION: Synthetic Construct

<400> SEQUENCE: 127

```
Glu Glu Glu Leu Gln Ile Ile Gln Pro Asp Lys Ser Val Leu Val Ala
1               5                   10                  15
Ala Gly Glu Thr Ala Thr Leu Arg Cys Thr Ile Thr Ser Leu Phe Pro
            20                  25                  30
Val Gly Pro Ile Gln Trp Phe Arg Gly Ala Gly Pro Gly Arg Val Leu
        35                  40                  45
Ile Tyr Asn Gln Arg Gln Gly Pro Phe Pro Arg Val Thr Thr Val Ser
    50                  55                  60
Asp Thr Thr Lys Arg Asn Asn Met Asp Phe Ser Ile Arg Ile Gly Asn
65                  70                  75                  80
Ile Thr Pro Ala Asp Ala Gly Thr Tyr Tyr Cys Ile Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Glu Arg Lys Cys Cys Val Glu Cys Pro
        115                 120                 125
Pro Cys Pro Ala Pro Pro Val Ala Gly Pro Ser Val Phe Leu Phe Pro
    130                 135                 140
Pro Lys Pro Lys Asp Thr Leu Met Ile Ser Arg Thr Pro Glu Val Thr
145                 150                 155                 160
Cys Val Val Val Asp Val Ser His Glu Asp Pro Glu Val Gln Phe Asn
                165                 170                 175
Trp Tyr Val Asp Gly Val Glu Val His Asn Ala Lys Thr Lys Pro Arg
            180                 185                 190
Glu Glu Gln Phe Asn Ser Thr Phe Arg Val Val Ser Val Leu Thr Val
        195                 200                 205
Val His Gln Asp Trp Leu Asn Gly Lys Glu Tyr Lys Cys Lys Val Ser
    210                 215                 220
Asn Lys Gly Leu Pro Ser Ser Ile Glu Lys Thr Ile Ser Lys Thr Lys
225                 230                 235                 240
Gly Gln Pro Arg Glu Pro Gln Val Tyr Thr Leu Pro Pro Ser Arg Glu
                245                 250                 255
Glu Met Thr Lys Asn Gln Val Ser Leu Thr Cys Leu Val Lys Gly Phe
            260                 265                 270
Tyr Pro Ser Asp Ile Ala Val Glu Trp Glu Ser Asn Gly Gln Pro Glu
        275                 280                 285
Asn Asn Tyr Lys Thr Thr Pro Pro Met Leu Asp Ser Asp Gly Ser Phe
    290                 295                 300
Phe Leu Tyr Ser Lys Leu Thr Val Asp Lys Ser Arg Trp Gln Gln Gly
305                 310                 315                 320
Asn Val Phe Ser Cys Ser Val Met His Glu Ala Leu His Asn His Tyr
                325                 330                 335
Thr Gln Lys Ser Leu Ser Leu Ser Pro Gly Lys
            340                 345
```

<210> SEQ ID NO 128
<211> LENGTH: 347
<212> TYPE: PRT
<213> ORGANISM: Artificial Sequence
<220> FEATURE:
<223> OTHER INFORMATION: Synthetic Construct

<400> SEQUENCE: 128

```
Glu Glu Glu Leu Gln Ile Ile Gln Pro Asp Lys Ser Val Leu Val Ala
1               5                   10                  15
Ala Gly Glu Thr Ala Thr Leu Arg Cys Thr Ile Thr Ser Leu Phe Pro
            20                  25                  30
Val Gly Pro Ile Gln Trp Phe Arg Gly Ala Gly Pro Gly Arg Val Leu
        35                  40                  45
Ile Tyr Asn Gln Arg Gln Gly Pro Phe Pro Arg Val Thr Thr Val Ser
    50                  55                  60
Asp Thr Thr Lys Arg Asn Asn Met Asp Phe Ser Ile Arg Ile Gly Asn
65                  70                  75                  80
Ile Thr Pro Ala Asp Ala Gly Thr Tyr Tyr Cys Ile Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Glu Arg Lys Cys Cys Val Glu Cys Pro
        115                 120                 125
Pro Cys Pro Ala Pro Val Ala Gly Pro Ser Val Phe Leu Phe Pro
130                 135                 140
Pro Lys Pro Lys Asp Thr Leu Met Ile Ser Arg Thr Pro Glu Val Thr
145                 150                 155                 160
Cys Val Val Val Asp Val Ser His Glu Asp Pro Glu Val Gln Phe Asn
                165                 170                 175
Trp Tyr Val Asp Gly Val Glu Val His Asn Ala Lys Thr Lys Pro Arg
            180                 185                 190
Glu Glu Gln Phe Ala Ser Thr Phe Arg Val Val Ser Val Leu Thr Val
        195                 200                 205
Val His Gln Asp Trp Leu Asn Gly Lys Glu Tyr Lys Cys Lys Val Ser
    210                 215                 220
Asn Lys Gly Leu Pro Ala Pro Ile Glu Lys Thr Ile Ser Lys Thr Lys
225                 230                 235                 240
Gly Gln Pro Arg Glu Pro Gln Val Tyr Thr Leu Pro Pro Ser Arg Glu
                245                 250                 255
Glu Met Thr Lys Asn Gln Val Ser Leu Thr Cys Leu Val Lys Gly Phe
            260                 265                 270
Tyr Pro Ser Asp Ile Ala Val Glu Trp Glu Ser Asn Gly Gln Pro Glu
        275                 280                 285
Asn Asn Tyr Lys Thr Thr Pro Pro Met Leu Asp Ser Asp Gly Ser Phe
    290                 295                 300
Phe Leu Tyr Ser Lys Leu Thr Val Asp Lys Ser Arg Trp Gln Gln Gly
305                 310                 315                 320
Asn Val Phe Ser Cys Ser Val Met His Glu Ala Leu His Asn His Tyr
                325                 330                 335
Thr Gln Lys Ser Leu Ser Leu Ser Pro Gly Lys
            340                 345
```

<210> SEQ ID NO 129
<211> LENGTH: 347
<212> TYPE: PRT
<213> ORGANISM: Artificial Sequence
<220> FEATURE:
<223> OTHER INFORMATION: Synthetic Construct

<400> SEQUENCE: 129

```
Glu Glu Glu Leu Gln Ile Ile Gln Pro Asp Lys Ser Val Leu Val Ala
1               5                   10                  15
Ala Gly Glu Thr Ala Thr Leu Arg Cys Thr Ile Thr Ser Leu Phe Pro
            20                  25                  30
Val Gly Pro Ile Gln Trp Phe Arg Gly Ala Gly Pro Gly Arg Val Leu
        35                  40                  45
Ile Tyr Asn Gln Arg Gln Gly Pro Phe Pro Arg Val Thr Thr Val Ser
    50                  55                  60
Asp Thr Thr Lys Arg Asn Asn Met Asp Phe Ser Ile Arg Ile Gly Asn
65                  70                  75                  80
Ile Thr Pro Ala Asp Ala Gly Thr Tyr Tyr Cys Ile Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Glu Arg Lys Cys Cys Val Glu Cys Pro
        115                 120                 125
Pro Cys Pro Ala Pro Pro Val Ala Gly Pro Ser Val Phe Leu Phe Pro
    130                 135                 140
Pro Lys Pro Lys Asp Thr Leu Met Ile Ser Arg Thr Pro Glu Val Thr
145                 150                 155                 160
Cys Val Val Val Asp Val Ser His Glu Asp Pro Glu Val Gln Phe Asn
                165                 170                 175
Trp Tyr Val Asp Gly Val Glu Val His Asn Ala Lys Thr Lys Pro Arg
            180                 185                 190
Glu Glu Gln Phe Ala Ser Thr Phe Arg Val Val Ser Val Leu Thr Val
        195                 200                 205
Val His Gln Asp Trp Leu Asn Gly Lys Glu Tyr Lys Cys Lys Val Ser
    210                 215                 220
Asn Lys Gly Leu Pro Ser Ser Ile Glu Lys Thr Ile Ser Lys Thr Lys
225                 230                 235                 240
Gly Gln Pro Arg Glu Pro Gln Val Tyr Thr Leu Pro Pro Ser Arg Glu
                245                 250                 255
Glu Met Thr Lys Asn Gln Val Ser Leu Thr Cys Leu Val Lys Gly Phe
            260                 265                 270
Tyr Pro Ser Asp Ile Ala Val Glu Trp Glu Ser Asn Gly Gln Pro Glu
        275                 280                 285
Asn Asn Tyr Lys Thr Thr Pro Pro Met Leu Asp Ser Asp Gly Ser Phe
    290                 295                 300
Phe Leu Tyr Ser Lys Leu Thr Val Asp Lys Ser Arg Trp Gln Gln Gly
305                 310                 315                 320
Asn Val Phe Ser Cys Ser Val Met His Glu Ala Leu His Asn His Tyr
                325                 330                 335
Thr Gln Lys Ser Leu Ser Leu Ser Pro Gly Lys
            340                 345
```

<210> SEQ ID NO 130
<211> LENGTH: 347
<212> TYPE: PRT
<213> ORGANISM: Artificial Sequence
<220> FEATURE:
<223> OTHER INFORMATION: Synthetic Construct

<400> SEQUENCE: 130

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Glu Ser Lys Tyr Gly Pro Pro Cys Pro Ser
        115                 120                 125

Cys Pro Ala Pro Glu Phe Leu Gly Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser Gln Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Asn Ser Thr Tyr Arg Val Val Ser Val Leu Thr Val
        195                 200                 205

Leu His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Ala Lys
225                 230                 235                 240

Gly Gln Pro Arg Glu Pro Gln Val Tyr Thr Leu Pro Pro Ser Gln Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Val Leu Asp Ser Asp Gly Ser Phe
    290                 295                 300

Phe Leu Tyr Ser Arg Leu Thr Val Asp Lys Ser Arg Trp Gln Glu Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Leu Gly Lys
            340                 345

<210> SEQ ID NO 131
<211> LENGTH: 348
<212> TYPE: PRT
<213> ORGANISM: Artificial Sequence
<220> FEATURE:
<223> OTHER INFORMATION: Synthetic Construct

<400> SEQUENCE: 131

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Ser Lys Tyr Gly Pro Pro Cys Pro
        115                 120                 125

Pro Cys Pro Ala Pro Glu Phe Leu Gly Gly Pro Ser Val Phe Leu Phe
130                 135                 140

Pro Pro Lys Pro Lys Asp Thr Leu Met Ile Ser Arg Thr Pro Glu Val
145                 150                 155                 160

Thr Cys Val Val Val Asp Val Ser Gln Glu Asp Pro Glu Val Gln Phe
                165                 170                 175

Asn Trp Tyr Val Asp Gly Val Glu Val His Asn Ala Lys Thr Lys Pro
            180                 185                 190

Arg Glu Glu Gln Phe Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Gly Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Gln
                245                 250                 255

Glu Glu Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Tyr Ser Arg Leu Thr Val Asp Lys Ser Arg Trp Gln Glu
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Leu Gly Lys
            340                 345

<210> SEQ ID NO 132
<211> LENGTH: 348
<212> TYPE: PRT
<213> ORGANISM: Artificial Sequence
<220> FEATURE:
<223> OTHER INFORMATION: Synthetic Construct

<400> SEQUENCE: 132

| | | | | | | | | | | | | | | |
|---|---|---|---|---|---|---|---|---|---|---|---|---|---|---|
| Glu | Glu | Glu | Leu | Gln | Ile | Ile | Gln | Pro | Asp | Lys | Ser | Val | Leu | Val | Ala |
| 1 | | | | 5 | | | | | 10 | | | | | 15 | |
| Ala | Gly | Glu | Thr | Ala | Thr | Leu | Arg | Cys | Thr | Ile | Thr | Ser | Leu | Phe | Pro |
| | | | 20 | | | | | 25 | | | | | 30 | | |
| Val | Gly | Pro | Ile | Gln | Trp | Phe | Arg | Gly | Ala | Gly | Pro | Gly | Arg | Glu | Leu |
| | | 35 | | | | | 40 | | | | | 45 | | | |
| Ile | Tyr | Asn | Gln | Arg | Glu | Gly | Pro | Phe | Pro | Arg | Val | Thr | Thr | Val | Ser |
| | 50 | | | | | 55 | | | | | 60 | | | | |
| Asp | Thr | Thr | Lys | Arg | Asn | Asn | Met | Asp | Phe | Ser | Ile | Arg | Ile | Gly | Ala |
| 65 | | | | | 70 | | | | | 75 | | | | | 80 |
| Ile | Thr | Pro | Ala | Asp | Ala | Gly | Thr | Tyr | Tyr | Cys | Val | Lys | Phe | Arg | Lys |
| | | | | 85 | | | | | 90 | | | | | 95 | |
| Gly | Ser | Pro | Asp | Asp | Val | Glu | Phe | Lys | Ser | Gly | Ala | Gly | Thr | Glu | Leu |
| | | | 100 | | | | | 105 | | | | | 110 | | |
| Ser | Val | Arg | Ala | Lys | Pro | Ser | Glu | Ser | Lys | Tyr | Gly | Pro | Pro | Cys | Pro |
| | | 115 | | | | | 120 | | | | | 125 | | | |
| Pro | Cys | Pro | Ala | Pro | Glu | Phe | Glu | Gly | Gly | Pro | Ser | Val | Phe | Leu | Phe |
| | 130 | | | | | 135 | | | | | 140 | | | | |
| Pro | Pro | Lys | Pro | Lys | Asp | Thr | Leu | Met | Ile | Ser | Arg | Thr | Pro | Glu | Val |
| 145 | | | | | 150 | | | | | 155 | | | | | 160 |
| Thr | Cys | Val | Val | Val | Asp | Val | Ser | Gln | Glu | Asp | Pro | Glu | Val | Gln | Phe |
| | | | | 165 | | | | | 170 | | | | | 175 | |
| Asn | Trp | Tyr | Val | Asp | Gly | Val | Glu | Val | His | Asn | Ala | Lys | Thr | Lys | Pro |
| | | | 180 | | | | | 185 | | | | | 190 | | |
| Arg | Glu | Glu | Gln | Phe | Asn | Ser | Thr | Tyr | Arg | Val | Val | Ser | Val | Leu | Thr |
| | | 195 | | | | | 200 | | | | | 205 | | | |
| Val | Leu | His | Gln | Asp | Trp | Leu | Asn | Gly | Lys | Glu | Tyr | Lys | Cys | Lys | Val |
| | 210 | | | | | 215 | | | | | 220 | | | | |
| Ser | Asn | Lys | Gly | Leu | Pro | Ser | Ser | Ile | Glu | Lys | Thr | Ile | Ser | Lys | Ala |
| 225 | | | | | 230 | | | | | 235 | | | | | 240 |
| Lys | Gly | Gln | Pro | Arg | Glu | Pro | Gln | Val | Tyr | Thr | Leu | Pro | Pro | Ser | Gln |
| | | | | 245 | | | | | 250 | | | | | 255 | |
| Glu | Glu | Met | Thr | Lys | Asn | Gln | Val | Ser | Leu | Thr | Cys | Leu | Val | Lys | Gly |
| | | | 260 | | | | | 265 | | | | | 270 | | |
| Phe | Tyr | Pro | Ser | Asp | Ile | Ala | Val | Glu | Trp | Glu | Ser | Asn | Gly | Gln | Pro |
| | | 275 | | | | | 280 | | | | | 285 | | | |
| Glu | Asn | Asn | Tyr | Lys | Thr | Thr | Pro | Pro | Val | Leu | Asp | Ser | Asp | Gly | Ser |
| | 290 | | | | | 295 | | | | | 300 | | | | |
| Phe | Phe | Leu | Tyr | Ser | Arg | Leu | Thr | Val | Asp | Lys | Ser | Arg | Trp | Gln | Glu |
| 305 | | | | | 310 | | | | | 315 | | | | | 320 |
| Gly | Asn | Val | Phe | Ser | Cys | Ser | Val | Met | His | Glu | Ala | Leu | His | Asn | His |
| | | | | 325 | | | | | 330 | | | | | 335 | |
| Tyr | Thr | Gln | Lys | Ser | Leu | Ser | Leu | Ser | Leu | Gly | Lys | | | | |
| | | | 340 | | | | | 345 | | | | | | | |

<210> SEQ ID NO 133
<211> LENGTH: 347
<212> TYPE: PRT
<213> ORGANISM: Artificial Sequence
<220> FEATURE:
<223> OTHER INFORMATION: Synthetic Construct

<400> SEQUENCE: 133

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Ser Lys Tyr Gly Pro Pro Cys Pro
        115                 120                 125

Pro Cys Pro Ala Pro Val Ala Gly Pro Ser Val Phe Leu Phe Pro
130                 135                 140

Pro Lys Pro Lys Asp Thr Leu Met Ile Ser Arg Thr Pro Glu Val Thr
145                 150                 155                 160

Cys Val Val Val Asp Val Ser Gln Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Asn Ser Thr Tyr Arg Val Val Ser Val Leu Thr Val
        195                 200                 205

Leu His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Ala Lys
225                 230                 235                 240

Gly Gln Pro Arg Glu Pro Gln Val Tyr Thr Leu Pro Pro Ser Gln Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Val Leu Asp Ser Asp Gly Ser Phe
    290                 295                 300

Phe Leu Tyr Ser Arg Leu Thr Val Asp Lys Ser Arg Trp Gln Glu Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Leu Gly Lys
            340                 345

<210> SEQ ID NO 134
<211> LENGTH: 346
<212> TYPE: PRT
<213> ORGANISM: Artificial Sequence
<220> FEATURE:
<223> OTHER INFORMATION: Synthetic Construct

<400> SEQUENCE: 134

```
Glu Glu Glu Leu Gln Ile Ile Gln Pro Asp Lys Ser Val Leu Val Ala
1               5                   10                  15
Ala Gly Glu Thr Ala Thr Leu Arg Cys Thr Ile Thr Ser Leu Phe Pro
            20                  25                  30
Val Gly Pro Ile Gln Trp Phe Arg Gly Ala Gly Pro Gly Arg Val Leu
        35                  40                  45
Ile Tyr Asn Gln Arg Gln Gly Pro Phe Pro Arg Val Thr Thr Val Ser
    50                  55                  60
Asp Thr Thr Lys Arg Asn Asn Met Asp Phe Ser Ile Arg Ile Gly Asn
65                  70                  75                  80
Ile Thr Pro Ala Asp Ala Gly Thr Tyr Tyr Cys Ile Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Ala Ala Pro Pro Cys Pro Pro Cys
            115                 120                 125
Pro Ala Pro Glu Phe Leu Gly Gly Pro Ser Val Phe Leu Phe Pro Pro
130                 135                 140
Lys Pro Lys Asp Thr Leu Met Ile Ser Arg Thr Pro Glu Val Thr Cys
145                 150                 155                 160
Val Val Val Asp Val Ser Gln Glu Asp Pro Glu Val Gln Phe Asn Trp
                165                 170                 175
Tyr Val Asp Gly Val Glu Val His Asn Ala Lys Thr Lys Pro Arg Glu
            180                 185                 190
Glu Gln Phe Asn Ser Thr Tyr Arg Val Val Ser Val Leu Thr Val Leu
        195                 200                 205
His Gln Asp Trp Leu Asn Gly Lys Glu Tyr Lys Cys Lys Val Ser Asn
    210                 215                 220
Lys Gly Leu Pro Ser Ser Ile Glu Lys Thr Ile Ser Lys Ala Lys Gly
225                 230                 235                 240
Gln Pro Arg Glu Pro Gln Val Tyr Thr Leu Pro Pro Ser Gln Glu Glu
                245                 250                 255
Met Thr Lys Asn Gln Val Ser Leu Thr Cys Leu Val Lys Gly Phe Tyr
            260                 265                 270
Pro Ser Asp Ile Ala Val Glu Trp Glu Ser Asn Gly Gln Pro Glu Asn
        275                 280                 285
Asn Tyr Lys Thr Thr Pro Pro Val Leu Asp Ser Asp Gly Ser Phe Phe
    290                 295                 300
Leu Tyr Ser Arg Leu Thr Val Asp Lys Ser Arg Trp Gln Glu Gly Asn
305                 310                 315                 320
Val Phe Ser Cys Ser Val Met His Glu Ala Leu His Asn His Tyr Thr
                325                 330                 335
Gln Lys Ser Leu Ser Leu Ser Pro Gly Lys
            340                 345
```

<210> SEQ ID NO 135
<211> LENGTH: 345
<212> TYPE: PRT
<213> ORGANISM: Artificial Sequence
<220> FEATURE:
<223> OTHER INFORMATION: Synthetic Construct

<400> SEQUENCE: 135

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly
            340                 345

<210> SEQ ID NO 136
<211> LENGTH: 345
<212> TYPE: PRT
<213> ORGANISM: Artificial Sequence
<220> FEATURE:
<223> OTHER INFORMATION: Synthetic Construct

<400> SEQUENCE: 136

```
Glu Glu Glu Leu Gln Ile Ile Gln Pro Asp Lys Ser Val Leu Val Ala
1               5                   10                  15
Ala Gly Glu Thr Ala Thr Leu Arg Cys Thr Ile Thr Ser Leu Phe Pro
            20                  25                  30
Val Gly Pro Ile Gln Trp Phe Arg Gly Ala Gly Pro Gly Arg Glu Leu
        35                  40                  45
Ile Tyr Asn Gln Arg Glu Gly Pro Phe Pro Arg Val Thr Thr Val Ser
50                  55                  60
Asp Thr Thr Lys Arg Asn Asn Met Asp Phe Ser Ile Arg Ile Gly Ala
65                  70                  75                  80
Ile Thr Pro Ala Asp Ala Gly Thr Tyr Tyr Cys Val Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Asp Lys Thr His Thr Cys Pro Pro Cys
        115                 120                 125
Pro Ala Pro Glu Ala Ala Gly Ala Pro Ser Val Phe Leu Phe Pro Pro
130                 135                 140
Lys Pro Lys Asp Thr Leu Met Ile Ser Arg Thr Pro Glu Val Thr Cys
145                 150                 155                 160
Val Val Val Asp Val Ser His Glu Asp Pro Glu Val Lys Phe Asn Trp
                165                 170                 175
Tyr Val Asp Gly Val Glu Val His Asn Ala Lys Thr Lys Pro Arg Glu
            180                 185                 190
Glu Gln Tyr Ala Ser Thr Tyr Arg Val Val Ser Val Leu Thr Val Leu
        195                 200                 205
His Gln Asp Trp Leu Asn Gly Lys Glu Tyr Lys Cys Lys Val Ser Asn
210                 215                 220
Lys Ala Leu Pro Ala Pro Ile Glu Lys Thr Ile Ser Lys Ala Lys Gly
225                 230                 235                 240
Gln Pro Arg Glu Pro Gln Val Tyr Thr Leu Pro Pro Ser Arg Glu Glu
                245                 250                 255
Met Thr Lys Asn Gln Val Ser Leu Thr Cys Leu Val Lys Gly Phe Tyr
            260                 265                 270
Pro Ser Asp Ile Ala Val Glu Trp Glu Ser Asn Gly Gln Pro Glu Asn
        275                 280                 285
Asn Tyr Lys Thr Thr Pro Pro Val Leu Asp Ser Asp Gly Ser Phe Phe
290                 295                 300
Leu Tyr Ser Lys Leu Thr Val Asp Lys Ser Arg Trp Gln Gln Gly Asn
305                 310                 315                 320
Val Phe Ser Cys Ser Val Met His Glu Ala Leu His Asn His Tyr Thr
                325                 330                 335
Gln Lys Ser Leu Ser Leu Ser Pro Gly
            340                 345
```

<210> SEQ ID NO 137
<211> LENGTH: 345
<212> TYPE: PRT
<213> ORGANISM: Artificial Sequence
<220> FEATURE:
<223> OTHER INFORMATION: Synthetic Construct

<400> SEQUENCE: 137

| | | | | | | | | | | | | | | | |
|---|---|---|---|---|---|---|---|---|---|---|---|---|---|---|---|

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Glu Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly
            340                 345

<210> SEQ ID NO 138
<211> LENGTH: 346
<212> TYPE: PRT
<213> ORGANISM: Artificial Sequence
<220> FEATURE:
<223> OTHER INFORMATION: Synthetic Construct

<400> SEQUENCE: 138

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Trp Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 139
<211> LENGTH: 227
<212> TYPE: PRT
<213> ORGANISM: Artificial Sequence
<220> FEATURE:
<223> OTHER INFORMATION: Synthetic Construct

<400> SEQUENCE: 139

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys
225
```

<210> SEQ ID NO 140
<211> LENGTH: 346
<212> TYPE: PRT
<213> ORGANISM: Artificial Sequence
<220> FEATURE:
<223> OTHER INFORMATION: Synthetic Construct

<400> SEQUENCE: 140

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
            35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110
```

```
Ser Val Arg Ala Lys Pro Ser Asp Lys Thr His Thr Cys Pro Pro Cys
            115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Ser Cys Ala Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Val Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 141
<211> LENGTH: 227
<212> TYPE: PRT
<213> ORGANISM: Artificial Sequence
<220> FEATURE:
<223> OTHER INFORMATION: Synthetic Construct

<400> SEQUENCE: 141

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125
```

```
Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 142
<211> LENGTH: 346
<212> TYPE: PRT
<213> ORGANISM: Artificial Sequence
<220> FEATURE:
<223> OTHER INFORMATION: Synthetic Construct

<400> SEQUENCE: 142

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255
```

Met Thr Lys Asn Gln Val Ser Leu Trp Cys Leu Val Lys Gly Phe Tyr
                260                 265                 270

Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
        290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 143
<211> LENGTH: 346
<212> TYPE: PRT
<213> ORGANISM: Artificial Sequence
<220> FEATURE:
<223> OTHER INFORMATION: Synthetic Construct

<400> SEQUENCE: 143

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Ser Cys Ala Val Lys Gly Phe Tyr
            260                 265                 270

```
Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
        290                 295                 300

Leu Val Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 144
<211> LENGTH: 449
<212> TYPE: PRT
<213> ORGANISM: Artificial Sequence
<220> FEATURE:
<223> OTHER INFORMATION: Synthetic Construct

<400> SEQUENCE: 144

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Arg Lys
    210                 215                 220

Thr His Thr Cys Pro Arg Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 145
<211> LENGTH: 346
<212> TYPE: PRT
<213> ORGANISM: Artificial Sequence
<220> FEATURE:
<223> OTHER INFORMATION: Synthetic Construct

<400> SEQUENCE: 145

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Lys Thr His Thr Cys Pro Glu Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190
```

```
Glu Gln Tyr Ala Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Glu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 146
<211> LENGTH: 346
<212> TYPE: PRT
<213> ORGANISM: Artificial Sequence
<220> FEATURE:
<223> OTHER INFORMATION: Synthetic Construct

<400> SEQUENCE: 146

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205
```

```
His Gln Asp Trp Leu Asn Gly Lys Glu Tyr Lys Cys Lys Val Ser Asn
            210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Trp Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 147
<211> LENGTH: 227
<212> TYPE: PRT
<213> ORGANISM: Artificial Sequence
<220> FEATURE:
<223> OTHER INFORMATION: Synthetic Construct

<400> SEQUENCE: 147

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220
```

Pro Gly Lys
225

<210> SEQ ID NO 148
<211> LENGTH: 346
<212> TYPE: PRT
<213> ORGANISM: Artificial Sequence
<220> FEATURE:
<223> OTHER INFORMATION: Synthetic Construct

<400> SEQUENCE: 148

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Ser Cys Ala Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Val Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 149
<211> LENGTH: 227
<212> TYPE: PRT
<213> ORGANISM: Artificial Sequence
<220> FEATURE:
<223> OTHER INFORMATION: Synthetic Construct

<400> SEQUENCE: 149

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161
<211> LENGTH: 226
<212> TYPE: PRT
<213> ORGANISM: Artificial Sequence
<220> FEATURE:
<223> OTHER INFORMATION: Synthetic Construct

<400> SEQUENCE: 161

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

```
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
            115                 120                 125
Tyr Thr Leu Pro Pro Ser Arg Glu Glu Met Thr Lys Asn Gln Val Ser
        130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
            195                 200                 205
His Glu Ala Leu His Asn His Tyr Thr Gln Lys Ser Leu Ser Leu Ser
        210                 215                 220
Pro Gly
225

<210> SEQ ID NO 162
<211> LENGTH: 227
<212> TYPE: PRT
<213> ORGANISM: Artificial Sequence
<220> FEATURE:
<223> OTHER INFORMATION: Synthetic Construct

<400> SEQUENCE: 162

Glu Arg Lys Cys Cys Val Glu Cys Pro Pro Cys Pro Ala Pro Pro Val
1               5                   10                  15
Ala Gly Pro Ser Val Phe Leu Phe Pro Pro Lys Pro Lys Asp Thr Leu
            20                  25                  30
Met Ile Ser Arg Thr Pro Glu Val Thr Cys Val Val Val Asp Val Ser
        35                  40                  45
His Glu Asp Pro Glu Val Gln Phe Asn Trp Tyr Val Asp Gly Val Glu
    50                  55                  60
Val His Asn Ala Lys Thr Lys Pro Arg Glu Glu Gln Phe Asn Ser Thr
65                  70                  75                  80
Phe Arg Val Val Ser Val Leu Thr Val His Gln Asp Trp Leu Asn Gly
                85                  90                  95
Lys Glu Tyr Lys Cys Lys Val Ser Asn Lys Gly Leu Pro Ala Pro Ile
            100                 105                 110
Glu Lys Thr Ile Ser Lys Thr Lys Gly Gln Pro Arg Glu Pro Gln Val
            115                 120                 125
Tyr Thr Leu Pro Pro Ser Arg Glu Glu Met Thr Lys Asn Gln Val Ser
        130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Met Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val
            195                 200                 205
```

Met His Glu Ala Leu His Asn His Tyr Thr Gln Lys Ser Leu Ser Leu
    210                 215                 220

Ser Pro Gly
225

<210> SEQ ID NO 163
<211> LENGTH: 5
<212> TYPE: PRT
<213> ORGANISM: Artificial Sequence
<220> FEATURE:
<223> OTHER INFORMATION: Synthetic Construct

<400> SEQUENCE: 163

Gly Gly Gly Gly Ser
1               5

<210> SEQ ID NO 164
<211> LENGTH: 4
<212> TYPE: PRT
<213> ORGANISM: Artificial Sequence
<220> FEATURE:
<223> OTHER INFORMATION: Synthetic Construct

<400> SEQUENCE: 164

Gly Gly Ser Gly
1

<210> SEQ ID NO 165
<211> LENGTH: 4
<212> TYPE: PRT
<213> ORGANISM: Artificial Sequence
<220> FEATURE:
<223> OTHER INFORMATION: Synthetic Construct

<400> SEQUENCE: 165

Ser Gly Gly Gly
1

<210> SEQ ID NO 166
<211> LENGTH: 4
<212> TYPE: PRT
<213> ORGANISM: Artificial Sequence
<220> FEATURE:
<223> OTHER INFORMATION: Synthetic Construct

<400> SEQUENCE: 166

Gly Ser Gly Ser
1

<210> SEQ ID NO 167
<211> LENGTH: 6
<212> TYPE: PRT
<213> ORGANISM: Artificial Sequence
<220> FEATURE:
<223> OTHER INFORMATION: Synthetic Construct

<400> SEQUENCE: 167

Gly Ser Gly Ser Gly Ser
1               5

<210> SEQ ID NO 168
<211> LENGTH: 8
<212> TYPE: PRT
<213> ORGANISM: Artificial Sequence
<220> FEATURE:
<223> OTHER INFORMATION: Synthetic Construct

<400> SEQUENCE: 168

Gly Ser Gly Ser Gly Ser Gly Ser
1               5

<210> SEQ ID NO 169
<211> LENGTH: 10
<212> TYPE: PRT
<213> ORGANISM: Artificial Sequence
<220> FEATURE:
<223> OTHER INFORMATION: Synthetic Construct

<400> SEQUENCE: 169

Gly Ser Gly Ser Gly Ser Gly Ser Gly Ser
1               5                   10

<210> SEQ ID NO 170
<211> LENGTH: 12
<212> TYPE: PRT
<213> ORGANISM: Artificial Sequence
<220> FEATURE:
<223> OTHER INFORMATION: Synthetic Construct

<400> SEQUENCE: 170

Gly Ser Gly Ser Gly Ser Gly Ser Gly Ser Gly Ser
1               5                   10

<210> SEQ ID NO 171
<211> LENGTH: 6
<212> TYPE: PRT
<213> ORGANISM: Artificial Sequence
<220> FEATURE:
<223> OTHER INFORMATION: Synthetic Construct

<400> SEQUENCE: 171

Gly Gly Ser Gly Gly Ser
1               5

<210> SEQ ID NO 172
<211> LENGTH: 9
<212> TYPE: PRT
<213> ORGANISM: Artificial Sequence
<220> FEATURE:
<223> OTHER INFORMATION: Synthetic Construct

<400> SEQUENCE: 172

Gly Gly Ser Gly Gly Ser Gly Gly Ser
1               5

<210> SEQ ID NO 173
<211> LENGTH: 12
<212> TYPE: PRT
<213> ORGANISM: Artificial Sequence
<220> FEATURE:
<223> OTHER INFORMATION: Synthetic Construct

<400> SEQUENCE: 173

Gly Gly Ser Gly Gly Ser Gly Gly Ser Gly Gly Ser
1               5                   10

<210> SEQ ID NO 174
<211> LENGTH: 8
<212> TYPE: PRT
<213> ORGANISM: Artificial Sequence
<220> FEATURE:
<223> OTHER INFORMATION: Synthetic Construct

<400> SEQUENCE: 174

Gly Gly Ser Gly Gly Ser Gly
1               5

<210> SEQ ID NO 175
<211> LENGTH: 12
<212> TYPE: PRT
<213> ORGANISM: Artificial Sequence
<220> FEATURE:
<223> OTHER INFORMATION: Synthetic Construct

<400> SEQUENCE: 175

Gly Gly Ser Gly Gly Gly Ser Gly Gly Gly Ser Gly
1               5                   10

<210> SEQ ID NO 176
<211> LENGTH: 15
<212> TYPE: PRT
<213> ORGANISM: Artificial Sequence
<220> FEATURE:
<223> OTHER INFORMATION: Synthetic Construct

<400> SEQUENCE: 176

Gly Gly Gly Gly Ser Gly Gly Gly Gly Ser Gly Gly Gly Gly Ser
1               5                   10                  15

<210> SEQ ID NO 177
<211> LENGTH: 3
<212> TYPE: PRT
<213> ORGANISM: Artificial Sequence
<220> FEATURE:
<223> OTHER INFORMATION: Synthetic Construct

<400> SEQUENCE: 177

Ala Ala Ser
1

<210> SEQ ID NO 178
<211> LENGTH: 4
<212> TYPE: PRT
<213> ORGANISM: Artificial Sequence
<220> FEATURE:
<223> OTHER INFORMATION: Synthetic Construct

<400> SEQUENCE: 178

Ala Ala Ala Leu
1

<210> SEQ ID NO 179
<211> LENGTH: 4
<212> TYPE: PRT
<213> ORGANISM: Artificial Sequence
<220> FEATURE:
<223> OTHER INFORMATION: Synthetic Construct

<400> SEQUENCE: 179

Ala Ala Ala Lys
1

<210> SEQ ID NO 180
<211> LENGTH: 4
<212> TYPE: PRT
<213> ORGANISM: Artificial Sequence
<220> FEATURE:
<223> OTHER INFORMATION: Synthetic Construct

```
<400> SEQUENCE: 180

Ala Ala Ala Arg
1

<210> SEQ ID NO 181
<211> LENGTH: 14
<212> TYPE: PRT
<213> ORGANISM: Artificial Sequence
<220> FEATURE:
<223> OTHER INFORMATION: Synthetic Construct

<400> SEQUENCE: 181

Glu Gly Lys Ser Ser Gly Ser Gly Ser Glu Ser Lys Ser Thr
1               5                   10

<210> SEQ ID NO 182
<211> LENGTH: 12
<212> TYPE: PRT
<213> ORGANISM: Artificial Sequence
<220> FEATURE:
<223> OTHER INFORMATION: Synthetic Construct

<400> SEQUENCE: 182

Gly Ser Ala Gly Ser Ala Ala Gly Ser Gly Glu Phe
1               5                   10

<210> SEQ ID NO 183
<211> LENGTH: 12
<212> TYPE: PRT
<213> ORGANISM: Artificial Sequence
<220> FEATURE:
<223> OTHER INFORMATION: Synthetic Construct

<400> SEQUENCE: 183

Ala Glu Ala Ala Ala Lys Glu Ala Ala Ala Lys Ala
1               5                   10

<210> SEQ ID NO 184
<211> LENGTH: 18
<212> TYPE: PRT
<213> ORGANISM: Artificial Sequence
<220> FEATURE:
<223> OTHER INFORMATION: Synthetic Construct

<400> SEQUENCE: 184

Lys Glu Ser Gly Ser Val Ser Ser Glu Gln Leu Ala Gln Phe Arg Ser
1               5                   10                  15

Leu Asp

<210> SEQ ID NO 185
<211> LENGTH: 9
<212> TYPE: PRT
<213> ORGANISM: Artificial Sequence
<220> FEATURE:
<223> OTHER INFORMATION: Synthetic Construct

<400> SEQUENCE: 185

Gly Gly Gly Gly Ala Gly Gly Gly Gly
1               5

<210> SEQ ID NO 186
<211> LENGTH: 10
<212> TYPE: PRT
<213> ORGANISM: Artificial Sequence
<220> FEATURE:
<223> OTHER INFORMATION: Synthetic Construct
```

<400> SEQUENCE: 186

Gly Glu Asn Leu Tyr Phe Gln Ser Gly Gly
1               5                   10

<210> SEQ ID NO 187
<211> LENGTH: 8
<212> TYPE: PRT
<213> ORGANISM: Artificial Sequence
<220> FEATURE:
<223> OTHER INFORMATION: Synthetic Construct

<400> SEQUENCE: 187

Ser Ala Cys Tyr Cys Glu Leu Ser
1               5

<210> SEQ ID NO 188
<211> LENGTH: 5
<212> TYPE: PRT
<213> ORGANISM: Artificial Sequence
<220> FEATURE:
<223> OTHER INFORMATION: Synthetic Construct

<400> SEQUENCE: 188

Arg Ser Ile Ala Thr
1               5

<210> SEQ ID NO 189
<211> LENGTH: 17
<212> TYPE: PRT
<213> ORGANISM: Artificial Sequence
<220> FEATURE:
<223> OTHER INFORMATION: Synthetic Construct

<400> SEQUENCE: 189

Arg Pro Ala Cys Lys Ile Pro Asn Asp Leu Lys Gln Lys Val Met Asn
1               5                   10                  15

His

<210> SEQ ID NO 190
<211> LENGTH: 36
<212> TYPE: PRT
<213> ORGANISM: Artificial Sequence
<220> FEATURE:
<223> OTHER INFORMATION: Synthetic Construct

<400> SEQUENCE: 190

Gly Gly Ser Ala Gly Gly Ser Gly Ser Gly Ser Ser Gly Ser Ser
1               5                   10                  15

Gly Ala Ser Gly Thr Gly Thr Ala Gly Gly Thr Gly Ser Gly Ser Gly
            20                  25                  30

Thr Gly Ser Gly
            35

<210> SEQ ID NO 191
<211> LENGTH: 17
<212> TYPE: PRT
<213> ORGANISM: Artificial Sequence
<220> FEATURE:
<223> OTHER INFORMATION: Synthetic Construct

<400> SEQUENCE: 191

Ala Ala Ala Asn Ser Ser Ile Asp Leu Ile Ser Val Pro Val Asp Ser
1               5                   10                  15

Arg

<210> SEQ ID NO 192
<211> LENGTH: 36
<212> TYPE: PRT
<213> ORGANISM: Artificial Sequence
<220> FEATURE:
<223> OTHER INFORMATION: Synthetic Construct

<400> SEQUENCE: 192

Gly Gly Ser Gly Gly Gly Ser Glu Gly Gly Gly Ser Glu Gly Gly Gly
1               5                   10                  15

Ser Glu Gly Gly Gly Ser Glu Gly Gly Gly Ser Glu Gly Gly Gly Ser
                20                  25                  30

Gly Gly Gly Ser
        35

<210> SEQ ID NO 193
<211> LENGTH: 5
<212> TYPE: PRT
<213> ORGANISM: Artificial Sequence
<220> FEATURE:
<223> OTHER INFORMATION: Synthetic Construct

<400> SEQUENCE: 193

Glu Ala Ala Ala Lys
1               5

<210> SEQ ID NO 194
<211> LENGTH: 5
<212> TYPE: PRT
<213> ORGANISM: Artificial Sequence
<220> FEATURE:
<223> OTHER INFORMATION: Synthetic Construct

<400> SEQUENCE: 194

Pro Ala Pro Ala Pro
1               5

<210> SEQ ID NO 195
<211> LENGTH: 119
<212> TYPE: PRT
<213> ORGANISM: Artificial Sequence
<220> FEATURE:
<223> OTHER INFORMATION: Synthetic Construct

<400> SEQUENCE: 195

Glu Glu Glu Leu Gln Ile Ile Gln Pro Asp Lys Ser Val Leu Val Ala
1               5                   10                  15

Ala Gly Glu Thr Ala Thr Leu Arg Cys Thr Met Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
        50                  55                  60

Asp Thr Thr Lys Arg Asn Asn Met Asp Phe Ser Ile Arg Ile Gly Ala
65                  70                  75                  80

```
Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 196
<211> LENGTH: 119
<212> TYPE: PRT
<213> ORGANISM: Artificial Sequence
<220> FEATURE:
<223> OTHER INFORMATION: Synthetic Construct

<400> SEQUENCE: 196

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Lys Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 197
<211> LENGTH: 119
<212> TYPE: PRT
<213> ORGANISM: Artificial Sequence
<220> FEATURE:
<223> OTHER INFORMATION: Synthetic Construct

<400> SEQUENCE: 197

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Arg Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115
```

```
<210> SEQ ID NO 198
<211> LENGTH: 119
<212> TYPE: PRT
<213> ORGANISM: Artificial Sequence
<220> FEATURE:
<223> OTHER INFORMATION: Synthetic Construct

<400> SEQUENCE: 198

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Tyr Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 199
<211> LENGTH: 119
<212> TYPE: PRT
<213> ORGANISM: Artificial Sequence
<220> FEATURE:
<223> OTHER INFORMATION: Synthetic Construct

<400> SEQUENCE: 199

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Asp Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 200
<211> LENGTH: 119
<212> TYPE: PRT
<213> ORGANISM: Artificial Sequence
<220> FEATURE:
<223> OTHER INFORMATION: Synthetic Construct

<400> SEQUENCE: 200

Glu Glu Glu Leu Gln Ile Ile Gln Pro Asp Lys Ser Val Leu Val Ala
1               5                   10                  15
```

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
            85                  90                  95

Gly Ile Pro Asp Asp Val Glu Phe Lys Ser Gly Ala Gly Thr Glu Leu
            100                 105                 110

Ser Val Arg Ala Lys Pro Ser
        115

<210> SEQ ID NO 201
<211> LENGTH: 119
<212> TYPE: PRT
<213> ORGANISM: Artificial Sequence
<220> FEATURE:
<223> OTHER INFORMATION: Synthetic Construct

<400> SEQUENCE: 201

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
            85                  90                  95

Gly Met Pro Asp Asp Val Glu Phe Lys Ser Gly Ala Gly Thr Glu Leu
            100                 105                 110

Ser Val Arg Ala Lys Pro Ser
        115

<210> SEQ ID NO 202
<211> LENGTH: 118
<212> TYPE: PRT
<213> ORGANISM: Artificial Sequence
<220> FEATURE:
<223> OTHER INFORMATION: Synthetic Construct

<400> SEQUENCE: 202

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Val Glu Phe Lys Ser Gly Ala Gly Thr Glu Leu Ser
            100                 105                 110

Val Arg Ala Lys Pro Ser
        115

<210> SEQ ID NO 203
<211> LENGTH: 120
<212> TYPE: PRT
<213> ORGANISM: Artificial Sequence
<220> FEATURE:
<223> OTHER INFORMATION: Synthetic Construct

<400> SEQUENCE: 203

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Ser Glu Pro Asp Val Glu Phe Lys Ser Gly Ala Gly Thr Glu
            100                 105                 110

Leu Ser Val Arg Ala Lys Pro Ser
        115                 120

<210> SEQ ID NO 204
<211> LENGTH: 119
<212> TYPE: PRT
<213> ORGANISM: Artificial Sequence
<220> FEATURE:
<223> OTHER INFORMATION: Synthetic Construct

<400> SEQUENCE: 204

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Arg Pro
            20                  25                  30

Val Gly Pro Ile Gln Trp Phe Arg Gly Ala Gly Pro Gly Arg Glu Leu
        35                  40                  45

Ile Tyr Asn Gln Arg Asp Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser
        115

<210> SEQ ID NO 205
<211> LENGTH: 119
<212> TYPE: PRT
<213> ORGANISM: Artificial Sequence
<220> FEATURE:
<223> OTHER INFORMATION: Synthetic Construct

<400> SEQUENCE: 205

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Arg Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ile Pro Asp Asp Val Glu Phe Lys Ser Gly Ala Gly Thr Glu Leu
                100                 105                 110

Ser Val Arg Ala Lys Pro Ser
        115

<210> SEQ ID NO 206
<211> LENGTH: 119
<212> TYPE: PRT
<213> ORGANISM: Artificial Sequence
<220> FEATURE:
<223> OTHER INFORMATION: Synthetic Construct

<400> SEQUENCE: 206

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Arg Pro
            20                  25                  30

Val Gly Pro Ile Gln Trp Phe Arg Gly Ala Gly Pro Gly Arg Glu Leu
        35                  40                  45

Ile Tyr Asn Gln Arg Asp Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ile Pro Asp Asp Val Glu Phe Lys Ser Gly Ala Gly Thr Glu Leu
                100                 105                 110

Ser Val Arg Ala Lys Pro Ser
        115

<210> SEQ ID NO 207
<211> LENGTH: 119
<212> TYPE: PRT

<213> ORGANISM: Artificial Sequence
<220> FEATURE:
<223> OTHER INFORMATION: Synthetic Construct

<400> SEQUENCE: 207

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Tyr Pro
            20                  25                  30

Val Gly Pro Ile Gln Trp Phe Arg Gly Ala Gly Pro Gly Arg Glu Leu
        35                  40                  45

Ile Tyr Asn Gln Arg Asp Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115
```

<210> SEQ ID NO 208
<211> LENGTH: 119
<212> TYPE: PRT
<213> ORGANISM: Artificial Sequence
<220> FEATURE:
<223> OTHER INFORMATION: Synthetic Construct

<400> SEQUENCE: 208

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Tyr Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ile Pro Asp Asp Val Glu Phe Lys Ser Gly Ala Gly Thr Glu Leu
            100                 105                 110

Ser Val Arg Ala Lys Pro Ser
        115
```

<210> SEQ ID NO 209
<211> LENGTH: 119
<212> TYPE: PRT
<213> ORGANISM: Artificial Sequence
<220> FEATURE:
<223> OTHER INFORMATION: Synthetic Construct

<400> SEQUENCE: 209

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Tyr Pro
            20                  25                  30
```

-continued

Val Gly Pro Ile Gln Trp Phe Arg Gly Ala Gly Pro Gly Arg Glu Leu
            35                  40                  45

Ile Tyr Asn Gln Arg Asp Gly Pro Phe Pro Arg Val Thr Thr Val Ser
 50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ile Pro Asp Asp Val Glu Phe Lys Ser Gly Ala Gly Thr Glu Leu
            100                 105                 110

Ser Val Arg Ala Lys Pro Ser
            115

<210> SEQ ID NO 210
<211> LENGTH: 119
<212> TYPE: PRT
<213> ORGANISM: Artificial Sequence
<220> FEATURE:
<223> OTHER INFORMATION: Synthetic Construct

<400> SEQUENCE: 210

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
            35                  40                  45

Ile Tyr Asn Gln Arg Asp Gly Pro Phe Pro Arg Val Thr Thr Val Ser
 50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ile Pro Asp Asp Val Glu Phe Lys Ser Gly Ala Gly Thr Glu Leu
            100                 105                 110

Ser Val Arg Ala Lys Pro Ser
            115

<210> SEQ ID NO 211
<211> LENGTH: 345
<212> TYPE: PRT
<213> ORGANISM: Artificial Sequence
<220> FEATURE:
<223> OTHER INFORMATION: Synthetic Construct

<400> SEQUENCE: 211

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Arg Pro
            20                  25                  30

Val Gly Pro Ile Gln Trp Phe Arg Gly Ala Gly Pro Gly Arg Glu Leu
            35                  40                  45

Ile Tyr Asn Gln Arg Asp Gly Pro Phe Pro Arg Val Thr Thr Val Ser
 50                  55                  60

Asp Thr Thr Lys Arg Asn Asn Met Asp Phe Ser Ile Arg Ile Gly Ala
65                  70                  75                  80

```
Ile Thr Pro Ala Asp Ala Gly Thr Tyr Tyr Cys Val Lys Phe Arg Lys
             85                  90                  95

Gly Ile Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
            115                 120                 125

Pro Ala Pro Glu Ala Ala Gly Ala Pro Ser Val Phe Leu Phe Pro Pro
        130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
                180                 185                 190

Glu Gln Tyr Ala Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
                260                 265                 270

Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
        290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly
            340                 345

<210> SEQ ID NO 212
<211> LENGTH: 118
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V, L, I
<220> FEATURE:
<221> NAME/KEY: VARIANT
<222> LOCATION: 27
<223> OTHER INFORMATION: Xaa = V, I, L
<220> FEATURE:
<221> NAME/KEY: VARIANT
<222> LOCATION: 31
<223> OTHER INFORMATION: Xaa = I, T, S, F
<220> FEATURE:
<221> NAME/KEY: VARIANT
<222> LOCATION: 53
<223> OTHER INFORMATION: Xaa = K, R
<220> FEATURE:
<221> NAME/KEY: VARIANT
<222> LOCATION: 56
<223> OTHER INFORMATION: Xaa = H, P, R
```

```
<220> FEATURE:
<221> NAME/KEY: VARIANT
<222> LOCATION: 66
<223> OTHER INFORMATION: Xaa = S, T, G
<220> FEATURE:
<221> NAME/KEY: VARIANT
<222> LOCATION: 80
<223> OTHER INFORMATION: Xaa = N, A

<400> SEQUENCE: 212

Glu Glu Glu Leu Gln Xaa Ile Gln Pro Asp Lys Ser Val Ser Val Ala
1               5                   10                  15

Ala Gly Glu Ser Ala Ile Leu His Cys Thr Xaa Thr Ser Leu Xaa Pro
            20                  25                  30

Val Gly Pro Ile Gln Trp Phe Arg Gly Ala Gly Pro Ala Arg Glu Leu
        35                  40                  45

Ile Tyr Asn Gln Xaa Glu Gly Xaa Phe Pro Arg Val Thr Thr Val Ser
    50                  55                  60

Glu Xaa Thr Lys Arg Glu Asn Met Asp Phe Ser Ile Ser Ile Ser Xaa
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 213
<211> LENGTH: 119
<212> TYPE: PRT
<213> ORGANISM: Artificial Sequence
<220> FEATURE:
<223> OTHER INFORMATION: Synthetic Construct

<400> SEQUENCE: 213

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Val Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 214
<211> LENGTH: 346
<212> TYPE: PRT
<213> ORGANISM: Artificial Sequence
<220> FEATURE:
<223> OTHER INFORMATION: Synthetic Construct
```

<400> SEQUENCE: 214

```
Glu Glu Glu Leu Gln Val Ile Gln Pro Asp Lys Ser Val Leu Val Ala
1               5                   10                  15
Ala Gly Glu Thr Ala Thr Leu Arg Cys Thr Ala Thr Ser Leu Phe Pro
            20                  25                  30
Val Gly Pro Ile Gln Trp Phe Arg Gly Ala Gly Pro Gly Arg Glu Leu
        35                  40                  45
Ile Tyr Asn Gln Arg Glu Gly Pro Phe Pro Arg Val Thr Thr Val Ser
    50                  55                  60
Asp Leu Thr Lys Arg Asn Asn Met Asp Phe Ser Ile Arg Ile Gly Ala
65                  70                  75                  80
Ile Thr Pro Ala Asp Ala Gly Thr Tyr Tyr Cys Val Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Glu Arg Lys Ser Ser Val Glu Cys Pro
        115                 120                 125
Pro Cys Pro Ala Pro Val Ala Gly Pro Ser Val Phe Leu Phe Pro
130                 135                 140
Pro Lys Pro Lys Asp Thr Leu Met Ile Ser Arg Thr Pro Glu Val Thr
145                 150                 155                 160
Cys Val Val Val Asp Val Ser His Glu Asp Pro Glu Val Gln Phe Asn
                165                 170                 175
Trp Tyr Val Asp Gly Val Glu Val His Asn Ala Lys Thr Lys Pro Arg
            180                 185                 190
Glu Glu Gln Phe Ala Ser Thr Phe Arg Val Val Ser Val Leu Thr Val
        195                 200                 205
Val His Gln Asp Trp Leu Asn Gly Lys Glu Tyr Lys Cys Lys Val Ser
    210                 215                 220
Asn Lys Gly Leu Pro Ser Ser Ile Glu Lys Thr Ile Ser Lys Thr Lys
225                 230                 235                 240
Gly Gln Pro Arg Glu Pro Gln Val Tyr Thr Leu Pro Pro Ser Arg Glu
                245                 250                 255
Glu Met Thr Lys Asn Gln Val Ser Leu Thr Cys Leu Val Lys Gly Phe
            260                 265                 270
Tyr Pro Ser Asp Ile Ala Val Glu Trp Glu Ser Asn Gly Gln Pro Glu
        275                 280                 285
Asn Asn Tyr Lys Thr Thr Pro Pro Met Leu Asp Ser Asp Gly Ser Phe
    290                 295                 300
Phe Leu Tyr Ser Lys Leu Thr Val Asp Lys Ser Arg Trp Gln Gln Gly
305                 310                 315                 320
Asn Val Phe Ser Cys Ser Val Met His Glu Ala Leu His Asn His Tyr
                325                 330                 335
Thr Gln Lys Ser Leu Ser Leu Ser Pro Gly
            340                 345
```

<210> SEQ ID NO 215

<400> SEQUENCE: 215

000

<210> SEQ ID NO 216
<211> LENGTH: 346

<212> TYPE: PRT
<213> ORGANISM: Artificial Sequence
<220> FEATURE:
<223> OTHER INFORMATION: Synthetic Construct

<400> SEQUENCE: 216

| | | | | | | | | | | | | | | |
|---|---|---|---|---|---|---|---|---|---|---|---|---|---|---|
| Glu | Glu | Glu | Leu | Gln | Ile | Ile | Gln | Pro | Asp | Lys | Ser | Val | Leu | Val | Ala |
| 1 | | | | 5 | | | | | 10 | | | | | 15 | |
| Ala | Gly | Glu | Thr | Ala | Thr | Leu | Arg | Cys | Thr | Ile | Thr | Ser | Leu | Phe | Pro |
| | | | 20 | | | | | 25 | | | | | 30 | | |
| Val | Gly | Pro | Ile | Gln | Trp | Phe | Arg | Gly | Ala | Gly | Pro | Gly | Arg | Val | Leu |
| | | | 35 | | | | | 40 | | | | | 45 | | |
| Ile | Tyr | Asn | Gln | Arg | Gln | Gly | Pro | Phe | Pro | Arg | Val | Thr | Thr | Val | Ser |
| | 50 | | | | | 55 | | | | | 60 | | | | |
| Asp | Thr | Thr | Lys | Arg | Asn | Asn | Met | Asp | Phe | Ser | Ile | Arg | Ile | Gly | Asn |
| 65 | | | | | 70 | | | | | 75 | | | | | 80 |
| Ile | Thr | Pro | Ala | Asp | Ala | Gly | Thr | Tyr | Tyr | Cys | Ile | Lys | Phe | Arg | Lys |
| | | | | 85 | | | | | 90 | | | | | 95 | |
| Gly | Ser | Pro | Asp | Asp | Val | Glu | Phe | Lys | Ser | Gly | Ala | Gly | Thr | Glu | Leu |
| | | | 100 | | | | | 105 | | | | | 110 | | |
| Ser | Val | Arg | Ala | Lys | Pro | Ser | Asp | Lys | Thr | His | Thr | Cys | Pro | Pro | Cys |
| | | | 115 | | | | | 120 | | | | | 125 | | |
| Pro | Ala | Pro | Glu | Leu | Leu | Gly | Gly | Pro | Ser | Val | Phe | Leu | Phe | Pro | Pro |
| | | 130 | | | | | 135 | | | | | 140 | | | |
| Lys | Pro | Lys | Asp | Thr | Leu | Met | Ile | Ser | Arg | Thr | Pro | Glu | Val | Thr | Cys |
| 145 | | | | | 150 | | | | | 155 | | | | | 160 |
| Val | Val | Val | Asp | Val | Ser | His | Glu | Asp | Pro | Glu | Val | Lys | Phe | Asn | Trp |
| | | | | 165 | | | | | 170 | | | | | 175 | |
| Tyr | Val | Asp | Gly | Val | Glu | Val | His | Asn | Ala | Lys | Thr | Lys | Pro | Arg | Glu |
| | | | 180 | | | | | 185 | | | | | 190 | | |
| Glu | Gln | Tyr | Asn | Ser | Thr | Tyr | Arg | Val | Val | Ser | Val | Leu | Thr | Val | Leu |
| | | | 195 | | | | | 200 | | | | | 205 | | |
| His | Gln | Asp | Trp | Leu | Asn | Gly | Lys | Glu | Tyr | Lys | Cys | Lys | Val | Ser | Asn |
| | | 210 | | | | | 215 | | | | | 220 | | | |
| Lys | Ala | Leu | Pro | Ala | Pro | Ile | Glu | Lys | Thr | Ile | Ser | Lys | Ala | Lys | Gly |
| 225 | | | | | 230 | | | | | 235 | | | | | 240 |
| Gln | Pro | Arg | Glu | Pro | Gln | Val | Tyr | Thr | Leu | Pro | Pro | Ser | Arg | Glu | Glu |
| | | | | 245 | | | | | 250 | | | | | 255 | |
| Met | Thr | Lys | Asn | Gln | Val | Ser | Leu | Thr | Cys | Leu | Val | Lys | Gly | Phe | Tyr |
| | | | 260 | | | | | 265 | | | | | 270 | | |
| Pro | Ser | Asp | Ile | Ala | Val | Glu | Trp | Glu | Ser | Asn | Gly | Gln | Pro | Glu | Asn |
| | | 275 | | | | | 280 | | | | | 285 | | | |
| Asn | Tyr | Lys | Thr | Thr | Pro | Pro | Val | Leu | Asp | Ser | Asp | Gly | Ser | Phe | Phe |
| | 290 | | | | | 295 | | | | | 300 | | | | |
| Leu | Tyr | Ser | Lys | Leu | Thr | Val | Asp | Lys | Ser | Arg | Trp | Gln | Gln | Gly | Asn |
| 305 | | | | | 310 | | | | | 315 | | | | | 320 |
| Val | Phe | Ser | Cys | Ser | Val | Met | His | Glu | Ala | Leu | His | Asn | His | Tyr | Thr |
| | | | | 325 | | | | | 330 | | | | | 335 | |
| Gln | Lys | Ser | Leu | Ser | Leu | Ser | Pro | Gly | Lys | | | | | | |
| | | | 340 | | | | | 345 | | | | | | | |

<210> SEQ ID NO 217
<211> LENGTH: 346
<212> TYPE: PRT
<213> ORGANISM: Artificial Sequence
<220> FEATURE:

<223> OTHER INFORMATION: Synthetic Construct

<400> SEQUENCE: 217

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Lys Thr His Thr Cys Pro Glu Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Glu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 218
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT

```
<222> LOCATION: 6
<223> OTHER INFORMATION: Xaa = V, L, or I
<220> FEATURE:
<221> NAME/KEY: VARIANT
<222> LOCATION: 27
<223> OTHER INFORMATION: Xaa = A, V, L, or I
<220> FEATURE:
<221> NAME/KEY: VARIANT
<222> LOCATION: 31
<223> OTHER INFORMATION: Xaa = I, S, T, or F
<220> FEATURE:
<221> NAME/KEY: VARIANT
<222> LOCATION: 47
<223> OTHER INFORMATION: Xaa = E, L, or V
<220> FEATURE:
<221> NAME/KEY: VARIANT
<222> LOCATION: 53
<223> OTHER INFORMATION: Xaa = K or R
<220> FEATURE:
<221> NAME/KEY: VARIANT
<222> LOCATION: 54
<223> OTHER INFORMATION: Xaa = E or Q
<220> FEATURE:
<221> NAME/KEY: VARIANT
<222> LOCATION: 56
<223> OTHER INFORMATION: Xaa = H, R or P
<220> FEATURE:
<221> NAME/KEY: VARIANT
<222> LOCATION: 66
<223> OTHER INFORMATION: Xaa = S,G, L or  T
<220> FEATURE:
<221> NAME/KEY: VARIANT
<222> LOCATION: 80
<223> OTHER INFORMATION: Xaa = Any Amino Acid
<220> FEATURE:
<221> NAME/KEY: VARIANT
<222> LOCATION: 81
<223> OTHER INFORMATION: Xaa = Any Amino Acid
<220> FEATURE:
<221> NAME/KEY: VARIANT
<222> LOCATION: 82
<223> OTHER INFORMATION: Xaa = Any Amino Acid
<220> FEATURE:
<221> NAME/KEY: VARIANT
<222> LOCATION: 83
<223> OTHER INFORMATION: Xaa = Any Amino Acid
<220> FEATURE:
<221> NAME/KEY: VARIANT
<222> LOCATION: 92
<223> OTHER INFORMATION: Xaa = V or I

<400> SEQUENCE: 218

Glu Glu Glu Leu Gln Xaa Ile Gln Pro Asp Lys Ser Val Leu Val Ala
1               5                   10                  15

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Lys Arg Asn Asn Met Asp Phe Ser Ile Arg Ile Gly Xaa
65                  70                  75                  80

Xaa Xaa Xaa Ala Asp Ala Gly Thr Tyr Tyr Cys Xaa Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 219
```

```
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V, L or I
<220> FEATURE:
<221> NAME/KEY: VARIANT
<222> LOCATION: 27
<223> OTHER INFORMATION: Xaa = A, V, L, or I
<220> FEATURE:
<221> NAME/KEY: VARIANT
<222> LOCATION: 31
<223> OTHER INFORMATION: Xaa = I, S, T or F
<220> FEATURE:
<221> NAME/KEY: VARIANT
<222> LOCATION: 47
<223> OTHER INFORMATION: Xaa = E, L, or V
<220> FEATURE:
<221> NAME/KEY: VARIANT
<222> LOCATION: 53
<223> OTHER INFORMATION: Xaa = K or R
<220> FEATURE:
<221> NAME/KEY: VARIANT
<222> LOCATION: 54
<223> OTHER INFORMATION: Xaa = E or Q
<220> FEATURE:
<221> NAME/KEY: VARIANT
<222> LOCATION: 56
<223> OTHER INFORMATION: Xaa = H, R or P
<220> FEATURE:
<221> NAME/KEY: VARIANT
<222> LOCATION: 66
<223> OTHER INFORMATION: Xaa = S,G, L, or T
<220> FEATURE:
<221> NAME/KEY: VARIANT
<222> LOCATION: 80
<223> OTHER INFORMATION: Xaa = N
<220> FEATURE:
<221> NAME/KEY: VARIANT
<222> LOCATION: 83
<223> OTHER INFORMATION: Xaa = any amino acid other than P
<220> FEATURE:
<221> NAME/KEY: VARIANT
<222> LOCATION: 92
<223> OTHER INFORMATION: Xaa = V or I

<400> SEQUENCE: 219

Glu Glu Glu Leu Gln Xaa Ile Gln Pro Asp Lys Ser Val Leu Val Ala
1               5                   10                  15

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
50                  55                  60

Asp Xaa Thr Lys Arg Asn Asn Met Asp Phe Ser Ile Arg Ile Gly Xaa
65                  70                  75                  80

Ile Thr Xaa Ala Asp Ala Gly Thr Tyr Tyr Cys Xaa Lys Phe Arg Lys
            85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 220
```

-continued

<400> SEQUENCE: 220

000

<210> SEQ ID NO 221
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V or I
<220> FEATURE:
<221> NAME/KEY: VARIANT
<222> LOCATION: 27
<223> OTHER INFORMATION: Xaa = A or I
<220> FEATURE:
<221> NAME/KEY: VARIANT
<222> LOCATION: 31
<223> OTHER INFORMATION: Xaa = I or F
<220> FEATURE:
<221> NAME/KEY: VARIANT
<222> LOCATION: 47
<223> OTHER INFORMATION: Xaa = E or V
<220> FEATURE:
<221> NAME/KEY: VARIANT
<222> LOCATION: 53
<223> OTHER INFORMATION: Xaa = K or R
<220> FEATURE:
<221> NAME/KEY: VARIANT
<222> LOCATION: 56
<223> OTHER INFORMATION: Xaa = H or P
<220> FEATURE:
<221> NAME/KEY: VARIANT
<222> LOCATION: 66
<223> OTHER INFORMATION: Xaa = L or T
<220> FEATURE:
<221> NAME/KEY: VARIANT
<222> LOCATION: 80
<223> OTHER INFORMATION: Xaa = any amino acid other than N
<220> FEATURE:
<221> NAME/KEY: VARIANT
<222> LOCATION: 92
<223> OTHER INFORMATION: Xaa = V or I

<400> SEQUENCE: 221

Glu Glu Glu Leu Gln Xaa Ile Gln Pro Asp Lys Ser Val Leu Val Ala
1               5                   10                  15

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Glu Gly Xaa Phe Pro Arg Val Thr Thr Val Ser
    50                  55                  60

Asp Xaa Thr Lys Arg Asn Asn Met Asp Phe Ser Ile Arg Ile Gly Xaa
65                  70                  75                  80

Ile Thr Pro Ala Asp Ala Gly Thr Tyr Tyr Cys Xaa Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 222
<211> LENGTH: 119
<212> TYPE: PRT
<213> ORGANISM: Artificial Sequence

```
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V, L, or I
<220> FEATURE:
<221> NAME/KEY: VARIANT
<222> LOCATION: 27
<223> OTHER INFORMATION: Xaa = A, I, or L
<220> FEATURE:
<221> NAME/KEY: VARIANT
<222> LOCATION: 31
<223> OTHER INFORMATION: Xaa = I, T, S, or F
<220> FEATURE:
<221> NAME/KEY: VARIANT
<222> LOCATION: 53
<223> OTHER INFORMATION: Xaa = K or R
<220> FEATURE:
<221> NAME/KEY: VARIANT
<222> LOCATION: 56
<223> OTHER INFORMATION: Xaa = H or P
<220> FEATURE:
<221> NAME/KEY: VARIANT
<222> LOCATION: 66
<223> OTHER INFORMATION: Xaa = L, T, or G
<220> FEATURE:
<221> NAME/KEY: VARIANT
<222> LOCATION: 80
<223> OTHER INFORMATION: Xaa = N or A

<400> SEQUENCE: 222

Glu Glu Glu Leu Gln Xaa Ile Gln Pro Asp Lys Ser Val Leu Val Ala
1               5                   10                  15

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Glu Leu
        35                  40                  45

Ile Tyr Asn Gln Xaa Glu Gly Xaa Phe Pro Arg Val Thr Thr Val Ser
    50                  55                  60

Asp Xaa Thr Lys Arg Asn Asn Met Asp Phe Ser Ile Arg Ile Gly Xaa
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 223
<211> LENGTH: 6
<212> TYPE: PRT
<213> ORGANISM: Artificial Sequence
<220> FEATURE:
<223> OTHER INFORMATION: Synthetic Construct

<400> SEQUENCE: 223

His His His His His His
1               5

<210> SEQ ID NO 224
<211> LENGTH: 10
<212> TYPE: PRT
<213> ORGANISM: Artificial Sequence
<220> FEATURE:
<223> OTHER INFORMATION: Synthetic Construct
```

```
<400> SEQUENCE: 224

His His His His His His His His His
1               5                   10
```